US009512190B2

(12) United States Patent
Ueno et al.

(10) Patent No.: US 9,512,190 B2
(45) Date of Patent: Dec. 6, 2016

(54) MALARIA VACCINE

(71) Applicant: VLP Therapeutics, LLC, Wilmington, DE (US)

(72) Inventors: Ryuji Ueno, Saint Michaels, MD (US); Wataru Akahata, Kensington, MD (US)

(73) Assignee: VLP Thereapeutics, LLC, Wilmington, DE (US)

( * ) Notice: Subject to any disclaimer, the term of this patent is extended or adjusted under 35 U.S.C. 154(b) by 0 days.

(21) Appl. No.: 14/294,968

(22) Filed: Jun. 3, 2014

(65) Prior Publication Data

US 2014/0363458 A1 Dec. 11, 2014

Related U.S. Application Data

(60) Provisional application No. 61/906,583, filed on Nov. 20, 2013, provisional application No. 61/830,436, filed on Jun. 3, 2013.

(51) Int. Cl.

| | |
|---|---|
| ***C07K 14/445*** | (2006.01) |
| ***A61K 39/12*** | (2006.01) |
| ***A61K 39/193*** | (2006.01) |
| ***C07K 14/005*** | (2006.01) |
| ***A61K 39/015*** | (2006.01) |
| ***A61K 38/16*** | (2006.01) |
| *A61K 39/00* | (2006.01) |

(52) U.S. Cl.

CPC ........... *C07K 14/445* (2013.01); *A61K 38/162* (2013.01); *A61K 39/015* (2013.01); *A61K 39/12* (2013.01); *A61K 39/193* (2013.01); *C07K 14/005* (2013.01); *A61K 2039/5258* (2013.01); *C07K 2319/85* (2013.01); *C12N 2770/36034* (2013.01)

(58) Field of Classification Search

None

See application file for complete search history.

(56) References Cited

U.S. PATENT DOCUMENTS

2012/0003266 A1 1/2012 Nable et al.
2016/0040134 A1 2/2016 Akahata et al.

FOREIGN PATENT DOCUMENTS

WO 9310152 A1 5/1993
WO 2004043399 A2 5/2004
WO 2006040334 A1 4/2006
WO 2007003384 A1 1/2007
WO 2008025067 A1 3/2008
WO 2011035004 A1 3/2011
WO 2012006180 A1 1/2012
WO 2012023995 A1 2/2012
WO 2012106356 A2 8/2012
WO 2013122262 A1 8/2013

OTHER PUBLICATIONS

Oliveira-Ferreira et al. Immunogenicity of Ty-VLP bearing a CD8(+) T cell epitope of the CS protein of P. yoelii: enhanced memory response by boosting with recombinant vaccinia virus. Vaccine. Mar. 6, 2000;18(17):1863-9.*

GenBank: AAW78190.1. circumsporozoite protein, partial [Plasmodium falciparum]. Dec. 29, 2006. http://www.ncbi.nlm.nih.gov/protein/58429573?report=genbank&log$=protalign&blast_rank=18&RID=P92DM05R01R.*

Gregson et al. Phase I Trial of an Alhydrogel Adjuvanted Hepatitis B Core Virus-Like Particle Containing Epitopes of Plasmodium falciparum Circumsporozoite Protein. PLoS ONE. Feb. 2008 | vol. 3 | Issue 2 | e1556.*

Adams et al. The expression of hybrid HIV:Ty virus-like particles in yeast. Nature. Sep. 3-9, 1987;329(6134):68-70.*

GenBank: ADG95942.1 structural polyprotein [Chikungunya virus] http://www.ncbi.nlm.nih.gov/protein/296124572?report=genbank&log$=protalign&blast_rank=2&RID=PBR7NT0U015. Dec. 28, 2010.*

Calvo-Calle et al. A Linear Peptide Containing Minimal T- and B-Cell Epitopes of Plasmodium falciparum Circumsporozoite Protein Elicits Protection against Transgenic Sporozoite Challenge. Infection and Immunity, Dec. 2006, p. 6929-6939. vol. 74, No. 12.*

Federico M. Virus-like particles show promise as candidates for new vaccine strategies. Future Virol. (2010) 5(4), 371-374.*

Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445.

Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.

Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi:10.1371/journal.pone.0079538.

Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648.

Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371.

Ghasparian A et al., Engineered synthetic virus-like particles and their use in vaccine delivery, Chembiochem, 2011, vol. 12, No. 1, pp. 100-109.

Dobano C et al., Alphavirus replicon particles are highly immunogenic in the murine Malaria model by homologous or heterologous immunization, Open Vaccine Journal, vol. 1, 2008, pp. 27-37.

Lechner F et al., Virus-like particles as a modular system for novel vaccines, Intervirology, 2002, vol. 45, No. 4-6, pp. 212-217.

(Continued)

*Primary Examiner* — Nick Zou

(74) *Attorney, Agent, or Firm* — Sughrue Mion, PLLC

(57) ABSTRACT

The present invention provides a particle comprising a polypeptide and at least one malaria antigen, and a composition or vaccine comprising thereof, its use in medicine, particularly in the prevention or treatment of malaria infections.

18 Claims, 6 Drawing Sheets

(56) References Cited

OTHER PUBLICATIONS

Gilbert SC et al., A protein particle vaccine containing multiple Malaria epitopes, Nat. Biotechnol., 1997, vol. 15, No. 12, pp. 1280-1284.
Allsopp CE et al., Comparison of numerous delivery systems for the induction of cytotoxic T lymphocytes by immunization, Eur. J. Immunol., 1996, vol. 26, No. 8, pp. 1951-1959.
International Search Report and Written Opinion dated Sep. 16, 2014, issued by the International Searching Authority in counterpart International Application No. PCT/JP2014/065166.
Carvalho et al., "Malaria Vaccine: Candidate Antigens, Mechanisms, Constraints and Prospects", Scand. J. Immunol., Blackwell Science Ltd., Jul. 1, 2002, vol. 56, pp. 327-343.
Akahata et al., "A VLP vaccine for epidemic Chikungunya virus protects nonhuman primates against infection", NIH Public Access Author Manuscript, Sep. 1, 2010 for Nat. Med., Mar. 2010, vol. 16, No. 3, pp. 334-338, doi:10.1038/nm.2105 (12 pages total).
Roldao et al., "Virus-like particles in vaccine development", Expert Reviews Vaccines, Expert Reviews Ltd., 2010, vol. 9, No. 10, pp. 1149-1176.
Crompton et al, "Advances and challenges in malaria vaccine development", Science in medicine, The Journal of Clinical Investigation, Dec. 2010, vol. 120, No. 12, pp. 4168-4178.

SEQUENCE LISTING

<160> NUMBER OF SEQ ID NOS: 56

<210> SEQ ID NO 1
<211> LENGTH: 1248
<212> TYPE: PRT
<213> ORGANISM: Chikungunya virus

<400> SEQUENCE: 1

Met Glu Phe Ile Pro Thr Gln Thr Phe Tyr Asn Arg Arg Tyr Gln Pro
1 5 10 15

Arg Pro Trp Thr Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Lys Gln Lys Gln Gln Ala Pro Gln Asn Asn
65 70 75 80

Thr Asn Gln Lys Lys Gln Pro Pro Lys Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Thr Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Ile Pro Val Met Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Glu Thr Leu Arg Met Leu Glu Asp Asn Val Met
290 295 300

Arg Pro Gly Tyr Tyr Gln Leu Leu Gln Ala Ser Leu Thr Cys Ser Pro
305 310 315 320

His Arg Gln Arg Arg Ser Thr Lys Asp Asn Phe Asn Val Tyr Lys Ala
325 330 335

-continued

```
Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750
```

-continued

```
Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Val  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Met  Pro Ile Ser Ile Asp  Ile Pro Glu Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Ala Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
```

```
    1160                1165                1170

Phe Arg  Val Gln Val Cys Ser  Thr Gln Val His Cys  Ala Ala Glu
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp
    1205                1210                1215

Val Gln  Lys Ile Thr Gly Gly  Val Gly Leu Val Val  Ala Val Ala
    1220                1225                1230

Ala Leu  Ile Leu Ile Val Val  Leu Cys Val Ser Phe  Ser Arg His
    1235                1240                1245


<210> SEQ ID NO 2
<211> LENGTH: 1248
<212> TYPE: PRT
<213> ORGANISM: Chikungunya virus

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285
```

```
Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
```

-continued

```
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Ile  Pro Ile Ser Ile Asp  Ile Pro Asp Ala Ala  Phe Thr Arg
    1085                 1090                 1095

Val Val  Asp Ala Pro Ser Val  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125
```

```
Tyr Thr  Ala Ser Lys Lys Gly  Lys Cys Ala Val His  Ser Met Thr
    1130                 1135                 1140

Asn Ala  Val Thr Ile Arg Glu  Ala Asp Val Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Ala
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Thr Thr Ala  Met Ser Trp
    1205                 1210                 1215

Val Gln  Lys Ile Thr Gly Gly  Val Gly Leu Ile Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 3
<211> LENGTH: 1255
<212> TYPE: PRT
<213> ORGANISM: Venesuelan equine encephalitis virus

<400> SEQUENCE: 3

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
```

-continued

```
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
        595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670
```

-continued

```
Trp Ala Gln Glu Thr Ala Pro Gly Asn Pro His Gly Leu Pro His Glu
        675                 680                 685

Val Ile Thr His Tyr Tyr His Arg Tyr Pro Met Ser Thr Ile Leu Gly
    690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
        755                 760                 765

Asn Asn Asn Gln Gln Met Phe Trp Ile Gln Leu Leu Ile Pro Leu Ala
    770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
                805                 810                 815

Ala Thr Thr Met Pro Ser Gln Ala Gly Ile Ser Tyr Asn Thr Ile Val
            820                 825                 830

Asn Arg Ala Gly Tyr Ala Pro Leu Pro Ile Ser Ile Thr Pro Thr Lys
        835                 840                 845

Ile Lys Leu Ile Pro Thr Val Asn Leu Glu Tyr Val Thr Cys His Tyr
    850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr  Asp Phe Pro Glu Tyr  Gly Ala Gly
        995                 1000                 1005

Gln Pro  Gly Ala Phe Gly Asp  Ile Gln Ser Arg Thr  Val Ser Ser
    1010                 1015                 1020

Ser Asp  Leu Tyr Ala Asn Thr  Asn Leu Val Leu Gln  Arg Pro Lys
    1025                 1030                 1035

Ala Gly  Ala Ile His Val Pro  Tyr Thr Gln Ala Pro  Ser Gly Phe
    1040                 1045                 1050

Glu Gln  Trp Lys Lys Asp Lys  Ala Pro Ser Leu Lys  Phe Thr Ala
    1055                 1060                 1065

Pro Phe  Gly Cys Glu Ile Tyr  Thr Asn Pro Ile Arg  Ala Glu Asn
    1070                 1075                 1080
```

```
Cys Ala  Val Gly Ser Ile Pro  Leu Ala Phe Asp Ile  Pro Asp Ala
    1085                 1090                 1095

Leu Phe  Thr Arg Val Ser Glu  Thr Pro Thr Leu Ser  Ala Ala Glu
    1100                 1105                 1110

Cys Thr  Leu Asn Glu Cys Val  Tyr Ser Ser Asp Phe  Gly Gly Ile
    1115                 1120                 1125

Ala Thr  Val Lys Tyr Ser Ala  Ser Lys Ser Gly Lys  Cys Ala Val
    1130                 1135                 1140

His Val  Pro Ser Gly Thr Ala  Thr Leu Lys Glu Ala  Ala Val Glu
    1145                 1150                 1155

Leu Thr  Glu Gln Gly Ser Ala  Thr Ile His Phe Ser  Thr Ala Asn
    1160                 1165                 1170

Ile His  Pro Glu Phe Arg Leu  Gln Ile Cys Thr Ser  Tyr Val Thr
    1175                 1180                 1185

Cys Lys  Gly Asp Cys His Pro  Pro Lys Asp His Ile  Val Thr His
    1190                 1195                 1200

Pro Gln  Tyr His Ala Gln Thr  Phe Thr Ala Ala Val  Ser Lys Thr
    1205                 1210                 1215

Ala Trp  Thr Trp Leu Thr Ser  Leu Leu Gly Gly Ser  Ala Val Ile
    1220                 1225                 1230

Ile Ile  Ile Gly Leu Val Leu  Ala Thr Ile Val Ala  Met Tyr Val
    1235                 1240                 1245

Leu Thr  Asn Gln Lys His Asn
    1250                 1255


<210> SEQ ID NO 4
<211> LENGTH: 2964
<212> TYPE: DNA
<213> ORGANISM: Chikungunya virus

<400> SEQUENCE: 4

atgagcctcg ccctcccggt cttgtgcctg ttggcaaaca ctacattccc ctgctctcag     60

ccgccttgca caccctgctg ctacgaaaag gaaccggaaa gcaccttgcg catgcttgag    120

gacaacgtga tgagacccgg atactaccag ctactaaaag catcgctgac ttgctctccc    180

caccgccaaa gacgcagtac taaggacaat tttaatgtct ataaagccac aagaccatat    240

ctagctcatt gtcctgactg cggagaaggg cattcgtgcc acagccctat cgcattggag    300

cgcatcagaa atgaagcaac ggacggaacg ctgaaaatcc aggtctcttt gcagatcggg    360

ataaagacag atgacagcca cgattggacc aagctgcgct atatggatag ccatacgcca    420

gcggacgcgg agcgagccgg attgcttgta aggacttcag caccgtgcac gatcaccggg    480

accatgggac actttattct cgcccgatgc ccgaaaggag agacgctgac agtgggattt    540

acggacagca gaaagatcag ccacacatgc acacacccgt tccatcatga accacctgtg    600

ataggtaggg agaggttcca ctctcgacca caacatggta aagagttacc ttgcagcacg    660

tacgtgcaga gcaccgctgc cactgctgag gagatagagg tgcatatgcc cccagatact    720

cctgaccgca cgctgatgac gcagcagtct ggcaacgtga agatcacagt taatgggcag    780

acggtgcggt acaagtgcaa ctgcggtggc tcaaacgagg gactgacaac cacagacaaa    840

gtgatcaata actgcaaaat tgatcagtgc catgctgcag tcactaatca caagaattgg    900

caatacaact cccctttagt cccgcgcaac gctgaactcg gggaccgtaa aggaaagatc    960

cacatcccat tcccattggc aaacgtgact tgcagagtgc caaaagcaag aaaccctaca   1020

gtaacttacg gaaaaaacca agtcaccatg ctgctgtatc ctgaccatcc gacactcttg   1080
```

tcttaccgta acatgggaca ggaaccaaat taccacgagg agtgggtgac acacaagaag 1140
gaggttacct tgaccgtgcc tactgagggt ctggaggtca cttggggcaa caacgaacca 1200
tacaagtact ggccgcagat gtctacgaac ggtactgctc atggtcaccc acatgagata 1260
atcttgtact attatgagct gtaccccact atgactgtag tcattgtgtc ggtggcctcg 1320
ttcgtgcttc tgtcgatggt gggcacagca gtgggaatgt gtgtgtgcgc acggcgcaga 1380
tgcattacac catatgaatt aacaccagga gccactgttc ccttcctgct cagcctgcta 1440
tgctgcgtca gaacgaccaa ggcggccaca tattacgagg ctgcggcata tctatggaac 1500
gaacagcagc ccctgttctg gttgcaggct cttatcccgc tggccgcctt gatcgtcctg 1560
tgcaactgtc tgaaactctt gccatgctgc tgtaagaccc tggctttttt agccgtaatg 1620
agcatcggtg cccacactgt gagcgcgtac gaacacgtaa cagtgatccc gaacacggtg 1680
ggagtaccgt ataagactct tgtcaacaga ccgggttaca gccccatggt gttggagatg 1740
gagctacaat cagtcacctt ggaaccaaca ctgtcacttg actacatcac gtgcgagtac 1800
aaaactgtca tcccctcccc gtacgtgaag tgctgtggta cagcagagtg caaggacaag 1860
agcctaccag actacagctg caaggtcttt actggagtct acccatttat gtggggcggc 1920
gcctactgct tttgcgacgc cgaaaatacg caattgagcg aggcacatgt agagaaatct 1980
gaatcttgca aaacagagtt tgcatcggcc tacagagccc acaccgcatc ggcgtcggcg 2040
aagctccgcg tcctttacca aggaaacaac attaccgtag ctgcctacgc taacggtgac 2100
catgccgtca cagtaaagga cgccaagttt gtcgtgggcc caatgtcctc cgcctggaca 2160
ccttttgaca acaaaatcgt ggtgtacaaa ggcgacgtct acaacatgga ctacccacct 2220
tttggcgcag gaagaccagg acaatttggt gacattcaaa gtcgtacacc ggaaagtaaa 2280
gacgtttatg ccaacactca gttggtacta cagaggccag cagcaggcac ggtacatgta 2340
ccatactctc aggcaccatc tggcttcaag tattggctga aggaacgagg agcatcgcta 2400
cagcacacgg caccgttcgg ttgccagatt gcgacaaacc cggtaagagc tgtaaattgc 2460
gctgtgggga acataccaat ttccatcgac ataccggatg cggcctttac tagggttgtc 2520
gatgcaccct ctgtaacgga catgtcatgc gaagtaccag cctgcactca ctcctccgac 2580
tttgggggcg tcgccatcat caaatacaca gctagcaaga aaggtaaatg tgcagtacat 2640
tcgatgacca acgccgttac cattcgagaa gccgacgtag aagtagaggg gaactcccag 2700
ctgcaaatat ccttctcaac agccctggca agcgccgagt ttcgcgtgca agtgtgctcc 2760
acacaagtac actgcgcagc cgcatgccac cctccaaagg accacatagt caattaccca 2820
gcatcacaca ccacccttgg ggtccaggat atatccacaa cggcaatgtc ttgggtgcag 2880
aagattacgg gaggagtagg attaattgtt gctgttgctg ccttaatttt aattgtggtg 2940
ctatgcgtgt cgtttagcag gcac 2964

<210> SEQ ID NO 5
<211> LENGTH: 2964
<212> TYPE: DNA
<213> ORGANISM: Chikungunya virus

<400> SEQUENCE: 5
atgagtcttg ccatcccagt tatgtgcctg ttggcaaaca ccacgttccc ctgctcccag 60 ccccttgca cgccctgctg ctacgaaaag gaaccggagg aaaccctacg catgcttgag 120
gacaacgtca tgagacctgg gtactatcag ctgctacaag catccttaac atgttctccc 180

```
caccgccagc gacgcagcac caaggacaac ttcaatgtct ataaagccac aagaccatac    240
ttagctcact gtcccgactg tggagaaggg cactcgtgcc atagtcccgt agcactagaa    300
cgcatcagaa atgaagcgac agacgggacg ctgaaaatcc aggtctcctt gcaaatcgga    360
ataaagacgg atgacagcca cgattggacc aagctgcgtt atatggacaa ccacatgcca    420
gcagacgcag agagggcggg gctatttgta agaacatcag caccgtgtac gattactgga    480
acaatgggac acttcatcct ggcccgatgt ccaaaagggg aaactctgac ggtgggattc    540
actgacagta ggaagattag tcactcatgt acgcacccat ttcaccacga ccctcctgtg    600
ataggtcggg aaaaattcca ttcccgaccg cagcacggta aagagctacc ttgcagcacg    660
tacgtgcaga gcaccgccgc aactaccgag gagatagagg tacacatgcc cccagacacc    720
cctgatcgca cattaatgtc acaacagtcc ggcaacgtaa agatcacagt caatggccag    780
acggtgcggt acaagtgtaa ttgcggtggc tcaaatgaag gactaacaac tacagacaaa    840
gtgattaata actgcaaggt tgatcaatgt catgccgcgg tcaccaatca caaaaagtgg    900
cagtataact cccctctggt cccgcgtaat gctgaacttg ggaccgaaaa aggaaaaatt    960
cacatcccgt ttccgctggc aaatgtaaca tgcagggtgc ctaaagcaag gaaccccacc   1020
gtgacgtacg ggaaaaacca agtcatcatg ctactgtatc ctgaccaccc aacactcctg   1080
tcctaccgga atatgggaga agaaccaaac tatcaagaag agtgggtgat gcataagaag   1140
gaagtcgtgc taaccgtgcc gactgaaggg ctcgaggtca cgtggggcaa caacgagccg   1200
tataagtatt ggccgcagtt atctacaaac ggtacagccc atggccaccc gcatgagata   1260
attctgtatt attatgagct gtaccccact atgactgtag tagttgtgtc agtggccacg   1320
ttcatactcc tgtcgatggt gggtatggca gcggggatgt gcatgtgtgc acgacgcaga   1380
tgcatcacac cgtatgaact gacaccagga gctaccgtcc ctttcctgct tagcctaata   1440
tgctgcatca gaacagctaa agcggccaca taccaagagg ctgcgatata cctgtggaac   1500
gagcagcaac ctttgttttg gctacaagcc cttattccgc tggcagccct gattgttcta   1560
tgcaactgtc tgagactctt accatgctgc tgtaaaacgt tggctttttt agccgtaatg   1620
agcgtcggtg cccacactgt gagcgcgtac gaacacgtaa cagtgatccc gaacacggtg   1680
ggagtaccgt ataagactct agtcaataga cctggctaca gccccatggt attggagatg   1740
gaactactgt cagtcacttt ggagccaaca ctatcgcttg attacatcac gtgcgagtac   1800
aaaaccgtca tcccgtctcc gtacgtgaag tgctgcggta cagcagagtg caaggacaaa   1860
aacctacctg actacagctg taaggtcttc accggcgtct acccatttat gtggggcggc   1920
gcctactgct tctgcgacgc tgaaaacacg cagttgagcg aagcacacgt ggagaagtcc   1980
gaatcatgca aaacagaatt tgcatcagca tacagggctc ataccgcatc tgcatcagct   2040
aagctccgcg tcctttacca aggaaataac atcactgtaa ctgcctatgc aaacggcgac   2100
catgccgtca cagttaagga cgccaaattc attgtggggc caatgtcttc agcctggaca   2160
cctttcgaca acaaaattgt ggtgtacaaa ggtgacgtct ataacatgga ctacccgccc   2220
tttggcgcag gaagaccagg acaatttggc gatatccaaa gtcgcacacc tgagagtaaa   2280
gacgtctatg ctaatacaca actggtactg cagagaccgg ctgtgggtac ggtacacgtg   2340
ccatactctc aggcaccatc tggctttaag tattggctaa aagaacgcgg ggcgtcgctg   2400
cagcacacag caccatttgg ctgccaaata gcaacaaacc cggtaagagc ggtgaactgc   2460
gccgtaggga acatgcccat ctccatcgac ataccggaag cggccttcac tagggtcgtc   2520
gacgcgccct ctttaacgga catgtcgtgc gaggtaccag cctgcaccca ttcctcagac   2580
```

```
tttgggggcg tcgccattat taaatatgca gccagcaaga aaggcaagtg tgcggtgcat   2640

tcgatgacta acgccgtcac tattcgggaa gctgagatag aagttgaagg gaattctcag   2700

ctgcaaatct ctttctcgac ggccttagcc agcgccgaat tccgcgtaca agtctgttct   2760

acacaagtac actgtgcagc cgagtgccac cccccgaagg accacatagt caactacccg   2820

gcgtcacata ccaccctcgg ggtccaggac atctccgcta cggcgatgtc atgggtgcag   2880

aagatcacgg gaggtgtggg actggttgtt gctgttgccg cactgattct aatcgtggtg   2940

ctatgcgtgt cgttcagcag gcac                                          2964


<210> SEQ ID NO 6
<211> LENGTH: 3747
<212> TYPE: DNA
<213> ORGANISM: Chikungunya virus

<400> SEQUENCE: 6

atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080

cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380

ataggtaggg agaggttcca ctctcgacca caacatggta aagagttacc ttgcagcacg   1440

tacgtgcaga gcaccgctgc cactgctgag gagatagagg tgcatatgcc cccagatact   1500

cctgaccgca cgctgatgac gcagcagtct ggcaacgtga agatcacagt taatgggcag   1560

acggtgcggt acaagtgcaa ctgcggtggc tcaaacgagg gactgacaac cacagacaaa   1620

gtgatcaata actgcaaaat tgatcagtgc catgctgcag tcactaatca caagaattgg   1680
```

-continued

```
caatacaact cccctttagt cccgcgcaac gctgaactcg gggaccgtaa aggaaagatc   1740
cacatcccat tcccattggc aaacgtgact tgcagagtgc caaaagcaag aaaccctaca   1800
gtaacttacg gaaaaaacca agtcaccatg ctgctgtatc ctgaccatcc gacactcttg   1860
tcttaccgta acatgggaca ggaaccaaat taccacgagg agtgggtgac acacaagaag   1920
gaggttacct tgaccgtgcc tactgagggt ctggaggtca cttggggcaa caacgaacca   1980
tacaagtact ggccgcagat gtctacgaac ggtactgctc atggtcaccc acatgagata   2040
atcttgtact attatgagct gtaccccact atgactgtag tcattgtgtc ggtggcctcg   2100
ttcgtgcttc tgtcgatggt gggcacagca gtgggaatgt gtgtgtgcgc acggcgcaga   2160
tgcattacac catatgaatt aacaccagga gccactgttc ccttcctgct cagcctgcta   2220
tgctgcgtca gaacgaccaa ggcggccaca tattacgagg ctgcggcata tctatggaac   2280
gaacagcagc ccctgttctg gttgcaggct cttatcccgc tggccgcctt gatcgtcctg   2340
tgcaactgtc tgaaactctt gccatgctgc tgtaagaccc tggctttttt agccgtaatg   2400
agcatcggtg cccacactgt gagcgcgtac gaacacgtaa cagtgatccc gaacacggtg   2460
ggagtaccgt ataagactct tgtcaacaga ccgggttaca gccccatggt gttggagatg   2520
gagctacaat cagtcacctt ggaaccaaca ctgtcacttg actacatcac gtgcgagtac   2580
aaaactgtca tcccctcccc gtacgtgaag tgctgtggta cagcagagtg caaggacaag   2640
agcctaccag actacagctg caaggtcttt actggagtct acccatttat gtggggcggc   2700
gcctactgct tttgcgacgc cgaaaatacg caattgagcg aggcacatgt agagaaatct   2760
gaatcttgca aaacagagtt tgcatcggcc tacagagccc acaccgcatc ggcgtcggcg   2820
aagctccgcg tcctttacca aggaaacaac attaccgtag ctgcctacgc taacggtgac   2880
catgccgtca cagtaaagga cgccaagttt gtcgtgggcc caatgtcctc cgcctggaca   2940
ccttttgaca acaaaatcgt ggtgtacaaa ggcgacgtct acaacatgga ctacccacct   3000
tttggcgcag gaagaccagg acaatttggt gacattcaaa gtcgtacacc ggaaagtaaa   3060
gacgtttatg ccaacactca gttggtacta cagaggccag cagcaggcac ggtacatgta   3120
ccatactctc aggcaccatc tggcttcaag tattggctga aggaacgagg agcatcgcta   3180
cagcacacgg caccgttcgg ttgccagatt gcgacaaacc cggtaagagc tgtaaattgc   3240
gctgtgggga acataccaat ttccatcgac ataccggatg cggcctttac tagggttgtc   3300
gatgcaccct ctgtaacgga catgtcatgc gaagtaccag cctgcactca ctcctccgac   3360
tttgggggcg tcgccatcat caaatacaca gctagcaaga aaggtaaatg tgcagtacat   3420
tcgatgacca acgccgttac cattcgagaa gccgacgtag aagtagaggg gaactcccag   3480
ctgcaaatat ccttctcaac agccctggca agcgccgagt ttcgcgtgca agtgtgctcc   3540
acacaagtac actgcgcagc cgcatgccac cctccaaagg accacatagt caattaccca   3600
gcatcacaca ccacccttgg ggtccaggat atatccacaa cggcaatgtc ttgggtgcag   3660
aagattacgg gaggagtagg attaattgtt gctgttgctg ccttaatttt aattgtggtg   3720
ctatgcgtgt cgtttagcag gcactaa                                        3747
```

<210> SEQ ID NO 7
<211> LENGTH: 3747
<212> TYPE: DNA
<213> ORGANISM: Chikungunya virus

<400> SEQUENCE: 7

```
atggagttca tcccaaccca aactttttac aataggaggt accagcctcg accctggact     60
```

```
ccgcgcccta ctatccaagt catcaggccc agaccgcgcc ctcagaggca agctgggcaa    120
cttgcccagc tgatctcagc agttaataaa ctgacaatgc gcgcggtacc acaacagaag    180
ccacgcagga atcggaagaa taagaagcaa aagcaaaaac aacaggcgcc acaaaacaac    240
acaaatcaaa agaagcagcc acctaaaaag aaaccggctc aaaagaaaaa gaagccgggc    300
cgcagagaga ggatgtgcat gaaaatcgaa aatgattgta ttttcgaagt caagcacgaa    360
ggtaaggtaa caggttacgc gtgcctggtg ggggacaaag taatgaaacc agcacacgta    420
aaggggacca tcgataacgc ggacctggcc aaactggcct ttaagcggtc atctaagtat    480
gaccttgaat gcgcgcagat acccgtgcac atgaagtccg acgcttcgaa gttcacccat    540
gagaaaccgg aggggtacta caactggcac cacggagcag tacagtactc aggaggccgg    600
ttcaccatcc ctacaggtgc tggcaaacca ggggacagcg gcagaccgat cttcgacaac    660
aagggacgcg tggtggccat agtcttagga ggagctaatg aaggagcccg tacagccctc    720
tcggtggtga cctggaataa agacattgtc actaaaatca cccccgaggg ggccgaagag    780
tggagtcttg ccatcccagt tatgtgcctg ttggcaaaca ccacgttccc ctgctcccag    840
ccccccttgca cgccctgctg ctacgaaaag gaaccggagg aaaccctacg catgcttgag    900
gacaacgtca tgagacctgg gtactatcag ctgctacaag catccttaac atgttctccc    960
caccgccagc gacgcagcac caaggacaac ttcaatgtct ataaagccac aagaccatac   1020
ttagctcact gtcccgactg tggagaaggg cactcgtgcc atagtcccgt agcactagaa   1080
cgcatcagaa atgaagcgac agacgggacg ctgaaaatcc aggtctcctt gcaaatcgga   1140
ataaagacgg atgacagcca cgattggacc aagctgcgtt atatggacaa ccacatgcca   1200
gcagacgcag agagggcggg gctatttgta agaacatcag caccgtgtac gattactgga   1260
acaatgggac acttcatcct ggcccgatgt ccaaaagggg aaactctgac ggtgggattc   1320
actgacagta ggaagattag tcactcatgt acgcacccat ttcaccacga ccctcctgtg   1380
ataggtcggg aaaaattcca ttcccgaccg cagcacggta aagagctacc ttgcagcacg   1440
tacgtgcaga gcaccgccgc aactaccgag gagatagagg tacacatgcc cccagacacc   1500
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaaagtgg   1680
cagtataact cccctctggt cccgcgtaat gctgaacttg gggaccgaaa aggaaaaatt   1740
cacatcccgt ttccgctggc aaatgtaaca tgcagggtgc ctaaagcaag gaaccccacc   1800
gtgacgtacg ggaaaaacca agtcatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatgagata   2040
attctgtatt attatgagct gtaccccact atgactgtag tagttgtgtc agtggccacg   2100
ttcatactcc tgtcgatggt gggtatggca gcggggatgt gcatgtgtgc acgacgcaga   2160
tgcatcacac cgtatgaact gacaccagga gctaccgtcc ctttcctgct tagcctaata   2220
tgctgcatca gaacagctaa agcggccaca taccaagagg ctgcgatata cctgtggaac   2280
gagcagcaac ctttgttttg gctacaagcc cttattccgc tggcagccct gattgttcta   2340
tgcaactgtc tgagactctt accatgctgc tgtaaaacgt tggctttttt agccgtaatg   2400
```

```
agcgtcggtg cccacactgt gagcgcgtac gaacacgtaa cagtgatccc gaacacggtg   2460

ggagtaccgt ataagactct agtcaataga cctggctaca gccccatggt attggagatg   2520

gaactactgt cagtcacttt ggagccaaca ctatcgcttg attacatcac gtgcgagtac   2580

aaaaccgtca tcccgtctcc gtacgtgaag tgctgcggta cagcagagtg caaggacaaa   2640

aacctacctg actacagctg taaggtcttc accggcgtct acccatttat gtggggcggc   2700

gcctactgct tctgcgacgc tgaaaacacg cagttgagcg aagcacacgt ggagaagtcc   2760

gaatcatgca aaacagaatt tgcatcagca tacagggctc ataccgcatc tgcatcagct   2820

aagctccgcg tcctttacca aggaaataac atcactgtaa ctgcctatgc aaacggcgac   2880

catgccgtca cagttaagga cgccaaattc attgtggggc caatgtcttc agcctggaca   2940

cctttcgaca acaaaattgt ggtgtacaaa ggtgacgtct ataacatgga ctacccgccc   3000

tttggcgcag gaagaccagg acaatttggc gatatccaaa gtcgcacacc tgagagtaaa   3060

gacgtctatg ctaatacaca actggtactg cagagaccgg ctgtgggtac ggtacacgtg   3120

ccatactctc aggcaccatc tggctttaag tattggctaa aagaacgcgg ggcgtcgctg   3180

cagcacacag caccatttgg ctgccaaata gcaacaaacc cggtaagagc ggtgaactgc   3240

gccgtaggga acatgcccat ctccatcgac ataccggaag cggccttcac tagggtcgtc   3300

gacgcgccct ctttaacgga catgtcgtgc gaggtaccag cctgcaccca ttcctcagac   3360

tttgggggcg tcgccattat taaatatgca gccagcaaga aaggcaagtg tgcggtgcat   3420

tcgatgacta acgccgtcac tattcgggaa gctgagatag aagttgaagg gaattctcag   3480

ctgcaaatct ctttctcgac ggccttagcc agcgccgaat tccgcgtaca agtctgttct   3540

acacaagtac actgtgcagc cgagtgccac cccccgaagg accacatagt caactacccg   3600

gcgtcacata ccaccctcgg ggtccaggac atctccgcta cggcgatgtc atgggtgcag   3660

aagatcacgg gaggtgtggg actggttgtt gctgttgccg cactgattct aatcgtggtg   3720

ctatgcgtgt cgttcagcag gcactaa                                       3747
```

<210> SEQ ID NO 8
<211> LENGTH: 8404
<212> TYPE: DNA
<213> ORGANISM: Artificial Sequence
<220> FEATURE:
<223> OTHER INFORMATION: Synthetic vector VLP_CHI512

<400> SEQUENCE: 8

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720
```

```
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtccggagg atccaacgtg aagatcacag   2460
ttaatgggca gacggtgcgg tacaagtgca actgcggtgg ctcaaacgag ggactgacaa   2520
ccacagacaa agtgatcaat aactgcaaaa ttgatcagtg ccatgctgca gtcactaatc   2580
acaagaattg gcaatacaac tcccctttag tcccgcgcaa cgctgaactc ggggaccgta   2640
aaggaaagat ccacatccca ttcccattgg caaacgtgac ttgcagagtg ccaaaagcaa   2700
gaaaccctac agtaacttac ggaaaaaacc aagtcaccat gctgctgtat cctgaccatc   2760
cgacactctt gtcttaccgt aacatgggac aggaaccaaa ttaccacgag gagtgggtga   2820
cacacaagaa ggaggttacc ttgaccgtgc ctactgaggg tctggaggtc acttggggca   2880
acaacgaacc atacaagtac tggccgcaga tgtctacgaa cggtactgct catggtcacc   2940
cacatgagat aatcttgtac tattatgagc tgtaccccac tatgactgta gtcattgtgt   3000
cggtggcctc gttcgtgctt ctgtcgatgg tgggcacagc agtgggaatg tgtgtgtgcg   3060
```

-continued

```
cacggcgcag atgcattaca ccatatgaat taacaccagg agccactgtt cccttcctgc   3120
tcagcctgct atgctgcgtc agaacgacca aggcggccac atattacgag gctgcggcat   3180
atctatggaa cgaacagcag cccctgttct ggttgcaggc tcttatcccg ctggccgcct   3240
tgatcgtcct gtgcaactgt ctgaaactct tgccatgctg ctgtaagacc ctggcttttt   3300
tagccgtaat gagcatcggt gcccacactg tgagcgcgta cgaacacgta acagtgatcc   3360
cgaacacggt gggagtaccg tataagactc ttgtcaacag accgggttac agccccatgg   3420
tgttggagat ggagctacaa tcagtcacct tggaaccaac actgtcactt gactacatca   3480
cgtgcgagta caaaactgtc atcccctccc cgtacgtgaa gtgctgtggt acagcagagt   3540
gcaaggacaa gagcctacca gactacagct gcaaggtctt tactggagtc tacccattta   3600
tgtggggcgg cgcctactgc ttttgcgacg ccgaaaatac gcaattgagc gaggcacatg   3660
tagagaaatc tgaatcttgc aaaacagagt ttgcatcggc ctacagagcc cacaccgcat   3720
cggcgtcggc gaagctccgc gtcctttacc aaggaaacaa cattaccgta gctgcctacg   3780
ctaacggtga ccatgccgtc acagtaaagg acgccaagtt tgtcgtgggc ccaatgtcct   3840
ccgcctggac accttttgac aacaaaatcg tggtgtacaa aggcgacgtc tacaacatgg   3900
actacccacc ttttggcgca ggaagaccag gacaatttgg tgacattcaa agtcgtacac   3960
cggaaagtaa agacgtttat gccaacactc agttggtact acagaggcca gcagcaggca   4020
cggtacatgt accatactct caggcaccat ctggcttcaa gtattggctg aaggaacgag   4080
gagcatcgct acagcacacg gcaccgttcg gttgccagat tgcgacaaac ccggtaagag   4140
ctgtaaattg cgctgtgggg aacataccaa tttccatcga cataccggat gcggccttta   4200
ctagggttgt cgatgcaccc tctgtaacgg acatgtcatg cgaagtacca gcctgcactc   4260
actcctccga ctttgggggc gtcgccatca tcaaatacac agctagcaag aaaggtaaat   4320
gtgcagtaca ttcgatgacc aacgccgtta ccattcgaga agccgacgta gaagtagagg   4380
ggaactccca gctgcaaata tccttctcaa cagccctggc aagcgccgag tttcgcgtgc   4440
aagtgtgctc cacacaagta cactgcgcag ccgcatgcca ccctccaaag gaccacatag   4500
tcaattaccc agcatcacac accacccttg ggtccagga tatatccaca acggcaatgt    4560
cttgggtgca gaagattacg ggaggagtag gattaattgt tgctgttgct gccttaattt   4620
taattgtggt gctatgcgtg tcgtttagca ggcactaagg atctagatct gctgtgcctt   4680
ctagttgcca gccatctgtt gtttgcccct cccccgtgcc ttccttgacc ctggaaggtg   4740
ccactcccac tgtcctttcc taataaaatg aggaaattgc atcgcattgt ctgagtaggt   4800
gtcattctat tctggggggt ggggtggggc aggacagcaa gggggaggat tgggaagaca   4860
atagcaggca tgctggggat gcggtgggct ctatgggtac ccaggtgctg aagaattgac   4920
ccggttcctc ctgggccaga aagaagcagg cacatcccct tctctgtgac acaccctgtc   4980
cacgcccctg gttcttagtt ccagccccac tcataggaca ctcatagctc aggagggctc   5040
cgccttcaat cccacccgct aaagtacttg gagcggtctc tccctccctc atcagcccac   5100
caaaccaaac ctagcctcca agagtgggaa gaaattaaag caagataggc tattaagtgc   5160
agagggagag aaaatgcctc caacatgtga ggaagtaatg agagaaatca tagaatttta   5220
aggccatgat ttaaggccat catggcctaa gcttgaaagg agataggatc aaagcttggc   5280
gtaatcatgg tcatagctgt ttcctgtgtg aaattgttat ccgctcacaa ttccacacaa   5340
catacgagcc ggaagcataa agtgtaaagc ctggggtgcc taatgagtga gctaactcac   5400
attaattgcg ttgcgctcac tgcccgcttt ccagtcggga aacctgtcgt gccagctgca   5460
```

-continued

```
ttaatgaatc ggccaacgcg cggggagagg cggtttgcgt attgggcgct cttccgcttc   5520
ctcgctcact gactcgctgc gctcggtcgt tcggctgcgg cgagcggtat cagctcactc   5580
aaaggcggta atacggttat ccacagaatc aggggataac gcaggaaaga acatgtgagc   5640
aaaaggccag caaaaggcca ggaaccgtaa aaaggccgcg ttgctggcgt ttttccatag   5700
gctccgcccc cctgacgagc atcacaaaaa tcgacgctca agtcagaggt ggcgaaaccc   5760
gacaggacta taaagatacc aggcgtttcc ccctggaagc tccctcgtgc gctctcctgt   5820
tccgaccctg ccgcttaccg gatacctgtc cgcctttctc ccttcgggaa gcgtggcgct   5880
ttctcatagc tcacgctgta ggtatctcag ttcggtgtag gtcgttcgct ccaagctggg   5940
ctgtgtgcac gaaccccccg ttcagcccga ccgctgcgcc ttatccggta actatcgtct   6000
tgagtccaac ccggtaagac acgacttatc gccactggca gcagccactg gtaacaggat   6060
tagcagagcg aggtatgtag gcggtgctac agagttcttg aagtggtggc ctaactacgg   6120
ctacactaga agaacagtat ttggtatctg cgctctgctg aagccagtta ccttcggaaa   6180
aagagttggt agctcttgat ccggcaaaca aaccaccgct ggtagcggtg gtttttttgt   6240
ttgcaagcag cagattacgc gcagaaaaaa aggatctcaa gaagatcctt tgatcttttc   6300
tacggggtct gacgctcagt ggaacgaaaa ctcacgttaa gggattttgg tcatgagatt   6360
atcaaaaagg atcttcacct agatcctttt aaattaaaaa tgaagtttta aatcaatcta   6420
aagtatatat gagtaaactt ggtctgacag ttaccaatgc ttaatcagtg aggcacctat   6480
ctcagcgatc tgtctatttc gttcatccat agttgcctga ctccccgtcg tgtagataac   6540
tacgatacgg gagggcttac catctggccc cagtgctgca atgataccgc gagaaccacg   6600
ctcaccggct ccagatttat cagcaataaa ccagccagcc ggaagggccg agcgcagaag   6660
tggtcctgca actttatccg cctccatcca gtctattaat tgttgccggg aagctagagt   6720
aagtagttcg ccagttaata gtttgcgcaa cgttgttgcc attgctacag gcatcgtggt   6780
gtcacgctcg tcgtttggta tggcttcatt cagctccggt tcccaacgat caaggcgagt   6840
tacatgatcc cccatgttgt gcaaaaaagc ggttagctcc ttcggtcctc cgatcgttgt   6900
cagaagtaag ttggccgcag tgttatcact catggttatg gcagcactgc ataattctct   6960
tactgtcatg ccatccgtaa gatgcttttc tgtgactggt gagtactcaa ccaagtcatt   7020
ctgagaatag tgtatgcggc gaccgagttg ctcttgcccg gcgtcaatac gggataatac   7080
cgcgccacat agcagaactt taaaagtgct catcattgga aaacgttctt cggggcgaaa   7140
actctcaagg atcttaccgc tgttgagatc cagttcgatg taacccactc gtgcacccaa   7200
ctgatcttca gcatctttta ctttcaccag cgtttctggg tgagcaaaaa caggaaggca   7260
aaatgccgca aaaaagggaa taagggcgac acggaaatgt tgaatactca tactcttcct   7320
ttttcaatat tattgaagca tttatcaggg ttattgtctc atgagcggat acatatttga   7380
atgtatttag aaaaataaac aaataggggt tccgcgcaca tttccccgaa aagtgccacc   7440
tgacgtctaa gaaaccatta ttatcatgac attaacctat aaaaataggc gtatcacgag   7500
gccctttcgg gtcgcgcgtt tcggtgatga cggtgaaaac ctctgacaca tgcagctccc   7560
gttgacggtc acagcttgtc tgtaagcgga tgccgggagc agacaagccc gtcagggcgc   7620
gtcagcgggt gttggcgggt gtcggggctg gcttaactat gcggcatcag agcagattgt   7680
actgagagtg caccataaaa ttgtaaacgt taatattttg ttaaaattcg cgttaaattt   7740
ttgttaaatc agctcatttt ttaaccaata ggccgaaatc ggcaaaatcc cttataaatc   7800
```

-continued

```
aaaagaatag cccgagatag ggttgagtgt tgttccagtt tggaacaaga gtccactatt   7860

aaagaacgtg gactccaacg tcaaagggcg aaaaaccgtc tatcagggcg atggcccact   7920

acgtgaacca tcacccaaat caagtttttt ggggtcgagg tgccgtaaag cactaaatcg   7980

gaaccctaaa gggagccccc gatttagagc ttgacgggga aagccggcga acgtggcgag   8040

aaaggaaggg aagaaagcga aaggagcggg cgctagggcg ctggcaagtg tagcggtcac   8100

gctgcgcgta accaccacac ccgccgcgct taatgcgccg ctacagggcg cgtactatgg   8160

ttgctttgac gtatgcggtg tgaaataccg cacagatgcg taaggagaaa ataccgcatc   8220

aggcgccatt cgccattcag gctgcgcaac tgttgggaag ggcgatcggt gcgggcctct   8280

tcgctattac gccagctggc gaaaggggga tgtgctgcaa ggcgattaag ttgggtaacg   8340

ccagggtttt cccagtcacg acgttgtaaa acgacggcca gtgaattcca tggtctcaac   8400

tttc                                                                8404
```

<210> SEQ ID NO 9
<211> LENGTH: 8410
<212> TYPE: DNA
<213> ORGANISM: Artificial Sequence
<220> FEATURE:
<223> OTHER INFORMATION: Synthetic vector VLP_CHI 532

<400> SEQUENCE: 9

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttccatggg tcttttctgc agtcaccgtc gtcgacacgt gtgatcagat atcgcggccg    900

ccaccatgga gttcatcccg acgcaaactt tctataacag aaggtaccaa ccccgaccct    960

gggccccacg ccctacaatt caagtaatta gacctagacc acgtccacag aggcaggctg   1020

ggcaactcgc ccagctgatc tccgcagtca acaaattgac catgcgcgcg gtacctcaac   1080

agaagcctcg cagaaatcgg aaaaacaaga agcaaaggca gaagaagcag gcgccgcaaa   1140

acgacccaaa gcaaaagaag caaccaccac aaaagaagcc ggctcaaaag aagaagaaac   1200

caggccgtag ggagagaatg tgcatgaaaa ttgaaaatga ttgcatcttc gaagtcaagc   1260

atgaaggcaa agtgatgggc tacgcatgcc tggtgggggga taaagtaatg aaaccagcac   1320

atgtgaaggg aactatcgac aatgccgatc tggctaaact ggcctttaag cggtcgtcta   1380

aatacgatct tgaatgtgca cagataccgg tgcacatgaa gtctgatgcc tcgaagttta   1440
```

-continued

```
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
ggcagacggt gcggtacaag tgcaactgcg gtggctccgg aagtggatcc aacgagggac   2520
tgacaaccac agacaaagtg atcaataact gcaaaattga tcagtgccat gctgcagtca   2580
ctaatcacaa gaattggcaa tacaactccc ctttagtccc gcgcaacgct gaactcgggg   2640
accgtaaagg aaagatccac atcccattcc cattggcaaa cgtgacttgc agagtgccaa   2700
aagcaagaaa ccctacagta acttacggaa aaaaccaagt caccatgctg ctgtatcctg   2760
accatccgac actcttgtct taccgtaaca tgggacagga accaaattac cacgaggagt   2820
gggtgacaca caagaaggag gttaccttga ccgtgcctac tgagggtctg gaggtcactt   2880
ggggcaacaa cgaaccatac aagtactggc cgcagatgtc tacgaacggt actgctcatg   2940
gtcacccaca tgagataatc ttgtactatt atgagctgta ccccactatg actgtagtca   3000
ttgtgtcggt ggcctcgttc gtgcttctgt cgatggtggg cacagcagtg ggaatgtgtg   3060
tgtgcgcacg gcgcagatgc attacaccat atgaattaac accaggagcc actgttccct   3120
tcctgctcag cctgctatgc tgcgtcagaa cgaccaaggc ggccacatat tacgaggctg   3180
cggcatatct atggaacgaa cagcagcccc tgttctggtt gcaggctctt atcccgctgg   3240
ccgccttgat cgtcctgtgc aactgtctga aactcttgcc atgctgctgt aagaccctgg   3300
ctttttttagc cgtaatgagc atcggtgccc acactgtgag cgcgtacgaa cacgtaacag   3360
tgatcccgaa cacggtggga gtaccgtata agactcttgt caacagaccg ggttacagcc   3420
ccatggtgtt ggagatggag ctacaatcag tcaccttgga accaacactg tcacttgact   3480
acatcacgtg cgagtacaaa actgtcatcc cctccccgta cgtgaagtgc tgtggtacag   3540
cagagtgcaa ggacaagagc ctaccagact acagctgcaa ggtctttact ggagtctacc   3600
catttatgtg gggcggcgcc tactgctttt gcgacgccga aaatacgcaa ttgagcgagg   3660
cacatgtaga gaaatctgaa tcttgcaaaa cagagtttgc atcggcctac agagcccaca   3720
ccgcatcggc gtcggcgaag ctccgcgtcc tttaccaagg aaacaacatt accgtagctg   3780
```

-continued

```
cctacgctaa cggtgaccat gccgtcacag taaaggacgc caagtttgtc gtgggcccaa   3840
tgtcctccgc ctggacacct tttgacaaca aaatcgtggt gtacaaaggc gacgtctaca   3900
acatggacta cccacctttt ggcgcaggaa gaccaggaca atttggtgac attcaaagtc   3960
gtacaccgga aagtaaagac gtttatgcca acactcagtt ggtactacag aggccagcag   4020
caggcacggt acatgtacca tactctcagg caccatctgg cttcaagtat tggctgaagg   4080
aacgaggagc atcgctacag cacacggcac cgttcggttg ccagattgcg acaaacccgg   4140
taagagctgt aaattgcgct gtggggaaca taccaatttc catcgacata ccggatgcgg   4200
cctttactag ggttgtcgat gcaccctctg taacggacat gtcatgcgaa gtaccagcct   4260
gcactcactc ctccgacttt gggggcgtcg ccatcatcaa atacacagct agcaagaaag   4320
gtaaatgtgc agtacattcg atgaccaacg ccgttaccat tcgagaagcc gacgtagaag   4380
tagaggggaa ctcccagctg caaatatcct tctcaacagc cctggcaagc gccgagtttc   4440
gcgtgcaagt gtgctccaca caagtacact gcgcagccgc atgccaccct ccaaaggacc   4500
acatagtcaa ttacccagca tcacacacca cccttggggt ccaggatata tccacaacgg   4560
caatgtcttg ggtgcagaag attacgggag gagtaggatt aattgttgct gttgctgcct   4620
taattttaat tgtggtgcta tgcgtgtcgt ttagcaggca ctaaggatct agatctgctg   4680
tgccttctag ttgccagcca tctgttgttt gcccctcccc cgtgccttcc ttgaccctgg   4740
aaggtgccac tcccactgtc ctttcctaat aaaatgagga aattgcatcg cattgtctga   4800
gtaggtgtca ttctattctg gggggtgggg tggggcagga cagcaagggg gaggattggg   4860
aagacaatag caggcatgct ggggatgcgg tgggctctat gggtacccag gtgctgaaga   4920
attgacccgg ttcctcctgg gccagaaaga agcaggcaca tcccctctc tgtgacacac   4980
cctgtccacg cccctggttc ttagttccag ccccactcat aggacactca tagctcagga   5040
gggctccgcc ttcaatccca cccgctaaag tacttggagc ggtctctccc tccctcatca   5100
gcccaccaaa ccaaacctag cctccaagag tgggaagaaa ttaaagcaag ataggctatt   5160
aagtgcagag ggagagaaaa tgcctccaac atgtgaggaa gtaatgagag aaatcataga   5220
attttaaggc catgatttaa ggccatcatg gcctaagctt gaaaggagat aggatccaag   5280
cttggcgtaa tcatggtcat agctgtttcc tgtgtgaaat tgttatccgc tcacaattcc   5340
acacaacata cgagccggaa gcataaagtg taaagcctgg ggtgcctaat gagtgagcta   5400
actcacatta attgcgttgc gctcactgcc cgctttccag tcgggaaacc tgtcgtgcca   5460
gctgcattaa tgaatcggcc aacgcgcggg gagaggcggt ttgcgtattg ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac cccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagaa cagtatttgg tatctgcgct ctgctgaagc cagttacctt   6180
```

-continued

```
cggaaaaaga gttggtagct cttgatccgg caaacaaacc accgctggta gcggtggttt   6240
ttttgtttgc aagcagcaga ttacgcgcag aaaaaaagga tctcaagaag atcctttgat   6300
cttttctacg gggtctgacg ctcagtggaa cgaaaactca cgttaaggga ttttggtcat   6360
gagattatca aaaaggatct tcacctagat ccttttaaat taaaaatgaa gttttaaatc   6420
aatctaaagt atatatgagt aaacttggtc tgacagttac caatgcttaa tcagtgaggc   6480
acctatctca gcgatctgtc tatttcgttc atccatagtt gcctgactcc ccgtcgtgta   6540
gataactacg atacgggagg gcttaccatc tggccccagt gctgcaatga taccgcgaga   6600
accacgctca ccggctccag atttatcagc aataaaccag ccagccggaa gggccgagcg   6660
cagaagtggt cctgcaactt tatccgcctc catccagtct attaattgtt gccgggaagc   6720
tagagtaagt agttcgccag ttaatagttt gcgcaacgtt gttgccattg ctacaggcat   6780
cgtggtgtca cgctcgtcgt ttggtatggc ttcattcagc tccggttccc aacgatcaag   6840
gcgagttaca tgatccccca tgttgtgcaa aaaagcggtt agctccttcg gtcctccgat   6900
cgttgtcaga agtaagttgg ccgcagtgtt atcactcatg gttatggcag cactgcataa   6960
ttctcttact gtcatgccat ccgtaagatg cttttctgtg actggtgagt actcaaccaa   7020
gtcattctga gaatagtgta tgcggcgacc gagttgctct tgcccggcgt caatacggga   7080
taataccgcg ccacatagca gaactttaaa agtgctcatc attggaaaac gttcttcggg   7140
gcgaaaactc tcaaggatct taccgctgtt gagatccagt tcgatgtaac ccactcgtgc   7200
acccaactga tcttcagcat cttttacttt caccagcgtt tctgggtgag caaaaacagg   7260
aaggcaaaat gccgcaaaaa agggaataag ggcgacacgg aaatgttgaa tactcatact   7320
cttccttttt caatattatt gaagcattta tcagggttat tgtctcatga gcggatacat   7380
atttgaatgt atttagaaaa ataaacaaat aggggttccg cgcacatttc cccgaaaagt   7440
gccacctgac gtctaagaaa ccattattat catgacatta acctataaaa ataggcgtat   7500
cacgaggccc tttcgggtcg cgcgtttcgg tgatgacggt gaaaacctct gacacatgca   7560
gctcccgttg acggtcacag cttgtctgta agcggatgcc gggagcagac aagcccgtca   7620
gggcgcgtca gcgggtgttg gcgggtgtcg gggctggctt aactatgcgg catcagagca   7680
gattgtactg agagtgcacc ataaaattgt aaacgttaat attttgttaa aattcgcgtt   7740
aaatttttgt taaatcagct cattttttaa ccaataggcc gaaatcggca aaatccctta   7800
taaatcaaaa gaatagcccg agatagggtt gagtgttgtt ccagtttgga acaagagtcc   7860
actattaaag aacgtggact ccaacgtcaa agggcgaaaa accgtctatc agggcgatgg   7920
cccactacgt gaaccatcac ccaaatcaag ttttttgggg tcgaggtgcc gtaaagcact   7980
aaatcggaac cctaaaggga gcccccgatt tagagcttga cggggaaagc cggcgaacgt   8040
ggcgagaaag gaagggaaga aagcgaaagg agcgggcgct agggcgctgg caagtgtagc   8100
ggtcacgctg cgcgtaacca ccacacccgc cgcgcttaat gcgccgctac agggcgcgta   8160
ctatggttgc tttgacgtat gcggtgtgaa ataccgcaca gatgcgtaag gagaaaatac   8220
cgcatcaggc gccattcgcc attcaggctg cgcaactgtt gggaagggcg atcggtgcgg   8280
gcctcttcgc tattacgcca gctggcgaaa gggggatgtg ctgcaaggcg attaagttgg   8340
gtaacgccag ggttttccca gtcacgacgt tgtaaaacga cggccagtga attccatggt   8400
ctcaactttc                                                          8410
```

<210> SEQ ID NO 10

<211> LENGTH: 8431
<212> TYPE: DNA
<213> ORGANISM: Artificial Sequence
<220> FEATURE:
<223> OTHER INFORMATION: Synthetic vector VLP_VEEV VLP 518

<400> SEQUENCE: 10
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgtt cccgttccag ccaatgtatc cgatgcagcc aatgccctat cgcaacccgt 960
tcgcggcccc gcgcaggccc tggttcccca gaaccgaccc ttttctggcg atgcaggtgc 1020
aggaattaac ccgctcgatg gctaacctga cgttcaagca acgccgggac gcgccacctg 1080
aggggccatc cgctaataaa ccgaagaagg aggcctcgca aaaacagaaa gggggaggcc 1140
aagggaagaa gaagaagaac caagggaaga agaaggctaa gacagggccg cctaatccga 1200
aggcacagaa tggaaacaag aagaagacca acaagaaacc aggcaagaga cagcgcatgg 1260
tcatgaaatt ggaatctgac aagacgttcc caatcatgtt ggaagggaag ataaacggct 1320
acgcttgtgt ggtcggaggg aagttattca ggccgatgca tgtggaaggc aagatcgaca 1380
acgacgttct ggccgcgctt aagacgaaga aagcatccaa atacgatctt gagtatgcag 1440
atgtgccaca gaacatgcgg gccgatacat tcaaatacac ccatgagaaa ccccaaggct 1500
attacagctg gcatcatgga gcagtccaat atgaaaatgg gcgtttcacg gtgccgaaag 1560
gagttggggc caagggagac agcggacgac ccattctgga taaccaggga cgggtggtcg 1620
ctattgtgct gggaggtgtg aatgaaggat ctaggacagc cctttcagtc gtcatgtgga 1680
acgagaaggg agttaccgtg aagtatactc cagagaactg cgagcaatgg tcactagtga 1740
ccaccatgtg tctgctcgcc aatgtgacgt tcccatgtgc tcaaccacca atttgctacg 1800
acagaaaacc agcagagact ttggccatgc tcagcgttaa cgttgacaac ccgggctacg 1860
atgagctgct ggaagcagct gttaagtgcc ccggaaggaa aaggagatcc accgaggagc 1920
tgtttaatga gtataagcta acgcgccctt acatggccag atgcatcaga tgtgcagttg 1980
ggagctgcca tagtccaata gcaatcgagg cagtaaagag cgacgggcac gacggttatg 2040
ttagacttca gacttcctcg cagtatggcc tggattcctc cggcaactta aagggcagga 2100
ccatgcggta tgacatgcac gggaccatta aagagatacc actacatcaa gtgtcactct 2160

-continued

```
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggctccg   2460
gaggatccag ttcagtcacc gtgacacctc ctgatgggac tagcgccctg gtggaatgcg   2520
agtgtggcgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
gatcagtgtc actgaaactg caccctaaga atcccacata tctaatcacc cgccaacttg   2820
ctgatgagcc tcactacacg cacgagctca tatctgaacc agctgttagg aattttaccg   2880
tcaccgaaaa agggtgggag tttgtatggg gaaaccaccc gccgaaaagg ttttgggcac   2940
aggaaacagc acccggaaat ccacatgggc taccgcacga ggtgataact cattattacc   3000
acagataccc tatgtccacc atcctgggtt tgtcaatttg tgccgccatt gcaaccgttt   3060
ccgttgcagc gtctacctgg ctgttttgca gatcaagagt tgcgtgccta actccttacc   3120
ggctaacacc taacgctagg ataccatttt gtctggctgt gctttgctgc gcccgcactg   3180
cccgggccga gaccacctgg gagtccttgg atcacctatg gaacaataac caacagatgt   3240
tctggattca attgctgatc cctctggccg ccttgatcgt agtgactcgc ctgctcaggt   3300
gcgtgtgctg tgtcgtgcct tttttagtca tggccggcgc cgcaggcgcc ggcgcctacg   3360
agcacgcgac cacgatgccg agccaagcgg gaatctcgta taacactata gtcaacagag   3420
caggctacgc accactccct atcagcataa caccaacaaa gatcaagctg atacctacag   3480
tgaacttgga gtacgtcacc tgccactaca aaacaggaat ggattcacca gccatcaaat   3540
gctgcggatc tcaggaatgc actccaactt acaggcctga tgaacagtgc aaagtcttca   3600
caggggttta cccgttcatg tggggtggtg catattgctt ttgcgacact gagaacaccc   3660
aagtcagcaa ggcctacgta atgaaatctg acgactgcct tgcggatcat gctgaagcat   3720
ataaagcgca cacagcctca gtgcaggcgt tcctcaacat cacagtggga gaacactcta   3780
ttgtgactac cgtgtatgtg aatggagaaa ctcctgtgaa tttcaatggg gtcaaaataa   3840
ctgcaggtcc gctttccaca gcttggacac cctttgatcg caaaatcgtg cagtatgccg   3900
gggagatcta taattatgat tttcctgagt atggggcagg acaaccagga gcatttggag   3960
atatacaatc cagaacagtc tcaagctctg atctgtatgc caataccaac ctagtgctgc   4020
agagacccaa agcaggagcg atccacgtgc catacactca ggcaccttcg ggttttgagc   4080
aatggaagaa agataaagct ccatcattga aatttaccgc ccctttcgga tgcgaaatat   4140
atacaaaccc cattcgcgcc gaaaactgtg ctgtagggtc aattccatta gcctttgaca   4200
ttcccgacgc cttgttcacc agggtgtcag aaacaccgac actttcagcg gccgaatgca   4260
ctcttaacga gtgcgtgtat tcttccgact ttggtgggat cgccacggtc aagtactcgg   4320
ccagcaagtc aggcaagtgc gcagtccatg tgccatcagg gactgctacc ctaaaagaag   4380
cagcagtcga gctaaccgag caagggtcgg cgactatcca tttctcgacc gcaaatatcc   4440
acccggagtt caggctccaa atatgcacat catatgttac gtgcaaaggt gattgtcacc   4500
```

-continued

```
ccccgaaaga ccatattgtg acacaccctc agtatcacgc ccaaacattt acagccgcgg   4560
tgtcaaaaac cgcgtggacg tggttaacat ccctgctggg aggatcagcc gtaattatta   4620
taattggctt ggtgctggct actattgtgg ccatgtacgt gctgaccaac cagaaacata   4680
attaaggatc tagatctgct gtgccttcta gttgccagcc atctgttgtt tgcccctccc   4740
ccgtgccttc cttgaccctg gaaggtgcca ctcccactgt cctttcctaa taaaatgagg   4800
aaattgcatc gcattgtctg agtaggtgtc attctattct ggggggtggg gtggggcagg   4860
acagcaaggg ggaggattgg gaagacaata gcaggcatgc tggggatgcg gtgggctcta   4920
tgggtaccca ggtgctgaag aattgacccg gttcctcctg ggccagaaag aagcaggcac   4980
atccccttct ctgtgacaca ccctgtccac gcccctggtt cttagttcca gccccactca   5040
taggacactc atagctcagg agggctccgc cttcaatccc acccgctaaa gtacttggag   5100
cggtctctcc ctccctcatc agcccaccaa accaaaccta gcctccaaga gtgggaagaa   5160
attaaagcaa gataggctat taagtgcaga gggagagaaa atgcctccaa catgtgagga   5220
agtaatgaga gaaatcatag aattttaagg ccatgattta aggccatcat ggcctaagct   5280
tgaaaggaga taggatcaaa gcttggcgta atcatggtca tagctgtttc ctgtgtgaaa   5340
ttgttatccg ctcacaattc cacacaacat acgagccgga agcataaagt gtaaagcctg   5400
gggtgcctaa tgagtgagct aactcacatt aattgcgttg cgctcactgc ccgctttcca   5460
gtcgggaaac ctgtcgtgcc agctgcatta atgaatcggc caacgcgcgg ggagaggcgg   5520
tttgcgtatt gggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgcccccct gacgagcatc acaaaaatcg   5760
acgctcaagt cagaggtggc gaaacccgac aggactataa agataccagg cgtttccccc   5820
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
actggcagca gccactggta acaggattag cagagcgagg tatgtaggcg gtgctacaga   6120
gttcttgaag tggtggccta actacggcta cactagaaga acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac ggggtctgac gctcagtgga acgaaaactc   6360
acgttaaggg attttggtca tgagattatc aaaaaggatc ttcacctaga tccttttaaa   6420
ttaaaaatga agttttaaat caatctaaag tatatatgag taaacttggt ctgacagtta   6480
ccaatgctta atcagtgagg cacctatctc agcgatctgt ctatttcgtt catccatagt   6540
tgcctgactc cccgtcgtgt agataactac gatacgggag ggcttaccat ctggccccag   6600
tgctgcaatg ataccgcgag aaccacgctc accggctcca gatttatcag caataaacca   6660
gccagccgga agggccgagc gcagaagtgg tcctgcaact ttatccgcct ccatccagtc   6720
tattaattgt tgccgggaag ctagagtaag tagttcgcca gttaatagtt tgcgcaacgt   6780
tgttgccatt gctacaggca tcgtggtgtc acgctcgtcg tttggtatgg cttcattcag   6840
ctccggttcc caacgatcaa ggcgagttac atgatccccc atgttgtgca aaaaagcggt   6900
```

```
tagctccttc ggtcctccga tcgttgtcag aagtaagttg gccgcagtgt tatcactcat   6960

ggttatggca gcactgcata attctcttac tgtcatgcca tccgtaagat gcttttctgt   7020

gactggtgag tactcaacca agtcattctg agaatagtgt atgcggcgac cgagttgctc   7080

ttgcccggcg tcaatacggg ataataccgc gccacatagc agaactttaa aagtgctcat   7140

cattggaaaa cgttcttcgg ggcgaaaact ctcaaggatc ttaccgctgt tgagatccag   7200

ttcgatgtaa cccactcgtg cacccaactg atcttcagca tcttttactt tcaccagcgt   7260

ttctgggtga gcaaaaacag gaaggcaaaa tgccgcaaaa aagggaataa gggcgacacg   7320

gaaatgttga atactcatac tcttcctttt tcaatattat tgaagcattt atcagggtta   7380

ttgtctcatg agcggataca tatttgaatg tatttagaaa aataaacaaa taggggttcc   7440

gcgcacattt ccccgaaaag tgccacctga cgtctaagaa accattatta tcatgacatt   7500

aacctataaa aataggcgta tcacgaggcc ctttcgggtc gcgcgtttcg gtgatgacgg   7560

tgaaaacctc tgacacatgc agctcccgtt gacggtcaca gcttgtctgt aagcggatgc   7620

cgggagcaga caagcccgtc agggcgcgtc agcgggtgtt ggcgggtgtc ggggctggct   7680

taactatgcg gcatcagagc agattgtact gagagtgcac cataaaattg taaacgttaa   7740

tattttgtta aaattcgcgt taaatttttg ttaaatcagc tcatttttta accaataggc   7800

cgaaatcggc aaaatccctt ataaatcaaa agaatagccc gagatagggt tgagtgttgt   7860

tccagtttgg aacaagagtc cactattaaa gaacgtggac tccaacgtca aagggcgaaa   7920

aaccgtctat cagggcgatg gcccactacg tgaaccatca cccaaatcaa gttttttggg   7980

gtcgaggtgc cgtaaagcac taaatcggaa ccctaaaggg agcccccgat ttagagcttg   8040

acggggaaag ccggcgaacg tggcgagaaa ggaagggaag aaagcgaaag gagcgggcgc   8100

tagggcgctg gcaagtgtag cggtcacgct gcgcgtaacc accacacccg ccgcgcttaa   8160

tgcgccgcta cagggcgcgt actatggttg ctttgacgta tgcggtgtga aataccgcac   8220

agatgcgtaa ggagaaaata ccgcatcagg cgccattcgc cattcaggct gcgcaactgt   8280

tgggaagggc gatcggtgcg ggcctcttcg ctattacgcc agctggcgaa agggggatgt   8340

gctgcaaggc gattaagttg ggtaacgcca gggttttccc agtcacgacg ttgtaaaacg   8400

acggccagtg aattccatgg tctcaacttt c                                  8431
```

<210> SEQ ID NO 11
<211> LENGTH: 8431
<212> TYPE: DNA
<213> ORGANISM: Artificial Sequence
<220> FEATURE:
<223> OTHER INFORMATION: Synthetic vector VLP_VEEV VLP 519

<400> SEQUENCE: 11

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480
```

-continued

```
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa gggggaggcc   1140
aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
ccggaggatc ctcagtcacc gtgacacctc ctgatgggac tagcgccctg gtggaatgcg   2520
agtgtggcgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
gatcagtgtc actgaaactg caccctaaga atcccacata tctaatcacc cgccaacttg   2820
ctgatgagcc tcactacacg cacgagctca tatctgaacc agctgttagg aattttaccg   2880
```

tcaccgaaaa agggtgggag tttgtatggg gaaaccaccc gccgaaaagg ttttgggcac 2940
aggaaacagc acccggaaat ccacatgggc taccgcacga ggtgataact cattattacc 3000
acagataccc tatgtccacc atcctgggtt tgtcaatttg tgccgccatt gcaaccgttt 3060
ccgttgcagc gtctacctgg ctgttttgca gatcaagagt tgcgtgccta actccttacc 3120
ggctaacacc taacgctagg ataccatttt gtctggctgt gctttgctgc gcccgcactg 3180
cccgggccga gaccacctgg gagtccttgg atcacctatg gaacaataac caacagatgt 3240
tctggattca attgctgatc cctctggccg ccttgatcgt agtgactcgc ctgctcaggt 3300
gcgtgtgctg tgtcgtgcct tttttagtca tggccggcgc cgcaggcgcc ggcgcctacg 3360
agcacgcgac cacgatgccg agccaagcgg gaatctcgta taacactata gtcaacagag 3420
caggctacgc accactccct atcagcataa caccaacaaa gatcaagctg atacctacag 3480
tgaacttgga gtacgtcacc tgccactaca aaacaggaat ggattcacca gccatcaaat 3540
gctgcggatc tcaggaatgc actccaactt acaggcctga tgaacagtgc aaagtcttca 3600
caggggttta cccgttcatg tggggtggtg catattgctt ttgcgacact gagaacaccc 3660
aagtcagcaa ggcctacgta atgaaatctg acgactgcct tgcggatcat gctgaagcat 3720
ataaagcgca cacagcctca gtgcaggcgt tcctcaacat cacagtggga gaacactcta 3780
ttgtgactac cgtgtatgtg aatggagaaa ctcctgtgaa tttcaatggg gtcaaaataa 3840
ctgcaggtcc gctttccaca gcttggacac cctttgatcg caaaatcgtg cagtatgccg 3900
gggagatcta taattatgat tttcctgagt atggggcagg acaaccagga gcatttggag 3960
atatacaatc cagaacagtc tcaagctctg atctgtatgc caataccaac ctagtgctgc 4020
agagacccaa agcaggagcg atccacgtgc catacactca ggcaccttcg ggttttgagc 4080
aatggaagaa agataaagct ccatcattga aatttaccgc cccttttcgga tgcgaaatat 4140
atacaaaccc cattcgcgcc gaaaactgtg ctgtagggtc aattccatta gcctttgaca 4200
ttcccgacgc cttgttcacc agggtgtcag aaacaccgac actttcagcg gccgaatgca 4260
ctcttaacga gtgcgtgtat tcttccgact ttggtgggat cgccacggtc aagtactcgg 4320
ccagcaagtc aggcaagtgc gcagtccatg tgccatcagg gactgctacc ctaaaagaag 4380
cagcagtcga gctaaccgag caagggtcgg cgactatcca tttctcgacc gcaaatatcc 4440
acccggagtt caggctccaa atatgcacat catatgttac gtgcaaaggt gattgtcacc 4500
ccccgaaaga ccatattgtg acacaccctc agtatcacgc ccaaacattt acagccgcgg 4560
tgtcaaaaac cgcgtggacg tggttaacat ccctgctggg aggatcagcc gtaattatta 4620
taattggctt ggtgctggct actattgtgg ccatgtacgt gctgaccaac cagaaacata 4680
attaaggatc tagatctgct gtgccttcta gttgccagcc atctgttgtt tgcccctccc 4740
ccgtgccttc cttgaccctg gaaggtgcca ctcccactgt cctttcctaa taaaatgagg 4800
aaattgcatc gcattgtctg agtaggtgtc attctattct ggggggtggg gtggggcagg 4860
acagcaaggg ggaggattgg gaagacaata gcaggcatgc tggggatgcg gtgggctcta 4920
tgggtaccca ggtgctgaag aattgacccg gttcctcctg ggccagaaag aagcaggcac 4980
atccccttct ctgtgacaca ccctgtccac gcccctggtt cttagttcca gccccactca 5040
taggacactc atagctcagg agggctccgc cttcaatccc acccgctaaa gtacttggag 5100
cggtctctcc ctccctcatc agcccaccaa accaaaccta gcctccaaga gtgggaagaa 5160
attaaagcaa gataggctat taagtgcaga gggagagaaa atgcctccaa catgtgagga 5220

-continued agtaatgaga gaaatcatag aattttaagg ccatgattta aggccatcat ggcctaagct 5280
tgaaaggaga taggatcaaa gcttggcgta atcatggtca tagctgtttc ctgtgtgaaa 5340
ttgttatccg ctcacaattc cacacaacat acgagccgga agcataaagt gtaaagcctg 5400
gggtgcctaa tgagtgagct aactcacatt aattgcgttg cgctcactgc ccgctttcca 5460
gtcgggaaac ctgtcgtgcc agctgcatta atgaatcggc caacgcgcgg ggagaggcgg 5520
tttgcgtatt gggcgctctt ccgcttcctc gctcactgac tcgctgcgct cggtcgttcg 5580
gctgcggcga gcggtatcag ctcactcaaa ggcggtaata cggttatcca cagaatcagg 5640
ggataacgca ggaaagaaca tgtgagcaaa aggccagcaa aaggccagga accgtaaaaa 5700
ggccgcgttg ctggcgtttt tccataggct ccgcccccct gacgagcatc acaaaaatcg 5760
acgctcaagt cagaggtggc gaaacccgac aggactataa agataccagg cgtttccccc 5820
tggaagctcc ctcgtgcgct ctcctgttcc gaccctgccg cttaccggat acctgtccgc 5880
ctttctccct tcgggaagcg tggcgctttc tcatagctca cgctgtaggt atctcagttc 5940
ggtgtaggtc gttcgctcca agctgggctg tgtgcacgaa ccccccgttc agcccgaccg 6000
ctgcgcctta tccggtaact atcgtcttga gtccaacccg gtaagacacg acttatcgcc 6060
actggcagca gccactggta acaggattag cagagcgagg tatgtaggcg gtgctacaga 6120
gttcttgaag tggtggccta actacggcta cactagaaga acagtatttg gtatctgcgc 6180
tctgctgaag ccagttacct tcggaaaaag agttggtagc tcttgatccg gcaaacaaac 6240
caccgctggt agcggtggtt tttttgtttg caagcagcag attacgcgca gaaaaaaagg 6300
atctcaagaa gatcctttga tcttttctac ggggtctgac gctcagtgga acgaaaactc 6360
acgttaaggg attttggtca tgagattatc aaaaaggatc ttcacctaga tccttttaaa 6420
ttaaaaatga agttttaaat caatctaaag tatatatgag taaacttggt ctgacagtta 6480
ccaatgctta atcagtgagg cacctatctc agcgatctgt ctatttcgtt catccatagt 6540
tgcctgactc cccgtcgtgt agataactac gatacgggag ggcttaccat ctggccccag 6600
tgctgcaatg ataccgcgag aaccacgctc accggctcca gatttatcag caataaacca 6660
gccagccgga agggccgagc gcagaagtgg tcctgcaact ttatccgcct ccatccagtc 6720
tattaattgt tgccgggaag ctagagtaag tagttcgcca gttaatagtt tgcgcaacgt 6780
tgttgccatt gctacaggca tcgtggtgtc acgctcgtcg tttggtatgg cttcattcag 6840
ctccggttcc caacgatcaa ggcgagttac atgatccccc atgttgtgca aaaaagcggt 6900
tagctccttc ggtcctccga tcgttgtcag aagtaagttg gccgcagtgt tatcactcat 6960
ggttatggca gcactgcata attctcttac tgtcatgcca tccgtaagat gcttttctgt 7020
gactggtgag tactcaacca agtcattctg agaatagtgt atgcggcgac cgagttgctc 7080
ttgcccggcg tcaatacggg ataataccgc gccacatagc agaactttaa aagtgctcat 7140
cattggaaaa cgttcttcgg ggcgaaaact ctcaaggatc ttaccgctgt tgagatccag 7200
ttcgatgtaa cccactcgtg cacccaactg atcttcagca tcttttactt tcaccagcgt 7260
ttctgggtga gcaaaaacag gaaggcaaaa tgccgcaaaa aagggaataa gggcgacacg 7320
gaaatgttga atactcatac tcttcctttt tcaatattat tgaagcattt atcagggtta 7380
ttgtctcatg agcggataca tatttgaatg tatttagaaa aataaacaaa taggggttcc 7440
gcgcacattt ccccgaaaag tgccacctga cgtctaagaa accattatta tcatgacatt 7500
aacctataaa aataggcgta tcacgaggcc ctttcgggtc gcgcgtttcg gtgatgacgg 7560
tgaaaacctc tgacacatgc agctcccgtt gacggtcaca gcttgtctgt aagcggatgc 7620

-continued cgggagcaga caagcccgtc agggcgcgtc agcgggtgtt ggcgggtgtc ggggctggct 7680
taactatgcg gcatcagagc agattgtact gagagtgcac cataaaattg taaacgttaa 7740
tattttgtta aaattcgcgt taaatttttg ttaaatcagc tcatttttta accaataggc 7800
cgaaatcggc aaaatccctt ataaatcaaa agaatagccc gagatagggt tgagtgttgt 7860
tccagtttgg aacaagagtc cactattaaa gaacgtggac tccaacgtca aagggcgaaa 7920
aaccgtctat cagggcgatg gcccactacg tgaaccatca cccaaatcaa gttttttggg 7980
gtcgaggtgc cgtaaagcac taaatcggaa ccctaaaggg agcccccgat ttagagcttg 8040
acggggaaag ccggcgaacg tggcgagaaa ggaagggaag aaagcgaaag gagcgggcgc 8100
tagggcgctg gcaagtgtag cggtcacgct gcgcgtaacc accacacccg ccgcgcttaa 8160
tgcgccgcta cagggcgcgt actatggttg ctttgacgta tgcggtgtga aataccgcac 8220
agatgcgtaa ggagaaaata ccgcatcagg cgccattcgc cattcaggct gcgcaactgt 8280
tgggaagggc gatcggtgcg ggcctcttcg ctattacgcc agctggcgaa agggggatgt 8340
gctgcaaggc gattaagttg ggtaacgcca gggttttccc agtcacgacg ttgtaaaacg 8400
acggccagtg aattccatgg tctcaacttt c 8431

<210> SEQ ID NO 12
<211> LENGTH: 8431
<212> TYPE: DNA
<213> ORGANISM: Artificial Sequence
<220> FEATURE:
<223> OTHER INFORMATION: Synthetic vector VLP_VEEV VLP 538

<400> SEQUENCE: 12
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgtt cccgttccag ccaatgtatc cgatgcagcc aatgccctat cgcaacccgt 960
tcgcggcccc gcgcaggccc tggttcccca gaaccgaccc ttttctggcg atgcaggtgc 1020
aggaattaac ccgctcgatg gctaacctga cgttcaagca acgccgggac gcgccacctg 1080
aggggccatc cgctaataaa ccgaagaagg aggcctcgca aaaacagaaa gggggaggcc 1140
aagggaagaa gaagaagaac caagggaaga agaaggctaa gacagggccg cctaatccga 1200

-continued

```
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
cagtcaccgt gacacctcct gatgggacta gcgccctggt ggaatgcgag tgtggctccg   2520
gaggatccgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
gatcagtgtc actgaaactg caccctaaga atcccacata tctaatcacc cgccaacttg   2820
ctgatgagcc tcactacacg cacgagctca tatctgaacc agctgttagg aattttaccg   2880
tcaccgaaaa agggtgggag tttgtatggg gaaaccaccc gccgaaaagg ttttgggcac   2940
aggaaacagc acccggaaat ccacatgggc taccgcacga ggtgataact cattattacc   3000
acagataccc tatgtccacc atcctgggtt tgtcaatttg tgccgccatt gcaaccgttt   3060
ccgttgcagc gtctacctgg ctgttttgca gatcaagagt tgcgtgccta actccttacc   3120
ggctaacacc taacgctagg ataccatttt gtctggctgt gctttgctgc gcccgcactg   3180
cccgggccga gaccacctgg gagtccttgg atcacctatg gaacaataac caacagatgt   3240
tctggattca attgctgatc cctctggccg ccttgatcgt agtgactcgc ctgctcaggt   3300
gcgtgtgctg tgtcgtgcct tttttagtca tggccggcgc cgcaggcgcc ggcgcctacg   3360
agcacgcgac cacgatgccg agccaagcgg gaatctcgta taacactata gtcaacagag   3420
caggctacgc accactccct atcagcataa caccaacaaa gatcaagctg atacctacag   3480
tgaacttgga gtacgtcacc tgccactaca aaacaggaat ggattcacca gccatcaaat   3540
gctgcggatc tcaggaatgc actccaactt acaggcctga tgaacagtgc aaagtcttca   3600
```

-continued

```
cagggggttta cccgttcatg tggggtggtg catattgctt ttgcgacact gagaacaccc   3660
aagtcagcaa ggcctacgta atgaaatctg acgactgcct tgcggatcat gctgaagcat   3720
ataaagcgca cacagcctca gtgcaggcgt tcctcaacat cacagtggga gaacactcta   3780
ttgtgactac cgtgtatgtg aatggagaaa ctcctgtgaa tttcaatggg gtcaaaataa   3840
ctgcaggtcc gctttccaca gcttggacac cctttgatcg caaaatcgtg cagtatgccg   3900
gggagatcta taattatgat tttcctgagt atggggcagg acaaccagga gcatttggag   3960
atatacaatc cagaacagtc tcaagctctg atctgtatgc caataccaac ctagtgctgc   4020
agagacccaa agcaggagcg atccacgtgc catacactca ggcaccttcg ggttttgagc   4080
aatggaagaa agataaagct ccatcattga aatttaccgc ccctttcgga tgcgaaatat   4140
atacaaaccc cattcgcgcc gaaaactgtg ctgtagggtc aattccatta gcctttgaca   4200
ttcccgacgc cttgttcacc agggtgtcag aaacaccgac actttcagcg gccgaatgca   4260
ctcttaacga gtgcgtgtat tcttccgact ttggtgggat cgccacggtc aagtactcgg   4320
ccagcaagtc aggcaagtgc gcagtccatg tgccatcagg gactgctacc ctaaaagaag   4380
cagcagtcga gctaaccgag caagggtcgg cgactatcca tttctcgacc gcaaatatcc   4440
acccggagtt caggctccaa atatgcacat catatgttac gtgcaaaggt gattgtcacc   4500
ccccgaaaga ccatattgtg acacaccctc agtatcacgc ccaaacattt acagccgcgg   4560
tgtcaaaaac cgcgtggacg tggttaacat ccctgctggg aggatcagcc gtaattatta   4620
taattggctt ggtgctggct actattgtgg ccatgtacgt gctgaccaac cagaaacata   4680
attaaggatc tagatctgct gtgccttcta gttgccagcc atctgttgtt tgcccctccc   4740
ccgtgccttc cttgaccctg gaaggtgcca ctcccactgt cctttcctaa taaaatgagg   4800
aaattgcatc gcattgtctg agtaggtgtc attctattct ggggggtggg gtggggcagg   4860
acagcaaggg ggaggattgg gaagacaata gcaggcatgc tggggatgcg gtgggctcta   4920
tgggtaccca ggtgctgaag aattgacccg gttcctcctg ggccagaaag aagcaggcac   4980
atccccttct ctgtgacaca ccctgtccac gcccctggtt cttagttcca gccccactca   5040
taggacactc atagctcagg agggctccgc cttcaatccc acccgctaaa gtacttggag   5100
cggtctctcc ctccctcatc agcccaccaa accaaaccta gcctccaaga gtgggaagaa   5160
attaaagcaa gataggctat taagtgcaga gggagagaaa atgcctccaa catgtgagga   5220
agtaatgaga gaaatcatag aattttaagg ccatgattta aggccatcat ggcctaagct   5280
tgaaaggaga taggatcaaa gcttggcgta atcatggtca tagctgtttc ctgtgtgaaa   5340
ttgttatccg ctcacaattc cacacaacat acgagccgga agcataaagt gtaaagcctg   5400
gggtgcctaa tgagtgagct aactcacatt aattgcgttg cgctcactgc ccgctttcca   5460
gtcgggaaac ctgtcgtgcc agctgcatta atgaatcggc caacgcgcgg ggagaggcgg   5520
tttgcgtatt gggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgcccccct gacgagcatc acaaaaatcg   5760
acgctcaagt cagaggtggc gaaacccgac aggactataa agataccagg cgtttccccc   5820
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
```

-continued

```
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
actggcagca gccactggta acaggattag cagagcgagg tatgtaggcg gtgctacaga   6120
gttcttgaag tggtggccta actacggcta cactagaaga acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac ggggtctgac gctcagtgga acgaaaactc   6360
acgttaaggg attttggtca tgagattatc aaaaaggatc ttcacctaga tccttttaaa   6420
ttaaaaatga agttttaaat caatctaaag tatatatgag taaacttggt ctgacagtta   6480
ccaatgctta atcagtgagg cacctatctc agcgatctgt ctatttcgtt catccatagt   6540
tgcctgactc cccgtcgtgt agataactac gatacgggag ggcttaccat ctggccccag   6600
tgctgcaatg ataccgcgag aaccacgctc accggctcca gatttatcag caataaacca   6660
gccagccgga agggccgagc gcagaagtgg tcctgcaact ttatccgcct ccatccagtc   6720
tattaattgt tgccgggaag ctagagtaag tagttcgcca gttaatagtt tgcgcaacgt   6780
tgttgccatt gctacaggca tcgtggtgtc acgctcgtcg tttggtatgg cttcattcag   6840
ctccggttcc caacgatcaa ggcgagttac atgatccccc atgttgtgca aaaaagcggt   6900
tagctccttc ggtcctccga tcgttgtcag aagtaagttg gccgcagtgt tatcactcat   6960
ggttatggca gcactgcata attctcttac tgtcatgcca tccgtaagat gcttttctgt   7020
gactggtgag tactcaacca agtcattctg agaatagtgt atgcggcgac cgagttgctc   7080
ttgcccggcg tcaatacggg ataataccgc gccacatagc agaactttaa aagtgctcat   7140
cattggaaaa cgttcttcgg ggcgaaaact ctcaaggatc ttaccgctgt tgagatccag   7200
ttcgatgtaa cccactcgtg cacccaactg atcttcagca tcttttactt tcaccagcgt   7260
ttctgggtga gcaaaaacag gaaggcaaaa tgccgcaaaa aagggaataa gggcgacacg   7320
gaaatgttga atactcatac tcttcctttt tcaatattat tgaagcattt atcagggtta   7380
ttgtctcatg agcggataca tatttgaatg tatttagaaa aataaacaaa taggggttcc   7440
gcgcacattt ccccgaaaag tgccacctga cgtctaagaa accattatta tcatgacatt   7500
aacctataaa aataggcgta tcacgaggcc ctttcgggtc gcgcgtttcg gtgatgacgg   7560
tgaaaacctc tgacacatgc agctcccgtt gacggtcaca gcttgtctgt aagcggatgc   7620
cgggagcaga caagcccgtc agggcgcgtc agcgggtgtt ggcgggtgtc ggggctggct   7680
taactatgcg gcatcagagc agattgtact gagagtgcac cataaaattg taaacgttaa   7740
tattttgtta aaattcgcgt taaatttttg ttaaatcagc tcattttttta accaataggc   7800
cgaaatcggc aaaatccctt ataaatcaaa agaatagccc gagatagggt tgagtgttgt   7860
tccagtttgg aacaagagtc cactattaaa gaacgtggac tccaacgtca aagggcgaaa   7920
aaccgtctat cagggcgatg gcccactacg tgaaccatca cccaaatcaa gttttttggg   7980
gtcgaggtgc cgtaaagcac taaatcggaa ccctaaaggg agcccccgat ttagagcttg   8040
acggggaaag ccggcgaacg tggcgagaaa ggaagggaag aaagcgaaag gagcgggcgc   8100
tagggcgctg gcaagtgtag cggtcacgct gcgcgtaacc accacacccg ccgcgcttaa   8160
tgcgccgcta cagggcgcgt actatggttg ctttgacgta tgcggtgtga aataccgcac   8220
agatgcgtaa ggagaaaata ccgcatcagg cgccattcgc cattcaggct gcgcaactgt   8280
tgggaagggc gatcggtgcg ggcctcttcg ctattacgcc agctggcgaa agggggatgt   8340
```

gctgcaaggc gattaagttg ggtaacgcca gggttttccc agtcacgacg ttgtaaaacg 8400
acggccagtg aattccatgg tctcaacttt c 8431

<210> SEQ ID NO 13
<211> LENGTH: 3750
<212> TYPE: DNA
<213> ORGANISM: Artificial Sequence
<220> FEATURE:
<223> OTHER INFORMATION: Synthetic vector VLP_CHI 512 -CHIKV VLP

<400> SEQUENCE: 13
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
caccgccaaa gacgcagtac taaggacaat tttaatgtct ataaagccac aagaccatat 1020
ctagctcatt gtcctgactg cggagaaggg cattcgtgcc acagccctat cgcattggag 1080
cgcatcagaa atgaagcaac ggacggaacg ctgaaaatcc aggtctcttt gcagatcggg 1140
ataaagacag atgacagcca cgattggacc aagctgcgct atatggatag ccatacgcca 1200
gcggacgcgg agcgagccgg attgcttgta aggacttcag caccgtgcac gatcaccggg 1260
accatgggac actttattct cgcccgatgc ccgaaaggag agacgctgac agtgggattt 1320
acggacagca gaaagatcag ccacacatgc acacacccgt tccatcatga accacctgtg 1380
ataggtaggg agaggttcca ctctcgacca caacatggta aagagttacc ttgcagcacg 1440
tacgtgcaga gcaccgctgc cactgctgag gagatagagg tgcatatgcc cccagatact 1500
cctgaccgca cgctgatgac gcagcagtcc ggaggatcca acgtgaagat cacagttaat 1560
gggcagacgg tgcggtacaa gtgcaactgc ggtggctcaa acgagggact gacaaccaca 1620
gacaaagtga tcaataactg caaaattgat cagtgccatg ctgcagtcac taatcacaag 1680
aattggcaat acaactcccc tttagtcccg cgcaacgctg aactcgggga ccgtaaagga 1740
aagatccaca tcccattccc attggcaaac gtgacttgca gagtgccaaa agcaagaaac 1800
cctacagtaa cttacggaaa aaaccaagtc accatgctgc tgtatcctga ccatccgaca 1860
ctcttgtctt accgtaacat gggacaggaa ccaaattacc acgaggagtg ggtgacacac 1920

-continued

```
aagaaggagg ttaccttgac cgtgcctact gagggtctgg aggtcacttg gggcaacaac   1980

gaaccataca agtactggcc gcagatgtct acgaacggta ctgctcatgg tcacccacat   2040

gagataatct tgtactatta tgagctgtac cccactatga ctgtagtcat tgtgtcggtg   2100

gcctcgttcg tgcttctgtc gatggtgggc acagcagtgg gaatgtgtgt gtgcgcacgg   2160

cgcagatgca ttacaccata tgaattaaca ccaggagcca ctgttccctt cctgctcagc   2220

ctgctatgct gcgtcagaac gaccaaggcg gccacatatt acgaggctgc ggcatatcta   2280

tggaacgaac agcagcccct gttctggttg caggctctta tcccgctggc cgccttgatc   2340

gtcctgtgca actgtctgaa actcttgcca tgctgctgta agaccctggc tttttttagcc   2400

gtaatgagca tcggtgccca cactgtgagc gcgtacgaac acgtaacagt gatcccgaac   2460

acggtgggag taccgtataa gactcttgtc aacagaccgg gttacagccc catggtgttg   2520

gagatggagc tacaatcagt caccttggaa ccaacactgt cacttgacta catcacgtgc   2580

gagtacaaaa ctgtcatccc ctccccgtac gtgaagtgct gtggtacagc agagtgcaag   2640

gacaagagcc taccagacta cagctgcaag gtctttactg gagtctaccc atttatgtgg   2700

ggcggcgcct actgcttttg cgacgccgaa aatacgcaat tgagcgaggc acatgtagag   2760

aaatctgaat cttgcaaaac agagtttgca tcggcctaca gagcccacac cgcatcggcg   2820

tcggcgaagc tccgcgtcct ttaccaagga aacaacatta ccgtagctgc ctacgctaac   2880

ggtgaccatg ccgtcacagt aaaggacgcc aagtttgtcg tgggcccaat gtcctccgcc   2940

tggacacctt ttgacaacaa aatcgtggtg tacaaaggcg acgtctacaa catggactac   3000

ccaccttttg gcgcaggaag accaggacaa tttggtgaca ttcaaagtcg tacaccggaa   3060

agtaaagacg tttatgccaa cactcagttg gtactacaga ggccagcagc aggcacggta   3120

catgtaccat actctcaggc accatctggc ttcaagtatt ggctgaagga acgaggagca   3180

tcgctacagc acacggcacc gttcggttgc cagattgcga caaacccggt aagagctgta   3240

aattgcgctg tggggaacat accaatttcc atcgacatac cggatgcggc ctttactagg   3300

gttgtcgatg caccctctgt aacggacatg tcatgcgaag taccagcctg cactcactcc   3360

tccgactttg ggggcgtcgc catcatcaaa tacacagcta gcaagaaagg taaatgtgca   3420

gtacattcga tgaccaacgc cgttaccatt cgagaagccg acgtagaagt agaggggaac   3480

tcccagctgc aaatatcctt ctcaacagcc ctggcaagcg ccgagtttcg cgtgcaagtg   3540

tgctccacac aagtacactg cgcagccgca tgccaccctc caaaggacca catagtcaat   3600

tacccagcat cacacaccac ccttggggtc caggatatat ccacaacggc aatgtcttgg   3660

gtgcagaaga ttacgggagg agtaggatta attgttgctg ttgctgcctt aattttaatt   3720

gtggtgctat gcgtgtcgtt tagcaggcac                                    3750
```

<210> SEQ ID NO 14
<211> LENGTH: 1250
<212> TYPE: PRT
<213> ORGANISM: Artificial Sequence
<220> FEATURE:
<223> OTHER INFORMATION: Synthetic vector VLP_CHI 512 -CHIKV VLP

<400> SEQUENCE: 14

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
```

-continued

```
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460
```

-continued

```
Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Gly
            500                 505                 510

Ser Asn Val Lys Ile Thr Val Asn Gly Gln Thr Val Arg Tyr Lys Cys
        515                 520                 525

Asn Cys Gly Gly Ser Asn Glu Gly Leu Thr Thr Thr Asp Lys Val Ile
    530                 535                 540

Asn Asn Cys Lys Ile Asp Gln Cys His Ala Ala Val Thr Asn His Lys
545                 550                 555                 560

Asn Trp Gln Tyr Asn Ser Pro Leu Val Pro Arg Asn Ala Glu Leu Gly
                565                 570                 575

Asp Arg Lys Gly Lys Ile His Ile Pro Phe Pro Leu Ala Asn Val Thr
            580                 585                 590

Cys Arg Val Pro Lys Ala Arg Asn Pro Thr Val Thr Tyr Gly Lys Asn
        595                 600                 605

Gln Val Thr Met Leu Leu Tyr Pro Asp His Pro Thr Leu Leu Ser Tyr
    610                 615                 620

Arg Asn Met Gly Gln Glu Pro Asn Tyr His Glu Glu Trp Val Thr His
625                 630                 635                 640

Lys Lys Glu Val Thr Leu Thr Val Pro Thr Glu Gly Leu Glu Val Thr
                645                 650                 655

Trp Gly Asn Asn Glu Pro Tyr Lys Tyr Trp Pro Gln Met Ser Thr Asn
            660                 665                 670

Gly Thr Ala His Gly His Pro His Glu Ile Ile Leu Tyr Tyr Tyr Glu
        675                 680                 685

Leu Tyr Pro Thr Met Thr Val Val Ile Val Ser Val Ala Ser Phe Val
    690                 695                 700

Leu Leu Ser Met Val Gly Thr Ala Val Gly Met Cys Val Cys Ala Arg
705                 710                 715                 720

Arg Arg Cys Ile Thr Pro Tyr Glu Leu Thr Pro Gly Ala Thr Val Pro
                725                 730                 735

Phe Leu Leu Ser Leu Leu Cys Cys Val Arg Thr Thr Lys Ala Ala Thr
            740                 745                 750

Tyr Tyr Glu Ala Ala Ala Tyr Leu Trp Asn Glu Gln Gln Pro Leu Phe
        755                 760                 765

Trp Leu Gln Ala Leu Ile Pro Leu Ala Ala Leu Ile Val Leu Cys Asn
    770                 775                 780

Cys Leu Lys Leu Leu Pro Cys Cys Cys Lys Thr Leu Ala Phe Leu Ala
785                 790                 795                 800

Val Met Ser Ile Gly Ala His Thr Val Ser Ala Tyr Glu His Val Thr
                805                 810                 815

Val Ile Pro Asn Thr Val Gly Val Pro Tyr Lys Thr Leu Val Asn Arg
            820                 825                 830

Pro Gly Tyr Ser Pro Met Val Leu Glu Met Glu Leu Gln Ser Val Thr
        835                 840                 845

Leu Glu Pro Thr Leu Ser Leu Asp Tyr Ile Thr Cys Glu Tyr Lys Thr
    850                 855                 860

Val Ile Pro Ser Pro Tyr Val Lys Cys Cys Gly Thr Ala Glu Cys Lys
865                 870                 875                 880
```

-continued

```
Asp Lys Ser Leu Pro Asp Tyr Ser Cys Lys Val Phe Thr Gly Val Tyr
                885                 890                 895

Pro Phe Met Trp Gly Gly Ala Tyr Cys Phe Cys Asp Ala Glu Asn Thr
            900                 905                 910

Gln Leu Ser Glu Ala His Val Glu Lys Ser Glu Ser Cys Lys Thr Glu
        915                 920                 925

Phe Ala Ser Ala Tyr Arg Ala His Thr Ala Ser Ala Ser Ala Lys Leu
    930                 935                 940

Arg Val Leu Tyr Gln Gly Asn Asn Ile Thr Val Ala Ala Tyr Ala Asn
945                 950                 955                 960

Gly Asp His Ala Val Thr Val Lys Asp Ala Lys Phe Val Val Gly Pro
                965                 970                 975

Met Ser Ser Ala Trp Thr Pro Phe Asp Asn Lys Ile Val Val Tyr Lys
            980                 985                 990

Gly Asp Val Tyr Asn Met Asp Tyr  Pro Pro Phe Gly Ala  Gly Arg Pro
        995                 1000                1005

Gly Gln  Phe Gly Asp Ile Gln  Ser Arg Thr Pro Glu  Ser Lys Asp
    1010                1015                1020

Val Tyr  Ala Asn Thr Gln Leu  Val Leu Gln Arg Pro  Ala Ala Gly
    1025                1030                1035

Thr Val  His Val Pro Tyr Ser  Gln Ala Pro Ser Gly  Phe Lys Tyr
    1040                1045                1050

Trp Leu  Lys Glu Arg Gly Ala  Ser Leu Gln His Thr  Ala Pro Phe
    1055                1060                1065

Gly Cys  Gln Ile Ala Thr Asn  Pro Val Arg Ala Val  Asn Cys Ala
    1070                1075                1080

Val Gly  Asn Ile Pro Ile Ser  Ile Asp Ile Pro Asp  Ala Ala Phe
    1085                1090                1095

Thr Arg  Val Val Asp Ala Pro  Ser Val Thr Asp Met  Ser Cys Glu
    1100                1105                1110

Val Pro  Ala Cys Thr His Ser  Ser Asp Phe Gly Gly  Val Ala Ile
    1115                1120                1125

Ile Lys  Tyr Thr Ala Ser Lys  Lys Gly Lys Cys Ala  Val His Ser
    1130                1135                1140

Met Thr  Asn Ala Val Thr Ile  Arg Glu Ala Asp Val  Glu Val Glu
    1145                1150                1155

Gly Asn  Ser Gln Leu Gln Ile  Ser Phe Ser Thr Ala  Leu Ala Ser
    1160                1165                1170

Ala Glu  Phe Arg Val Gln Val  Cys Ser Thr Gln Val  His Cys Ala
    1175                1180                1185

Ala Ala  Cys His Pro Pro Lys  Asp His Ile Val Asn  Tyr Pro Ala
    1190                1195                1200

Ser His  Thr Thr Leu Gly Val  Gln Asp Ile Ser Thr  Thr Ala Met
    1205                1210                1215

Ser Trp  Val Gln Lys Ile Thr  Gly Gly Val Gly Leu  Ile Val Ala
    1220                1225                1230

Val Ala  Ala Leu Ile Leu Ile  Val Val Leu Cys Val  Ser Phe Ser
    1235                1240                1245

Arg His
    1250
```

<210> SEQ ID NO 15
<211> LENGTH: 3756
<212> TYPE: DNA

<213> ORGANISM: Artificial Sequence
<220> FEATURE:
<223> OTHER INFORMATION: Synthetic vector VLP_CHI 532 -CHIKV VLP

<400> SEQUENCE: 15
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
caccgccaaa gacgcagtac taaggacaat tttaatgtct ataaagccac aagaccatat 1020
ctagctcatt gtcctgactg cggagaaggg cattcgtgcc acagccctat cgcattggag 1080
cgcatcagaa atgaagcaac ggacggaacg ctgaaaatcc aggtctcttt gcagatcggg 1140
ataaagacag atgacagcca cgattggacc aagctgcgct atatggatag ccatacgcca 1200
gcggacgcgg agcgagccgg attgcttgta aggacttcag caccgtgcac gatcaccggg 1260
accatgggac actttattct cgcccgatgc ccgaaaggag agacgctgac agtgggattt 1320
acggacagca gaaagatcag ccacacatgc acacacccgt tccatcatga accacctgtg 1380
ataggtaggg agaggttcca ctctcgacca caacatggta aagagttacc ttgcagcacg 1440
tacgtgcaga gcaccgctgc cactgctgag gagatagagg tgcatatgcc cccagatact 1500
cctgaccgca cgctgatgac gcagcagtct ggcaacgtga agatcacagt taatgggcag 1560
acggtgcggt acaagtgcaa ctgcggtggc tccggaagtg gatccaacga gggactgaca 1620
accacagaca aagtgatcaa taactgcaaa attgatcagt gccatgctgc agtcactaat 1680
cacaagaatt ggcaatacaa ctcccctttta gtcccgcgca acgctgaact cggggaccgt 1740
aaaggaaaga tccacatccc attcccattg gcaaacgtga cttgcagagt gccaaaagca 1800
agaaacccta cagtaactta cggaaaaaac caagtcacca tgctgctgta tcctgaccat 1860
ccgacactct tgtcttaccg taacatggga caggaaccaa attaccacga ggagtgggtg 1920
acacacaaga aggaggttac cttgaccgtg cctactgagg gtctggaggt cacttggggc 1980
aacaacgaac catacaagta ctggccgcag atgtctacga acggtactgc tcatggtcac 2040
ccacatgaga taatcttgta ctattatgag ctgtacccca ctatgactgt agtcattgtg 2100
tcggtggcct cgttcgtgct tctgtcgatg gtgggcacag cagtgggaat gtgtgtgtgc 2160
gcacggcgca gatgcattac accatatgaa ttaacaccag gagccactgt tcccttcctg 2220

-continued

```
ctcagcctgc tatgctgcgt cagaacgacc aaggcggcca catattacga ggctgcggca   2280

tatctatgga acgaacagca gcccctgttc tggttgcagg ctcttatccc gctggccgcc   2340

ttgatcgtcc tgtgcaactg tctgaaactc ttgccatgct gctgtaagac cctggctttt   2400

ttagccgtaa tgagcatcgg tgcccacact gtgagcgcgt acgaacacgt aacagtgatc   2460

ccgaacacgg tgggagtacc gtataagact cttgtcaaca gaccgggtta cagccccatg   2520

gtgttggaga tggagctaca atcagtcacc ttggaaccaa cactgtcact tgactacatc   2580

acgtgcgagt acaaaactgt catcccctcc ccgtacgtga agtgctgtgg tacagcagag   2640

tgcaaggaca agagcctacc agactacagc tgcaaggtct ttactggagt ctacccattt   2700

atgtggggcg gcgcctactg cttttgcgac gccgaaaata cgcaattgag cgaggcacat   2760

gtagagaaat ctgaatcttg caaaacagag tttgcatcgg cctacagagc ccacaccgca   2820

tcggcgtcgg cgaagctccg cgtcctttac caaggaaaca acattaccgt agctgcctac   2880

gctaacggtg accatgccgt cacagtaaag gacgccaagt ttgtcgtggg cccaatgtcc   2940

tccgcctgga caccttttga caacaaaatc gtggtgtaca aaggcgacgt ctacaacatg   3000

gactacccac cttttggcgc aggaagacca ggacaatttg gtgacattca aagtcgtaca   3060

ccggaaagta aagacgttta tgccaacact cagttggtac tacagaggcc agcagcaggc   3120

acggtacatg taccatactc tcaggcacca tctggcttca agtattggct gaaggaacga   3180

ggagcatcgc tacagcacac ggcaccgttc ggttgccaga ttgcgacaaa cccggtaaga   3240

gctgtaaatt gcgctgtggg gaacatacca atttccatcg acataccgga tgcggccttt   3300

actagggttg tcgatgcacc ctctgtaacg gacatgtcat gcgaagtacc agcctgcact   3360

cactcctccg actttggggg cgtcgccatc atcaaataca cagctagcaa gaaaggtaaa   3420

tgtgcagtac attcgatgac caacgccgtt accattcgag aagccgacgt agaagtagag   3480

gggaactccc agctgcaaat atccttctca acagccctgg caagcgccga gtttcgcgtg   3540

caagtgtgct ccacacaagt acactgcgca gccgcatgcc accctccaaa ggaccacata   3600

gtcaattacc cagcatcaca caccaccctt ggggtccagg atatatccac aacggcaatg   3660

tcttgggtgc agaagattac gggaggagta ggattaattg ttgctgttgc tgccttaatt   3720

ttaattgtgg tgctatgcgt gtcgtttagc aggcac                             3756


<210> SEQ ID NO 16
<211> LENGTH: 1252
<212> TYPE: PRT
<213> ORGANISM: Artificial Sequence
<220> FEATURE:
<223> OTHER INFORMATION: Synthetic vector VLP_CHI 532 -CHIKV VLP

<400> SEQUENCE: 16

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
```

-continued

```
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510
```

```
Val Lys Ile Thr Val Asn Gly Gln Thr Val Arg Tyr Lys Cys Asn Cys
        515                 520                 525

Gly Gly Ser Gly Ser Gly Ser Asn Glu Gly Leu Thr Thr Thr Asp Lys
    530                 535                 540

Val Ile Asn Asn Cys Lys Ile Asp Gln Cys His Ala Ala Val Thr Asn
545                 550                 555                 560

His Lys Asn Trp Gln Tyr Asn Ser Pro Leu Val Pro Arg Asn Ala Glu
                565                 570                 575

Leu Gly Asp Arg Lys Gly Lys Ile His Ile Pro Phe Pro Leu Ala Asn
            580                 585                 590

Val Thr Cys Arg Val Pro Lys Ala Arg Asn Pro Thr Val Thr Tyr Gly
        595                 600                 605

Lys Asn Gln Val Thr Met Leu Leu Tyr Pro Asp His Pro Thr Leu Leu
    610                 615                 620

Ser Tyr Arg Asn Met Gly Gln Glu Pro Asn Tyr His Glu Glu Trp Val
625                 630                 635                 640

Thr His Lys Lys Glu Val Thr Leu Thr Val Pro Thr Glu Gly Leu Glu
                645                 650                 655

Val Thr Trp Gly Asn Asn Glu Pro Tyr Lys Tyr Trp Pro Gln Met Ser
            660                 665                 670

Thr Asn Gly Thr Ala His Gly His Pro His Glu Ile Ile Leu Tyr Tyr
        675                 680                 685

Tyr Glu Leu Tyr Pro Thr Met Thr Val Val Ile Val Ser Val Ala Ser
    690                 695                 700

Phe Val Leu Leu Ser Met Val Gly Thr Ala Val Gly Met Cys Val Cys
705                 710                 715                 720

Ala Arg Arg Arg Cys Ile Thr Pro Tyr Glu Leu Thr Pro Gly Ala Thr
                725                 730                 735

Val Pro Phe Leu Leu Ser Leu Leu Cys Cys Val Arg Thr Thr Lys Ala
            740                 745                 750

Ala Thr Tyr Tyr Glu Ala Ala Ala Tyr Leu Trp Asn Glu Gln Gln Pro
        755                 760                 765

Leu Phe Trp Leu Gln Ala Leu Ile Pro Leu Ala Ala Leu Ile Val Leu
    770                 775                 780

Cys Asn Cys Leu Lys Leu Leu Pro Cys Cys Cys Lys Thr Leu Ala Phe
785                 790                 795                 800

Leu Ala Val Met Ser Ile Gly Ala His Thr Val Ser Ala Tyr Glu His
                805                 810                 815

Val Thr Val Ile Pro Asn Thr Val Gly Val Pro Tyr Lys Thr Leu Val
            820                 825                 830

Asn Arg Pro Gly Tyr Ser Pro Met Val Leu Glu Met Glu Leu Gln Ser
        835                 840                 845

Val Thr Leu Glu Pro Thr Leu Ser Leu Asp Tyr Ile Thr Cys Glu Tyr
    850                 855                 860

Lys Thr Val Ile Pro Ser Pro Tyr Val Lys Cys Cys Gly Thr Ala Glu
865                 870                 875                 880

Cys Lys Asp Lys Ser Leu Pro Asp Tyr Ser Cys Lys Val Phe Thr Gly
                885                 890                 895

Val Tyr Pro Phe Met Trp Gly Gly Ala Tyr Cys Phe Cys Asp Ala Glu
            900                 905                 910

Asn Thr Gln Leu Ser Glu Ala His Val Glu Lys Ser Glu Ser Cys Lys
        915                 920                 925
```

-continued

```
Thr Glu Phe Ala Ser Ala Tyr Arg Ala His Thr Ala Ser Ala Ser Ala
    930                 935                 940

Lys Leu Arg Val Leu Tyr Gln Gly Asn Asn Ile Thr Val Ala Ala Tyr
945                 950                 955                 960

Ala Asn Gly Asp His Ala Val Thr Val Lys Asp Ala Lys Phe Val Val
                965                 970                 975

Gly Pro Met Ser Ser Ala Trp Thr Pro Phe Asp Asn Lys Ile Val Val
            980                 985                 990

Tyr Lys Gly Asp Val Tyr Asn Met  Asp Tyr Pro Pro Phe  Gly Ala Gly
        995                 1000                 1005

Arg Pro  Gly Gln Phe Gly Asp  Ile Gln Ser Arg Thr  Pro Glu Ser
    1010                 1015                 1020

Lys Asp  Val Tyr Ala Asn Thr  Gln Leu Val Leu Gln  Arg Pro Ala
    1025                 1030                 1035

Ala Gly  Thr Val His Val Pro  Tyr Ser Gln Ala Pro  Ser Gly Phe
    1040                 1045                 1050

Lys Tyr  Trp Leu Lys Glu Arg  Gly Ala Ser Leu Gln  His Thr Ala
    1055                 1060                 1065

Pro Phe  Gly Cys Gln Ile Ala  Thr Asn Pro Val Arg  Ala Val Asn
    1070                 1075                 1080

Cys Ala  Val Gly Asn Ile Pro  Ile Ser Ile Asp Ile  Pro Asp Ala
    1085                 1090                 1095

Ala Phe  Thr Arg Val Val Asp  Ala Pro Ser Val Thr  Asp Met Ser
    1100                 1105                 1110

Cys Glu  Val Pro Ala Cys Thr  His Ser Ser Asp Phe  Gly Gly Val
    1115                 1120                 1125

Ala Ile  Ile Lys Tyr Thr Ala  Ser Lys Lys Gly Lys  Cys Ala Val
    1130                 1135                 1140

His Ser  Met Thr Asn Ala Val  Thr Ile Arg Glu Ala  Asp Val Glu
    1145                 1150                 1155

Val Glu  Gly Asn Ser Gln Leu  Gln Ile Ser Phe Ser  Thr Ala Leu
    1160                 1165                 1170

Ala Ser  Ala Glu Phe Arg Val  Gln Val Cys Ser Thr  Gln Val His
    1175                 1180                 1185

Cys Ala  Ala Ala Cys His Pro  Pro Lys Asp His Ile  Val Asn Tyr
    1190                 1195                 1200

Pro Ala  Ser His Thr Thr Leu  Gly Val Gln Asp Ile  Ser Thr Thr
    1205                 1210                 1215

Ala Met  Ser Trp Val Gln Lys  Ile Thr Gly Gly Val  Gly Leu Ile
    1220                 1225                 1230

Val Ala  Val Ala Ala Leu Ile  Leu Ile Val Val Leu  Cys Val Ser
    1235                 1240                 1245

Phe Ser  Arg His
    1250


<210> SEQ ID NO 17
<211> LENGTH: 3777
<212> TYPE: DNA
<213> ORGANISM: Artificial Sequence
<220> FEATURE:
<223> OTHER INFORMATION: Synthetic vector VLP_VEEV VLP 518 -VEEV VLP

<400> SEQUENCE: 17

atgttcccgt tccagccaat gtatccgatg cagccaatgc cctatcgcaa cccgttcgcg      60

gccccgcgca ggccctggtt ccccagaacc gaccctttc tggcgatgca ggtgcaggaa     120
```

-continued

```
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg ctccggagga   1560
tccagttcag tcaccgtgac acctcctgat gggactagcg ccctggtgga atgcgagtgt   1620
ggcggcacaa agatctccga gaccatcaac aagacaaaac agttcagcca gtgcacaaag   1680
aaggagcagt gcagagcata tcggctgcag aacgataagt gggtgtataa ttctgacaaa   1740
ctgcccaaag cagcgggagc caccttaaaa ggaaaactgc atgtcccatt cttgctggca   1800
gacggcaaat gcaccgtgcc tctagcacca gaacctatga taaccttcgg tttcagatca   1860
gtgtcactga aactgcaccc taagaatccc acatatctaa tcacccgcca acttgctgat   1920
gagcctcact acacgcacga gctcatatct gaaccagctg ttaggaattt taccgtcacc   1980
gaaaaagggt gggagtttgt atggggaaac cacccgccga aaaggttttg ggcacaggaa   2040
acagcacccg gaaatccaca tgggctaccg cacgaggtga taactcatta ttaccacaga   2100
taccctatgt ccaccatcct gggtttgtca atttgtgccg ccattgcaac cgtttccgtt   2160
gcagcgtcta cctggctgtt ttgcagatca agagttgcgt gcctaactcc ttaccggcta   2220
acacctaacg ctaggatacc attttgtctg gctgtgcttt gctgcgcccg cactgcccgg   2280
gccgagacca cctgggagtc cttggatcac ctatggaaca ataaccaaca gatgttctgg   2340
attcaattgc tgatccctct ggccgccttg atcgtagtga ctcgcctgct caggtgcgtg   2400
tgctgtgtcg tgcctttttt agtcatggcc ggcgccgcag gcgccggcgc ctacgagcac   2460
```

-continued

```
gcgaccacga tgccgagcca agcgggaatc tcgtataaca ctatagtcaa cagagcaggc   2520

tacgcaccac tccctatcag cataacacca acaaagatca agctgatacc tacagtgaac   2580

ttggagtacg tcacctgcca ctacaaaaca ggaatggatt caccagccat caaatgctgc   2640

ggatctcagg aatgcactcc aacttacagg cctgatgaac agtgcaaagt cttcacaggg   2700

gtttacccgt tcatgtgggg tggtgcatat tgcttttgcg acactgagaa cacccaagtc   2760

agcaaggcct acgtaatgaa atctgacgac tgccttgcgg atcatgctga agcatataaa   2820

gcgcacacag cctcagtgca ggcgttcctc aacatcacag tgggagaaca ctctattgtg   2880

actaccgtgt atgtgaatgg agaaactcct gtgaatttca atggggtcaa aataactgca   2940

ggtccgcttt ccacagcttg gacacccttt gatcgcaaaa tcgtgcagta tgccggggag   3000

atctataatt atgattttcc tgagtatggg gcaggacaac caggagcatt tggagatata   3060

caatccagaa cagtctcaag ctctgatctg tatgccaata ccaacctagt gctgcagaga   3120

cccaaagcag gagcgatcca cgtgccatac actcaggcac cttcgggttt tgagcaatgg   3180

aagaaagata aagctccatc attgaaattt accgcccctt tcggatgcga aatatataca   3240

aaccccattc gcgccgaaaa ctgtgctgta gggtcaattc cattagcctt tgacattccc   3300

gacgccttgt tcaccagggt gtcagaaaca ccgacacttt cagcggccga atgcactctt   3360

aacgagtgcg tgtattcttc cgactttggt gggatcgcca cggtcaagta ctcggccagc   3420

aagtcaggca agtgcgcagt ccatgtgcca tcagggactg ctaccctaaa agaagcagca   3480

gtcgagctaa ccgagcaagg gtcggcgact atccatttct cgaccgcaaa tatccacccg   3540

gagttcaggc tccaaatatg cacatcatat gttacgtgca aaggtgattg tcaccccccg   3600

aaagaccata ttgtgacaca ccctcagtat cacgcccaaa catttacagc cgcggtgtca   3660

aaaaccgcgt ggacgtggtt aacatccctg ctgggaggat cagccgtaat tattataatt   3720

ggcttggtgc tggctactat tgtggccatg tacgtgctga ccaaccagaa acataat      3777
```

```
<210> SEQ ID NO 18
<211> LENGTH: 1259
<212> TYPE: PRT
<213> ORGANISM: Artificial Sequence
<220> FEATURE:
<223> OTHER INFORMATION: Synthetic vector VLP_VEEV VLP 518 -VEEV VLP

<400> SEQUENCE: 18

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
```

-continued

```
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Gly Gly Ser Ser Ser Val Thr Val Thr Pro
        515                 520                 525

Pro Asp Gly Thr Ser Ala Leu Val Glu Cys Glu Cys Gly Gly Thr Lys
    530                 535                 540

Ile Ser Glu Thr Ile Asn Lys Thr Lys Gln Phe Ser Gln Cys Thr Lys
545                 550                 555                 560
```

```
Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605

Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655

Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830

Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880

Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925

Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975
```

-continued

```
Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                 1005

Tyr Gly  Ala Gly Gln Pro Gly  Ala Phe Gly Asp Ile  Gln Ser Arg
    1010                 1015                 1020

Thr Val  Ser Ser Ser Asp Leu  Tyr Ala Asn Thr Asn  Leu Val Leu
    1025                 1030                 1035

Gln Arg  Pro Lys Ala Gly Ala  Ile His Val Pro Tyr  Thr Gln Ala
    1040                 1045                 1050

Pro Ser  Gly Phe Glu Gln Trp  Lys Lys Asp Lys Ala  Pro Ser Leu
    1055                 1060                 1065

Lys Phe  Thr Ala Pro Phe Gly  Cys Glu Ile Tyr Thr  Asn Pro Ile
    1070                 1075                 1080

Arg Ala  Glu Asn Cys Ala Val  Gly Ser Ile Pro Leu  Ala Phe Asp
    1085                 1090                 1095

Ile Pro  Asp Ala Leu Phe Thr  Arg Val Ser Glu Thr  Pro Thr Leu
    1100                 1105                 1110

Ser Ala  Ala Glu Cys Thr Leu  Asn Glu Cys Val Tyr  Ser Ser Asp
    1115                 1120                 1125

Phe Gly  Gly Ile Ala Thr Val  Lys Tyr Ser Ala Ser  Lys Ser Gly
    1130                 1135                 1140

Lys Cys  Ala Val His Val Pro  Ser Gly Thr Ala Thr  Leu Lys Glu
    1145                 1150                 1155

Ala Ala  Val Glu Leu Thr Glu  Gln Gly Ser Ala Thr  Ile His Phe
    1160                 1165                 1170

Ser Thr  Ala Asn Ile His Pro  Glu Phe Arg Leu Gln  Ile Cys Thr
    1175                 1180                 1185

Ser Tyr  Val Thr Cys Lys Gly  Asp Cys His Pro Pro  Lys Asp His
    1190                 1195                 1200

Ile Val  Thr His Pro Gln Tyr  His Ala Gln Thr Phe  Thr Ala Ala
    1205                 1210                 1215

Val Ser  Lys Thr Ala Trp Thr  Trp Leu Thr Ser Leu  Leu Gly Gly
    1220                 1225                 1230

Ser Ala  Val Ile Ile Ile Ile  Gly Leu Val Leu Ala  Thr Ile Val
    1235                 1240                 1245

Ala Met  Tyr Val Leu Thr Asn  Gln Lys His Asn
    1250                 1255
```

<210> SEQ ID NO 19
<211> LENGTH: 3777
<212> TYPE: DNA
<213> ORGANISM: Artificial Sequence
<220> FEATURE:
<223> OTHER INFORMATION: Synthetic vector VLP_VEEV VLP 519 -VEEV VLP

<400> SEQUENCE: 19

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360
```

-continued

```
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggatcctcag tcaccgtgac acctcctgat gggactagcg ccctggtgga atgcgagtgt   1620
ggcggcacaa agatctccga gaccatcaac aagacaaaac agttcagcca gtgcacaaag   1680
aaggagcagt gcagagcata tcggctgcag aacgataagt gggtgtataa ttctgacaaa   1740
ctgcccaaag cagcgggagc caccttaaaa ggaaaactgc atgtcccatt cttgctggca   1800
gacggcaaat gcaccgtgcc tctagcacca gaacctatga taaccttcgg tttcagatca   1860
gtgtcactga aactgcaccc taagaatccc acatatctaa tcacccgcca acttgctgat   1920
gagcctcact acacgcacga gctcatatct gaaccagctg ttaggaattt taccgtcacc   1980
gaaaaagggt gggagtttgt atggggaaac cacccgccga aaaggttttg ggcacaggaa   2040
acagcacccg gaaatccaca tggctaccg cacgaggtga taactcatta ttaccacaga   2100
taccctatgt ccaccatcct gggtttgtca atttgtgccg ccattgcaac cgtttccgtt   2160
gcagcgtcta cctggctgtt ttgcagatca agagttgcgt gcctaactcc ttaccggcta   2220
acacctaacg ctaggatacc attttgtctg gctgtgcttt gctgcgcccg cactgcccgg   2280
gccgagacca cctgggagtc cttggatcac ctatggaaca ataaccaaca gatgttctgg   2340
attcaattgc tgatccctct ggccgccttg atcgtagtga ctcgcctgct caggtgcgtg   2400
tgctgtgtcg tgcctttttt agtcatggcc ggcgccgcag gcgccggcgc ctacgagcac   2460
gcgaccacga tgccgagcca agcgggaatc tcgtataaca ctatagtcaa cagagcaggc   2520
tacgcaccac tccctatcag cataacacca acaaagatca agctgatacc tacagtgaac   2580
ttggagtacg tcacctgcca ctacaaaaca ggaatggatt caccagccat caaatgctgc   2640
ggatctcagg aatgcactcc aacttacagg cctgatgaac agtgcaaagt cttcacaggg   2700
gtttacccgt tcatgtgggg tggtgcatat tgcttttgcg acactgagaa cacccaagtc   2760
```

```
agcaaggcct acgtaatgaa atctgacgac tgccttgcgg atcatgctga agcatataaa   2820

gcgcacacag cctcagtgca ggcgttcctc aacatcacag tgggagaaca ctctattgtg   2880

actaccgtgt atgtgaatgg agaaactcct gtgaatttca atggggtcaa aataactgca   2940

ggtccgcttt ccacagcttg gacacccttt gatcgcaaaa tcgtgcagta tgccggggag   3000

atctataatt atgattttcc tgagtatggg gcaggacaac caggagcatt tggagatata   3060

caatccagaa cagtctcaag ctctgatctg tatgccaata ccaacctagt gctgcagaga   3120

cccaaagcag gagcgatcca cgtgccatac actcaggcac cttcgggttt tgagcaatgg   3180

aagaaagata aagctccatc attgaaattt accgcccctt tcggatgcga aatatataca   3240

aaccccattc gcgccgaaaa ctgtgctgta gggtcaattc cattagcctt tgacattccc   3300

gacgccttgt tcaccagggt gtcagaaaca ccgacacttt cagcggccga atgcactctt   3360

aacgagtgcg tgtattcttc cgactttggt gggatcgcca cggtcaagta ctcggccagc   3420

aagtcaggca agtgcgcagt ccatgtgcca tcagggactg ctaccctaaa agaagcagca   3480

gtcgagctaa ccgagcaagg gtcggcgact atccatttct cgaccgcaaa tatccacccg   3540

gagttcaggc tccaaatatg cacatcatat gttacgtgca aaggtgattg tcaccccccg   3600

aaagaccata ttgtgacaca ccctcagtat cacgcccaaa catttacagc cgcggtgtca   3660

aaaaccgcgt ggacgtggtt aacatccctg ctgggaggat cagccgtaat tattataatt   3720

ggcttggtgc tggctactat tgtggccatg tacgtgctga ccaaccagaa acataat      3777
```

<210> SEQ ID NO 20
<211> LENGTH: 1259
<212> TYPE: PRT
<213> ORGANISM: Artificial Sequence
<220> FEATURE:
<223> OTHER INFORMATION: Synthetic vector VLP_VEEV VLP 519 -VEEV VLP

<400> SEQUENCE: 20

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
```

-continued

```
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Ser Ser Val Thr Val Thr Pro
        515                 520                 525

Pro Asp Gly Thr Ser Ala Leu Val Glu Cys Glu Cys Gly Gly Thr Lys
    530                 535                 540

Ile Ser Glu Thr Ile Asn Lys Thr Lys Gln Phe Ser Gln Cys Thr Lys
545                 550                 555                 560

Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605
```

-continued

```
Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655

Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830

Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880

Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925

Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975

Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                 1005

Tyr Gly  Ala Gly Gln Pro Gly  Ala Phe Gly Asp Ile  Gln Ser Arg
    1010                 1015                 1020
```

```
Thr Val  Ser Ser Ser Asp Leu  Tyr Ala Asn Thr Asn  Leu Val Leu
    1025                 1030                 1035

Gln Arg  Pro Lys Ala Gly Ala  Ile His Val Pro Tyr  Thr Gln Ala
    1040                 1045                 1050

Pro Ser  Gly Phe Glu Gln Trp  Lys Lys Asp Lys Ala  Pro Ser Leu
    1055                 1060                 1065

Lys Phe  Thr Ala Pro Phe Gly  Cys Glu Ile Tyr Thr  Asn Pro Ile
    1070                 1075                 1080

Arg Ala  Glu Asn Cys Ala Val  Gly Ser Ile Pro Leu  Ala Phe Asp
    1085                 1090                 1095

Ile Pro  Asp Ala Leu Phe Thr  Arg Val Ser Glu Thr  Pro Thr Leu
    1100                 1105                 1110

Ser Ala  Ala Glu Cys Thr Leu  Asn Glu Cys Val Tyr  Ser Ser Asp
    1115                 1120                 1125

Phe Gly  Gly Ile Ala Thr Val  Lys Tyr Ser Ala Ser  Lys Ser Gly
    1130                 1135                 1140

Lys Cys  Ala Val His Val Pro  Ser Gly Thr Ala Thr  Leu Lys Glu
    1145                 1150                 1155

Ala Ala  Val Glu Leu Thr Glu  Gln Gly Ser Ala Thr  Ile His Phe
    1160                 1165                 1170

Ser Thr  Ala Asn Ile His Pro  Glu Phe Arg Leu Gln  Ile Cys Thr
    1175                 1180                 1185

Ser Tyr  Val Thr Cys Lys Gly  Asp Cys His Pro Pro  Lys Asp His
    1190                 1195                 1200

Ile Val  Thr His Pro Gln Tyr  His Ala Gln Thr Phe  Thr Ala Ala
    1205                 1210                 1215

Val Ser  Lys Thr Ala Trp Thr  Trp Leu Thr Ser Leu  Leu Gly Gly
    1220                 1225                 1230

Ser Ala  Val Ile Ile Ile Ile  Gly Leu Val Leu Ala  Thr Ile Val
    1235                 1240                 1245

Ala Met  Tyr Val Leu Thr Asn  Gln Lys His Asn
    1250                 1255
```

<210> SEQ ID NO 21
<211> LENGTH: 3777
<212> TYPE: DNA
<213> ORGANISM: Artificial Sequence
<220> FEATURE:
<223> OTHER INFORMATION: Synthetic vector VLP_VEEV VLP 538 -VEEV VLP

<400> SEQUENCE: 21

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaacccca aggctattac    600

agctggcatc atggagcagt ccaatatgaa aatgggcgtt tcacggtgcc gaaaggagtt    660
```

-continued

```
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttcagtc   1560
accgtgacac ctcctgatgg gactagcgcc ctggtggaat gcgagtgtgg ctccggagga   1620
tccggcacaa agatctccga gaccatcaac aagacaaaac agttcagcca gtgcacaaag   1680
aaggagcagt gcagagcata tcggctgcag aacgataagt gggtgtataa ttctgacaaa   1740
ctgcccaaag cagcgggagc caccttaaaa ggaaaactgc atgtcccatt cttgctggca   1800
gacggcaaat gcaccgtgcc tctagcacca gaacctatga taaccttcgg tttcagatca   1860
gtgtcactga aactgcaccc taagaatccc acatatctaa tcacccgcca acttgctgat   1920
gagcctcact acacgcacga gctcatatct gaaccagctg ttaggaattt taccgtcacc   1980
gaaaaagggt gggagtttgt atggggaaac cacccgccga aaaggttttg ggcacaggaa   2040
acagcacccg gaaatccaca tgggctaccg cacgaggtga taactcatta ttaccacaga   2100
taccctatgt ccaccatcct gggtttgtca atttgtgccg ccattgcaac cgtttccgtt   2160
gcagcgtcta cctggctgtt ttgcagatca agagttgcgt gcctaactcc ttaccggcta   2220
acacctaacg ctaggatacc attttgtctg gctgtgcttt gctgcgcccg cactgcccgg   2280
gccgagacca cctgggagtc cttggatcac ctatggaaca ataaccaaca gatgttctgg   2340
attcaattgc tgatccctct ggccgccttg atcgtagtga ctcgcctgct caggtgcgtg   2400
tgctgtgtcg tgcctttttt agtcatggcc ggcgccgcag gcgccggcgc ctacgagcac   2460
gcgaccacga tgccgagcca agcgggaatc tcgtataaca ctatagtcaa cagagcaggc   2520
tacgcaccac tccctatcag cataacacca acaaagatca agctgatacc tacagtgaac   2580
ttggagtacg tcacctgcca ctacaaaaca ggaatggatt caccagccat caaatgctgc   2640
ggatctcagg aatgcactcc aacttacagg cctgatgaac agtgcaaagt cttcacaggg   2700
gtttacccgt tcatgtgggg tggtgcatat tgcttttgcg acactgagaa cacccaagtc   2760
agcaaggcct acgtaatgaa atctgacgac tgccttgcgg atcatgctga agcatataaa   2820
gcgcacacag cctcagtgca ggcgttcctc aacatcacag tgggagaaca ctctattgtg   2880
actaccgtgt atgtgaatgg agaaactcct gtgaatttca atggggtcaa aataactgca   2940
ggtccgcttt ccacagcttg gacacccttt gatcgcaaaa tcgtgcagta tgccggggag   3000
```

```
atctataatt atgattttcc tgagtatggg gcaggacaac caggagcatt tggagatata   3060

caatccagaa cagtctcaag ctctgatctg tatgccaata ccaacctagt gctgcagaga   3120

cccaaagcag gagcgatcca cgtgccatac actcaggcac cttcgggttt tgagcaatgg   3180

aagaaagata aagctccatc attgaaattt accgcccctt tcggatgcga aatatataca   3240

aaccccattc gcgccgaaaa ctgtgctgta gggtcaattc cattagcctt tgacattccc   3300

gacgccttgt tcaccagggt gtcagaaaca ccgacacttt cagcggccga atgcactctt   3360

aacgagtgcg tgtattcttc cgactttggt gggatcgcca cggtcaagta ctcggccagc   3420

aagtcaggca agtgcgcagt ccatgtgcca tcagggactg ctaccctaaa agaagcagca   3480

gtcgagctaa ccgagcaagg gtcggcgact atccatttct cgaccgcaaa tatccacccg   3540

gagttcaggc tccaaatatg cacatcatat gttacgtgca aaggtgattg tcaccccccg   3600

aaagaccata ttgtgacaca ccctcagtat cacgcccaaa catttacagc cgcggtgtca   3660

aaaaccgcgt ggacgtggtt aacatccctg ctgggaggat cagccgtaat tattataatt   3720

ggcttggtgc tggctactat tgtggccatg tacgtgctga ccaaccagaa acataat      3777
```

<210> SEQ ID NO 22
<211> LENGTH: 1259
<212> TYPE: PRT
<213> ORGANISM: Artificial Sequence
<220> FEATURE:
<223> OTHER INFORMATION: Synthetic vector VLP_VEEV VLP 538 -VEEV VLP

<400> SEQUENCE: 22

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
```

-continued

```
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Ser Gly Gly Ser Gly Thr Lys
    530                 535                 540

Ile Ser Glu Thr Ile Asn Lys Thr Lys Gln Phe Ser Gln Cys Thr Lys
545                 550                 555                 560

Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605

Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655
```

```
Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830

Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880

Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925

Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975

Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                1005

Tyr Gly  Ala Gly Gln Pro Gly  Ala Phe Gly Asp Ile  Gln Ser Arg
    1010                1015                1020

Thr Val  Ser Ser Ser Asp Leu  Tyr Ala Asn Thr Asn  Leu Val Leu
    1025                1030                1035

Gln Arg  Pro Lys Ala Gly Ala  Ile His Val Pro Tyr  Thr Gln Ala
    1040                1045                1050

Pro Ser  Gly Phe Glu Gln Trp  Lys Lys Asp Lys Ala  Pro Ser Leu
    1055                1060                1065
```

Lys Phe Thr Ala Pro Phe Gly Cys Glu Ile Tyr Thr Asn Pro Ile
1070 1075 1080

Arg Ala Glu Asn Cys Ala Val Gly Ser Ile Pro Leu Ala Phe Asp
1085 1090 1095

Ile Pro Asp Ala Leu Phe Thr Arg Val Ser Glu Thr Pro Thr Leu
1100 1105 1110

Ser Ala Ala Glu Cys Thr Leu Asn Glu Cys Val Tyr Ser Ser Asp
1115 1120 1125

Phe Gly Gly Ile Ala Thr Val Lys Tyr Ser Ala Ser Lys Ser Gly
1130 1135 1140

Lys Cys Ala Val His Val Pro Ser Gly Thr Ala Thr Leu Lys Glu
1145 1150 1155

Ala Ala Val Glu Leu Thr Glu Gln Gly Ser Ala Thr Ile His Phe
1160 1165 1170

Ser Thr Ala Asn Ile His Pro Glu Phe Arg Leu Gln Ile Cys Thr
1175 1180 1185

Ser Tyr Val Thr Cys Lys Gly Asp Cys His Pro Pro Lys Asp His
1190 1195 1200

Ile Val Thr His Pro Gln Tyr His Ala Gln Thr Phe Thr Ala Ala
1205 1210 1215

Val Ser Lys Thr Ala Trp Thr Trp Leu Thr Ser Leu Leu Gly Gly
1220 1225 1230

Ser Ala Val Ile Ile Ile Ile Gly Leu Val Leu Ala Thr Ile Val
1235 1240 1245

Ala Met Tyr Val Leu Thr Asn Gln Lys His Asn
1250 1255

<210> SEQ ID NO 23
<211> LENGTH: 8416
<212> TYPE: DNA
<213> ORGANISM: Artificial Sequence
<220> FEATURE:
<223> OTHER INFORMATION: Synthetic vector VLP_CHI 520

<400> SEQUENCE: 23
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900

-continued

```
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
gctccggagg atccggcggg cagacggtgc ggtacaagtg caactgcggt ggctcaaacg   2520
agggactgac aaccacagac aaagtgatca ataactgcaa aattgatcag tgccatgctg   2580
cagtcactaa tcacaagaat tggcaataca actccccttt agtcccgcgc aacgctgaac   2640
tcggggaccg taaaggaaag atccacatcc cattcccatt ggcaaacgtg acttgcagag   2700
tgccaaaagc aagaaaccct acagtaactt acggaaaaaa ccaagtcacc atgctgctgt   2760
atcctgacca tccgacactc ttgtcttacc gtaacatggg acaggaacca aattaccacg   2820
aggagtgggt gacacacaag aaggaggtta ccttgaccgt gcctactgag ggtctggagg   2880
tcacttgggg caacaacgaa ccatacaagt actggccgca gatgtctacg aacggtactg   2940
ctcatggtca cccacatgag ataatcttgt actattatga gctgtacccc actatgactg   3000
tagtcattgt gtcggtggcc tcgttcgtgc ttctgtcgat ggtgggcaca gcagtgggaa   3060
tgtgtgtgtg cgcacggcgc agatgcatta caccatatga attaacacca ggagccactg   3120
ttcccttcct gctcagcctg ctatgctgcg tcagaacgac caaggcggcc acatattacg   3180
aggctgcggc atatctatgg aacgaacagc agcccctgtt ctggttgcag gctcttatcc   3240
cgctggccgc cttgatcgtc ctgtgcaact gtctgaaact cttgccatgc tgctgtaaga   3300
```

-continued

```
ccctggcttt tttagccgta atgagcatcg gtgcccacac tgtgagcgcg tacgaacacg   3360
taacagtgat cccgaacacg gtgggagtac cgtataagac tcttgtcaac agaccgggtt   3420
acagccccat ggtgttggag atggagctac aatcagtcac cttggaacca acactgtcac   3480
ttgactacat cacgtgcgag tacaaaactg tcatcccctc cccgtacgtg aagtgctgtg   3540
gtacagcaga gtgcaaggac aagagcctac cagactacag ctgcaaggtc tttactggag   3600
tctacccatt tatgtggggc ggcgcctact gcttttgcga cgccgaaaat acgcaattga   3660
gcgaggcaca tgtagagaaa tctgaatctt gcaaaacaga gtttgcatcg gcctacagag   3720
cccacaccgc atcggcgtcg gcgaagctcc gcgtccttta ccaaggaaac aacattaccg   3780
tagctgccta cgctaacggt gaccatgccg tcacagtaaa ggacgccaag tttgtcgtgg   3840
gcccaatgtc ctccgcctgg acaccttttg acaacaaaat cgtggtgtac aaaggcgacg   3900
tctacaacat ggactaccca ccttttggcg caggaagacc aggacaattt ggtgacattc   3960
aaagtcgtac accggaaagt aaagacgttt atgccaacac tcagttggta ctacagaggc   4020
cagcagcagg cacggtacat gtaccatact ctcaggcacc atctggcttc aagtattggc   4080
tgaaggaacg aggagcatcg ctacagcaca cggcaccgtt cggttgccag attgcgacaa   4140
acccggtaag agctgtaaat tgcgctgtgg ggaacatacc aatttccatc gacataccgg   4200
atgcggcctt tactagggtt gtcgatgcac cctctgtaac ggacatgtca tgcgaagtac   4260
cagcctgcac tcactcctcc gactttgggg gcgtcgccat catcaaatac acagctagca   4320
agaaaggtaa atgtgcagta cattcgatga ccaacgccgt taccattcga gaagccgacg   4380
tagaagtaga ggggaactcc cagctgcaaa tatccttctc aacagccctg gcaagcgccg   4440
agtttcgcgt gcaagtgtgc tccacacaag tacactgcgc agccgcatgc caccctccaa   4500
aggaccacat agtcaattac ccagcatcac acaccaccct tggggtccag gatatatcca   4560
caacggcaat gtcttgggtg cagaagatta cgggaggagt aggattaatt gttgctgttg   4620
ctgccttaat tttaattgtg gtgctatgcg tgtcgtttag caggcactaa ggatctagat   4680
ctgctgtgcc ttctagttgc cagccatctg ttgtttgccc ctcccccgtg ccttccttga   4740
ccctggaagg tgccactccc actgtccttt cctaataaaa tgaggaaatt gcatcgcatt   4800
gtctgagtag gtgtcattct attctggggg gtggggtggg gcaggacagc aagggggagg   4860
attgggaaga caatagcagg catgctgggg atgcggtggg ctctatgggt acccaggtgc   4920
tgaagaattg acccggttcc tcctgggcca gaaagaagca ggcacatccc cttctctgtg   4980
acacaccctg tccacgcccc tggttcttag ttccagcccc actcatagga cactcatagc   5040
tcaggagggc tccgccttca atcccacccg ctaaagtact tggagcggtc tctccctccc   5100
tcatcagccc accaaaccaa acctagcctc caagagtggg aagaaattaa agcaagatag   5160
gctattaagt gcagagggag agaaaatgcc tccaacatgt gaggaagtaa tgagagaaat   5220
catagaattt taaggccatg atttaaggcc atcatggcct aagcttgaaa ggagatagga   5280
tcaaagcttg gcgtaatcat ggtcatagct gtttcctgtg tgaaattgtt atccgctcac   5340
aattccacac aacatacgag ccggaagcat aaagtgtaaa gcctggggtg cctaatgagt   5400
gagctaactc acattaattg cgttgcgctc actgcccgct ttccagtcgg gaaacctgtc   5460
gtgccagctg cattaatgaa tcggccaacg cgcggggaga ggcggtttgc gtattgggcg   5520
ctcttccgct tcctcgctca ctgactcgct gcgctcggtc gttcggctgc ggcgagcggt   5580
atcagctcac tcaaaggcgg taatacggtt atccacagaa tcaggggata acgcaggaaa   5640
```

-continued gaacatgtga gcaaaaggcc agcaaaaggc caggaaccgt aaaaaggccg cgttgctggc 5700
gtttttccat aggctccgcc cccctgacga gcatcacaaa aatcgacgct caagtcagag 5760
gtggcgaaac ccgacaggac tataaagata ccaggcgttt ccccctggaa gctccctcgt 5820
gcgctctcct gttccgaccc tgccgcttac cggatacctg tccgcctttc tcccttcggg 5880
aagcgtggcg ctttctcata gctcacgctg taggtatctc agttcggtgt aggtcgttcg 5940
ctccaagctg ggctgtgtgc acgaaccccc cgttcagccc gaccgctgcg ccttatccgg 6000
taactatcgt cttgagtcca acccggtaag acacgactta tcgccactgg cagcagccac 6060
tggtaacagg attagcagag cgaggtatgt aggcggtgct acagagttct tgaagtggtg 6120
gcctaactac ggctacacta gaagaacagt atttggtatc tgcgctctgc tgaagccagt 6180
taccttcgga aaaagagttg gtagctcttg atccggcaaa caaaccaccg ctggtagcgg 6240
tggttttttt gtttgcaagc agcagattac gcgcagaaaa aaaggatctc aagaagatcc 6300
tttgatcttt tctacggggt ctgacgctca gtggaacgaa aactcacgtt aagggatttt 6360
ggtcatgaga ttatcaaaaa ggatcttcac ctagatcctt ttaaattaaa aatgaagttt 6420
taaatcaatc taaagtatat atgagtaaac ttggtctgac agttaccaat gcttaatcag 6480
tgaggcacct atctcagcga tctgtctatt tcgttcatcc atagttgcct gactccccgt 6540
cgtgtagata actacgatac gggagggctt accatctggc cccagtgctg caatgatacc 6600
gcgagaacca cgctcaccgg ctccagattt atcagcaata aaccagccag ccggaagggc 6660
cgagcgcaga agtggtcctg caactttatc cgcctccatc cagtctatta attgttgccg 6720
ggaagctaga gtaagtagtt cgccagttaa tagtttgcgc aacgttgttg ccattgctac 6780
aggcatcgtg gtgtcacgct cgtcgtttgg tatggcttca ttcagctccg gttcccaacg 6840
atcaaggcga gttacatgat cccccatgtt gtgcaaaaaa gcggttagct ccttcggtcc 6900
tccgatcgtt gtcagaagta agttggccgc agtgttatca ctcatggtta tggcagcact 6960
gcataattct cttactgtca tgccatccgt aagatgcttt tctgtgactg gtgagtactc 7020
aaccaagtca ttctgagaat agtgtatgcg gcgaccgagt tgctcttgcc cggcgtcaat 7080
acgggataat accgcgccac atagcagaac tttaaaagtg ctcatcattg gaaaacgttc 7140
ttcggggcga aaactctcaa ggatcttacc gctgttgaga tccagttcga tgtaacccac 7200
tcgtgcaccc aactgatctt cagcatcttt tactttcacc agcgtttctg ggtgagcaaa 7260
aacaggaagg caaaatgccg caaaaaaggg aataagggcg acacggaaat gttgaatact 7320
catactcttc ctttttcaat attattgaag catttatcag ggttattgtc tcatgagcgg 7380
atacatattt gaatgtattt agaaaaataa acaaataggg gttccgcgca catttccccg 7440
aaaagtgcca cctgacgtct aagaaaccat tattatcatg acattaacct ataaaaatag 7500
gcgtatcacg aggccctttc gggtcgcgcg tttcggtgat gacggtgaaa acctctgaca 7560
catgcagctc ccgttgacgg tcacagcttg tctgtaagcg gatgccggga gcagacaagc 7620
ccgtcagggc gcgtcagcgg gtgttggcgg gtgtcggggc tggcttaact atgcggcatc 7680
agagcagatt gtactgagag tgcaccataa aattgtaaac gttaatattt tgttaaaatt 7740
cgcgttaaat ttttgttaaa tcagctcatt ttttaaccaa taggccgaaa tcggcaaaat 7800
cccttataaa tcaaaagaat agcccgagat agggttgagt gttgttccag tttggaacaa 7860
gagtccacta ttaaagaacg tggactccaa cgtcaaaggg cgaaaaaccg tctatcaggg 7920
cgatggccca ctacgtgaac catcacccaa atcaagtttt ttggggtcga ggtgccgtaa 7980
agcactaaat cggaacccta aagggagccc ccgatttaga gcttgacggg gaaagccggc 8040

```
gaacgtggcg agaaaggaag ggaagaaagc gaaaggagcg ggcgctaggg cgctggcaag   8100

tgtagcggtc acgctgcgcg taaccaccac acccgccgcg cttaatgcgc cgctacaggg   8160

cgcgtactat ggttgctttg acgtatgcgg tgtgaaatac cgcacagatg cgtaaggaga   8220

aaataccgca tcaggcgcca ttcgccattc aggctgcgca actgttggga agggcgatcg   8280

gtgcgggcct cttcgctatt acgccagctg gcgaaagggg gatgtgctgc aaggcgatta   8340

agttgggtaa cgccagggtt ttcccagtca cgacgttgta aaacgacggc cagtgaattc   8400

catggtctca actttc                                                   8416
```

<210> SEQ ID NO 24
<211> LENGTH: 3762
<212> TYPE: DNA
<213> ORGANISM: Artificial Sequence
<220> FEATURE:
<223> OTHER INFORMATION: Synthetic vector insert VLP_CHI 520

<400> SEQUENCE: 24

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080

cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380

ataggtaggg agaggttcca ctctcgacca caacatggta aagagttacc ttgcagcacg   1440

tacgtgcaga gcaccgctgc cactgctgag gagatagagg tgcatatgcc cccagatact   1500

cctgaccgca cgctgatgac gcagcagtct ggcaacgtga agatcacagt taatggctcc   1560

ggaggatccg gcgggcagac ggtgcggtac aagtgcaact gcggtggctc aaacgaggga   1620
```

```
ctgacaacca cagacaaagt gatcaataac tgcaaaattg atcagtgcca tgctgcagtc   1680
actaatcaca agaattggca atacaactcc cctttagtcc cgcgcaacgc tgaactcggg   1740
gaccgtaaag gaaagatcca catcccattc ccattggcaa acgtgacttg cagagtgcca   1800
aaagcaagaa accctacagt aacttacgga aaaaaccaag tcaccatgct gctgtatcct   1860
gaccatccga cactcttgtc ttaccgtaac atgggacagg aaccaaatta ccacgaggag   1920
tgggtgacac acaagaagga ggttaccttg accgtgccta ctgagggtct ggaggtcact   1980
tggggcaaca acgaaccata caagtactgg ccgcagatgt ctacgaacgg tactgctcat   2040
ggtcacccac atgagataat cttgtactat tatgagctgt accccactat gactgtagtc   2100
attgtgtcgg tggcctcgtt cgtgcttctg tcgatggtgg gcacagcagt gggaatgtgt   2160
gtgtgcgcac ggcgcagatg cattacacca tatgaattaa caccaggagc cactgttccc   2220
ttcctgctca gcctgctatg ctgcgtcaga acgaccaagg cggccacata ttacgaggct   2280
gcggcatatc tatggaacga acagcagccc ctgttctggt tgcaggctct tatcccgctg   2340
gccgccttga tcgtcctgtg caactgtctg aaactcttgc catgctgctg taagaccctg   2400
gctttttttag ccgtaatgag catcggtgcc cacactgtga gcgcgtacga acacgtaaca   2460
gtgatcccga acacggtggg agtaccgtat aagactcttg tcaacagacc gggttacagc   2520
cccatggtgt tggagatgga gctacaatca gtcaccttgg aaccaacact gtcacttgac   2580
tacatcacgt gcgagtacaa aactgtcatc ccctccccgt acgtgaagtg ctgtggtaca   2640
gcagagtgca aggacaagag cctaccagac tacagctgca aggtctttac tggagtctac   2700
ccatttatgt ggggcggcgc ctactgcttt tgcgacgccg aaaatacgca attgagcgag   2760
gcacatgtag agaaatctga atcttgcaaa acagagtttg catcggccta cagagcccac   2820
accgcatcgg cgtcggcgaa gctccgcgtc ctttaccaag gaaacaacat taccgtagct   2880
gcctacgcta acggtgacca tgccgtcaca gtaaaggacg ccaagtttgt cgtgggccca   2940
atgtcctccg cctggacacc ttttgacaac aaaatcgtgg tgtacaaagg cgacgtctac   3000
aacatggact acccaccttt tggcgcagga agaccaggac aatttggtga cattcaaagt   3060
cgtacaccgg aaagtaaaga cgtttatgcc aacactcagt tggtactaca gaggccagca   3120
gcaggcacgg tacatgtacc atactctcag gcaccatctg gcttcaagta ttggctgaag   3180
gaacgaggag catcgctaca gcacacggca ccgttcggtt gccagattgc gacaaacccg   3240
gtaagagctg taaattgcgc tgtggggaac ataccaattt ccatcgacat accggatgcg   3300
gcctttacta gggttgtcga tgcaccctct gtaacggaca tgtcatgcga agtaccagcc   3360
tgcactcact cctccgactt tgggggcgtc gccatcatca aatacacagc tagcaagaaa   3420
ggtaaatgtg cagtacattc gatgaccaac gccgttacca ttcgagaagc cgacgtagaa   3480
gtagagggga actcccagct gcaaatatcc ttctcaacag ccctggcaag cgccgagttt   3540
cgcgtgcaag tgtgctccac acaagtacac tgcgcagccg catgccaccc tccaaaggac   3600
cacatagtca attacccagc atcacacacc acccttgggg tccaggatat atccacaacg   3660
gcaatgtctt gggtgcagaa gattacggga ggagtaggat taattgttgc tgttgctgcc   3720
ttaattttaa ttgtggtgct atgcgtgtcg tttagcaggc ac                       3762
```

<210> SEQ ID NO 25
<211> LENGTH: 1254
<212> TYPE: PRT
<213> ORGANISM: Artificial Sequence
<220> FEATURE:
<223> OTHER INFORMATION: Synthetic vector VLP_CHI 520

<400> SEQUENCE: 25

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Leu Pro Val Leu Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Ser Thr Leu Arg Met Leu Glu Asp Asn Val Met
290 295 300

Arg Pro Gly Tyr Tyr Gln Leu Leu Lys Ala Ser Leu Thr Cys Ser Pro
305 310 315 320

His Arg Gln Arg Arg Ser Thr Lys Asp Asn Phe Asn Val Tyr Lys Ala
325 330 335

Thr Arg Pro Tyr Leu Ala His Cys Pro Asp Cys Gly Glu Gly His Ser
340 345 350

Cys His Ser Pro Ile Ala Leu Glu Arg Ile Arg Asn Glu Ala Thr Asp
355 360 365

Gly Thr Leu Lys Ile Gln Val Ser Leu Gln Ile Gly Ile Lys Thr Asp
370 375 380

Asp Ser His Asp Trp Thr Lys Leu Arg Tyr Met Asp Ser His Thr Pro
385 390 395 400

Ala Asp Ala Glu Arg Ala Gly Leu Leu Val Arg Thr Ser Ala Pro Cys

-continued

```
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Ser Gly Gly Ser Gly Gly Gln Thr Val
        515                 520                 525

Arg Tyr Lys Cys Asn Cys Gly Gly Ser Asn Glu Gly Leu Thr Thr Thr
    530                 535                 540

Asp Lys Val Ile Asn Asn Cys Lys Ile Asp Gln Cys His Ala Ala Val
545                 550                 555                 560

Thr Asn His Lys Asn Trp Gln Tyr Asn Ser Pro Leu Val Pro Arg Asn
                565                 570                 575

Ala Glu Leu Gly Asp Arg Lys Gly Lys Ile His Ile Pro Phe Pro Leu
            580                 585                 590

Ala Asn Val Thr Cys Arg Val Pro Lys Ala Arg Asn Pro Thr Val Thr
        595                 600                 605

Tyr Gly Lys Asn Gln Val Thr Met Leu Leu Tyr Pro Asp His Pro Thr
    610                 615                 620

Leu Leu Ser Tyr Arg Asn Met Gly Gln Glu Pro Asn Tyr His Glu Glu
625                 630                 635                 640

Trp Val Thr His Lys Lys Glu Val Thr Leu Thr Val Pro Thr Glu Gly
                645                 650                 655

Leu Glu Val Thr Trp Gly Asn Asn Glu Pro Tyr Lys Tyr Trp Pro Gln
            660                 665                 670

Met Ser Thr Asn Gly Thr Ala His Gly His Pro His Glu Ile Ile Leu
        675                 680                 685

Tyr Tyr Tyr Glu Leu Tyr Pro Thr Met Thr Val Val Ile Val Ser Val
    690                 695                 700

Ala Ser Phe Val Leu Leu Ser Met Val Gly Thr Ala Val Gly Met Cys
705                 710                 715                 720

Val Cys Ala Arg Arg Arg Cys Ile Thr Pro Tyr Glu Leu Thr Pro Gly
                725                 730                 735

Ala Thr Val Pro Phe Leu Leu Ser Leu Leu Cys Cys Val Arg Thr Thr
            740                 745                 750

Lys Ala Ala Thr Tyr Tyr Glu Ala Ala Ala Tyr Leu Trp Asn Glu Gln
        755                 760                 765

Gln Pro Leu Phe Trp Leu Gln Ala Leu Ile Pro Leu Ala Ala Leu Ile
    770                 775                 780

Val Leu Cys Asn Cys Leu Lys Leu Leu Pro Cys Cys Cys Lys Thr Leu
785                 790                 795                 800

Ala Phe Leu Ala Val Met Ser Ile Gly Ala His Thr Val Ser Ala Tyr
                805                 810                 815

Glu His Val Thr Val Ile Pro Asn Thr Val Gly Val Pro Tyr Lys Thr
            820                 825                 830
```

```
Leu Val Asn Arg Pro Gly Tyr Ser Pro Met Val Leu Glu Met Glu Leu
        835                 840                 845

Gln Ser Val Thr Leu Glu Pro Thr Leu Ser Leu Asp Tyr Ile Thr Cys
    850                 855                 860

Glu Tyr Lys Thr Val Ile Pro Ser Pro Tyr Val Lys Cys Cys Gly Thr
865                 870                 875                 880

Ala Glu Cys Lys Asp Lys Ser Leu Pro Asp Tyr Ser Cys Lys Val Phe
                885                 890                 895

Thr Gly Val Tyr Pro Phe Met Trp Gly Gly Ala Tyr Cys Phe Cys Asp
            900                 905                 910

Ala Glu Asn Thr Gln Leu Ser Glu Ala His Val Glu Lys Ser Glu Ser
        915                 920                 925

Cys Lys Thr Glu Phe Ala Ser Ala Tyr Arg Ala His Thr Ala Ser Ala
    930                 935                 940

Ser Ala Lys Leu Arg Val Leu Tyr Gln Gly Asn Asn Ile Thr Val Ala
945                 950                 955                 960

Ala Tyr Ala Asn Gly Asp His Ala Val Thr Val Lys Asp Ala Lys Phe
                965                 970                 975

Val Val Gly Pro Met Ser Ser Ala Trp Thr Pro Phe Asp Asn Lys Ile
            980                 985                 990

Val Val Tyr Lys Gly Asp Val Tyr  Asn Met Asp Tyr Pro  Pro Phe Gly
        995                 1000                1005

Ala Gly  Arg Pro Gly Gln Phe  Gly Asp Ile Gln Ser  Arg Thr Pro
    1010                1015                1020

Glu Ser  Lys Asp Val Tyr Ala  Asn Thr Gln Leu Val  Leu Gln Arg
    1025                1030                1035

Pro Ala  Ala Gly Thr Val His  Val Pro Tyr Ser Gln  Ala Pro Ser
    1040                1045                1050

Gly Phe  Lys Tyr Trp Leu Lys  Glu Arg Gly Ala Ser  Leu Gln His
    1055                1060                1065

Thr Ala  Pro Phe Gly Cys Gln  Ile Ala Thr Asn Pro  Val Arg Ala
    1070                1075                1080

Val Asn  Cys Ala Val Gly Asn  Ile Pro Ile Ser Ile  Asp Ile Pro
    1085                1090                1095

Asp Ala  Ala Phe Thr Arg Val  Val Asp Ala Pro Ser  Val Thr Asp
    1100                1105                1110

Met Ser  Cys Glu Val Pro Ala  Cys Thr His Ser Ser  Asp Phe Gly
    1115                1120                1125

Gly Val  Ala Ile Ile Lys Tyr  Thr Ala Ser Lys Lys  Gly Lys Cys
    1130                1135                1140

Ala Val  His Ser Met Thr Asn  Ala Val Thr Ile Arg  Glu Ala Asp
    1145                1150                1155

Val Glu  Val Glu Gly Asn Ser  Gln Leu Gln Ile Ser  Phe Ser Thr
    1160                1165                1170

Ala Leu  Ala Ser Ala Glu Phe  Arg Val Gln Val Cys  Ser Thr Gln
    1175                1180                1185

Val His  Cys Ala Ala Ala Cys  His Pro Pro Lys Asp  His Ile Val
    1190                1195                1200

Asn Tyr  Pro Ala Ser His Thr  Thr Leu Gly Val Gln  Asp Ile Ser
    1205                1210                1215

Thr Thr  Ala Met Ser Trp Val  Gln Lys Ile Thr Gly  Gly Val Gly
    1220                1225                1230
```

```
Leu Ile  Val Ala Val Ala Ala  Leu Ile Leu Ile Val  Val Leu Cys
    1235                1240                1245

Val Ser  Phe Ser Arg His
    1250


<210> SEQ ID NO 26
<211> LENGTH: 8485
<212> TYPE: DNA
<213> ORGANISM: Artificial Sequence
<220> FEATURE:
<223> OTHER INFORMATION: Synthetic VLP74_11 (CHI VLP 532_NPNAx6)
      sequence

<400> SEQUENCE: 26

gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttccatggg tcttttctgc agtcaccgtc gtcgacacgt gtgatcagat atcgcggccg    900

ccaccatgga gttcatcccg acgcaaactt tctataacag aaggtaccaa ccccgaccct    960

gggccccacg ccctacaatt caagtaatta gacctagacc acgtccacag aggcaggctg   1020

ggcaactcgc ccagctgatc tccgcagtca acaaattgac catgcgcgcg gtacctcaac   1080

agaagcctcg cagaaatcgg aaaaacaaga agcaaaggca gaagaagcag gcgccgcaaa   1140

acgacccaaa gcaaaagaag caaccaccac aaaagaagcc ggctcaaaag aagaagaaac   1200

caggccgtag ggagagaatg tgcatgaaaa ttgaaaatga ttgcatcttc gaagtcaagc   1260

atgaaggcaa agtgatgggc tacgcatgcc tggtggggga taaagtaatg aaaccagcac   1320

atgtgaaggg aactatcgac aatgccgatc tggctaaact ggcctttaag cggtcgtcta   1380

aatacgatct tgaatgtgca cagataccgg tgcacatgaa gtctgatgcc tcgaagttta   1440

cccacgagaa acccgagggg tactataact ggcatcacgg agcagtgcag tattcaggag   1500

gccggttcac tatcccgacg ggtgcaggca agccgggaga cagcggcaga ccgatcttcg   1560

acaacaaagg acgggtggtg gccatcgtcc taggaggggc caacgaaggt gcccgcacgg   1620

ccctctccgt ggtgacgtgg aacaaagaca tcgtcacaaa aattacccct gagggagccg   1680

aagagtggag cctcgccctc ccggtcttgt gcctgttggc aaacactaca ttcccctgct   1740

ctcagccgcc ttgcacaccc tgctgctacg aaaaggaacc ggaaagcacc ttgcgcatgc   1800

ttgaggacaa cgtgatgaga cccggatact accagctact aaaagcatcg ctgacttgct   1860
```

-continued

```
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
ggcagacggt gcggtacaag tgcaactgcg gtggctccgg aggaaacccg aatgccaatc   2520
ccaacgcgaa ccccaatgct aacccaaatg ccaacccaaa cgccaacccc aacgctggtg   2580
gatccaacga gggactgaca accacagaca aagtgatcaa taactgcaaa attgatcagt   2640
gccatgctgc agtcactaat cacaagaatt ggcaatacaa ctccccttta gtcccgcgca   2700
acgctgaact cggggaccgt aaaggaaaga tccacatccc attcccattg gcaaacgtga   2760
cttgcagagt gccaaaagca agaaacccta cagtaactta cggaaaaaac caagtcacca   2820
tgctgctgta tcctgaccat ccgacactct tgtcttaccg taacatggga caggaaccaa   2880
attaccacga ggagtgggtg acacacaaga aggaggttac cttgaccgtg cctactgagg   2940
gtctggaggt cacttggggc aacaacgaac catacaagta ctggccgcag atgtctacga   3000
acggtactgc tcatggtcac ccacatgaga taatcttgta ctattatgag ctgtacccca   3060
ctatgactgt agtcattgtg tcggtggcct cgttcgtgct tctgtcgatg gtgggcacag   3120
cagtgggaat gtgtgtgtgc gcacggcgca gatgcattac accatatgaa ttaacaccag   3180
gagccactgt tcccttcctg ctcagcctgc tatgctgcgt cagaacgacc aaggcggcca   3240
catattacga ggctgcggca tatctatgga acgaacagca gcccctgttc tggttgcagg   3300
ctcttatccc gctggccgcc ttgatcgtcc tgtgcaactg tctgaaactc ttgccatgct   3360
gctgtaagac cctggctttt ttagccgtaa tgagcatcgg tgcccacact gtgagcgcgt   3420
acgaacacgt aacagtgatc ccgaacacgg tgggagtacc gtataagact cttgtcaaca   3480
gaccgggtta cagccccatg gtgttggaga tggagctaca atcagtcacc ttggaaccaa   3540
cactgtcact tgactacatc acgtgcgagt acaaaactgt catcccctcc ccgtacgtga   3600
agtgctgtgg tacagcagag tgcaaggaca agagcctacc agactacagc tgcaaggtct   3660
ttactggagt ctacccattt atgtggggcg gcgcctactg cttttgcgac gccgaaaata   3720
cgcaattgag cgaggcacat gtagagaaat ctgaatcttg caaaacagag tttgcatcgg   3780
cctacagagc ccacaccgca tcggcgtcgg cgaagctccg cgtcctttac caaggaaaca   3840
acattaccgt agctgcctac gctaacggtg accatgccgt cacagtaaag gacgccaagt   3900
ttgtcgtggg ccccaatgtcc tccgcctgga cacctttga caacaaaatc gtggtgtaca   3960
aaggcgacgt ctacaacatg gactacccac cttttggcgc aggaagacca ggacaatttg   4020
gtgacattca aagtcgtaca ccggaaagta aagacgttta tgccaacact cagttggtac   4080
tacagaggcc agcagcaggc acggtacatg taccatactc tcaggcacca tctggcttca   4140
agtattggct gaaggaacga ggagcatcgc tacagcacac ggcaccgttc ggttgccaga   4200
ttgcgacaaa cccggtaaga gctgtaaatt gcgctgtggg gaacatacca atttccatcg   4260
```

-continued acataccgga tgcggccttt actagggttg tcgatgcacc ctctgtaacg gacatgtcat 4320
gcgaagtacc agcctgcact cactcctccg actttggggg cgtcgccatc atcaaataca 4380
cagctagcaa gaaaggtaaa tgtgcagtac attcgatgac caacgccgtt accattcgag 4440
aagccgacgt agaagtagag gggaactccc agctgcaaat atccttctca acagccctgg 4500
caagcgccga gtttcgcgtg caagtgtgct ccacacaagt acactgcgca gccgcatgcc 4560
accctccaaa ggaccacata gtcaattacc cagcatcaca caccaccctt ggggtccagg 4620
atatatccac aacggcaatg tcttgggtgc agaagattac gggaggagta ggattaattg 4680
ttgctgttgc tgccttaatt ttaattgtgg tgctatgcgt gtcgtttagc aggcactaag 4740
gatctagatc tgctgtgcct tctagttgcc agccatctgt tgtttgcccc tcccccgtgc 4800
cttccttgac cctggaaggt gccactccca ctgtcctttc ctaataaaat gaggaaattg 4860
catcgcattg tctgagtagg tgtcattcta ttctgggggg tggggtgggg caggacagca 4920
agggggagga ttgggaagac aatagcaggc atgctgggga tgcggtgggc tctatgggta 4980
cccaggtgct gaagaattga cccggttcct cctgggccag aaagaagcag gcacatcccc 5040
ttctctgtga cacaccctgt ccacgcccct ggttcttagt tccagcccca ctcataggac 5100
actcatagct caggagggct ccgccttcaa tcccacccgc taaagtactt ggagcggtct 5160
ctccctccct catcagccca ccaaaccaaa cctagcctcc aagagtggga agaaattaaa 5220
gcaagatagg ctattaagtg cagagggaga gaaaatgcct ccaacatgtg aggaagtaat 5280
gagagaaatc atagaatttt aaggccatga tttaaggcca tcatggccta agcttgaaag 5340
gagataggat caaagcttgg cgtaatcatg gtcatagctg tttcctgtgt gaaattgtta 5400
tccgctcaca attccacaca acatacgagc cggaagcata aagtgtaaag cctggggtgc 5460
ctaatgagtg agctaactca cattaattgc gttgcgctca ctgcccgctt tccagtcggg 5520
aaacctgtcg tgccagctgc attaatgaat cggccaacgc gcggggagag gcggtttgcg 5580
tattgggcgc tcttccgctt cctcgctcac tgactcgctg cgctcggtcg ttcggctgcg 5640
gcgagcggta tcagctcact caaaggcggt aatacggtta tccacagaat caggggataa 5700
cgcaggaaag aacatgtgag caaaaggcca gcaaaaggcc aggaaccgta aaaaggccgc 5760
gttgctggcg tttttccata ggctccgccc ccctgacgag catcacaaaa atcgacgctc 5820
aagtcagagg tggcgaaacc cgacaggact ataaagatac caggcgtttc cccctggaag 5880
ctccctcgtg cgctctcctg ttccgaccct gccgcttacc ggatacctgt ccgcctttct 5940
cccttcggga agcgtggcgc tttctcatag ctcacgctgt aggtatctca gttcggtgta 6000
ggtcgttcgc tccaagctgg gctgtgtgca cgaacccccc gttcagcccg accgctgcgc 6060
cttatccggt aactatcgtc ttgagtccaa cccggtaaga cacgacttat cgccactggc 6120
agcagccact ggtaacagga ttagcagagc gaggtatgta ggcggtgcta cagagttctt 6180
gaagtggtgg cctaactacg gctacactag aagaacagta tttggtatct gcgctctgct 6240
gaagccagtt accttcggaa aaagagttgg tagctcttga tccggcaaac aaaccaccgc 6300
tggtagcggt ggtttttttg tttgcaagca gcagattacg cgcagaaaaa aaggatctca 6360
agaagatcct ttgatctttt ctacggggtc tgacgctcag tggaacgaaa actcacgtta 6420
agggattttg gtcatgagat tatcaaaaag gatcttcacc tagatccttt taaattaaaa 6480
atgaagtttt aaatcaatct aaagtatata tgagtaaact tggtctgaca gttaccaatg 6540
cttaatcagt gaggcaccta tctcagcgat ctgtctattt cgttcatcca tagttgcctg 6600
actccccgtc gtgtagataa ctacgatacg ggagggctta ccatctggcc ccagtgctgc 6660
aatgataccg cgagaaccac gctcaccggc tccagattta tcagcaataa accagccagc 6720
cggaagggcc gagcgcagaa gtggtcctgc aactttatcc gcctccatcc agtctattaa 6780
ttgttgccgg gaagctagag taagtagttc gccagttaat agtttgcgca acgttgttgc 6840
cattgctaca ggcatcgtgg tgtcacgctc gtcgtttggt atggcttcat tcagctccgg 6900
ttcccaacga tcaaggcgag ttacatgatc ccccatgttg tgcaaaaaag cggttagctc 6960
cttcggtcct ccgatcgttg tcagaagtaa gttggccgca gtgttatcac tcatggttat 7020
ggcagcactg cataattctc ttactgtcat gccatccgta agatgctttt ctgtgactgg 7080
tgagtactca accaagtcat tctgagaata gtgtatgcgg cgaccgagtt gctcttgccc 7140
ggcgtcaata cgggataata ccgcgccaca tagcagaact ttaaaagtgc tcatcattgg 7200
aaaacgttct tcggggcgaa aactctcaag gatcttaccg ctgttgagat ccagttcgat 7260
gtaacccact cgtgcaccca actgatcttc agcatctttt actttcacca gcgtttctgg 7320
gtgagcaaaa acaggaaggc aaaatgccgc aaaaaaggga ataagggcga cacggaaatg 7380
ttgaatactc atactcttcc tttttcaata ttattgaagc atttatcagg gttattgtct 7440
catgagcgga tacatatttg aatgtattta gaaaaataaa caaatagggg ttccgcgcac 7500
atttccccga aaagtgccac ctgacgtcta agaaaccatt attatcatga cattaaccta 7560
taaaaatagg cgtatcacga ggccctttcg ggtcgcgcgt ttcggtgatg acggtgaaaa 7620
cctctgacac atgcagctcc cgttgacggt cacagcttgt ctgtaagcgg atgccgggag 7680
cagacaagcc cgtcagggcg cgtcagcggg tgttggcggg tgtcggggct ggcttaacta 7740
tgcggcatca gagcagattg tactgagagt gcaccataaa attgtaaacg ttaatatttt 7800
gttaaaattc gcgttaaatt tttgttaaat cagctcattt tttaaccaat aggccgaaat 7860
cggcaaaatc ccttataaat caaaagaata gcccgagata gggttgagtg ttgttccagt 7920
ttggaacaag agtccactat taaagaacgt ggactccaac gtcaaagggc gaaaaaccgt 7980
ctatcagggc gatggcccac tacgtgaacc atcacccaaa tcaagttttt tggggtcgag 8040
gtgccgtaaa gcactaaatc ggaaccctaa agggagcccc cgatttagag cttgacgggg 8100
aaagccggcg aacgtggcga gaaaggaagg gaagaaagcg aaaggagcgg gcgctagggc 8160
gctggcaagt gtagcggtca cgctgcgcgt aaccaccaca cccgccgcgc ttaatgcgcc 8220
gctacagggc gcgtactatg gttgctttga cgtatgcggt gtgaaatacc gcacagatgc 8280
gtaaggagaa aataccgcat caggcgccat tcgccattca ggctgcgcaa ctgttgggaa 8340
gggcgatcgg tgcgggcctc ttcgctatta cgccagctgg cgaaaggggg atgtgctgca 8400
aggcgattaa gttgggtaac gccagggttt tcccagtcac gacgttgtaa aacgacggcc 8460
agtgaattcc atggtctcaa ctttc 8485

<210> SEQ ID NO 27
<211> LENGTH: 3831
<212> TYPE: DNA
<213> ORGANISM: Artificial Sequence
<220> FEATURE:
<223> OTHER INFORMATION: Synthetic VLP74_11 (CHI VLP 532 NPNAx6) CHIKV-NPNAx6 sequence

<400> SEQUENCE: 27
atggagttca tcccgacgca aactttctat aacagaaggt accaaccccg accctgggcc 60
ccacgcccta caattcaagt aattagacct agaccacgtc cacagaggca ggctgggcaa 120

-continued

```
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccggaggaa acccgaatgc caatcccaac   1620
gcgaacccca atgctaaccc aaatgccaac ccaaacgcca accccaacgc tggtggatcc   1680
aacgagggac tgacaaccac agacaaagtg atcaataact gcaaaattga tcagtgccat   1740
gctgcagtca ctaatcacaa gaattggcaa tacaactccc ctttagtccc gcgcaacgct   1800
gaactcgggg accgtaaagg aaagatccac atcccattcc cattggcaaa cgtgacttgc   1860
agagtgccaa aagcaagaaa ccctacagta acttacggaa aaaaccaagt caccatgctg   1920
ctgtatcctg accatccgac actcttgtct taccgtaaca tgggacagga accaaattac   1980
cacgaggagt gggtgacaca caagaaggag gttaccttga ccgtgcctac tgagggtctg   2040
gaggtcactt ggggcaacaa cgaaccatac aagtactggc cgcagatgtc tacgaacggt   2100
actgctcatg gtcacccaca tgagataatc ttgtactatt atgagctgta ccccactatg   2160
actgtagtca ttgtgtcggt ggcctcgttc gtgcttctgt cgatggtggg cacagcagtg   2220
ggaatgtgtg tgtgcgcacg gcgcagatgc attacaccat atgaattaac accaggagcc   2280
actgttccct tcctgctcag cctgctatgc tgcgtcagaa cgaccaaggc ggccacatat   2340
tacgaggctg cggcatatct atggaacgaa cagcagcccc tgttctggtt gcaggctctt   2400
atcccgctgg ccgccttgat cgtcctgtgc aactgtctga aactcttgcc atgctgctgt   2460
aagaccctgg ctttttttagc cgtaatgagc atcggtgccc acactgtgag cgcgtacgaa   2520
```

```
cacgtaacag tgatcccgaa cacggtggga gtaccgtata agactcttgt caacagaccg   2580

ggttacagcc ccatggtgtt ggagatggag ctacaatcag tcaccttgga accaacactg   2640

tcacttgact acatcacgtg cgagtacaaa actgtcatcc cctccccgta cgtgaagtgc   2700

tgtggtacag cagagtgcaa ggacaagagc ctaccagact acagctgcaa ggtctttact   2760

ggagtctacc catttatgtg gggcggcgcc tactgctttt gcgacgccga aaatacgcaa   2820

ttgagcgagg cacatgtaga gaaatctgaa tcttgcaaaa cagagtttgc atcggcctac   2880

agagcccaca ccgcatcggc gtcggcgaag ctccgcgtcc tttaccaagg aaacaacatt   2940

accgtagctg cctacgctaa cggtgaccat gccgtcacag taaaggacgc caagtttgtc   3000

gtgggcccaa tgtcctccgc ctggacacct tttgacaaca aaatcgtggt gtacaaaggc   3060

gacgtctaca acatggacta cccacctttt ggcgcaggaa gaccaggaca atttggtgac   3120

attcaaagtc gtacaccgga aagtaaagac gtttatgcca acactcagtt ggtactacag   3180

aggccagcag caggcacggt acatgtacca tactctcagg caccatctgg cttcaagtat   3240

tggctgaagg aacgaggagc atcgctacag cacacggcac cgttcggttg ccagattgcg   3300

acaaacccgg taagagctgt aaattgcgct gtggggaaca taccaatttc catcgacata   3360

ccggatgcgg cctttactag ggttgtcgat gcaccctctg taacggacat gtcatgcgaa   3420

gtaccagcct gcactcactc ctccgacttt gggggcgtcg ccatcatcaa atacacagct   3480

agcaagaaag gtaaatgtgc agtacattcg atgaccaacg ccgttaccat tcgagaagcc   3540

gacgtagaag tagaggggaa ctcccagctg caaatatcct tctcaacagc cctggcaagc   3600

gccgagtttc gcgtgcaagt gtgctccaca caagtacact gcgcagccgc atgccaccct   3660

ccaaaggacc acatagtcaa ttacccagca tcacacacca cccttggggt ccaggatata   3720

tccacaacgg caatgtcttg ggtgcagaag attacgggag gagtaggatt aattgttgct   3780

gttgctgcct taattttaat tgtggtgcta tgcgtgtcgt ttagcaggca c            3831
```

<210> SEQ ID NO 28
<211> LENGTH: 1277
<212> TYPE: PRT
<213> ORGANISM: Artificial Sequence
<220> FEATURE:
<223> OTHER INFORMATION: Synthetic VLP74_11 (CHI VLP 532 NPNAx6) sequence

<400> SEQUENCE: 28

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125
```

-continued

```
Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Asn Pro Asn Ala Asn Pro Asn Ala Asn Pro Asn
    530                 535                 540
```

-continued

```
Ala Asn Pro Asn Ala Asn Pro Asn Ala Asn Pro Asn Ala Gly Gly Ser
545                 550                 555                 560

Asn Glu Gly Leu Thr Thr Thr Asp Lys Val Ile Asn Asn Cys Lys Ile
                565                 570                 575

Asp Gln Cys His Ala Ala Val Thr Asn His Lys Asn Trp Gln Tyr Asn
            580                 585                 590

Ser Pro Leu Val Pro Arg Asn Ala Glu Leu Gly Asp Arg Lys Gly Lys
        595                 600                 605

Ile His Ile Pro Phe Pro Leu Ala Asn Val Thr Cys Arg Val Pro Lys
    610                 615                 620

Ala Arg Asn Pro Thr Val Thr Tyr Gly Lys Asn Gln Val Thr Met Leu
625                 630                 635                 640

Leu Tyr Pro Asp His Pro Thr Leu Leu Ser Tyr Arg Asn Met Gly Gln
                645                 650                 655

Glu Pro Asn Tyr His Glu Glu Trp Val Thr His Lys Lys Glu Val Thr
            660                 665                 670

Leu Thr Val Pro Thr Glu Gly Leu Glu Val Thr Trp Gly Asn Asn Glu
        675                 680                 685

Pro Tyr Lys Tyr Trp Pro Gln Met Ser Thr Asn Gly Thr Ala His Gly
    690                 695                 700

His Pro His Glu Ile Ile Leu Tyr Tyr Tyr Glu Leu Tyr Pro Thr Met
705                 710                 715                 720

Thr Val Val Ile Val Ser Val Ala Ser Phe Val Leu Leu Ser Met Val
                725                 730                 735

Gly Thr Ala Val Gly Met Cys Val Cys Ala Arg Arg Arg Cys Ile Thr
            740                 745                 750

Pro Tyr Glu Leu Thr Pro Gly Ala Thr Val Pro Phe Leu Leu Ser Leu
        755                 760                 765

Leu Cys Cys Val Arg Thr Thr Lys Ala Ala Thr Tyr Tyr Glu Ala Ala
    770                 775                 780

Ala Tyr Leu Trp Asn Glu Gln Gln Pro Leu Phe Trp Leu Gln Ala Leu
785                 790                 795                 800

Ile Pro Leu Ala Ala Leu Ile Val Leu Cys Asn Cys Leu Lys Leu Leu
                805                 810                 815

Pro Cys Cys Cys Lys Thr Leu Ala Phe Leu Ala Val Met Ser Ile Gly
            820                 825                 830

Ala His Thr Val Ser Ala Tyr Glu His Val Thr Val Ile Pro Asn Thr
        835                 840                 845

Val Gly Val Pro Tyr Lys Thr Leu Val Asn Arg Pro Gly Tyr Ser Pro
    850                 855                 860

Met Val Leu Glu Met Glu Leu Gln Ser Val Thr Leu Glu Pro Thr Leu
865                 870                 875                 880

Ser Leu Asp Tyr Ile Thr Cys Glu Tyr Lys Thr Val Ile Pro Ser Pro
                885                 890                 895

Tyr Val Lys Cys Cys Gly Thr Ala Glu Cys Lys Asp Lys Ser Leu Pro
            900                 905                 910

Asp Tyr Ser Cys Lys Val Phe Thr Gly Val Tyr Pro Phe Met Trp Gly
        915                 920                 925

Gly Ala Tyr Cys Phe Cys Asp Ala Glu Asn Thr Gln Leu Ser Glu Ala
    930                 935                 940

His Val Glu Lys Ser Glu Ser Cys Lys Thr Glu Phe Ala Ser Ala Tyr
945                 950                 955                 960

Arg Ala His Thr Ala Ser Ala Ser Ala Lys Leu Arg Val Leu Tyr Gln
```

-continued

```
            965                 970                 975

Gly Asn Asn Ile Thr Val Ala Ala Tyr Ala Asn Gly Asp His Ala Val
        980                 985                 990

Thr Val Lys Asp Ala Lys Phe Val  Val Gly Pro Met Ser  Ser Ala Trp
    995                 1000                1005

Thr Pro  Phe Asp Asn Lys Ile  Val Val Tyr Lys Gly  Asp Val Tyr
    1010                 1015                1020

Asn Met  Asp Tyr Pro Pro Phe  Gly Ala Gly Arg Pro  Gly Gln Phe
    1025                 1030                1035

Gly Asp  Ile Gln Ser Arg Thr  Pro Glu Ser Lys Asp  Val Tyr Ala
    1040                 1045                1050

Asn Thr  Gln Leu Val Leu Gln  Arg Pro Ala Ala Gly  Thr Val His
    1055                 1060                1065

Val Pro  Tyr Ser Gln Ala Pro  Ser Gly Phe Lys Tyr  Trp Leu Lys
    1070                 1075                1080

Glu Arg  Gly Ala Ser Leu Gln  His Thr Ala Pro Phe  Gly Cys Gln
    1085                 1090                1095

Ile Ala  Thr Asn Pro Val Arg  Ala Val Asn Cys Ala  Val Gly Asn
    1100                 1105                1110

Ile Pro  Ile Ser Ile Asp Ile  Pro Asp Ala Ala Phe  Thr Arg Val
    1115                 1120                1125

Val Asp  Ala Pro Ser Val Thr  Asp Met Ser Cys Glu  Val Pro Ala
    1130                 1135                1140

Cys Thr  His Ser Ser Asp Phe  Gly Gly Val Ala Ile  Ile Lys Tyr
    1145                 1150                1155

Thr Ala  Ser Lys Lys Gly Lys  Cys Ala Val His Ser  Met Thr Asn
    1160                 1165                1170

Ala Val  Thr Ile Arg Glu Ala  Asp Val Glu Val Glu  Gly Asn Ser
    1175                 1180                1185

Gln Leu  Gln Ile Ser Phe Ser  Thr Ala Leu Ala Ser  Ala Glu Phe
    1190                 1195                1200

Arg Val  Gln Val Cys Ser Thr  Gln Val His Cys Ala  Ala Ala Cys
    1205                 1210                1215

His Pro  Pro Lys Asp His Ile  Val Asn Tyr Pro Ala  Ser His Thr
    1220                 1225                1230

Thr Leu  Gly Val Gln Asp Ile  Ser Thr Thr Ala Met  Ser Trp Val
    1235                 1240                1245

Gln Lys  Ile Thr Gly Gly Val  Gly Leu Ile Val Ala  Val Ala Ala
    1250                 1255                1260

Leu Ile  Leu Ile Val Val Leu  Cys Val Ser Phe Ser  Arg His
    1265                 1270                1275
```

<210> SEQ ID NO 29
<211> LENGTH: 8713
<212> TYPE: DNA
<213> ORGANISM: Artificial Sequence
<220> FEATURE:
<223> OTHER INFORMATION: Synthetic VLP78_11 (CHI VLP 532 NPNAx25) sequence

<400> SEQUENCE: 29

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180
```

-continued

```
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
ggcagacggt gcggtacaag tgcaactgcg gtggctccgg aggaaacccg aatgccaatc   2520
ccaacgcgaa ccccaacgct aaccccaacg ccaatccgaa tgcaaacccg aacgttgacc   2580
```

caaacgccaa cccgaatgcc aatcccaacg cgaaccccaa tgctaaccca aatgccaacc 2640
caaacgccaa ccccaacgct aatccaaacg ccaaccctaa cgccaatccc aacgcgaatc 2700
ctaacgctaa tcccaacgca aatcccaatg ctaatccgaa cgcgaaccct aatgcaaacc 2760
ccaacgccaa cccgaacgct aacccgaacg ctaatcccaa cgccggtgga tccaacgagg 2820
gactgacaac cacagacaaa gtgatcaata actgcaaaat tgatcagtgc catgctgcag 2880
tcactaatca caagaattgg caatacaact cccctttagt cccgcgcaac gctgaactcg 2940
gggaccgtaa aggaaagatc cacatcccat tcccattggc aaacgtgact tgcagagtgc 3000
caaaagcaag aaaccctaca gtaacttacg gaaaaaacca agtcaccatg ctgctgtatc 3060
ctgaccatcc gacactcttg tcttaccgta acatgggaca ggaaccaaat taccacgagg 3120
agtgggtgac acacaagaag gaggttacct tgaccgtgcc tactgagggt ctggaggtca 3180
cttggggcaa caacgaacca tacaagtact ggccgcagat gtctacgaac ggtactgctc 3240
atggtcaccc acatgagata atcttgtact attatgagct gtaccccact atgactgtag 3300
tcattgtgtc ggtggcctcg ttcgtgcttc tgtcgatggt gggcacagca gtgggaatgt 3360
gtgtgtgcgc acggcgcaga tgcattacac catatgaatt aacaccagga gccactgttc 3420
ccttcctgct cagcctgcta tgctgcgtca gaacgaccaa ggcggccaca tattacgagg 3480
ctgcggcata tctatggaac gaacagcagc ccctgttctg gttgcaggct cttatcccgc 3540
tggccgcctt gatcgtcctg tgcaactgtc tgaaactctt gccatgctgc tgtaagaccc 3600
tggctttttt agccgtaatg agcatcggtg cccacactgt gagcgcgtac gaacacgtaa 3660
cagtgatccc gaacacggtg ggagtaccgt ataagactct tgtcaacaga ccgggttaca 3720
gccccatggt gttggagatg gagctacaat cagtcacctt ggaaccaaca ctgtcacttg 3780
actacatcac gtgcgagtac aaaactgtca tcccctcccc gtacgtgaag tgctgtggta 3840
cagcagagtg caaggacaag agcctaccag actacagctg caaggtcttt actggagtct 3900
acccatttat gtggggcggc gcctactgct tttgcgacgc cgaaaatacg caattgagcg 3960
aggcacatgt agagaaatct gaatcttgca aaacagagtt tgcatcggcc tacagagccc 4020
acaccgcatc ggcgtcggcg aagctccgcg tcctttacca aggaaacaac attaccgtag 4080
ctgcctacgc taacggtgac catgccgtca cagtaaagga cgccaagttt gtcgtgggcc 4140
caatgtcctc cgcctggaca ccttttgaca acaaaatcgt ggtgtacaaa ggcgacgtct 4200
acaacatgga ctacccacct tttggcgcag gaagaccagg acaatttggt gacattcaaa 4260
gtcgtacacc ggaaagtaaa gacgtttatg ccaacactca gttggtacta cagaggccag 4320
cagcaggcac ggtacatgta ccatactctc aggcaccatc tggcttcaag tattggctga 4380
aggaacgagg agcatcgcta cagcacacgg caccgttcgg ttgccagatt gcgacaaacc 4440
cggtaagagc tgtaaattgc gctgtgggga acataccaat ttccatcgac ataccggatg 4500
cggcctttac tagggttgtc gatgcaccct ctgtaacgga catgtcatgc gaagtaccag 4560
cctgcactca ctcctccgac tttgggggcg tcgccatcat caaatacaca gctagcaaga 4620
aaggtaaatg tgcagtacat tcgatgacca acgccgttac cattcgagaa gccgacgtag 4680
aagtagaggg gaactcccag ctgcaaatat ccttctcaac agccctggca agcgccgagt 4740
ttcgcgtgca agtgtgctcc acacaagtac actgcgcagc cgcatgccac cctccaaagg 4800
accacatagt caattaccca gcatcacaca ccacccttgg ggtccaggat atatccacaa 4860
cggcaatgtc ttgggtgcag aagattacgg gaggagtagg attaattgtt gctgttgctg 4920

-continued

```
ccttaatttt aattgtggtg ctatgcgtgt cgtttagcag gcactaagga tctagatctg   4980
ctgtgccttc tagttgccag ccatctgttg tttgcccctc ccccgtgcct tccttgaccc   5040
tggaaggtgc cactcccact gtcctttcct aataaaatga ggaaattgca tcgcattgtc   5100
tgagtaggtg tcattctatt ctggggggtg gggtggggca ggacagcaag ggggaggatt   5160
gggaagacaa tagcaggcat gctggggatg cggtgggctc tatgggtacc caggtgctga   5220
agaattgacc cggttcctcc tgggccagaa agaagcaggc acatcccctt ctctgtgaca   5280
caccctgtcc acgcccctgg ttcttagttc cagccccact cataggacac tcatagctca   5340
ggagggctcc gccttcaatc ccacccgcta aagtacttgg agcggtctct ccctccctca   5400
tcagcccacc aaaccaaacc tagcctccaa gagtgggaag aaattaaagc aagataggct   5460
attaagtgca gagggagaga aaatgcctcc aacatgtgag gaagtaatga gagaaatcat   5520
agaattttaa ggccatgatt taaggccatc atggcctaag cttgaaagga gataggatca   5580
aagcttggcg taatcatggt catagctgtt tcctgtgtga aattgttatc cgctcacaat   5640
tccacacaac atacgagccg gaagcataaa gtgtaaagcc tggggtgcct aatgagtgag   5700
ctaactcaca ttaattgcgt tgcgctcact gcccgctttc cagtcgggaa acctgtcgtg   5760
ccagctgcat taatgaatcg gccaacgcgc ggggagaggc ggtttgcgta ttgggcgctc   5820
ttccgcttcc tcgctcactg actcgctgcg ctcggtcgtt cggctgcggc gagcggtatc   5880
agctcactca aaggcggtaa tacggttatc cacagaatca ggggataacg caggaaagaa   5940
catgtgagca aaaggccagc aaaaggccag gaaccgtaaa aaggccgcgt tgctggcgtt   6000
tttccatagg ctccgccccc ctgacgagca tcacaaaaat cgacgctcaa gtcagaggtg   6060
gcgaaacccg acaggactat aaagatacca ggcgtttccc cctggaagct ccctcgtgcg   6120
ctctcctgtt ccgaccctgc cgcttaccgg atacctgtcc gcctttctcc cttcgggaag   6180
cgtggcgctt tctcatagct cacgctgtag gtatctcagt tcggtgtagg tcgttcgctc   6240
caagctgggc tgtgtgcacg aaccccccgt tcagcccgac cgctgcgcct tatccggtaa   6300
ctatcgtctt gagtccaacc cggtaagaca cgacttatcg ccactggcag cagccactgg   6360
taacaggatt agcagagcga ggtatgtagg cggtgctaca gagttcttga agtggtggcc   6420
taactacggc tacactagaa gaacagtatt tggtatctgc gctctgctga agccagttac   6480
cttcggaaaa agagttggta gctcttgatc cggcaaacaa accaccgctg gtagcggtgg   6540
tttttttgtt tgcaagcagc agattacgcg cagaaaaaaa ggatctcaag aagatccttt   6600
gatcttttct acggggtctg acgctcagtg gaacgaaaac tcacgttaag ggattttggt   6660
catgagatta tcaaaaagga tcttcaccta gatcctttta aattaaaaat gaagttttaa   6720
atcaatctaa agtatatatg agtaaacttg gtctgacagt taccaatgct taatcagtga   6780
ggcacctatc tcagcgatct gtctatttcg ttcatccata gttgcctgac tccccgtcgt   6840
gtagataact acgatacggg agggcttacc atctggcccc agtgctgcaa tgataccgcg   6900
agaaccacgc tcaccggctc cagatttatc agcaataaac cagccagccg gaagggccga   6960
gcgcagaagt ggtcctgcaa ctttatccgc ctccatccag tctattaatt gttgccggga   7020
agctagagta agtagttcgc cagttaatag tttgcgcaac gttgttgcca ttgctacagg   7080
catcgtggtg tcacgctcgt cgtttggtat ggcttcattc agctccggtt cccaacgatc   7140
aaggcgagtt acatgatccc ccatgttgtg caaaaaagcg gttagctcct tcggtcctcc   7200
gatcgttgtc agaagtaagt tggccgcagt gttatcactc atggttatgg cagcactgca   7260
taattctctt actgtcatgc catccgtaag atgcttttct gtgactggtg agtactcaac   7320
```

caagtcattc tgagaatagt gtatgcggcg accgagttgc tcttgcccgg cgtcaatacg 7380
ggataatacc gcgccacata gcagaacttt aaaagtgctc atcattggaa aacgttcttc 7440
ggggcgaaaa ctctcaagga tcttaccgct gttgagatcc agttcgatgt aacccactcg 7500
tgcacccaac tgatcttcag catcttttac tttcaccagc gtttctgggt gagcaaaaac 7560
aggaaggcaa aatgccgcaa aaaagggaat aagggcgaca cggaaatgtt gaatactcat 7620
actcttcctt tttcaatatt attgaagcat ttatcagggt tattgtctca tgagcggata 7680
catatttgaa tgtatttaga aaaataaaca aataggggtt ccgcgcacat ttccccgaaa 7740
agtgccacct gacgtctaag aaaccattat tatcatgaca ttaacctata aaaataggcg 7800
tatcacgagg ccctttcggg tcgcgcgttt cggtgatgac ggtgaaaacc tctgacacat 7860
gcagctcccg ttgacggtca cagcttgtct gtaagcggat gccgggagca gacaagcccg 7920
tcagggcgcg tcagcgggtg ttggcgggtg tcggggctgg cttaactatg cggcatcaga 7980
gcagattgta ctgagagtgc accataaaat tgtaaacgtt aatattttgt taaaattcgc 8040
gttaaatttt tgttaaatca gctcattttt taaccaatag gccgaaatcg gcaaaatccc 8100
ttataaatca aaagaatagc ccgagatagg gttgagtgtt gttccagttt ggaacaagag 8160
tccactatta aagaacgtgg actccaacgt caaagggcga aaaaccgtct atcagggcga 8220
tggcccacta cgtgaaccat cacccaaatc aagttttttg gggtcgaggt gccgtaaagc 8280
actaaatcgg aaccctaaag ggagcccccg atttagagct tgacggggaa agccggcgaa 8340
cgtggcgaga aaggaaggga agaaagcgaa aggagcgggc gctagggcgc tggcaagtgt 8400
agcggtcacg ctgcgcgtaa ccaccacacc cgccgcgctt aatgcgccgc tacagggcgc 8460
gtactatggt tgctttgacg tatgcggtgt gaaataccgc acagatgcgt aaggagaaaa 8520
taccgcatca ggcgccattc gccattcagg ctgcgcaact gttgggaagg gcgatcggtg 8580
cgggcctctt cgctattacg ccagctggcg aaagggggat gtgctgcaag gcgattaagt 8640
tgggtaacgc cagggttttc ccagtcacga cgttgtaaaa cgacggccag tgaattccat 8700
ggtctcaact ttc 8713

<210> SEQ ID NO 30
<211> LENGTH: 4059
<212> TYPE: DNA
<213> ORGANISM: Artificial Sequence
<220> FEATURE:
<223> OTHER INFORMATION: Synthetic VLP78_11 (CHI VLP 532 NPNAx25)
CHIKV-NPNAx25 sequence

<400> SEQUENCE: 30
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600

-continued

```
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccggaggaa acccgaatgc caatcccaac   1620
gcgaacccca acgctaaccc caacgccaat ccgaatgcaa acccgaacgt tgacccaaac   1680
gccaacccga atgccaatcc caacgcgaac cccaatgcta acccaaatgc caacccaaac   1740
gccaacccca acgctaatcc aaacgccaac cctaacgcca atcccaacgc gaatcctaac   1800
gctaatccca acgcaaatcc caatgctaat ccgaacgcga accctaatgc aaaccccaac   1860
gccaacccga acgctaaccc gaacgctaat cccaacgccg gtggatccaa cgagggactg   1920
acaaccacag acaaagtgat caataactgc aaaattgatc agtgccatgc tgcagtcact   1980
aatcacaaga attggcaata caactcccct ttagtcccgc gcaacgctga actcggggac   2040
cgtaaaggaa agatccacat cccattccca ttggcaaacg tgacttgcag agtgccaaaa   2100
gcaagaaacc ctacagtaac ttacggaaaa aaccaagtca ccatgctgct gtatcctgac   2160
catccgacac tcttgtctta ccgtaacatg ggacaggaac caaattacca cgaggagtgg   2220
gtgacacaca agaaggaggt taccttgacc gtgcctactg agggtctgga ggtcacttgg   2280
ggcaacaacg aaccatacaa gtactggccg cagatgtcta cgaacggtac tgctcatggt   2340
cacccacatg agataatctt gtactattat gagctgtacc ccactatgac tgtagtcatt   2400
gtgtcggtgg cctcgttcgt gcttctgtcg atggtgggca cagcagtggg aatgtgtgtg   2460
tgcgcacggc gcagatgcat tacaccatat gaattaacac caggagccac tgttcccttc   2520
ctgctcagcc tgctatgctg cgtcagaacg accaaggcgg ccacatatta cgaggctgcg   2580
gcatatctat ggaacgaaca gcagcccctg ttctggttgc aggctcttat cccgctggcc   2640
gccttgatcg tcctgtgcaa ctgtctgaaa ctcttgccat gctgctgtaa gaccctggct   2700
tttttagccg taatgagcat cggtgcccac actgtgagcg cgtacgaaca cgtaacagtg   2760
atcccgaaca cggtgggagt accgtataag actcttgtca acagaccggg ttacagcccc   2820
atggtgttgg agatggagct acaatcagtc accttggaac caacactgtc acttgactac   2880
atcacgtgcg agtacaaaac tgtcatcccc tccccgtacg tgaagtgctg tggtacagca   2940
```

-continued gagtgcaagg acaagagcct accagactac agctgcaagg tctttactgg agtctaccca 3000
tttatgtggg gcggcgccta ctgcttttgc gacgccgaaa atacgcaatt gagcgaggca 3060
catgtagaga aatctgaatc ttgcaaaaca gagtttgcat cggcctacag agcccacacc 3120
gcatcggcgt cggcgaagct ccgcgtcctt taccaaggaa acaacattac cgtagctgcc 3180
tacgctaacg gtgaccatgc cgtcacagta aaggacgcca agtttgtcgt gggcccaatg 3240
tcctccgcct ggacaccttt tgacaacaaa atcgtggtgt acaaaggcga cgtctacaac 3300
atggactacc caccttttgg cgcaggaaga ccaggacaat ttggtgacat tcaaagtcgt 3360
acaccggaaa gtaaagacgt ttatgccaac actcagttgg tactacagag gccagcagca 3420
ggcacggtac atgtaccata ctctcaggca ccatctggct tcaagtattg gctgaaggaa 3480
cgaggagcat cgctacagca cacggcaccg ttcggttgcc agattgcgac aaacccggta 3540
agagctgtaa attgcgctgt ggggaacata ccaatttcca tcgacatacc ggatgcggcc 3600
tttactaggg ttgtcgatgc accctctgta acggacatgt catgcgaagt accagcctgc 3660
actcactcct ccgactttgg gggcgtcgcc atcatcaaat acacagctag caagaaaggt 3720
aaatgtgcag tacattcgat gaccaacgcc gttaccattc gagaagccga cgtagaagta 3780
gaggggaact cccagctgca aatatccttc tcaacagccc tggcaagcgc cgagtttcgc 3840
gtgcaagtgt gctccacaca agtacactgc gcagccgcat gccaccctcc aaaggaccac 3900
atagtcaatt acccagcatc acacaccacc cttggggtcc aggatatatc cacaacggca 3960
atgtcttggg tgcagaagat tacgggagga gtaggattaa ttgttgctgt tgctgcctta 4020
attttaattg tggtgctatg cgtgtcgttt agcaggcac 4059

<210> SEQ ID NO 31
<211> LENGTH: 1353
<212> TYPE: PRT
<213> ORGANISM: Artificial Sequence
<220> FEATURE:
<223> OTHER INFORMATION: Synthetic VLP78_11 (CHI VLP 532 NPNAx25) sequence

<400> SEQUENCE: 31

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

-continued

```
Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Asn Pro Asn Ala Asn Pro Asn Ala Asn Pro Asn
    530                 535                 540

Ala Asn Pro Asn Ala Asn Pro Asn Ala Asn Pro Asn Val Asp Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Ala Asn Pro Asn
```

-continued

```
            580                 585                 590

Ala Asn Pro Asn Ala Asn Pro Asn Ala Asn Pro Asn Ala Asn Pro Asn
        595                 600                 605

Ala Asn Pro Asn Ala Asn Pro Asn Ala Asn Pro Asn Ala Asn Pro Asn
    610                 615                 620

Ala Asn Pro Asn Ala Asn Pro Asn Ala Gly Gly Ser Asn Glu Gly Leu
625                 630                 635                 640

Thr Thr Thr Asp Lys Val Ile Asn Asn Cys Lys Ile Asp Gln Cys His
                645                 650                 655

Ala Ala Val Thr Asn His Lys Asn Trp Gln Tyr Asn Ser Pro Leu Val
            660                 665                 670

Pro Arg Asn Ala Glu Leu Gly Asp Arg Lys Gly Lys Ile His Ile Pro
        675                 680                 685

Phe Pro Leu Ala Asn Val Thr Cys Arg Val Pro Lys Ala Arg Asn Pro
    690                 695                 700

Thr Val Thr Tyr Gly Lys Asn Gln Val Thr Met Leu Leu Tyr Pro Asp
705                 710                 715                 720

His Pro Thr Leu Leu Ser Tyr Arg Asn Met Gly Gln Glu Pro Asn Tyr
                725                 730                 735

His Glu Glu Trp Val Thr His Lys Lys Glu Val Thr Leu Thr Val Pro
            740                 745                 750

Thr Glu Gly Leu Glu Val Thr Trp Gly Asn Asn Glu Pro Tyr Lys Tyr
        755                 760                 765

Trp Pro Gln Met Ser Thr Asn Gly Thr Ala His Gly His Pro His Glu
    770                 775                 780

Ile Ile Leu Tyr Tyr Tyr Glu Leu Tyr Pro Thr Met Thr Val Val Ile
785                 790                 795                 800

Val Ser Val Ala Ser Phe Val Leu Leu Ser Met Val Gly Thr Ala Val
                805                 810                 815

Gly Met Cys Val Cys Ala Arg Arg Arg Cys Ile Thr Pro Tyr Glu Leu
            820                 825                 830

Thr Pro Gly Ala Thr Val Pro Phe Leu Leu Ser Leu Leu Cys Cys Val
        835                 840                 845

Arg Thr Thr Lys Ala Ala Thr Tyr Tyr Glu Ala Ala Ala Tyr Leu Trp
    850                 855                 860

Asn Glu Gln Gln Pro Leu Phe Trp Leu Gln Ala Leu Ile Pro Leu Ala
865                 870                 875                 880

Ala Leu Ile Val Leu Cys Asn Cys Leu Lys Leu Leu Pro Cys Cys Cys
                885                 890                 895

Lys Thr Leu Ala Phe Leu Ala Val Met Ser Ile Gly Ala His Thr Val
            900                 905                 910

Ser Ala Tyr Glu His Val Thr Val Ile Pro Asn Thr Val Gly Val Pro
        915                 920                 925

Tyr Lys Thr Leu Val Asn Arg Pro Gly Tyr Ser Pro Met Val Leu Glu
    930                 935                 940

Met Glu Leu Gln Ser Val Thr Leu Glu Pro Thr Leu Ser Leu Asp Tyr
945                 950                 955                 960

Ile Thr Cys Glu Tyr Lys Thr Val Ile Pro Ser Pro Tyr Val Lys Cys
                965                 970                 975

Cys Gly Thr Ala Glu Cys Lys Asp Lys Ser Leu Pro Asp Tyr Ser Cys
            980                 985                 990

Lys Val Phe Thr Gly Val Tyr Pro  Phe Met Trp Gly Gly  Ala Tyr Cys
        995                 1000                1005
```

Phe Cys Asp Ala Glu Asn Thr Gln Leu Ser Glu Ala His Val Glu
1010 1015 1020

Lys Ser Glu Ser Cys Lys Thr Glu Phe Ala Ser Ala Tyr Arg Ala
1025 1030 1035

His Thr Ala Ser Ala Ser Ala Lys Leu Arg Val Leu Tyr Gln Gly
1040 1045 1050

Asn Asn Ile Thr Val Ala Ala Tyr Ala Asn Gly Asp His Ala Val
1055 1060 1065

Thr Val Lys Asp Ala Lys Phe Val Val Gly Pro Met Ser Ser Ala
1070 1075 1080

Trp Thr Pro Phe Asp Asn Lys Ile Val Val Tyr Lys Gly Asp Val
1085 1090 1095

Tyr Asn Met Asp Tyr Pro Pro Phe Gly Ala Gly Arg Pro Gly Gln
1100 1105 1110

Phe Gly Asp Ile Gln Ser Arg Thr Pro Glu Ser Lys Asp Val Tyr
1115 1120 1125

Ala Asn Thr Gln Leu Val Leu Gln Arg Pro Ala Ala Gly Thr Val
1130 1135 1140

His Val Pro Tyr Ser Gln Ala Pro Ser Gly Phe Lys Tyr Trp Leu
1145 1150 1155

Lys Glu Arg Gly Ala Ser Leu Gln His Thr Ala Pro Phe Gly Cys
1160 1165 1170

Gln Ile Ala Thr Asn Pro Val Arg Ala Val Asn Cys Ala Val Gly
1175 1180 1185

Asn Ile Pro Ile Ser Ile Asp Ile Pro Asp Ala Ala Phe Thr Arg
1190 1195 1200

Val Val Asp Ala Pro Ser Val Thr Asp Met Ser Cys Glu Val Pro
1205 1210 1215

Ala Cys Thr His Ser Ser Asp Phe Gly Gly Val Ala Ile Ile Lys
1220 1225 1230

Tyr Thr Ala Ser Lys Lys Gly Lys Cys Ala Val His Ser Met Thr
1235 1240 1245

Asn Ala Val Thr Ile Arg Glu Ala Asp Val Glu Val Glu Gly Asn
1250 1255 1260

Ser Gln Leu Gln Ile Ser Phe Ser Thr Ala Leu Ala Ser Ala Glu
1265 1270 1275

Phe Arg Val Gln Val Cys Ser Thr Gln Val His Cys Ala Ala Ala
1280 1285 1290

Cys His Pro Pro Lys Asp His Ile Val Asn Tyr Pro Ala Ser His
1295 1300 1305

Thr Thr Leu Gly Val Gln Asp Ile Ser Thr Thr Ala Met Ser Trp
1310 1315 1320

Val Gln Lys Ile Thr Gly Gly Val Gly Leu Ile Val Ala Val Ala
1325 1330 1335

Ala Leu Ile Leu Ile Val Val Leu Cys Val Ser Phe Ser Arg His
1340 1345 1350

<210> SEQ ID NO 32
<211> LENGTH: 8737
<212> TYPE: DNA
<213> ORGANISM: Artificial Sequence
<220> FEATURE:
<223> OTHER INFORMATION: Synthetic VLP78_21 (VEEV VLP 519 NPNAx25)
sequence

<400> SEQUENCE: 32
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgtt cccgttccag ccaatgtatc cgatgcagcc aatgccctat cgcaacccgt 960
tcgcggcccc gcgcaggccc tggttcccca gaaccgaccc ttttctggcg atgcaggtgc 1020
aggaattaac ccgctcgatg gctaacctga cgttcaagca acgccgggac gcgccacctg 1080
aggggccatc cgctaataaa ccgaagaagg aggcctcgca aaaacagaaa gggggaggcc 1140
aagggaagaa gaagaagaac caagggaaga agaaggctaa gacagggccg cctaatccga 1200
aggcacagaa tggaaacaag aagaagacca acaagaaacc aggcaagaga cagcgcatgg 1260
tcatgaaatt ggaatctgac aagacgttcc caatcatgtt ggaagggaag ataaacggct 1320
acgcttgtgt ggtcggaggg aagttattca ggccgatgca tgtggaaggc aagatcgaca 1380
acgacgttct ggccgcgctt aagacgaaga aagcatccaa atacgatctt gagtatgcag 1440
atgtgccaca gaacatgcgg gccgatacat tcaaatacac ccatgagaaa ccccaaggct 1500
attacagctg gcatcatgga gcagtccaat atgaaaatgg gcgtttcacg gtgccgaaag 1560
gagttggggc caagggagac agcggacgac ccattctgga taaccaggga cgggtggtcg 1620
ctattgtgct gggaggtgtg aatgaaggat ctaggacagc cctttcagtc gtcatgtgga 1680
acgagaaggg agttaccgtg aagtatactc cagagaactg cgagcaatgg tcactagtga 1740
ccaccatgtg tctgctcgcc aatgtgacgt tcccatgtgc tcaaccacca atttgctacg 1800
acagaaaacc agcagagact ttggccatgc tcagcgttaa cgttgacaac ccgggctacg 1860
atgagctgct ggaagcagct gttaagtgcc ccggaaggaa aaggagatcc accgaggagc 1920
tgtttaatga gtataagcta acgcgccctt acatggccag atgcatcaga tgtgcagttg 1980
ggagctgcca tagtccaata gcaatcgagg cagtaaagag cgacgggcac gacggttatg 2040
ttagacttca gacttcctcg cagtatggcc tggattcctc cggcaactta aagggcagga 2100
ccatgcggta tgacatgcac gggaccatta aagagatacc actacatcaa gtgtcactct 2160
atacatctcg cccgtgtcac attgtggatg ggcacggtta tttcctgctt gccaggtgcc 2220
cggcagggga ctccatcacc atggaattta agaaagattc cgtcagacac tcctgctcgg 2280
tgccgtatga agtgaaattt aatcctgtag gcagagaact ctatactcat cccccagaac 2340
acggagtaga gcaagcgtgc caagtctacg cacatgatgc acagaacaga ggagcttatg 2400
tcgagatgca cctcccgggc tcagaagtgg acagcagttt ggtttccttg agcggcagtt 2460
ccggaggaaa cccgaatgcc aatcccaacg cgaaccccaa cgctaacccc aacgccaatc 2520
cgaatgcaaa cccgaacgtt gacccaaacg ccaacccgaa tgccaatccc aacgcgaacc 2580
ccaatgctaa cccaaatgcc aacccaaacg ccaaccccaa cgctaatcca aacgccaacc 2640
ctaacgccaa tcccaacgcg aatcctaacg ctaatcccaa cgcaaatccc aatgctaatc 2700
cgaacgcgaa ccctaatgca aaccccaacg ccaacccgaa cgctaacccg aacgctaatc 2760
ccaacgccgg tggatcctca gtcaccgtga cacctcctga tgggactagc gccctggtgg 2820
aatgcgagtg tggcggcaca aagatctccg agaccatcaa caagacaaaa cagttcagcc 2880
agtgcacaaa gaaggagcag tgcagagcat atcggctgca gaacgataag tgggtgtata 2940
attctgacaa actgcccaaa gcagcgggag ccaccttaaa aggaaaactg catgtcccat 3000
tcttgctggc agacggcaaa tgcaccgtgc ctctagcacc agaacctatg ataaccttcg 3060
gtttcagatc agtgtcactg aaactgcacc ctaagaatcc cacatatcta atcacccgcc 3120
aacttgctga tgagcctcac tacacgcacg agctcatatc tgaaccagct gttaggaatt 3180
ttaccgtcac cgaaaaaggg tgggagtttg tatggggaaa ccacccgccg aaaaggtttt 3240
gggcacagga aacagcaccc ggaaatccac atgggctacc gcacgaggtg ataactcatt 3300
attaccacag ataccctatg tccaccatcc tgggtttgtc aatttgtgcc gccattgcaa 3360
ccgtttccgt tgcagcgtct acctggctgt tttgcagatc aagagttgcg tgcctaactc 3420
cttaccggct aacacctaac gctaggatac cattttgtct ggctgtgctt tgctgcgccc 3480
gcactgcccg ggccgagacc acctgggagt ccttggatca cctatggaac aataaccaac 3540
agatgttctg gattcaattg ctgatccctc tggccgcctt gatcgtagtg actcgcctgc 3600
tcaggtgcgt gtgctgtgtc gtgccttttt tagtcatggc cggcgccgca ggcgccggcg 3660
cctacgagca cgcgaccacg atgccgagcc aagcgggaat ctcgtataac actatagtca 3720
acagagcagg ctacgcacca ctccctatca gcataacacc aacaaagatc aagctgatac 3780
ctacagtgaa cttggagtac gtcacctgcc actacaaaac aggaatggat tcaccagcca 3840
tcaaatgctg cggatctcag gaatgcactc caacttacag gcctgatgaa cagtgcaaag 3900
tcttcacagg ggtttacccg ttcatgtggg gtggtgcata ttgcttttgc gacactgaga 3960
acacccaagt cagcaaggcc tacgtaatga aatctgacga ctgccttgcg gatcatgctg 4020
aagcatataa agcgcacaca gcctcagtgc aggcgttcct caacatcaca gtgggagaac 4080
actctattgt gactaccgtg tatgtgaatg gagaaactcc tgtgaatttc aatggggtca 4140
aaataactgc aggtccgctt tccacagctt ggacacccct tgatcgcaaa atcgtgcagt 4200
atgccgggga gatctataat tatgattttc ctgagtatgg ggcaggacaa ccaggagcat 4260
ttggagatat acaatccaga acagtctcaa gctctgatct gtatgccaat accaacctag 4320
tgctgcagag acccaaagca ggagcgatcc acgtgccata cactcaggca ccttcgggtt 4380
ttgagcaatg gaagaaagat aaagctccat cattgaaatt taccgcccct ttcggatgcg 4440
aaatatatac aaaccccatt cgcgccgaaa actgtgctgt agggtcaatt ccattagcct 4500
ttgacattcc cgacgccttg ttcaccaggg tgtcagaaac accgacactt tcagcggccg 4560
aatgcactct taacgagtgc gtgtattctt ccgactttgg tgggatcgcc acggtcaagt 4620
actcggccag caagtcaggc aagtgcgcag tccatgtgcc atcagggact gctaccctaa 4680

-continued aagaagcagc agtcgagcta accgagcaag ggtcggcgac tatccatttc tcgaccgcaa 4740
atatccaccc ggagttcagg ctccaaatat gcacatcata tgttacgtgc aaaggtgatt 4800
gtcacccccc gaaagaccat attgtgacac accctcagta tcacgcccaa acatttacag 4860
ccgcggtgtc aaaaaccgcg tggacgtggt taacatccct gctgggagga tcagccgtaa 4920
ttattataat tggcttggtg ctggctacta ttgtggccat gtacgtgctg accaaccaga 4980
aacataatta aggatctaga tctgctgtgc cttctagttg ccagccatct gttgtttgcc 5040
cctcccccgt gccttccttg accctggaag gtgccactcc cactgtcctt tcctaataaa 5100
atgaggaaat tgcatcgcat tgtctgagta ggtgtcattc tattctgggg ggtggggtgg 5160
ggcaggacag caagggggag gattgggaag acaatagcag gcatgctggg gatgcggtgg 5220
gctctatggg tacccaggtg ctgaagaatt gacccggttc ctcctgggcc agaaagaagc 5280
aggcacatcc ccttctctgt gacacaccct gtccacgccc ctggttctta gttccagccc 5340
cactcatagg acactcatag ctcaggaggg ctccgccttc aatcccaccc gctaaagtac 5400
ttggagcggt ctctccctcc ctcatcagcc caccaaacca aacctagcct ccaagagtgg 5460
gaagaaatta aagcaagata ggctattaag tgcagaggga gagaaaatgc ctccaacatg 5520
tgaggaagta atgagagaaa tcatagaatt ttaaggccat gatttaaggc catcatggcc 5580
taagcttgaa aggagatagg atcaaagctt ggcgtaatca tggtcatagc tgtttcctgt 5640
gtgaaattgt tatccgctca caattccaca caacatacga gccggaagca taaagtgtaa 5700
agcctggggt gcctaatgag tgagctaact cacattaatt gcgttgcgct cactgcccgc 5760
tttccagtcg ggaaacctgt cgtgccagct gcattaatga atcggccaac gcgcggggag 5820
aggcggtttg cgtattgggc gctcttccgc ttcctcgctc actgactcgc tgcgctcggt 5880
cgttcggctg cggcgagcgg tatcagctca ctcaaaggcg gtaatacggt tatccacaga 5940
atcaggggat aacgcaggaa agaacatgtg agcaaaaggc cagcaaaagg ccaggaaccg 6000
taaaaaggcc gcgttgctgg cgtttttcca taggctccgc ccccctgacg agcatcacaa 6060
aaatcgacgc tcaagtcaga ggtggcgaaa cccgacagga ctataaagat accaggcgtt 6120
tccccctgga agctccctcg tgcgctctcc tgttccgacc ctgccgctta ccggatacct 6180
gtccgccttt ctcccttcgg gaagcgtggc gctttctcat agctcacgct gtaggtatct 6240
cagttcggtg taggtcgttc gctccaagct gggctgtgtg cacgaacccc ccgttcagcc 6300
cgaccgctgc gccttatccg gtaactatcg tcttgagtcc aacccggtaa gacacgactt 6360
atcgccactg gcagcagcca ctggtaacag gattagcaga gcgaggtatg taggcggtgc 6420
tacagagttc ttgaagtggt ggcctaacta cggctacact agaagaacag tatttggtat 6480
ctgcgctctg ctgaagccag ttaccttcgg aaaaagagtt ggtagctctt gatccggcaa 6540
acaaaccacc gctggtagcg gtggtttttt tgtttgcaag cagcagatta cgcgcagaaa 6600
aaaaggatct caagaagatc ctttgatctt ttctacgggg tctgacgctc agtggaacga 6660
aaactcacgt taagggattt tggtcatgag attatcaaaa aggatcttca cctagatcct 6720
tttaaattaa aaatgaagtt ttaaatcaat ctaaagtata tatgagtaaa cttggtctga 6780
cagttaccaa tgcttaatca gtgaggcacc tatctcagcg atctgtctat ttcgttcatc 6840
catagttgcc tgactccccg tcgtgtagat aactacgata cgggagggct taccatctgg 6900
ccccagtgct gcaatgatac cgcgagaacc acgctcaccg gctccagatt tatcagcaat 6960
aaaccagcca gccggaaggg ccgagcgcag aagtggtcct gcaactttat ccgcctccat 7020
ccagtctatt aattgttgcc gggaagctag agtaagtagt tcgccagtta atagtttgcg 7080

```
caacgttgtt gccattgcta caggcatcgt ggtgtcacgc tcgtcgtttg gtatggcttc   7140

attcagctcc ggttcccaac gatcaaggcg agttacatga tcccccatgt tgtgcaaaaa   7200

agcggttagc tccttcggtc ctccgatcgt tgtcagaagt aagttggccg cagtgttatc   7260

actcatggtt atggcagcac tgcataattc tcttactgtc atgccatccg taagatgctt   7320

ttctgtgact ggtgagtact caaccaagtc attctgagaa tagtgtatgc ggcgaccgag   7380

ttgctcttgc ccggcgtcaa tacgggataa taccgcgcca catagcagaa ctttaaaagt   7440

gctcatcatt ggaaaacgtt cttcggggcg aaaactctca aggatcttac cgctgttgag   7500

atccagttcg atgtaaccca ctcgtgcacc caactgatct tcagcatctt ttactttcac   7560

cagcgtttct gggtgagcaa aaacaggaag gcaaaatgcc gcaaaaaagg gaataagggc   7620

gacacggaaa tgttgaatac tcatactctt cctttttcaa tattattgaa gcatttatca   7680

gggttattgt ctcatgagcg gatacatatt tgaatgtatt tagaaaaata aacaaatagg   7740

ggttccgcgc acatttcccc gaaaagtgcc acctgacgtc taagaaacca ttattatcat   7800

gacattaacc tataaaaata ggcgtatcac gaggcccttt cgggtcgcgc gtttcggtga   7860

tgacggtgaa aacctctgac acatgcagct cccgttgacg gtcacagctt gtctgtaagc   7920

ggatgccggg agcagacaag cccgtcaggg cgcgtcagcg ggtgttggcg ggtgtcgggg   7980

ctggcttaac tatgcggcat cagagcagat tgtactgaga gtgcaccata aaattgtaaa   8040

cgttaatatt ttgttaaaat tcgcgttaaa tttttgttaa atcagctcat tttttaacca   8100

ataggccgaa atcggcaaaa tcccttataa atcaaaagaa tagcccgaga tagggttgag   8160

tgttgttcca gtttggaaca agagtccact attaaagaac gtggactcca acgtcaaagg   8220

gcgaaaaacc gtctatcagg gcgatggccc actacgtgaa ccatcaccca aatcaagttt   8280

tttggggtcg aggtgccgta aagcactaaa tcggaaccct aaagggagcc cccgatttag   8340

agcttgacgg ggaaagccgg cgaacgtggc gagaaaggaa gggaagaaag cgaaaggagc   8400

gggcgctagg gcgctggcaa gtgtagcggt cacgctgcgc gtaaccacca cacccgccgc   8460

gcttaatgcg ccgctacagg gcgcgtacta tggttgcttt gacgtatgcg gtgtgaaata   8520

ccgcacagat gcgtaaggag aaaataccgc atcaggcgcc attcgccatt caggctgcgc   8580

aactgttggg aagggcgatc ggtgcgggcc tcttcgctat tacgccagct ggcgaaaggg   8640

ggatgtgctg caaggcgatt aagttgggta acgccagggt tttcccagtc acgacgttgt   8700

aaaacgacgg ccagtgaatt ccatggtctc aactttc                            8737
```

<210> SEQ ID NO 33
<211> LENGTH: 4086
<212> TYPE: DNA
<213> ORGANISM: Artificial Sequence
<220> FEATURE:
<223> OTHER INFORMATION: Synthetic VLP78_21 (VEEV VLP 519 NPNAx25)
VEEV-NPNAx25 sequence

<400> SEQUENCE: 33

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360
```

-continued

```
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaaccccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggaaacccga atgccaatcc caacgcgaac cccaacgcta accccaacgc caatccgaat   1620
gcaaacccga acgttgaccc aaacgccaac ccgaatgcca atcccaacgc gaaccccaat   1680
gctaacccaa atgccaaccc aaacgccaac cccaacgcta atccaaacgc caaccctaac   1740
gccaatccca acgcgaatcc taacgctaat cccaacgcaa atcccaatgc taatccgaac   1800
gcgaacccta atgcaaaccc caacgccaac ccgaacgcta acccgaacgc taatcccaac   1860
gccggtggat cctcagtcac cgtgacacct cctgatggga ctagcgccct ggtggaatgc   1920
gagtgtggcg gcacaaagat ctccgagacc atcaacaaga caaaacagtt cagccagtgc   1980
acaaagaagg agcagtgcag agcatatcgg ctgcagaacg ataagtgggt gtataattct   2040
gacaaactgc ccaaagcagc gggagccacc ttaaaaggaa aactgcatgt cccattcttg   2100
ctggcagacg gcaaatgcac cgtgcctcta gcaccagaac ctatgataac cttcggtttc   2160
agatcagtgt cactgaaact gcaccctaag aatcccacat atctaatcac ccgccaactt   2220
gctgatgagc ctcactacac gcacgagctc atatctgaac cagctgttag gaattttacc   2280
gtcaccgaaa aagggtggga gtttgtatgg ggaaaccacc cgccgaaaag gttttgggca   2340
caggaaacag cacccggaaa tccacatggg ctaccgcacg aggtgataac tcattattac   2400
cacagatacc ctatgtccac catcctgggt ttgtcaattt gtgccgccat tgcaaccgtt   2460
tccgttgcag cgtctacctg gctgttttgc agatcaagag ttgcgtgcct aactccttac   2520
cggctaacac ctaacgctag gataccattt tgtctggctg tgctttgctg cgcccgcact   2580
gcccgggccg agaccacctg ggagtccttg gatcacctat ggaacaataa ccaacagatg   2640
ttctggattc aattgctgat ccctctggcc gccttgatcg tagtgactcg cctgctcagg   2700
```

-continued

```
tgcgtgtgct gtgtcgtgcc ttttttagtc atggccggcg ccgcaggcgc cggcgcctac   2760

gagcacgcga ccacgatgcc gagccaagcg ggaatctcgt ataacactat agtcaacaga   2820

gcaggctacg caccactccc tatcagcata acaccaacaa agatcaagct gatacctaca   2880

gtgaacttgg agtacgtcac ctgccactac aaaacaggaa tggattcacc agccatcaaa   2940

tgctgcggat ctcaggaatg cactccaact tacaggcctg atgaacagtg caaagtcttc   3000

acaggggttt acccgttcat gtggggtggt gcatattgct tttgcgacac tgagaacacc   3060

caagtcagca aggcctacgt aatgaaatct gacgactgcc ttgcggatca tgctgaagca   3120

tataaagcgc acacagcctc agtgcaggcg ttcctcaaca tcacagtggg agaacactct   3180

attgtgacta ccgtgtatgt gaatggagaa actcctgtga atttcaatgg ggtcaaaata   3240

actgcaggtc cgctttccac agcttggaca ccctttgatc gcaaaatcgt gcagtatgcc   3300

ggggagatct ataattatga ttttcctgag tatggggcag gacaaccagg agcatttgga   3360

gatatacaat ccagaacagt ctcaagctct gatctgtatg ccaataccaa cctagtgctg   3420

cagagaccca aagcaggagc gatccacgtg ccatacactc aggcaccttc gggttttgag   3480

caatggaaga aagataaagc tccatcattg aaatttaccg ccccttctcgg atgcgaaata   3540

tatacaaacc ccattcgcgc cgaaaactgt gctgtagggt caattccatt agcctttgac   3600

attcccgacg ccttgttcac cagggtgtca gaaacaccga cactttcagc ggccgaatgc   3660

actcttaacg agtgcgtgta ttcttccgac tttggtggga tcgccacggt caagtactcg   3720

gccagcaagt caggcaagtg cgcagtccat gtgccatcag ggactgctac cctaaaagaa   3780

gcagcagtcg agctaaccga gcaagggtcg gcgactatcc atttctcgac cgcaaatatc   3840

cacccggagt tcaggctcca aatatgcaca tcatatgtta cgtgcaaagg tgattgtcac   3900

cccccgaaag accatattgt gacacaccct cagtatcacg cccaaacatt tacagccgcg   3960

gtgtcaaaaa ccgcgtggac gtggttaaca tccctgctgg gaggatcagc cgtaattatt   4020

ataattggct tggtgctggc tactattgtg gccatgtacg tgctgaccaa ccagaaacat   4080

aattaa                                                              4086


<210> SEQ ID NO 34
<211> LENGTH: 1361
<212> TYPE: PRT
<213> ORGANISM: Artificial Sequence
<220> FEATURE:
<223> OTHER INFORMATION: Synthetic VLP78_21 (VEEV VLP 519 NPNAx25)
      sequence

<400> SEQUENCE: 34

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110
```

-continued

```
Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Asn Pro Asn Ala Asn Pro Asn
        515                 520                 525
```

```
Ala Asn Pro Asn Ala Asn Pro Asn Ala Asn Pro Asn Ala Asn Pro Asn
    530                 535                 540

Val Asp Pro Asn Ala Asn Pro Asn Ala Asn Pro Asn Ala Asn Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Ala Asn Pro Asn
            580                 585                 590

Ala Asn Pro Asn Ala Asn Pro Asn Ala Asn Pro Asn Ala Asn Pro Asn
        595                 600                 605

Ala Asn Pro Asn Ala Asn Pro Asn Ala Asn Pro Asn Ala Gly Gly Ser
    610                 615                 620

Ser Val Thr Val Thr Pro Pro Asp Gly Thr Ser Ala Leu Val Glu Cys
625                 630                 635                 640

Glu Cys Gly Gly Thr Lys Ile Ser Glu Thr Ile Asn Lys Thr Lys Gln
                645                 650                 655

Phe Ser Gln Cys Thr Lys Lys Glu Gln Cys Arg Ala Tyr Arg Leu Gln
            660                 665                 670

Asn Asp Lys Trp Val Tyr Asn Ser Asp Lys Leu Pro Lys Ala Ala Gly
        675                 680                 685

Ala Thr Leu Lys Gly Lys Leu His Val Pro Phe Leu Leu Ala Asp Gly
    690                 695                 700

Lys Cys Thr Val Pro Leu Ala Pro Glu Pro Met Ile Thr Phe Gly Phe
705                 710                 715                 720

Arg Ser Val Ser Leu Lys Leu His Pro Lys Asn Pro Thr Tyr Leu Ile
                725                 730                 735

Thr Arg Gln Leu Ala Asp Glu Pro His Tyr Thr His Glu Leu Ile Ser
            740                 745                 750

Glu Pro Ala Val Arg Asn Phe Thr Val Thr Glu Lys Gly Trp Glu Phe
        755                 760                 765

Val Trp Gly Asn His Pro Pro Lys Arg Phe Trp Ala Gln Glu Thr Ala
    770                 775                 780

Pro Gly Asn Pro His Gly Leu Pro His Glu Val Ile Thr His Tyr Tyr
785                 790                 795                 800

His Arg Tyr Pro Met Ser Thr Ile Leu Gly Leu Ser Ile Cys Ala Ala
                805                 810                 815

Ile Ala Thr Val Ser Val Ala Ala Ser Thr Trp Leu Phe Cys Arg Ser
            820                 825                 830

Arg Val Ala Cys Leu Thr Pro Tyr Arg Leu Thr Pro Asn Ala Arg Ile
        835                 840                 845

Pro Phe Cys Leu Ala Val Leu Cys Cys Ala Arg Thr Ala Arg Ala Glu
    850                 855                 860

Thr Thr Trp Glu Ser Leu Asp His Leu Trp Asn Asn Asn Gln Gln Met
865                 870                 875                 880

Phe Trp Ile Gln Leu Leu Ile Pro Leu Ala Ala Leu Ile Val Val Thr
                885                 890                 895

Arg Leu Leu Arg Cys Val Cys Cys Val Val Pro Phe Leu Val Met Ala
            900                 905                 910

Gly Ala Ala Gly Ala Gly Ala Tyr Glu His Ala Thr Thr Met Pro Ser
        915                 920                 925

Gln Ala Gly Ile Ser Tyr Asn Thr Ile Val Asn Arg Ala Gly Tyr Ala
    930                 935                 940

Pro Leu Pro Ile Ser Ile Thr Pro Thr Lys Ile Lys Leu Ile Pro Thr
```

-continued

```
945                 950                 955                 960

Val Asn Leu Glu Tyr Val Thr Cys His Tyr Lys Thr Gly Met Asp Ser
                965                 970                 975

Pro Ala Ile Lys Cys Cys Gly Ser Gln Glu Cys Thr Pro Thr Tyr Arg
            980                 985                 990

Pro Asp Glu Gln Cys Lys Val Phe  Thr Gly Val Tyr Pro  Phe Met Trp
        995                 1000                 1005

Gly Gly  Ala Tyr Cys Phe Cys  Asp Thr Glu Asn Thr  Gln Val Ser
    1010                 1015                 1020

Lys Ala  Tyr Val Met Lys Ser  Asp Asp Cys Leu Ala  Asp His Ala
    1025                 1030                 1035

Glu Ala  Tyr Lys Ala His Thr  Ala Ser Val Gln Ala  Phe Leu Asn
    1040                 1045                 1050

Ile Thr  Val Gly Glu His Ser  Ile Val Thr Thr Val  Tyr Val Asn
    1055                 1060                 1065

Gly Glu  Thr Pro Val Asn Phe  Asn Gly Val Lys Ile  Thr Ala Gly
    1070                 1075                 1080

Pro Leu  Ser Thr Ala Trp Thr  Pro Phe Asp Arg Lys  Ile Val Gln
    1085                 1090                 1095

Tyr Ala  Gly Glu Ile Tyr Asn  Tyr Asp Phe Pro Glu  Tyr Gly Ala
    1100                 1105                 1110

Gly Gln  Pro Gly Ala Phe Gly  Asp Ile Gln Ser Arg  Thr Val Ser
    1115                 1120                 1125

Ser Ser  Asp Leu Tyr Ala Asn  Thr Asn Leu Val Leu  Gln Arg Pro
    1130                 1135                 1140

Lys Ala  Gly Ala Ile His Val  Pro Tyr Thr Gln Ala  Pro Ser Gly
    1145                 1150                 1155

Phe Glu  Gln Trp Lys Lys Asp  Lys Ala Pro Ser Leu  Lys Phe Thr
    1160                 1165                 1170

Ala Pro  Phe Gly Cys Glu Ile  Tyr Thr Asn Pro Ile  Arg Ala Glu
    1175                 1180                 1185

Asn Cys  Ala Val Gly Ser Ile  Pro Leu Ala Phe Asp  Ile Pro Asp
    1190                 1195                 1200

Ala Leu  Phe Thr Arg Val Ser  Glu Thr Pro Thr Leu  Ser Ala Ala
    1205                 1210                 1215

Glu Cys  Thr Leu Asn Glu Cys  Val Tyr Ser Ser Asp  Phe Gly Gly
    1220                 1225                 1230

Ile Ala  Thr Val Lys Tyr Ser  Ala Ser Lys Ser Gly  Lys Cys Ala
    1235                 1240                 1245

Val His  Val Pro Ser Gly Thr  Ala Thr Leu Lys Glu  Ala Ala Val
    1250                 1255                 1260

Glu Leu  Thr Glu Gln Gly Ser  Ala Thr Ile His Phe  Ser Thr Ala
    1265                 1270                 1275

Asn Ile  His Pro Glu Phe Arg  Leu Gln Ile Cys Thr  Ser Tyr Val
    1280                 1285                 1290

Thr Cys  Lys Gly Asp Cys His  Pro Pro Lys Asp His  Ile Val Thr
    1295                 1300                 1305

His Pro  Gln Tyr His Ala Gln  Thr Phe Thr Ala Ala  Val Ser Lys
    1310                 1315                 1320

Thr Ala  Trp Thr Trp Leu Thr  Ser Leu Leu Gly Gly  Ser Ala Val
    1325                 1330                 1335

Ile Ile  Ile Ile Gly Leu Val  Leu Ala Thr Ile Val  Ala Met Tyr
    1340                 1345                 1350
```

```
Val Leu  Thr Asn Gln Lys His  Asn
    1355                 1360


<210> SEQ ID NO 35
<211> LENGTH: 8509
<212> TYPE: DNA
<213> ORGANISM: Artificial Sequence
<220> FEATURE:
<223> OTHER INFORMATION: Synthetic VLP74_21 (VEEV VLP 519 NPNAx6)
      sequence

<400> SEQUENCE: 35

gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttccatggg tcttttctgc agtcaccgtc gtcgacacgt gtgatcagat atcgcggccg    900

ccaccatgtt cccgttccag ccaatgtatc cgatgcagcc aatgccctat cgcaacccgt    960

tcgcggcccc gcgcaggccc tggttcccca gaaccgaccc ttttctggcg atgcaggtgc   1020

aggaattaac ccgctcgatg gctaacctga cgttcaagca acgccgggac gcgccacctg   1080

aggggccatc cgctaataaa ccgaagaagg aggcctcgca aaaacagaaa gggggaggcc   1140

aagggaagaa gaagaagaac caagggaaga agaaggctaa gacagggccg cctaatccga   1200

aggcacagaa tggaaacaag aagaagacca acaagaaacc aggcaagaga cagcgcatgg   1260

tcatgaaatt ggaatctgac aagacgttcc caatcatgtt ggaagggaag ataaacggct   1320

acgcttgtgt ggtcggaggg aagttattca ggccgatgca tgtggaaggc aagatcgaca   1380

acgacgttct ggccgcgctt aagacgaaga aagcatccaa atacgatctt gagtatgcag   1440

atgtgccaca gaacatgcgg gccgatacat tcaaatacac ccatgagaaa ccccaaggct   1500

attacagctg gcatcatgga gcagtccaat atgaaaatgg gcgtttcacg gtgccgaaag   1560

gagttggggc caagggagac agcggacgac ccattctgga taaccaggga cgggtggtcg   1620

ctattgtgct gggaggtgtg aatgaaggat ctaggacagc cctttcagtc gtcatgtgga   1680

acgagaaggg agttaccgtg aagtatactc cagagaactg cgagcaatgg tcactagtga   1740

ccaccatgtg tctgctcgcc aatgtgacgt tcccatgtgc tcaaccacca atttgctacg   1800

acagaaaacc agcagagact ttggccatgc tcagcgttaa cgttgacaac ccgggctacg   1860

atgagctgct ggaagcagct gttaagtgcc ccggaaggaa aaggagatcc accgaggagc   1920
```

-continued

```
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
ccggaggaaa cccgaatgcc aatcccaacg cgaaccccaa tgctaaccca aatgccaacc   2520
caaacgccaa ccccaacgct ggtggatcct cagtcaccgt gacacctcct gatgggacta   2580
gcgccctggt ggaatgcgag tgtggcggca caaagatctc cgagaccatc aacaagacaa   2640
aacagttcag ccagtgcaca aagaaggagc agtgcagagc atatcggctg cagaacgata   2700
agtgggtgta taattctgac aaactgccca aagcagcggg agccacctta aaaggaaaac   2760
tgcatgtccc attcttgctg gcagacggca aatgcaccgt gcctctagca ccagaaccta   2820
tgataacctt cggtttcaga tcagtgtcac tgaaactgca ccctaagaat cccacatatc   2880
taatcacccg ccaacttgct gatgagcctc actacacgca cgagctcata tctgaaccag   2940
ctgttaggaa ttttaccgtc accgaaaaag ggtgggagtt tgtatgggga aaccacccgc   3000
cgaaaaggtt ttgggcacag gaaacagcac ccggaaatcc acatgggcta ccgcacgagg   3060
tgataactca ttattaccac agatacccta tgtccaccat cctgggtttg tcaatttgtg   3120
ccgccattgc aaccgtttcc gttgcagcgt ctacctggct gttttgcaga tcaagagttg   3180
cgtgcctaac tccttaccgg ctaacaccta acgctaggat accattttgt ctggctgtgc   3240
tttgctgcgc ccgcactgcc cgggccgaga ccacctggga gtccttggat cacctatgga   3300
acaataacca acagatgttc tggattcaat tgctgatccc tctggccgcc ttgatcgtag   3360
tgactcgcct gctcaggtgc gtgtgctgtg tcgtgccttt tttagtcatg gccggcgccg   3420
caggcgccgg cgcctacgag cacgcgacca cgatgccgag ccaagcggga atctcgtata   3480
acactatagt caacagagca ggctacgcac cactccctat cagcataaca ccaacaaaga   3540
tcaagctgat acctacagtg aacttggagt acgtcacctg ccactacaaa acaggaatgg   3600
attcaccagc catcaaatgc tgcggatctc aggaatgcac tccaacttac aggcctgatg   3660
aacagtgcaa agtcttcaca ggggtttacc cgttcatgtg ggtggtgca tattgctttt   3720
gcgacactga gaacacccaa gtcagcaagg cctacgtaat gaaatctgac gactgccttg   3780
cggatcatgc tgaagcatat aaagcgcaca cagcctcagt gcaggcgttc ctcaacatca   3840
cagtgggaga acactctatt gtgactaccg tgtatgtgaa tggagaaact cctgtgaatt   3900
tcaatggggt caaaataact gcaggtccgc tttccacagc ttggacaccc tttgatcgca   3960
aaatcgtgca gtatgccggg gagatctata attatgattt tcctgagtat ggggcaggac   4020
aaccaggagc atttggagat atacaatcca gaacagtctc aagctctgat ctgtatgcca   4080
ataccaacct agtgctgcag agacccaaag caggagcgat ccacgtgcca tacactcagg   4140
caccttcggg ttttgagcaa tggaagaaag ataaagctcc atcattgaaa tttaccgccc   4200
ctttcggatg cgaaatatat acaaacccca ttcgcgccga aaactgtgct gtagggtcaa   4260
ttccattagc ctttgacatt cccgacgcct tgttcaccag ggtgtcagaa acaccgacac   4320
```

-continued

```
tttcagcggc cgaatgcact cttaacgagt gcgtgtattc ttccgacttt ggtgggatcg   4380
ccacggtcaa gtactcggcc agcaagtcag gcaagtgcgc agtccatgtg ccatcaggga   4440
ctgctaccct aaaagaagca gcagtcgagc taaccgagca agggtcggcg actatccatt   4500
tctcgaccgc aaatatccac ccggagttca ggctccaaat atgcacatca tatgttacgt   4560
gcaaaggtga ttgtcacccc ccgaaagacc atattgtgac acaccctcag tatcacgccc   4620
aaacatttac agccgcggtg tcaaaaaccg cgtggacgtg gttaacatcc ctgctgggag   4680
gatcagccgt aattattata attggcttgg tgctggctac tattgtggcc atgtacgtgc   4740
tgaccaacca gaaacataat taaggatcta gatctgctgt gccttctagt tgccagccat   4800
ctgttgtttg cccctccccc gtgccttcct tgaccctgga aggtgccact cccactgtcc   4860
tttcctaata aaatgaggaa attgcatcgc attgtctgag taggtgtcat tctattctgg   4920
ggggtggggt ggggcaggac agcaaggggg aggattggga agacaatagc aggcatgctg   4980
gggatgcggt gggctctatg ggtacccagg tgctgaagaa ttgacccggt tcctcctggg   5040
ccagaaagaa gcaggcacat ccccttctct gtgacacacc ctgtccacgc ccctggttct   5100
tagttccagc cccactcata ggacactcat agctcaggag ggctccgcct tcaatcccac   5160
ccgctaaagt acttggagcg gtctctccct ccctcatcag cccaccaaac caaacctagc   5220
ctccaagagt gggaagaaat taaagcaaga taggctatta agtgcagagg gagagaaaat   5280
gcctccaaca tgtgaggaag taatgagaga aatcatagaa ttttaaggcc atgatttaag   5340
gccatcatgg cctaagcttg aaaggagata ggatcaaagc ttggcgtaat catggtcata   5400
gctgtttcct gtgtgaaatt gttatccgct cacaattcca cacaacatac gagccggaag   5460
cataaagtgt aaagcctggg gtgcctaatg agtgagctaa ctcacattaa ttgcgttgcg   5520
ctcactgccc gctttccagt cgggaaacct gtcgtgccag ctgcattaat gaatcggcca   5580
acgcgcgggg agaggcggtt tgcgtattgg gcgctcttcc gcttcctcgc tcactgactc   5640
gctgcgctcg gtcgttcggc tgcggcgagc ggtatcagct cactcaaagg cggtaatacg   5700
gttatccaca gaatcagggg ataacgcagg aaagaacatg tgagcaaaag gccagcaaaa   5760
ggccaggaac cgtaaaaagg ccgcgttgct ggcgtttttc cataggctcc gcccccctga   5820
cgagcatcac aaaaatcgac gctcaagtca gaggtggcga aacccgacag gactataaag   5880
ataccaggcg tttccccctg gaagctccct cgtgcgctct cctgttccga ccctgccgct   5940
taccggatac ctgtccgcct ttctcccttc gggaagcgtg gcgctttctc atagctcacg   6000
ctgtaggtat ctcagttcgg tgtaggtcgt tcgctccaag ctgggctgtg tgcacgaacc   6060
ccccgttcag cccgaccgct gcgccttatc cggtaactat cgtcttgagt ccaacccggt   6120
aagacacgac ttatcgccac tggcagcagc cactggtaac aggattagca gagcgaggta   6180
tgtaggcggt gctacagagt tcttgaagtg gtggcctaac tacggctaca ctagaagaac   6240
agtatttggt atctgcgctc tgctgaagcc agttaccttc ggaaaaagag ttggtagctc   6300
ttgatccggc aaacaaacca ccgctggtag cggtggtttt tttgtttgca agcagcagat   6360
tacgcgcaga aaaaaaggat ctcaagaaga tcctttgatc ttttctacgg ggtctgacgc   6420
tcagtggaac gaaaactcac gttaagggat tttggtcatg agattatcaa aaaggatctt   6480
cacctagatc cttttaaatt aaaaatgaag ttttaaatca atctaaagta tatatgagta   6540
aacttggtct gacagttacc aatgcttaat cagtgaggca cctatctcag cgatctgtct   6600
atttcgttca tccatagttg cctgactccc cgtcgtgtag ataactacga tacgggaggg   6660
```

-continued

```
cttaccatct ggccccagtg ctgcaatgat accgcgagaa ccacgctcac cggctccaga   6720

tttatcagca ataaaccagc cagccggaag ggccgagcgc agaagtggtc ctgcaacttt   6780

atccgcctcc atccagtcta ttaattgttg ccgggaagct agagtaagta gttcgccagt   6840

taatagtttg cgcaacgttg ttgccattgc tacaggcatc gtggtgtcac gctcgtcgtt   6900

tggtatggct tcattcagct ccggttccca acgatcaagg cgagttacat gatcccccat   6960

gttgtgcaaa aaagcggtta gctccttcgg tcctccgatc gttgtcagaa gtaagttggc   7020

cgcagtgtta tcactcatgg ttatggcagc actgcataat tctcttactg tcatgccatc   7080

cgtaagatgc ttttctgtga ctggtgagta ctcaaccaag tcattctgag aatagtgtat   7140

gcggcgaccg agttgctctt gcccggcgtc aatacgggat aataccgcgc cacatagcag   7200

aactttaaaa gtgctcatca ttggaaaacg ttcttcgggg cgaaaactct caaggatctt   7260

accgctgttg agatccagtt cgatgtaacc cactcgtgca cccaactgat cttcagcatc   7320

ttttactttc accagcgttt ctgggtgagc aaaaacagga aggcaaaatg ccgcaaaaaa   7380

gggaataagg gcgacacgga aatgttgaat actcatactc ttcctttttc aatattattg   7440

aagcatttat cagggttatt gtctcatgag cggatacata tttgaatgta tttagaaaaa   7500

taaacaaata ggggttccgc gcacatttcc ccgaaaagtg ccacctgacg tctaagaaac   7560

cattattatc atgacattaa cctataaaaa taggcgtatc acgaggccct ttcgggtcgc   7620

gcgtttcggt gatgacggtg aaaacctctg acacatgcag ctcccgttga cggtcacagc   7680

ttgtctgtaa gcggatgccg ggagcagaca agcccgtcag ggcgcgtcag cgggtgttgg   7740

cgggtgtcgg ggctggctta actatgcggc atcagagcag attgtactga gagtgcacca   7800

taaaattgta aacgttaata ttttgttaaa attcgcgtta aatttttgtt aaatcagctc   7860

atttttaac caataggccg aaatcggcaa aatcccttat aaatcaaaag aatagcccga   7920

gatagggttg agtgttgttc cagtttggaa caagagtcca ctattaaaga acgtggactc   7980

caacgtcaaa gggcgaaaaa ccgtctatca gggcgatggc ccactacgtg aaccatcacc   8040

caaatcaagt tttttggggt cgaggtgccg taaagcacta aatcggaacc ctaaagggag   8100

cccccgattt agagcttgac ggggaaagcc ggcgaacgtg gcgagaaagg aagggaagaa   8160

agcgaaagga gcgggcgcta gggcgctggc aagtgtagcg gtcacgctgc gcgtaaccac   8220

cacacccgcc gcgcttaatg cgccgctaca gggcgcgtac tatggttgct ttgacgtatg   8280

cggtgtgaaa taccgcacag atgcgtaagg agaaaatacc gcatcaggcg ccattcgcca   8340

ttcaggctgc gcaactgttg ggaagggcga tcggtgcggg cctcttcgct attacgccag   8400

ctggcgaaag ggggatgtgc tgcaaggcga ttaagttggg taacgccagg gttttcccag   8460

tcacgacgtt gtaaaacgac ggccagtgaa ttccatggtc tcaactttc              8509
```

<210> SEQ ID NO 36
<211> LENGTH: 3858
<212> TYPE: DNA
<213> ORGANISM: Artificial Sequence
<220> FEATURE:
<223> OTHER INFORMATION: Synthetic VLP74_21 (VEEV VLP 519 NPNAx6) VEEV-NPNAx6 sequence

<400> SEQUENCE: 36

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180
```

-continued

```
ccatccgcta ataaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggaaacccga atgccaatcc caacgcgaac cccaatgcta acccaaatgc caacccaaac   1620
gccaacccca acgctggtgg atcctcagtc accgtgacac ctcctgatgg gactagcgcc   1680
ctggtggaat gcgagtgtgg cggcacaaag atctccgaga ccatcaacaa gacaaaacag   1740
ttcagccagt gcacaaagaa ggagcagtgc agagcatatc ggctgcagaa cgataagtgg   1800
gtgtataatt ctgacaaact gcccaaagca gcgggagcca ccttaaaagg aaaactgcat   1860
gtcccattct tgctggcaga cggcaaatgc accgtgcctc tagcaccaga acctatgata   1920
accttcggtt tcagatcagt gtcactgaaa ctgcacccta agaatcccac atatctaatc   1980
acccgccaac ttgctgatga gcctcactac acgcacgagc tcatatctga accagctgtt   2040
aggaatttta ccgtcaccga aaaagggtgg gagtttgtat ggggaaacca cccgccgaaa   2100
aggttttggg cacaggaaac agcacccgga aatccacatg ggctaccgca cgaggtgata   2160
actcattatt accacagata ccctatgtcc accatcctgg gtttgtcaat ttgtgccgcc   2220
attgcaaccg tttccgttgc agcgtctacc tggctgtttt gcagatcaag agttgcgtgc   2280
ctaactcctt accggctaac acctaacgct aggataccat tttgtctggc tgtgctttgc   2340
tgcgcccgca ctgcccgggc cgagaccacc tgggagtcct tggatcacct atggaacaat   2400
aaccaacaga tgttctggat tcaattgctg atccctctgg ccgccttgat cgtagtgact   2460
cgcctgctca ggtgcgtgtg ctgtgtcgtg cctttttttag tcatggccgg cgccgcaggc   2520
gccggcgcct acgagcacgc gaccacgatg ccgagccaag cgggaatctc gtataacact   2580
```

```
atagtcaaca gagcaggcta cgcaccactc cctatcagca taacaccaac aaagatcaag   2640

ctgataccta cagtgaactt ggagtacgtc acctgccact acaaaacagg aatggattca   2700

ccagccatca aatgctgcgg atctcaggaa tgcactccaa cttacaggcc tgatgaacag   2760

tgcaaagtct tcacaggggt ttacccgttc atgtggggtg gtgcatattg cttttgcgac   2820

actgagaaca cccaagtcag caaggcctac gtaatgaaat ctgacgactg ccttgcggat   2880

catgctgaag catataaagc gcacacagcc tcagtgcagg cgttcctcaa catcacagtg   2940

ggagaacact ctattgtgac taccgtgtat gtgaatggag aaactcctgt gaatttcaat   3000

ggggtcaaaa taactgcagg tccgctttcc acagcttgga caccctttga tcgcaaaatc   3060

gtgcagtatg ccggggagat ctataattat gattttcctg agtatggggc aggacaacca   3120

ggagcatttg gagatataca atccagaaca gtctcaagct ctgatctgta tgccaatacc   3180

aacctagtgc tgcagagacc caaagcagga gcgatccacg tgccatacac tcaggcacct   3240

tcgggttttg agcaatggaa gaaagataaa gctccatcat tgaaatttac cgcccctttc   3300

ggatgcgaaa tatatacaaa ccccattcgc gccgaaaact gtgctgtagg gtcaattcca   3360

ttagcctttg acattcccga cgccttgttc accagggtgt cagaaacacc gacactttca   3420

gcggccgaat gcactcttaa cgagtgcgtg tattcttccg actttggtgg gatcgccacg   3480

gtcaagtact cggccagcaa gtcaggcaag tgcgcagtcc atgtgccatc agggactgct   3540

accctaaaag aagcagcagt cgagctaacc gagcaagggt cggcgactat ccatttctcg   3600

accgcaaata tccacccgga gttcaggctc caaatatgca catcatatgt tacgtgcaaa   3660

ggtgattgtc aaccccccgaa agaccatatt gtgacacacc ctcagtatca cgcccaaaca   3720

tttacagccg cggtgtcaaa aaccgcgtgg acgtggttaa catccctgct gggaggatca   3780

gccgtaatta ttataattgg cttggtgctg gctactattg tggccatgta cgtgctgacc   3840

aaccagaaac ataattaa                                                  3858
```

<210> SEQ ID NO 37
<211> LENGTH: 1285
<212> TYPE: PRT
<213> ORGANISM: Artificial Sequence
<220> FEATURE:
<223> OTHER INFORMATION: Synthetic VLP74_21 (VEEV VLP 519 NPNAx6) sequence

<400> SEQUENCE: 37

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125
```

-continued

```
Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Asn Pro Asn Ala Asn Pro Asn
        515                 520                 525

Ala Asn Pro Asn Ala Asn Pro Asn Ala Asn Pro Asn Ala Asn Pro Asn
    530                 535                 540
```

-continued

```
Ala Gly Gly Ser Ser Val Thr Val Thr Pro Pro Asp Gly Thr Ser Ala
545                 550                 555                 560

Leu Val Glu Cys Glu Cys Gly Gly Thr Lys Ile Ser Glu Thr Ile Asn
                565                 570                 575

Lys Thr Lys Gln Phe Ser Gln Cys Thr Lys Lys Glu Gln Cys Arg Ala
            580                 585                 590

Tyr Arg Leu Gln Asn Asp Lys Trp Val Tyr Asn Ser Asp Lys Leu Pro
        595                 600                 605

Lys Ala Ala Gly Ala Thr Leu Lys Gly Lys Leu His Val Pro Phe Leu
    610                 615                 620

Leu Ala Asp Gly Lys Cys Thr Val Pro Leu Ala Pro Glu Pro Met Ile
625                 630                 635                 640

Thr Phe Gly Phe Arg Ser Val Ser Leu Lys Leu His Pro Lys Asn Pro
                645                 650                 655

Thr Tyr Leu Ile Thr Arg Gln Leu Ala Asp Glu Pro His Tyr Thr His
            660                 665                 670

Glu Leu Ile Ser Glu Pro Ala Val Arg Asn Phe Thr Val Thr Glu Lys
        675                 680                 685

Gly Trp Glu Phe Val Trp Gly Asn His Pro Pro Lys Arg Phe Trp Ala
    690                 695                 700

Gln Glu Thr Ala Pro Gly Asn Pro His Gly Leu Pro His Glu Val Ile
705                 710                 715                 720

Thr His Tyr Tyr His Arg Tyr Pro Met Ser Thr Ile Leu Gly Leu Ser
                725                 730                 735

Ile Cys Ala Ala Ile Ala Thr Val Ser Val Ala Ala Ser Thr Trp Leu
            740                 745                 750

Phe Cys Arg Ser Arg Val Ala Cys Leu Thr Pro Tyr Arg Leu Thr Pro
        755                 760                 765

Asn Ala Arg Ile Pro Phe Cys Leu Ala Val Leu Cys Cys Ala Arg Thr
    770                 775                 780

Ala Arg Ala Glu Thr Thr Trp Glu Ser Leu Asp His Leu Trp Asn Asn
785                 790                 795                 800

Asn Gln Gln Met Phe Trp Ile Gln Leu Leu Ile Pro Leu Ala Ala Leu
                805                 810                 815

Ile Val Val Thr Arg Leu Leu Arg Cys Val Cys Cys Val Val Pro Phe
            820                 825                 830

Leu Val Met Ala Gly Ala Ala Gly Ala Gly Ala Tyr Glu His Ala Thr
        835                 840                 845

Thr Met Pro Ser Gln Ala Gly Ile Ser Tyr Asn Thr Ile Val Asn Arg
    850                 855                 860

Ala Gly Tyr Ala Pro Leu Pro Ile Ser Ile Thr Pro Thr Lys Ile Lys
865                 870                 875                 880

Leu Ile Pro Thr Val Asn Leu Glu Tyr Val Thr Cys His Tyr Lys Thr
                885                 890                 895

Gly Met Asp Ser Pro Ala Ile Lys Cys Cys Gly Ser Gln Glu Cys Thr
            900                 905                 910

Pro Thr Tyr Arg Pro Asp Glu Gln Cys Lys Val Phe Thr Gly Val Tyr
        915                 920                 925

Pro Phe Met Trp Gly Gly Ala Tyr Cys Phe Cys Asp Thr Glu Asn Thr
    930                 935                 940

Gln Val Ser Lys Ala Tyr Val Met Lys Ser Asp Asp Cys Leu Ala Asp
945                 950                 955                 960

His Ala Glu Ala Tyr Lys Ala His Thr Ala Ser Val Gln Ala Phe Leu
```

-continued

```
                965                 970                 975

Asn Ile Thr Val Gly Glu His Ser Ile Val Thr Thr Val Tyr Val Asn
            980                 985                 990

Gly Glu Thr Pro Val Asn Phe Asn  Gly Val Lys Ile Thr  Ala Gly Pro
        995                 1000                1005

Leu Ser  Thr Ala Trp Thr Pro  Phe Asp Arg Lys Ile  Val Gln Tyr
    1010                 1015                1020

Ala Gly  Glu Ile Tyr Asn Tyr  Asp Phe Pro Glu Tyr  Gly Ala Gly
    1025                 1030                1035

Gln Pro  Gly Ala Phe Gly Asp  Ile Gln Ser Arg Thr  Val Ser Ser
    1040                 1045                1050

Ser Asp  Leu Tyr Ala Asn Thr  Asn Leu Val Leu Gln  Arg Pro Lys
    1055                 1060                1065

Ala Gly  Ala Ile His Val Pro  Tyr Thr Gln Ala Pro  Ser Gly Phe
    1070                 1075                1080

Glu Gln  Trp Lys Lys Asp Lys  Ala Pro Ser Leu Lys  Phe Thr Ala
    1085                 1090                1095

Pro Phe  Gly Cys Glu Ile Tyr  Thr Asn Pro Ile Arg  Ala Glu Asn
    1100                 1105                1110

Cys Ala  Val Gly Ser Ile Pro  Leu Ala Phe Asp Ile  Pro Asp Ala
    1115                 1120                1125

Leu Phe  Thr Arg Val Ser Glu  Thr Pro Thr Leu Ser  Ala Ala Glu
    1130                 1135                1140

Cys Thr  Leu Asn Glu Cys Val  Tyr Ser Ser Asp Phe  Gly Gly Ile
    1145                 1150                1155

Ala Thr  Val Lys Tyr Ser Ala  Ser Lys Ser Gly Lys  Cys Ala Val
    1160                 1165                1170

His Val  Pro Ser Gly Thr Ala  Thr Leu Lys Glu Ala  Ala Val Glu
    1175                 1180                1185

Leu Thr  Glu Gln Gly Ser Ala  Thr Ile His Phe Ser  Thr Ala Asn
    1190                 1195                1200

Ile His  Pro Glu Phe Arg Leu  Gln Ile Cys Thr Ser  Tyr Val Thr
    1205                 1210                1215

Cys Lys  Gly Asp Cys His Pro  Pro Lys Asp His Ile  Val Thr His
    1220                 1225                1230

Pro Gln  Tyr His Ala Gln Thr  Phe Thr Ala Ala Val  Ser Lys Thr
    1235                 1240                1245

Ala Trp  Thr Trp Leu Thr Ser  Leu Leu Gly Gly Ser  Ala Val Ile
    1250                 1255                1260

Ile Ile  Ile Gly Leu Val Leu  Ala Thr Ile Val Ala  Met Tyr Val
    1265                 1270                1275

Leu Thr  Asn Gln Lys His Asn
    1280                 1285
```

<210> SEQ ID NO 38
<211> LENGTH: 7305
<212> TYPE: DNA
<213> ORGANISM: Artificial Sequence
<220> FEATURE:
<223> OTHER INFORMATION: Synthetic VLP74_15 (CHI VLP 532 NPNAx6) sequence

<400> SEQUENCE: 38

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120
```

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gacgcgtgtt ggcattgatt    420
attgactagt tattaatagt aatcaattac ggggtcatta gttcatagcc catatatgga    480
gttccgcgtt acataactta cggtaaatgg cccgcctggc tgaccgccca acgacccccg    540
cccattgacg tcaataatga cgtatgttcc catagtaacg ccaataggga ctttccattg    600
acgtcaatgg gtggagtatt tacggtaaac tgcccacttg gcagtacatc aagtgtatca    660
tatgccaagt acgcccccta ttgacgtcaa tgacggtaaa tggcccgcct ggcattatgc    720
ccagtacatg accttatggg actttcctac ttggcagtac atctacgtat tagtcatcgc    780
tattaccatg gtgatgcggt tttggcagta catcaatggg cgtggatagc ggtttgactc    840
acggggattt ccaagtctcc accccattga cgtcaatggg agtttgtttt ggcaccaaaa    900
tcaacgggac tttccaaaat gtcgtaacaa ctccgcccca ttgacgcaaa tgggcggtag    960
gcgtgtacgg tgggaggtct atataagcag agctcgttta gtgaaccgtc agataactgc   1020
aggtcgacga tatcgcggcc gccaccatgg agttcatccc gacgcaaact ttctataaca   1080
gaaggtacca accccgaccc tggccccac gccctacaat tcaagtaatt agacctagac    1140
cacgtccaca gaggcaggct gggcaactcg cccagctgat ctccgcagtc aacaaattga   1200
ccatgcgcgc ggtacctcaa cagaagcctc gcagaaatcg gaaaaacaag aagcaaaggc   1260
agaagaagca ggcgccgcaa aacgacccaa agcaaaagaa gcaaccacca caaaagaagc   1320
cggctcaaaa gaagaagaaa ccaggccgta gggagagaat gtgcatgaaa attgaaaatg   1380
attgcatctt cgaagtcaag catgaaggca aagtgatggg ctacgcatgc ctggtggggg   1440
ataaagtaat gaaaccagca catgtgaagg gaactatcga caatgccgat ctggctaaac   1500
tggcctttaa gcggtcgtct aaatacgatc ttgaatgtgc acagataccg gtgcacatga   1560
agtctgatgc ctcgaagttt acccacgaga aacccgaggg gtactataac tggcatcacg   1620
gagcagtgca gtattcagga ggccggttca ctatcccgac gggtgcaggc aagccgggag   1680
acagcggcag accgatcttc gacaacaaag gacgggtggt ggccatcgtc ctaggagggg   1740
ccaacgaagg tgcccgcacg gccctctccg tggtgacgtg gaacaaagac atcgtcacaa   1800
aaattacccc tgagggagcc gaagagtgga gcctcgccct cccggtcttg tgcctgttgg   1860
caaacactac attcccctgc tctcagccgc cttgcacacc ctgctgctac gaaaaggaac   1920
cggaaagcac cttgcgcatg cttgaggaca acgtgatgag acccggatac taccagctac   1980
taaaagcatc gctgacttgc tctccccacc gccaaagacg cagtactaag gacaatttta   2040
atgtctataa agccacaaga ccatatctag ctcattgtcc tgactgcgga gaagggcatt   2100
cgtgccacag ccctatcgca ttggagcgca tcagaaatga agcaacggac ggaacgctga   2160
aaatccaggt ctctttgcag atcgggataa agacagatga cagccacgat tggaccaagc   2220
tgcgctatat ggatagccat acgccagcgg acgcggagcg agccggattg cttgtaagga   2280
cttcagcacc gtgcacgatc accgggacca tgggacactt tattctcgcc cgatgcccga   2340
aaggagagac gctgacagtg ggatttacgg acagcagaaa gatcagccac acatgcacac   2400
acccgttcca tcatgaacca cctgtgatag gtagggagag gttccactct cgaccacaac   2460
```

-continued

```
atggtaaaga gttaccttgc agcacgtacg tgcagagcac cgctgccact gctgaggaga   2520
tagaggtgca tatgccccca gatactcctg accgcacgct gatgacgcag cagtctggca   2580
acgtgaagat cacagttaat gggcagacgg tgcggtacaa gtgcaactgc ggtggctccg   2640
gaggaaaccc gaatgccaat cccaacgcga accccaatgc taacccaaat gccaacccaa   2700
acgccaaccc caacgctggt ggatccaacg agggactgac aaccacagac aaagtgatca   2760
ataactgcaa aattgatcag tgccatgctg cagtcactaa tcacaagaat tggcaataca   2820
actccccttt agtcccgcgc aacgctgaac tcggggaccg taaaggaaag atccacatcc   2880
cattcccatt ggcaaacgtg acttgcagag tgccaaaagc aagaaaccct acagtaactt   2940
acggaaaaaa ccaagtcacc atgctgctgt atcctgacca tccgacactc ttgtcttacc   3000
gtaacatggg acaggaacca aattaccacg aggagtgggt gacacacaag aaggaggtta   3060
ccttgaccgt gcctactgag ggtctggagg tcacttgggg caacaacgaa ccatacaagt   3120
actggccgca gatgtctacg aacggtactg ctcatggtca cccacatgag ataatcttgt   3180
actattatga gctgtacccc actatgactg tagtcattgt gtcggtggcc tcgttcgtgc   3240
ttctgtcgat ggtgggcaca gcagtgggaa tgtgtgtgtg cgcacggcgc agatgcatta   3300
caccatatga attaacacca ggagccactg ttcccttcct gctcagcctg ctatgctgcg   3360
tcagaacgac caaggcggcc acatattacg aggctgcggc atatctatgg aacgaacagc   3420
agcccctgtt ctggttgcag gctcttatcc cgctggccgc cttgatcgtc ctgtgcaact   3480
gtctgaaact cttgccatgc tgctgtaaga ccctggcttt tttagccgta atgagcatcg   3540
gtgcccacac tgtgagcgcg tacgaacacg taacagtgat cccgaacacg gtgggagtac   3600
cgtataagac tcttgtcaac agaccgggtt acagccccat ggtgttggag atggagctac   3660
aatcagtcac cttggaacca acactgtcac ttgactacat cacgtgcgag tacaaaactg   3720
tcatcccctc cccgtacgtg aagtgctgtg gtacagcaga gtgcaaggac aagagcctac   3780
cagactacag ctgcaaggtc tttactggag tctacccatt tatgtggggc ggcgcctact   3840
gcttttgcga cgccgaaaat acgcaattga gcgaggcaca tgtagagaaa tctgaatctt   3900
gcaaaacaga gtttgcatcg gcctacagag cccacaccgc atcggcgtcg gcgaagctcc   3960
gcgtccttta ccaaggaaac aacattaccg tagctgccta cgctaacggt gaccatgccg   4020
tcacagtaaa ggacgccaag tttgtcgtgg gcccaatgtc ctccgcctgg acaccttttg   4080
acaacaaaat cgtggtgtac aaaggcgacg tctacaacat ggactaccca ccttttggcg   4140
caggaagacc aggacaattt ggtgacattc aaagtcgtac accggaaagt aaagacgttt   4200
atgccaacac tcagttggta ctacagaggc cagcagcagg cacggtacat gtaccatact   4260
ctcaggcacc atctggcttc aagtattggc tgaaggaacg aggagcatcg ctacagcaca   4320
cggcaccgtt cggttgccag attgcgacaa acccggtaag agctgtaaat tgcgctgtgg   4380
ggaacatacc aatttccatc gacataccgg atgcggcctt tactagggtt gtcgatgcac   4440
cctctgtaac ggacatgtca tgcgaagtac cagcctgcac tcactcctcc gactttgggg   4500
gcgtcgccat catcaaatac acagctagca agaaaggtaa atgtgcagta cattcgatga   4560
ccaacgccgt taccattcga gaagccgacg tagaagtaga ggggaactcc cagctgcaaa   4620
tatccttctc aacagccctg gcaagcgccg agtttcgcgt gcaagtgtgc tccacacaag   4680
tacactgcgc agccgcatgc caccctccaa aggaccacat agtcaattac ccagcatcac   4740
acaccaccct tggggtccag gatatatcca caacggcaat gtcttgggtg cagaagatta   4800
cgggaggagt aggattaatt gttgctgttg ctgccttaat tttaattgtg gtgctatgcg   4860
```

tgtcgtttag caggcactaa ggatctagat ctgctgtgcc ttctagttgc cagccatctg 4920
ttgtttgccc ctcccccgtg ccttccttga ccctggaagg tgccactccc actgtccttt 4980
cctaataaaa tgaggaaatt gcatcgcatt gtctgagtag gtgtcattct attctggggg 5040
gtggggtggg gcaggacagc aagggggagg attgggaaga caatagcagg catgctgggg 5100
atgcggtggg ctctatggct cgagcatggt catagctgtt tcctgtgtga aattgttatc 5160
cgctcacaat tccacacaac atacgagccg gaagcataaa gtgtaaagcc tggggtgcct 5220
aatgagtgag ctaactcaca ttaattgcgt tgcgctcact gcccgctttc cagtcgggaa 5280
acctgtcgtg ccagctgcat taatgaatcg gccaacgcgc ggggagaggc ggtttgcgta 5340
ttgggcgctc ttccgcttcc tcgctcactg actcgctgcg ctcggtcgtt cggctgcggc 5400
gagcggtatc agctcactca aaggcggtaa tacggttatc cacagaatca ggggataacg 5460
caggaaagaa catgtgagca aaaggccagc aaaaggccag gaaccgtaaa aaggccgcgt 5520
tgctggcgtt tttccatagg ctccgccccc ctgacgagca tcacaaaaat cgacgctcaa 5580
gtcagaggtg gcgaaacccg acaggactat aaagatacca ggcgtttccc cctggaagct 5640
ccctcgtgcg ctctcctgtt ccgaccctgc cgcttaccgg atacctgtcc gcctttctcc 5700
cttcgggaag cgtggcgctt tctcatagct cacgctgtag gtatctcagt tcggtgtagg 5760
tcgttcgctc caagctgggc tgtgtgcacg aaccccccgt tcagcccgac cgctgcgcct 5820
tatccggtaa ctatcgtctt gagtccaacc cggtaagaca cgacttatcg ccactggcag 5880
cagccactgg taacaggatt agcagagcga ggtatgtagg cggtgctaca gagttcttga 5940
agtggtggcc taactacggc tacactagaa gaacagtatt tggtatctgc gctctgctga 6000
agccagttac cttcggaaaa agagttggta gctcttgatc cggcaaacaa accaccgctg 6060
gtagcggtgg tttttttgtt tgcaagcagc agattacgcg cagaaaaaaa ggatctcaag 6120
aagatccttt gatcttttct acggggtctg acgctcagtg gaacgaaaac tcacgttaag 6180
ggattttggt catgagatta tcaaaaagga tcttcaccta gatcctttta aattaaaaat 6240
gaagttttaa atcaatctaa agtatatatg agtaaacttg gtctgacagt tagaaaaact 6300
catcgagcat caaatgaaac tgcaatttat tcatatcagg attatcaata ccatattttt 6360
gaaaaagccg tttctgtaat gaaggagaaa actcaccgag gcagttccat aggatggcaa 6420
gatcctggta tcggtctgcg attccgactc gtccaacatc aatacaacct attaatttcc 6480
cctcgtcaaa aataaggtta tcaagtgaga aatcaccatg agtgacgact gaatccggtg 6540
agaatggcaa aagtttatgc atttctttcc agacttgttc aacaggccag ccattacgct 6600
cgtcatcaaa atcactcgca tcaaccaaac cgttattcat tcgtgattgc gcctgagcga 6660
gacgaaatac gcgatcgctg ttaaaaggac aattacaaac aggaatcgaa tgcaaccggc 6720
gcaggaacac tgccagcgca tcaacaatat tttcacctga atcaggatat tcttctaata 6780
cctggaatgc tgttttccca gggatcgcag tggtgagtaa ccatgcatca tcaggagtac 6840
ggataaaatg cttgatggtc ggaagaggca taaattccgt cagccagttt agtctgacca 6900
tctcatctgt aacatcattg gcaacgctac ctttgccatg tttcagaaac aactctggcg 6960
catcgggctt cccatacaat cgatagattg tcgcacctga ttgcccgaca ttatcgcgag 7020
cccatttata cccatataaa tcagcatcca tgttggaatt taatcgcggc ctagagcaag 7080
acgtttcccg ttgaatatgg ctcatactct tcctttttca atattattga agcatttatc 7140
agggttattg tctcatgagc ggatacatat ttgaatgtat ttagaaaaat aaacaaatag 7200
gggttccgcg cacatttccc cgaaaagtgc cacctgacgt ctaagaaacc attattatca 7260
tgacattaac ctataaaaat aggcgtatca cgaggccctt tcgtc 7305

<210> SEQ ID NO 39
<211> LENGTH: 1277
<212> TYPE: PRT
<213> ORGANISM: Artificial Sequence
<220> FEATURE:
<223> OTHER INFORMATION: Synthetic VLP74_15 (CHI VLP 532 NPNAx6) sequence

<400> SEQUENCE: 39

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
```

```
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Asn Pro Asn Ala Asn Pro Asn Ala Asn Pro Asn
    530                 535                 540

Ala Asn Pro Asn Ala Asn Pro Asn Ala Asn Pro Asn Ala Gly Gly Ser
545                 550                 555                 560

Asn Glu Gly Leu Thr Thr Thr Asp Lys Val Ile Asn Asn Cys Lys Ile
                565                 570                 575

Asp Gln Cys His Ala Ala Val Thr Asn His Lys Asn Trp Gln Tyr Asn
            580                 585                 590

Ser Pro Leu Val Pro Arg Asn Ala Glu Leu Gly Asp Arg Lys Gly Lys
        595                 600                 605

Ile His Ile Pro Phe Pro Leu Ala Asn Val Thr Cys Arg Val Pro Lys
    610                 615                 620

Ala Arg Asn Pro Thr Val Thr Tyr Gly Lys Asn Gln Val Thr Met Leu
625                 630                 635                 640

Leu Tyr Pro Asp His Pro Thr Leu Leu Ser Tyr Arg Asn Met Gly Gln
                645                 650                 655

Glu Pro Asn Tyr His Glu Glu Trp Val Thr His Lys Lys Glu Val Thr
            660                 665                 670

Leu Thr Val Pro Thr Glu Gly Leu Glu Val Thr Trp Gly Asn Asn Glu
        675                 680                 685

Pro Tyr Lys Tyr Trp Pro Gln Met Ser Thr Asn Gly Thr Ala His Gly
    690                 695                 700

His Pro His Glu Ile Ile Leu Tyr Tyr Tyr Glu Leu Tyr Pro Thr Met
705                 710                 715                 720

Thr Val Val Ile Val Ser Val Ala Ser Phe Val Leu Leu Ser Met Val
                725                 730                 735

Gly Thr Ala Val Gly Met Cys Val Cys Ala Arg Arg Arg Cys Ile Thr
            740                 745                 750

Pro Tyr Glu Leu Thr Pro Gly Ala Thr Val Pro Phe Leu Leu Ser Leu
        755                 760                 765
```

```
Leu Cys Cys Val Arg Thr Thr Lys Ala Ala Thr Tyr Tyr Glu Ala Ala
    770                 775                 780

Ala Tyr Leu Trp Asn Glu Gln Gln Pro Leu Phe Trp Leu Gln Ala Leu
785                 790                 795                 800

Ile Pro Leu Ala Ala Leu Ile Val Leu Cys Asn Cys Leu Lys Leu Leu
                805                 810                 815

Pro Cys Cys Cys Lys Thr Leu Ala Phe Leu Ala Val Met Ser Ile Gly
            820                 825                 830

Ala His Thr Val Ser Ala Tyr Glu His Val Thr Val Ile Pro Asn Thr
        835                 840                 845

Val Gly Val Pro Tyr Lys Thr Leu Val Asn Arg Pro Gly Tyr Ser Pro
    850                 855                 860

Met Val Leu Glu Met Glu Leu Gln Ser Val Thr Leu Glu Pro Thr Leu
865                 870                 875                 880

Ser Leu Asp Tyr Ile Thr Cys Glu Tyr Lys Thr Val Ile Pro Ser Pro
                885                 890                 895

Tyr Val Lys Cys Cys Gly Thr Ala Glu Cys Lys Asp Lys Ser Leu Pro
            900                 905                 910

Asp Tyr Ser Cys Lys Val Phe Thr Gly Val Tyr Pro Phe Met Trp Gly
        915                 920                 925

Gly Ala Tyr Cys Phe Cys Asp Ala Glu Asn Thr Gln Leu Ser Glu Ala
    930                 935                 940

His Val Glu Lys Ser Glu Ser Cys Lys Thr Glu Phe Ala Ser Ala Tyr
945                 950                 955                 960

Arg Ala His Thr Ala Ser Ala Ser Ala Lys Leu Arg Val Leu Tyr Gln
                965                 970                 975

Gly Asn Asn Ile Thr Val Ala Ala Tyr Ala Asn Gly Asp His Ala Val
            980                 985                 990

Thr Val Lys Asp Ala Lys Phe Val  Val Gly Pro Met Ser  Ser Ala Trp
        995                 1000                1005

Thr Pro  Phe Asp Asn Lys Ile  Val Val Tyr Lys Gly  Asp Val Tyr
    1010                1015                1020

Asn Met  Asp Tyr Pro Pro Phe  Gly Ala Gly Arg Pro  Gly Gln Phe
    1025                1030                1035

Gly Asp  Ile Gln Ser Arg Thr  Pro Glu Ser Lys Asp  Val Tyr Ala
    1040                1045                1050

Asn Thr  Gln Leu Val Leu Gln  Arg Pro Ala Ala Gly  Thr Val His
    1055                1060                1065

Val Pro  Tyr Ser Gln Ala Pro  Ser Gly Phe Lys Tyr  Trp Leu Lys
    1070                1075                1080

Glu Arg  Gly Ala Ser Leu Gln  His Thr Ala Pro Phe  Gly Cys Gln
    1085                1090                1095

Ile Ala  Thr Asn Pro Val Arg  Ala Val Asn Cys Ala  Val Gly Asn
    1100                1105                1110

Ile Pro  Ile Ser Ile Asp Ile  Pro Asp Ala Ala Phe  Thr Arg Val
    1115                1120                1125

Val Asp  Ala Pro Ser Val Thr  Asp Met Ser Cys Glu  Val Pro Ala
    1130                1135                1140

Cys Thr  His Ser Ser Asp Phe  Gly Gly Val Ala Ile  Ile Lys Tyr
    1145                1150                1155

Thr Ala  Ser Lys Lys Gly Lys  Cys Ala Val His Ser  Met Thr Asn
    1160                1165                1170
```

```
Ala Val  Thr Ile Arg Glu Ala  Asp Val Glu Val Glu  Gly Asn Ser
    1175                 1180                 1185

Gln Leu  Gln Ile Ser Phe Ser  Thr Ala Leu Ala Ser  Ala Glu Phe
    1190                 1195                 1200

Arg Val  Gln Val Cys Ser Thr  Gln Val His Cys Ala  Ala Ala Cys
    1205                 1210                 1215

His Pro  Pro Lys Asp His Ile  Val Asn Tyr Pro Ala  Ser His Thr
    1220                 1225                 1230

Thr Leu  Gly Val Gln Asp Ile  Ser Thr Thr Ala Met  Ser Trp Val
    1235                 1240                 1245

Gln Lys  Ile Thr Gly Gly Val  Gly Leu Ile Val Ala  Val Ala Ala
    1250                 1255                 1260

Leu Ile  Leu Ile Val Val Leu  Cys Val Ser Phe Ser  Arg His
    1265                 1270                 1275
```

<210> SEQ ID NO 40
<211> LENGTH: 7533
<212> TYPE: DNA
<213> ORGANISM: Artificial Sequence
<220> FEATURE:
<223> OTHER INFORMATION: Synthetic VLP78_15 (CHI VLP 532 NPNAx25) sequence

<400> SEQUENCE: 40

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt gacgcgtgtt ggcattgatt    420

attgactagt tattaatagt aatcaattac ggggtcatta gttcatagcc catatatgga    480

gttccgcgtt acataactta cggtaaatgg cccgcctggc tgaccgccca acgacccccg    540

cccattgacg tcaataatga cgtatgttcc catagtaacg ccaataggga ctttccattg    600

acgtcaatgg gtggagtatt tacggtaaac tgcccacttg gcagtacatc aagtgtatca    660

tatgccaagt acgcccccta ttgacgtcaa tgacggtaaa tggcccgcct ggcattatgc    720

ccagtacatg accttatggg actttcctac ttggcagtac atctacgtat tagtcatcgc    780

tattaccatg gtgatgcggt tttggcagta catcaatggg cgtggatagc ggtttgactc    840

acggggattt ccaagtctcc accccattga cgtcaatggg agtttgtttt ggcaccaaaa    900

tcaacgggac tttccaaaat gtcgtaacaa ctccgcccca ttgacgcaaa tgggcggtag    960

gcgtgtacgg tgggaggtct atataagcag agctcgttta gtgaaccgtc agataactgc   1020

aggtcgacga tatcgcggcc gccaccatgg agttcatccc gacgcaaact ttctataaca   1080

gaaggtacca accccgaccc tgggccccac gccctacaat tcaagtaatt agacctagac   1140

cacgtccaca gaggcaggct gggcaactcg cccagctgat ctccgcagtc aacaaattga   1200

ccatgcgcgc ggtacctcaa cagaagcctc gcagaaatcg gaaaaacaag aagcaaaggc   1260

agaagaagca ggcgccgcaa aacgacccaa agcaaaagaa gcaaccacca caaaagaagc   1320

cggctcaaaa gaagaagaaa ccaggccgta gggagagaat gtgcatgaaa attgaaaatg   1380

attgcatctt cgaagtcaag catgaaggca aagtgatggg ctacgcatgc ctggtggggg   1440
```

ataaagtaat gaaaccagca catgtgaagg gaactatcga caatgccgat ctggctaaac 1500
tggcctttaa gcggtcgtct aaatacgatc ttgaatgtgc acagataccg gtgcacatga 1560
agtctgatgc ctcgaagttt acccacgaga aacccgaggg gtactataac tggcatcacg 1620
gagcagtgca gtattcagga ggccggttca ctatcccgac gggtgcaggc aagccgggag 1680
acagcggcag accgatcttc gacaacaaag gacgggtggt ggccatcgtc ctaggagggg 1740
ccaacgaagg tgcccgcacg gccctctccg tggtgacgtg gaacaaagac atcgtcacaa 1800
aaattacccc tgagggagcc gaagagtgga gcctcgccct cccggtcttg tgcctgttgg 1860
caaacactac attcccctgc tctcagccgc cttgcacacc ctgctgctac gaaaaggaac 1920
cggaaagcac cttgcgcatg cttgaggaca acgtgatgag acccggatac taccagctac 1980
taaaagcatc gctgacttgc tctccccacc gccaaagacg cagtactaag gacaatttta 2040
atgtctataa agccacaaga ccatatctag ctcattgtcc tgactgcgga gaagggcatt 2100
cgtgccacag ccctatcgca ttggagcgca tcagaaatga agcaacggac ggaacgctga 2160
aaatccaggt ctctttgcag atcgggataa agacagatga cagccacgat tggaccaagc 2220
tgcgctatat ggatagccat acgccagcgg acgcggagcg agccggattg cttgtaagga 2280
cttcagcacc gtgcacgatc accgggacca tgggacactt tattctcgcc cgatgcccga 2340
aaggagagac gctgacagtg ggatttacgg acagcagaaa gatcagccac acatgcacac 2400
acccgttcca tcatgaacca cctgtgatag gtagggagag gttccactct cgaccacaac 2460
atggtaaaga gttaccttgc agcacgtacg tgcagagcac cgctgccact gctgaggaga 2520
tagaggtgca tatgcccccca gatactcctg accgcacgct gatgacgcag cagtctggca 2580
acgtgaagat cacagttaat gggcagacgg tgcggtacaa gtgcaactgc ggtggctccg 2640
gaggaaaccc gaatgccaat cccaacgcga accccaacgc taaccccaac gccaatccga 2700
atgcaaaccc gaacgttgac ccaaacgcca acccgaatgc caatcccaac gcgaacccca 2760
atgctaaccc aaatgccaac ccaaacgcca accccaacgc taatccaaac gccaacccta 2820
acgccaatcc caacgcgaat cctaacgcta atcccaacgc aaatcccaat gctaatccga 2880
acgcgaaccc taatgcaaac cccaacgcca acccgaacgc taacccgaac gctaatccca 2940
acgccggtgg atccaacgag ggactgacaa ccacagacaa agtgatcaat aactgcaaaa 3000
ttgatcagtg ccatgctgca gtcactaatc acaagaattg gcaatacaac tcccctttag 3060
tcccgcgcaa cgctgaactc ggggaccgta aaggaaagat ccacatccca ttcccattgg 3120
caaacgtgac ttgcagagtg ccaaaagcaa gaaaccctac agtaacttac ggaaaaaacc 3180
aagtcaccat gctgctgtat cctgaccatc cgacactctt gtcttaccgt aacatgggac 3240
aggaaccaaa ttaccacgag gagtgggtga cacacaagaa ggaggttacc ttgaccgtgc 3300
ctactgaggg tctggaggtc acttggggca acaacgaacc atacaagtac tggccgcaga 3360
tgtctacgaa cggtactgct catggtcacc cacatgagat aatcttgtac tattatgagc 3420
tgtaccccac tatgactgta gtcattgtgt cggtggcctc gttcgtgctt ctgtcgatgg 3480
tgggcacagc agtgggaatg tgtgtgtgcg cacggcgcag atgcattaca ccatatgaat 3540
taacaccagg agccactgtt cccttcctgc tcagcctgct atgctgcgtc agaacgacca 3600
aggcggccac atattacgag gctgcggcat atctatggaa cgaacagcag cccctgttct 3660
ggttgcaggc tcttatcccg ctggccgcct tgatcgtcct gtgcaactgt ctgaaactct 3720
tgccatgctg ctgtaagacc ctggcttttt tagccgtaat gagcatcggt gcccacactg 3780

-continued

```
tgagcgcgta cgaacacgta acagtgatcc cgaacacggt gggagtaccg tataagactc   3840
ttgtcaacag accgggttac agccccatgg tgttggagat ggagctacaa tcagtcacct   3900
tggaaccaac actgtcactt gactacatca cgtgcgagta caaaactgtc atcccctccc   3960
cgtacgtgaa gtgctgtggt acagcagagt gcaaggacaa gagcctacca gactacagct   4020
gcaaggtctt tactggagtc tacccattta tgtggggcgg cgcctactgc ttttgcgacg   4080
ccgaaaatac gcaattgagc gaggcacatg tagagaaatc tgaatcttgc aaaacagagt   4140
ttgcatcggc ctacagagcc cacaccgcat cggcgtcggc gaagctccgc gtcctttacc   4200
aaggaaacaa cattaccgta gctgcctacg ctaacggtga ccatgccgtc acagtaaagg   4260
acgccaagtt tgtcgtgggc ccaatgtcct ccgcctggac accttttgac aacaaaatcg   4320
tggtgtacaa aggcgacgtc tacaacatgg actacccacc ttttggcgca ggaagaccag   4380
gacaatttgg tgacattcaa agtcgtacac cggaaagtaa agacgtttat gccaacactc   4440
agttggtact acagaggcca gcagcaggca cggtacatgt accatactct caggcaccat   4500
ctggcttcaa gtattggctg aaggaacgag gagcatcgct acagcacacg gcaccgttcg   4560
gttgccagat tgcgacaaac ccggtaagag ctgtaaattg cgctgtgggg aacataccaa   4620
tttccatcga cataccggat gcggccttta ctagggttgt cgatgcaccc tctgtaacgg   4680
acatgtcatg cgaagtacca gcctgcactc actcctccga ctttgggggc gtcgccatca   4740
tcaaatacac agctagcaag aaaggtaaat gtgcagtaca ttcgatgacc aacgccgtta   4800
ccattcgaga agccgacgta gaagtagagg ggaactccca gctgcaaata tccttctcaa   4860
cagccctggc aagcgccgag tttcgcgtgc aagtgtgctc cacacaagta cactgcgcag   4920
ccgcatgcca ccctccaaag gaccacatag tcaattaccc agcatcacac accacccttg   4980
gggtccagga tatatccaca acggcaatgt cttgggtgca gaagattacg ggaggagtag   5040
gattaattgt tgctgttgct gccttaattt taattgtggt gctatgcgtg tcgtttagca   5100
ggcactaagg atctagatct gctgtgcctt ctagttgcca gccatctgtt gtttgcccct   5160
cccccgtgcc ttccttgacc ctggaaggtg ccactcccac tgtcctttcc taataaaatg   5220
aggaaattgc atcgcattgt ctgagtaggt gtcattctat tctggggggt ggggtggggc   5280
aggacagcaa gggggaggat tgggaagaca atagcaggca tgctggggat gcggtgggct   5340
ctatggctcg agcatggtca tagctgtttc ctgtgtgaaa ttgttatccg ctcacaattc   5400
cacacaacat acgagccgga agcataaagt gtaaagcctg gggtgcctaa tgagtgagct   5460
aactcacatt aattgcgttg cgctcactgc ccgctttcca gtcgggaaac ctgtcgtgcc   5520
agctgcatta atgaatcggc caacgcgcgg ggagaggcgg tttgcgtatt gggcgctctt   5580
ccgcttcctc gctcactgac tcgctgcgct cggtcgttcg gctgcggcga gcggtatcag   5640
ctcactcaaa ggcggtaata cggttatcca cagaatcagg ggataacgca ggaaagaaca   5700
tgtgagcaaa aggccagcaa aaggccagga accgtaaaaa ggccgcgttg ctggcgtttt   5760
tccataggct ccgcccccct gacgagcatc acaaaaatcg acgctcaagt cagaggtggc   5820
gaaacccgac aggactataa agataccagg cgtttccccc tggaagctcc ctcgtgcgct   5880
ctcctgttcc gaccctgccg cttaccggat acctgtccgc ctttctccct tcgggaagcg   5940
tggcgctttc tcatagctca cgctgtaggt atctcagttc ggtgtaggtc gttcgctcca   6000
agctgggctg tgtgcacgaa ccccccgttc agcccgaccg ctgcgcctta tccggtaact   6060
atcgtcttga gtccaacccg gtaagacacg acttatcgcc actggcagca gccactggta   6120
acaggattag cagagcgagg tatgtaggcg gtgctacaga gttcttgaag tggtggccta   6180
```

```
actacggcta cactagaaga acagtatttg gtatctgcgc tctgctgaag ccagttacct   6240

tcggaaaaag agttggtagc tcttgatccg gcaaacaaac caccgctggt agcggtggtt   6300

tttttgtttg caagcagcag attacgcgca gaaaaaaagg atctcaagaa gatcctttga   6360

tcttttctac ggggtctgac gctcagtgga acgaaaactc acgttaaggg attttggtca   6420

tgagattatc aaaaaggatc ttcacctaga tccttttaaa ttaaaaatga agttttaaat   6480

caatctaaag tatatatgag taaacttggt ctgacagtta gaaaaactca tcgagcatca   6540

aatgaaactg caatttattc atatcaggat tatcaatacc atatttttga aaaagccgtt   6600

tctgtaatga aggagaaaac tcaccgaggc agttccatag gatggcaaga tcctggtatc   6660

ggtctgcgat tccgactcgt ccaacatcaa tacaacctat taatttcccc tcgtcaaaaa   6720

taaggttatc aagtgagaaa tcaccatgag tgacgactga atccggtgag aatggcaaaa   6780

gtttatgcat ttctttccag acttgttcaa caggccagcc attacgctcg tcatcaaaat   6840

cactcgcatc aaccaaaccg ttattcattc gtgattgcgc ctgagcgaga cgaaatacgc   6900

gatcgctgtt aaaaggacaa ttacaaacag gaatcgaatg caaccggcgc aggaacactg   6960

ccagcgcatc aacaatattt tcacctgaat caggatattc ttctaatacc tggaatgctg   7020

ttttcccagg gatcgcagtg gtgagtaacc atgcatcatc aggagtacgg ataaaatgct   7080

tgatggtcgg aagaggcata aattccgtca gccagtttag tctgaccatc tcatctgtaa   7140

catcattggc aacgctacct ttgccatgtt tcagaaacaa ctctggcgca tcgggcttcc   7200

catacaatcg atagattgtc gcacctgatt gcccgacatt atcgcgagcc catttatacc   7260

catataaatc agcatccatg ttggaattta atcgcggcct agagcaagac gtttcccgtt   7320

gaatatggct catactcttc ctttttcaat attattgaag catttatcag ggttattgtc   7380

tcatgagcgg atacatattt gaatgtattt agaaaaataa acaaataggg gttccgcgca   7440

catttccccg aaaagtgcca cctgacgtct aagaaaccat tattatcatg acattaacct   7500

ataaaaatag gcgtatcacg aggccctttc gtc                                7533
```

<210> SEQ ID NO 41
<211> LENGTH: 1353
<212> TYPE: PRT
<213> ORGANISM: Artificial Sequence
<220> FEATURE:
<223> OTHER INFORMATION: Synthetic VLP78_15 (CHI VLP 532 NPNAx25)
      sequence

<400> SEQUENCE: 41

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110
```

```
Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Asn Pro Asn Ala Asn Pro Asn Ala Asn Pro Asn
```

```
    530                 535                 540

Ala Asn Pro Asn Ala Asn Pro Asn Ala Asn Pro Asn Val Asp Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Ala Asn Pro Asn
            580                 585                 590

Ala Asn Pro Asn Ala Asn Pro Asn Ala Asn Pro Asn Ala Asn Pro Asn
        595                 600                 605

Ala Asn Pro Asn Ala Asn Pro Asn Ala Asn Pro Asn Ala Asn Pro Asn
    610                 615                 620

Ala Asn Pro Asn Ala Asn Pro Asn Ala Gly Gly Ser Asn Glu Gly Leu
625                 630                 635                 640

Thr Thr Thr Asp Lys Val Ile Asn Asn Cys Lys Ile Asp Gln Cys His
                645                 650                 655

Ala Ala Val Thr Asn His Lys Asn Trp Gln Tyr Asn Ser Pro Leu Val
            660                 665                 670

Pro Arg Asn Ala Glu Leu Gly Asp Arg Lys Gly Lys Ile His Ile Pro
        675                 680                 685

Phe Pro Leu Ala Asn Val Thr Cys Arg Val Pro Lys Ala Arg Asn Pro
    690                 695                 700

Thr Val Thr Tyr Gly Lys Asn Gln Val Thr Met Leu Leu Tyr Pro Asp
705                 710                 715                 720

His Pro Thr Leu Leu Ser Tyr Arg Asn Met Gly Gln Glu Pro Asn Tyr
                725                 730                 735

His Glu Glu Trp Val Thr His Lys Lys Glu Val Thr Leu Thr Val Pro
            740                 745                 750

Thr Glu Gly Leu Glu Val Thr Trp Gly Asn Asn Glu Pro Tyr Lys Tyr
        755                 760                 765

Trp Pro Gln Met Ser Thr Asn Gly Thr Ala His Gly His Pro His Glu
    770                 775                 780

Ile Ile Leu Tyr Tyr Tyr Glu Leu Tyr Pro Thr Met Thr Val Val Ile
785                 790                 795                 800

Val Ser Val Ala Ser Phe Val Leu Leu Ser Met Val Gly Thr Ala Val
                805                 810                 815

Gly Met Cys Val Cys Ala Arg Arg Arg Cys Ile Thr Pro Tyr Glu Leu
            820                 825                 830

Thr Pro Gly Ala Thr Val Pro Phe Leu Leu Ser Leu Leu Cys Cys Val
        835                 840                 845

Arg Thr Thr Lys Ala Ala Thr Tyr Tyr Glu Ala Ala Ala Tyr Leu Trp
    850                 855                 860

Asn Glu Gln Gln Pro Leu Phe Trp Leu Gln Ala Leu Ile Pro Leu Ala
865                 870                 875                 880

Ala Leu Ile Val Leu Cys Asn Cys Leu Lys Leu Leu Pro Cys Cys Cys
                885                 890                 895

Lys Thr Leu Ala Phe Leu Ala Val Met Ser Ile Gly Ala His Thr Val
            900                 905                 910

Ser Ala Tyr Glu His Val Thr Val Ile Pro Asn Thr Val Gly Val Pro
        915                 920                 925

Tyr Lys Thr Leu Val Asn Arg Pro Gly Tyr Ser Pro Met Val Leu Glu
    930                 935                 940

Met Glu Leu Gln Ser Val Thr Leu Glu Pro Thr Leu Ser Leu Asp Tyr
945                 950                 955                 960
```

```
Ile Thr Cys Glu Tyr Lys Thr Val Ile Pro Ser Pro Tyr Val Lys Cys
                965                 970                 975

Cys Gly Thr Ala Glu Cys Lys Asp Lys Ser Leu Pro Asp Tyr Ser Cys
            980                 985                 990

Lys Val Phe Thr Gly Val Tyr Pro  Phe Met Trp Gly Gly  Ala Tyr Cys
        995                 1000                 1005

Phe Cys  Asp Ala Glu Asn Thr  Gln Leu Ser Glu Ala  His Val Glu
    1010                 1015                 1020

Lys Ser  Glu Ser Cys Lys Thr  Glu Phe Ala Ser Ala  Tyr Arg Ala
    1025                 1030                 1035

His Thr  Ala Ser Ala Ser Ala  Lys Leu Arg Val Leu  Tyr Gln Gly
    1040                 1045                 1050

Asn Asn  Ile Thr Val Ala Ala  Tyr Ala Asn Gly Asp  His Ala Val
    1055                 1060                 1065

Thr Val  Lys Asp Ala Lys Phe  Val Val Gly Pro Met  Ser Ser Ala
    1070                 1075                 1080

Trp Thr  Pro Phe Asp Asn Lys  Ile Val Val Tyr Lys  Gly Asp Val
    1085                 1090                 1095

Tyr Asn  Met Asp Tyr Pro Pro  Phe Gly Ala Gly Arg  Pro Gly Gln
    1100                 1105                 1110

Phe Gly  Asp Ile Gln Ser Arg  Thr Pro Glu Ser Lys  Asp Val Tyr
    1115                 1120                 1125

Ala Asn  Thr Gln Leu Val Leu  Gln Arg Pro Ala Ala  Gly Thr Val
    1130                 1135                 1140

His Val  Pro Tyr Ser Gln Ala  Pro Ser Gly Phe Lys  Tyr Trp Leu
    1145                 1150                 1155

Lys Glu  Arg Gly Ala Ser Leu  Gln His Thr Ala Pro  Phe Gly Cys
    1160                 1165                 1170

Gln Ile  Ala Thr Asn Pro Val  Arg Ala Val Asn Cys  Ala Val Gly
    1175                 1180                 1185

Asn Ile  Pro Ile Ser Ile Asp  Ile Pro Asp Ala Ala  Phe Thr Arg
    1190                 1195                 1200

Val Val  Asp Ala Pro Ser Val  Thr Asp Met Ser Cys  Glu Val Pro
    1205                 1210                 1215

Ala Cys  Thr His Ser Ser Asp  Phe Gly Gly Val Ala  Ile Ile Lys
    1220                 1225                 1230

Tyr Thr  Ala Ser Lys Lys Gly  Lys Cys Ala Val His  Ser Met Thr
    1235                 1240                 1245

Asn Ala  Val Thr Ile Arg Glu  Ala Asp Val Glu Val  Glu Gly Asn
    1250                 1255                 1260

Ser Gln  Leu Gln Ile Ser Phe  Ser Thr Ala Leu Ala  Ser Ala Glu
    1265                 1270                 1275

Phe Arg  Val Gln Val Cys Ser  Thr Gln Val His Cys  Ala Ala Ala
    1280                 1285                 1290

Cys His  Pro Pro Lys Asp His  Ile Val Asn Tyr Pro  Ala Ser His
    1295                 1300                 1305

Thr Thr  Leu Gly Val Gln Asp  Ile Ser Thr Thr Ala  Met Ser Trp
    1310                 1315                 1320

Val Gln  Lys Ile Thr Gly Gly  Val Gly Leu Ile Val  Ala Val Ala
    1325                 1330                 1335

Ala Leu  Ile Leu Ile Val Val  Leu Cys Val Ser Phe  Ser Arg His
    1340                 1345                 1350
```

<210> SEQ ID NO 42
<211> LENGTH: 7329
<212> TYPE: DNA
<213> ORGANISM: Artificial Sequence
<220> FEATURE:
<223> OTHER INFORMATION: Synthetic VLP74_25 (VEEV VLP 519 NPNAx6) sequence

<400> SEQUENCE: 42
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt gacgcgtgtt ggcattgatt 420
attgactagt tattaatagt aatcaattac ggggtcatta gttcatagcc catatatgga 480
gttccgcgtt acataactta cggtaaatgg cccgcctggc tgaccgccca acgacccccg 540
cccattgacg tcaataatga cgtatgttcc catagtaacg ccaataggga ctttccattg 600
acgtcaatgg gtggagtatt tacggtaaac tgcccacttg gcagtacatc aagtgtatca 660
tatgccaagt acgcccccta ttgacgtcaa tgacggtaaa tggcccgcct ggcattatgc 720
ccagtacatg accttatggg actttcctac ttggcagtac atctacgtat tagtcatcgc 780
tattaccatg gtgatgcggt tttggcagta catcaatggg cgtggatagc ggtttgactc 840
acggggattt ccaagtctcc accccattga cgtcaatggg agtttgtttt ggcaccaaaa 900
tcaacgggac tttccaaaat gtcgtaacaa ctccgcccca ttgacgcaaa tgggcggtag 960
gcgtgtacgg tgggaggtct atataagcag agctcgttta gtgaaccgtc agataactgc 1020
aggtcgacga tatcgcggcc gccaccatgt tcccgttcca gccaatgtat ccgatgcagc 1080
caatgcccta tcgcaacccg ttcgcggccc cgcgcaggcc ctggttcccc agaaccgacc 1140
cttttctggc gatgcaggtg caggaattaa cccgctcgat ggctaacctg acgttcaagc 1200
aacgccggga cgcgccacct gaggggccat ccgctaataa accgaagaag gaggcctcgc 1260
aaaaacagaa agggggaggc caagggaaga agaagaagaa ccaagggaag aagaaggcta 1320
agacagggcc gcctaatccg aaggcacaga atggaaacaa gaagaagacc aacaagaaac 1380
caggcaagag acagcgcatg gtcatgaaat tggaatctga caagacgttc ccaatcatgt 1440
tggaagggaa gataaacggc tacgcttgtg tggtcggagg gaagttattc aggccgatgc 1500
atgtggaagg caagatcgac aacgacgttc tggccgcgct taagacgaag aaagcatcca 1560
aatacgatct tgagtatgca gatgtgccac agaacatgcg ggccgataca ttcaaataca 1620
cccatgagaa accccaaggc tattacagct ggcatcatgg agcagtccaa tatgaaaatg 1680
ggcgtttcac ggtgccgaaa ggagttgggg ccaagggaga cagcggacga cccattctgg 1740
ataaccaggg acgggtggtc gctattgtgc tgggaggtgt gaatgaagga tctaggacag 1800
ccctttcagt cgtcatgtgg aacgagaagg gagttaccgt gaagtatact ccagagaact 1860
gcgagcaatg gtcactagtg accaccatgt gtctgctcgc caatgtgacg ttcccatgtg 1920
ctcaaccacc aatttgctac gacagaaaac cagcagagac tttggccatg ctcagcgtta 1980
acgttgacaa cccgggctac gatgagctgc tggaagcagc tgttaagtgc cccggaagga 2040

-continued

```
aaaggagatc caccgaggag ctgtttaatg agtataagct aacgcgccct tacatggcca   2100
gatgcatcag atgtgcagtt gggagctgcc atagtccaat agcaatcgag gcagtaaaga   2160
gcgacgggca cgacggttat gttagacttc agacttcctc gcagtatggc ctggattcct   2220
ccggcaactt aaagggcagg accatgcggt atgacatgca cgggaccatt aaagagatac   2280
cactacatca agtgtcactc tatacatctc gcccgtgtca cattgtggat gggcacggtt   2340
atttcctgct tgccaggtgc ccggcagggg actccatcac catggaattt aagaaagatt   2400
ccgtcagaca ctcctgctcg gtgccgtatg aagtgaaatt taatcctgta ggcagagaac   2460
tctatactca tcccccagaa cacggagtag agcaagcgtg ccaagtctac gcacatgatg   2520
cacagaacag aggagcttat gtcgagatgc acctcccggg ctcagaagtg gacagcagtt   2580
tggtttcctt gagcggcagt tccggaggaa acccgaatgc caatcccaac gcgaacccca   2640
atgctaaccc aaatgccaac ccaaacgcca accccaacgc tggtggatcc tcagtcaccg   2700
tgacacctcc tgatgggact agcgccctgg tggaatgcga gtgtggcggc acaaagatct   2760
ccgagaccat caacaagaca aaacagttca gccagtgcac aaagaaggag cagtgcagag   2820
catatcggct gcagaacgat aagtgggtgt ataattctga caaactgccc aaagcagcgg   2880
gagccacctt aaaaggaaaa ctgcatgtcc cattcttgct ggcagacggc aaatgcaccg   2940
tgcctctagc accagaacct atgataacct tcggtttcag atcagtgtca ctgaaactgc   3000
accctaagaa tcccacatat ctaatcaccc gccaacttgc tgatgagcct cactacacgc   3060
acgagctcat atctgaacca gctgttagga attttaccgt caccgaaaaa gggtgggagt   3120
ttgtatgggg aaaccacccg ccgaaaaggt tttgggcaca ggaaacagca cccggaaatc   3180
cacatgggct accgcacgag gtgataactc attattacca cagataccct atgtccacca   3240
tcctgggttt gtcaatttgt gccgccattg caaccgtttc cgttgcagcg tctacctggc   3300
tgttttgcag atcaagagtt gcgtgcctaa ctccttaccg gctaacacct aacgctagga   3360
taccattttg tctggctgtg ctttgctgcg cccgcactgc ccgggccgag accacctggg   3420
agtccttgga tcacctatgg aacaataacc aacagatgtt ctggattcaa ttgctgatcc   3480
ctctggccgc cttgatcgta gtgactcgcc tgctcaggtg cgtgtgctgt gtcgtgcctt   3540
ttttagtcat ggccggcgcc gcaggcgccg gcgcctacga gcacgcgacc acgatgccga   3600
gccaagcggg aatctcgtat aacactatag tcaacagagc aggctacgca ccactcccta   3660
tcagcataac accaacaaag atcaagctga tacctacagt gaacttggag tacgtcacct   3720
gccactacaa aacaggaatg gattcaccag ccatcaaatg ctgcggatct caggaatgca   3780
ctccaactta caggcctgat gaacagtgca aagtcttcac aggggtttac ccgttcatgt   3840
ggggtggtgc atattgcttt tgcgacactg agaacaccca agtcagcaag gcctacgtaa   3900
tgaaatctga cgactgcctt gcggatcatg ctgaagcata taaagcgcac acagcctcag   3960
tgcaggcgtt cctcaacatc acagtgggag aacactctat tgtgactacc gtgtatgtga   4020
atggagaaac tcctgtgaat ttcaatgggg tcaaaataac tgcaggtccg ctttccacag   4080
cttggacacc ctttgatcgc aaaatcgtgc agtatgccgg ggagatatat aattatgatt   4140
ttcctgagta tggggcagga caaccaggag catttggaga tatacaatcc agaacagtct   4200
caagctctga tctgtatgcc aataccaacc tagtgctgca gagacccaaa gcaggagcga   4260
tccacgtgcc atacactcag gcaccttcgg gttttgagca atggaagaaa gataaagctc   4320
catcattgaa atttaccgcc cctttcggat gcgaaatata tacaaacccc attcgcgccg   4380
aaaactgtgc tgtagggtca attccattag cctttgacat tcccgacgcc ttgttcacca   4440
```

```
gggtgtcaga aacaccgaca ctttcagcgg ccgaatgcac tcttaacgag tgcgtgtatt   4500
cttccgactt tggtgggatc gccacggtca agtactcggc cagcaagtca ggcaagtgcg   4560
cagtccatgt gccatcaggg actgctaccc taaaagaagc agcagtcgag ctaaccgagc   4620
aagggtcggc gactatccat ttctcgaccg caaatatcca cccggagttc aggctccaaa   4680
tatgcacatc atatgttacg tgcaaaggtg attgtcaccc cccgaaagac catattgtga   4740
cacaccctca gtatcacgcc caaacattta cagccgcggt gtcaaaaacc gcgtggacgt   4800
ggttaacatc cctgctggga ggatcagccg taattattat aattggcttg gtgctggcta   4860
ctattgtggc catgtacgtg ctgaccaacc agaaacataa ttaaggatct agatctgctg   4920
tgccttctag ttgccagcca tctgttgttt gcccctcccc cgtgccttcc ttgaccctgg   4980
aaggtgccac tcccactgtc ctttcctaat aaaatgagga aattgcatcg cattgtctga   5040
gtaggtgtca ttctattctg gggggtgggg tggggcagga cagcaagggg gaggattggg   5100
aagacaatag caggcatgct ggggatgcgg tgggctctat ggctcgagca tggtcatagc   5160
tgtttcctgt gtgaaattgt tatccgctca caattccaca caacatacga gccggaagca   5220
taaagtgtaa agcctggggt gcctaatgag tgagctaact cacattaatt gcgttgcgct   5280
cactgcccgc tttccagtcg ggaaacctgt cgtgccagct gcattaatga atcggccaac   5340
gcgcggggag aggcggtttg cgtattgggc gctcttccgc ttcctcgctc actgactcgc   5400
tgcgctcggt cgttcggctg cggcgagcgg tatcagctca ctcaaaggcg gtaatacggt   5460
tatccacaga atcaggggat aacgcaggaa agaacatgtg agcaaaaggc cagcaaaagg   5520
ccaggaaccg taaaaaggcc gcgttgctgg cgtttttcca taggctccgc ccccctgacg   5580
agcatcacaa aaatcgacgc tcaagtcaga ggtggcgaaa cccgacagga ctataaagat   5640
accaggcgtt tccccctgga agctccctcg tgcgctctcc tgttccgacc ctgccgctta   5700
ccggatacct gtccgccttt ctcccttcgg gaagcgtggc gctttctcat agctcacgct   5760
gtaggtatct cagttcggtg taggtcgttc gctccaagct gggctgtgtg cacgaacccc   5820
ccgttcagcc cgaccgctgc gccttatccg gtaactatcg tcttgagtcc aacccggtaa   5880
gacacgactt atcgccactg gcagcagcca ctggtaacag gattagcaga gcgaggtatg   5940
taggcggtgc tacagagttc ttgaagtggt ggcctaacta cggctacact agaagaacag   6000
tatttggtat ctgcgctctg ctgaagccag ttaccttcgg aaaaagagtt ggtagctctt   6060
gatccggcaa acaaaccacc gctggtagcg gtggtttttt tgtttgcaag cagcagatta   6120
cgcgcagaaa aaaaggatct caagaagatc ctttgatctt ttctacgggg tctgacgctc   6180
agtggaacga aaactcacgt taagggattt tggtcatgag attatcaaaa aggatcttca   6240
cctagatcct tttaaattaa aaatgaagtt ttaaatcaat ctaaagtata tatgagtaaa   6300
cttggtctga cagttagaaa aactcatcga gcatcaaatg aaactgcaat ttattcatat   6360
caggattatc aataccatat ttttgaaaaa gccgtttctg taatgaagga gaaaactcac   6420
cgaggcagtt ccataggatg gcaagatcct ggtatcggtc tgcgattccg actcgtccaa   6480
catcaataca acctattaat ttcccctcgt caaaaataag gttatcaagt gagaaatcac   6540
catgagtgac gactgaatcc ggtgagaatg gcaaaagttt atgcatttct ttccagactt   6600
gttcaacagg ccagccatta cgctcgtcat caaaatcact cgcatcaacc aaaccgttat   6660
tcattcgtga ttgcgcctga gcgagacgaa atacgcgatc gctgttaaaa ggacaattac   6720
aaacaggaat cgaatgcaac cggcgcagga acactgccag cgcatcaaca atattttcac   6780
```

```
ctgaatcagg atattcttct aatacctgga atgctgtttt cccagggatc gcagtggtga   6840

gtaaccatgc atcatcagga gtacggataa aatgcttgat ggtcggaaga ggcataaatt   6900

ccgtcagcca gtttagtctg accatctcat ctgtaacatc attggcaacg ctacctttgc   6960

catgtttcag aaacaactct ggcgcatcgg gcttcccata caatcgatag attgtcgcac   7020

ctgattgccc gacattatcg cgagcccatt tatacccata taaatcagca tccatgttgg   7080

aatttaatcg cggcctagag caagacgttt cccgttgaat atggctcata ctcttccttt   7140

ttcaatatta ttgaagcatt tatcagggtt attgtctcat gagcggatac atatttgaat   7200

gtatttagaa aaataaacaa ataggggttc cgcgcacatt tccccgaaaa gtgccacctg   7260

acgtctaaga aaccattatt atcatgacat taacctataa aaataggcgt atcacgaggc   7320

cctttcgtc                                                           7329
```

<210> SEQ ID NO 43
<211> LENGTH: 1285
<212> TYPE: PRT
<213> ORGANISM: Artificial Sequence
<220> FEATURE:
<223> OTHER INFORMATION: Synthetic VLP74_25 (VEEV VLP 519 NPNAx6) sequence

<400> SEQUENCE: 43

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255
```

-continued

```
Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Asn Pro Asn Ala Asn Pro Asn
        515                 520                 525

Ala Asn Pro Asn Ala Asn Pro Asn Ala Asn Pro Asn Ala Asn Pro Asn
    530                 535                 540

Ala Gly Gly Ser Ser Val Thr Val Thr Pro Pro Asp Gly Thr Ser Ala
545                 550                 555                 560

Leu Val Glu Cys Glu Cys Gly Gly Thr Lys Ile Ser Glu Thr Ile Asn
                565                 570                 575

Lys Thr Lys Gln Phe Ser Gln Cys Thr Lys Lys Glu Gln Cys Arg Ala
            580                 585                 590

Tyr Arg Leu Gln Asn Asp Lys Trp Val Tyr Asn Ser Asp Lys Leu Pro
        595                 600                 605

Lys Ala Ala Gly Ala Thr Leu Lys Gly Lys Leu His Val Pro Phe Leu
    610                 615                 620

Leu Ala Asp Gly Lys Cys Thr Val Pro Leu Ala Pro Glu Pro Met Ile
625                 630                 635                 640

Thr Phe Gly Phe Arg Ser Val Ser Leu Lys Leu His Pro Lys Asn Pro
                645                 650                 655

Thr Tyr Leu Ile Thr Arg Gln Leu Ala Asp Glu Pro His Tyr Thr His
            660                 665                 670

Glu Leu Ile Ser Glu Pro Ala Val Arg Asn Phe Thr Val Thr Glu Lys
```

```
        675                 680                 685

Gly Trp Glu Phe Val Trp Gly Asn His Pro Pro Lys Arg Phe Trp Ala
    690                 695                 700

Gln Glu Thr Ala Pro Gly Asn Pro His Gly Leu Pro His Glu Val Ile
705                 710                 715                 720

Thr His Tyr Tyr His Arg Tyr Pro Met Ser Thr Ile Leu Gly Leu Ser
                725                 730                 735

Ile Cys Ala Ala Ile Ala Thr Val Ser Val Ala Ala Ser Thr Trp Leu
            740                 745                 750

Phe Cys Arg Ser Arg Val Ala Cys Leu Thr Pro Tyr Arg Leu Thr Pro
        755                 760                 765

Asn Ala Arg Ile Pro Phe Cys Leu Ala Val Leu Cys Cys Ala Arg Thr
    770                 775                 780

Ala Arg Ala Glu Thr Thr Trp Glu Ser Leu Asp His Leu Trp Asn Asn
785                 790                 795                 800

Asn Gln Gln Met Phe Trp Ile Gln Leu Leu Ile Pro Leu Ala Ala Leu
                805                 810                 815

Ile Val Val Thr Arg Leu Leu Arg Cys Val Cys Cys Val Val Pro Phe
            820                 825                 830

Leu Val Met Ala Gly Ala Ala Gly Ala Gly Ala Tyr Glu His Ala Thr
        835                 840                 845

Thr Met Pro Ser Gln Ala Gly Ile Ser Tyr Asn Thr Ile Val Asn Arg
    850                 855                 860

Ala Gly Tyr Ala Pro Leu Pro Ile Ser Ile Thr Pro Thr Lys Ile Lys
865                 870                 875                 880

Leu Ile Pro Thr Val Asn Leu Glu Tyr Val Thr Cys His Tyr Lys Thr
                885                 890                 895

Gly Met Asp Ser Pro Ala Ile Lys Cys Cys Gly Ser Gln Glu Cys Thr
            900                 905                 910

Pro Thr Tyr Arg Pro Asp Glu Gln Cys Lys Val Phe Thr Gly Val Tyr
        915                 920                 925

Pro Phe Met Trp Gly Gly Ala Tyr Cys Phe Cys Asp Thr Glu Asn Thr
    930                 935                 940

Gln Val Ser Lys Ala Tyr Val Met Lys Ser Asp Asp Cys Leu Ala Asp
945                 950                 955                 960

His Ala Glu Ala Tyr Lys Ala His Thr Ala Ser Val Gln Ala Phe Leu
                965                 970                 975

Asn Ile Thr Val Gly Glu His Ser Ile Val Thr Thr Val Tyr Val Asn
            980                 985                 990

Gly Glu Thr Pro Val Asn Phe Asn  Gly Val Lys Ile Thr  Ala Gly Pro
        995                 1000                1005

Leu Ser  Thr Ala Trp Thr Pro  Phe Asp Arg Lys Ile  Val Gln Tyr
    1010                 1015                 1020

Ala Gly  Glu Ile Tyr Asn Tyr  Asp Phe Pro Glu Tyr  Gly Ala Gly
    1025                 1030                 1035

Gln Pro  Gly Ala Phe Gly Asp  Ile Gln Ser Arg Thr  Val Ser Ser
    1040                 1045                 1050

Ser Asp  Leu Tyr Ala Asn Thr  Asn Leu Val Leu Gln  Arg Pro Lys
    1055                 1060                 1065

Ala Gly  Ala Ile His Val Pro  Tyr Thr Gln Ala Pro  Ser Gly Phe
    1070                 1075                 1080

Glu Gln  Trp Lys Lys Asp Lys  Ala Pro Ser Leu Lys  Phe Thr Ala
    1085                 1090                 1095
```

```
Pro Phe  Gly Cys Glu Ile Tyr  Thr Asn Pro Ile Arg  Ala Glu Asn
    1100                 1105                 1110

Cys Ala  Val Gly Ser Ile Pro  Leu Ala Phe Asp Ile  Pro Asp Ala
    1115                 1120                 1125

Leu Phe  Thr Arg Val Ser Glu  Thr Pro Thr Leu Ser  Ala Ala Glu
    1130                 1135                 1140

Cys Thr  Leu Asn Glu Cys Val  Tyr Ser Ser Asp Phe  Gly Gly Ile
    1145                 1150                 1155

Ala Thr  Val Lys Tyr Ser Ala  Ser Lys Ser Gly Lys  Cys Ala Val
    1160                 1165                 1170

His Val  Pro Ser Gly Thr Ala  Thr Leu Lys Glu Ala  Ala Val Glu
    1175                 1180                 1185

Leu Thr  Glu Gln Gly Ser Ala  Thr Ile His Phe Ser  Thr Ala Asn
    1190                 1195                 1200

Ile His  Pro Glu Phe Arg Leu  Gln Ile Cys Thr Ser  Tyr Val Thr
    1205                 1210                 1215

Cys Lys  Gly Asp Cys His Pro  Pro Lys Asp His Ile  Val Thr His
    1220                 1225                 1230

Pro Gln  Tyr His Ala Gln Thr  Phe Thr Ala Ala Val  Ser Lys Thr
    1235                 1240                 1245

Ala Trp  Thr Trp Leu Thr Ser  Leu Leu Gly Gly Ser  Ala Val Ile
    1250                 1255                 1260

Ile Ile  Ile Gly Leu Val Leu  Ala Thr Ile Val Ala  Met Tyr Val
    1265                 1270                 1275

Leu Thr  Asn Gln Lys His Asn
    1280                 1285


<210> SEQ ID NO 44
<211> LENGTH: 20
<212> TYPE: PRT
<213> ORGANISM: Plasmodium falciparum

<400> SEQUENCE: 44

Glu Tyr Leu Asn Lys Ile Gln Asn Ser Leu Ser Thr Glu Trp Ser Pro
1               5                   10                  15

Cys Ser Val Thr
            20


<210> SEQ ID NO 45
<211> LENGTH: 20
<212> TYPE: PRT
<213> ORGANISM: Plasmodium yoelii

<400> SEQUENCE: 45

Tyr Asn Arg Asn Ile Val Asn Arg Leu Leu Gly Asp Ala Leu Asn Gly
1               5                   10                  15

Pro Glu Glu Lys
            20


<210> SEQ ID NO 46
<211> LENGTH: 30
<212> TYPE: PRT
<213> ORGANISM: Artificial Sequence
<220> FEATURE:
<223> OTHER INFORMATION: Synthetic VLP74 insert

<400> SEQUENCE: 46

Ser Gly Gly Asn Pro Asn Ala Asn Pro Asn Ala Asn Pro Asn Ala Asn
```

```
1               5                   10                  15

Pro Asn Ala Asn Pro Asn Ala Asn Pro Asn Ala Gly Gly Ser
            20                  25                  30


<210> SEQ ID NO 47
<211> LENGTH: 90
<212> TYPE: DNA
<213> ORGANISM: Artificial Sequence
<220> FEATURE:
<223> OTHER INFORMATION: Synthetic VLP74 insert

<400> SEQUENCE: 47

tccggaggaa acccgaatgc caatcccaac gcgaacccca atgctaaccc aaatgccaac     60

ccaaacgcca accccaacgc tggtggatcc                                      90


<210> SEQ ID NO 48
<211> LENGTH: 106
<212> TYPE: PRT
<213> ORGANISM: Artificial Sequence
<220> FEATURE:
<223> OTHER INFORMATION: Synthetic VLP78 insert

<400> SEQUENCE: 48

Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Val Asp Pro Asn Ala Asn
            20                  25                  30

Pro Asn Ala Asn Pro Asn Ala Asn Pro Asn Ala Asn Pro Asn Ala Asn
        35                  40                  45

Pro Asn Ala Asn Pro Asn Ala Asn Pro Asn Ala Asn Pro Asn Ala Asn
    50                  55                  60

Pro Asn Ala Asn Pro Asn Ala Asn Pro Asn Ala Asn Pro Asn Ala Asn
65                  70                  75                  80

Pro Asn Ala Asn Pro Asn Ala Asn Pro Asn Ala Asn Pro Asn Ala Asn
                85                  90                  95

Pro Asn Ala Asn Pro Asn Ala Gly Gly Ser
            100                 105


<210> SEQ ID NO 49
<211> LENGTH: 318
<212> TYPE: DNA
<213> ORGANISM: Artificial Sequence
<220> FEATURE:
<223> OTHER INFORMATION: Synthetic VLP74 insert

<400> SEQUENCE: 49

tccggaggaa acccgaatgc caatcccaac gcgaacccca acgctaaccc caacgccaat     60

ccgaatgcaa acccgaacgt tgacccaaac gccaacccga atgccaatcc caacgcgaac    120

cccaatgcta acccaaatgc caacccaaac gccaacccca acgctaatcc aaacgccaac    180

cctaacgcca atcccaacgc gaatcctaac gctaatccca acgcaaatcc caatgctaat    240

ccgaacgcga accctaatgc aaaccccaac gccaacccga acgctaaccc gaacgctaat    300

cccaacgccg gtggatcc                                                  318


<210> SEQ ID NO 50
<211> LENGTH: 452
<212> TYPE: PRT
<213> ORGANISM: Artificial Sequence
<220> FEATURE:
<223> OTHER INFORMATION: Synthetic CHIKV E2-74 fusion protein
```

<400> SEQUENCE: 50

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Gly Gly
        195                 200                 205

Asn Pro Asn Ala Asn Pro Asn Ala Asn Pro Asn Ala Asn Pro Asn Ala
    210                 215                 220

Asn Pro Asn Ala Asn Pro Asn Ala Gly Gly Ser Asn Glu Gly Leu Thr
225                 230                 235                 240

Thr Thr Asp Lys Val Ile Asn Asn Cys Lys Ile Asp Gln Cys His Ala
                245                 250                 255

Ala Val Thr Asn His Lys Asn Trp Gln Tyr Asn Ser Pro Leu Val Pro
            260                 265                 270

Arg Asn Ala Glu Leu Gly Asp Arg Lys Gly Lys Ile His Ile Pro Phe
        275                 280                 285

Pro Leu Ala Asn Val Thr Cys Arg Val Pro Lys Ala Arg Asn Pro Thr
    290                 295                 300

Val Thr Tyr Gly Lys Asn Gln Val Thr Met Leu Leu Tyr Pro Asp His
305                 310                 315                 320

Pro Thr Leu Leu Ser Tyr Arg Asn Met Gly Gln Glu Pro Asn Tyr His
                325                 330                 335

Glu Glu Trp Val Thr His Lys Lys Glu Val Thr Leu Thr Val Pro Thr
            340                 345                 350

Glu Gly Leu Glu Val Thr Trp Gly Asn Asn Glu Pro Tyr Lys Tyr Trp
        355                 360                 365

Pro Gln Met Ser Thr Asn Gly Thr Ala His Gly His Pro His Glu Ile
    370                 375                 380

Ile Leu Tyr Tyr Tyr Glu Leu Tyr Pro Thr Met Thr Val Val Ile Val
385                 390                 395                 400

Ser Val Ala Ser Phe Val Leu Leu Ser Met Val Gly Thr Ala Val Gly
```

```
                405                 410                 415

Met Cys Val Cys Ala Arg Arg Arg Cys Ile Thr Pro Tyr Glu Leu Thr
            420                 425                 430

Pro Gly Ala Thr Val Pro Phe Leu Leu Ser Leu Leu Cys Cys Val Arg
        435                 440                 445

Thr Thr Lys Ala
    450


<210> SEQ ID NO 51
<211> LENGTH: 439
<212> TYPE: PRT
<213> ORGANISM: Artificial Sequence
<220> FEATURE:
<223> OTHER INFORMATION: Synthetic CHIKV E1

<400> SEQUENCE: 51

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
    290                 295                 300

Ala Cys Thr His Ser Ser Asp Phe Gly Gly Val Ala Ile Ile Lys Tyr
```

305 310 315 320

Thr Ala Ser Lys Lys Gly Lys Cys Ala Val His Ser Met Thr Asn Ala
325 330 335

Val Thr Ile Arg Glu Ala Asp Val Glu Val Glu Gly Asn Ser Gln Leu
340 345 350

Gln Ile Ser Phe Ser Thr Ala Leu Ala Ser Ala Glu Phe Arg Val Gln
355 360 365

Val Cys Ser Thr Gln Val His Cys Ala Ala Ala Cys His Pro Pro Lys
370 375 380

Asp His Ile Val Asn Tyr Pro Ala Ser His Thr Thr Leu Gly Val Gln
385 390 395 400

Asp Ile Ser Thr Thr Ala Met Ser Trp Val Gln Lys Ile Thr Gly Gly
405 410 415

Val Gly Leu Ile Val Ala Val Ala Ala Leu Ile Leu Ile Val Val Leu
420 425 430

Cys Val Ser Phe Ser Arg His
435

<210> SEQ ID NO 52
<211> LENGTH: 261
<212> TYPE: PRT
<213> ORGANISM: Artificial Sequence
<220> FEATURE:
<223> OTHER INFORMATION: Synthetic CHIKV capsid

<400> SEQUENCE: 52

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu

```
225                 230                 235                 240

Ser Val Val Thr Trp Asn Lys Asp Ile Val Thr Lys Ile Thr Pro Glu
                245                 250                 255

Gly Ala Glu Glu Trp
            260


<210> SEQ ID NO 53
<211> LENGTH: 453
<212> TYPE: PRT
<213> ORGANISM: Artificial Sequence
<220> FEATURE:
<223> OTHER INFORMATION: Synthetic VEEV E2-74 fusion protein

<400> SEQUENCE: 53

Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Arg His Ser Cys Ser Val Pro Tyr Glu
        115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Ser Gly Gly Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Ala Gly Gly Ser Ser Val Thr Val Thr Pro Pro Asp Gly Thr
    210                 215                 220

Ser Ala Leu Val Glu Cys Glu Cys Gly Gly Thr Lys Ile Ser Glu Thr
225                 230                 235                 240

Ile Asn Lys Thr Lys Gln Phe Ser Gln Cys Thr Lys Lys Glu Gln Cys
                245                 250                 255

Arg Ala Tyr Arg Leu Gln Asn Asp Lys Trp Val Tyr Asn Ser Asp Lys
            260                 265                 270

Leu Pro Lys Ala Ala Gly Ala Thr Leu Lys Gly Lys Leu His Val Pro
        275                 280                 285

Phe Leu Leu Ala Asp Gly Lys Cys Thr Val Pro Leu Ala Pro Glu Pro
    290                 295                 300

Met Ile Thr Phe Gly Phe Arg Ser Val Ser Leu Lys Leu His Pro Lys
305                 310                 315                 320

Asn Pro Thr Tyr Leu Ile Thr Arg Gln Leu Ala Asp Glu Pro His Tyr
```

```
                325                 330                 335

Thr His Glu Leu Ile Ser Glu Pro Ala Val Arg Asn Phe Thr Val Thr
            340                 345                 350

Glu Lys Gly Trp Glu Phe Val Trp Gly Asn His Pro Pro Lys Arg Phe
        355                 360                 365

Trp Ala Gln Glu Thr Ala Pro Gly Asn Pro His Gly Leu Pro His Glu
    370                 375                 380

Val Ile Thr His Tyr Tyr His Arg Tyr Pro Met Ser Thr Ile Leu Gly
385                 390                 395                 400

Leu Ser Ile Cys Ala Ala Ile Ala Thr Val Ser Val Ala Ala Ser Thr
                405                 410                 415

Trp Leu Phe Cys Arg Ser Arg Val Ala Cys Leu Thr Pro Tyr Arg Leu
            420                 425                 430

Thr Pro Asn Ala Arg Ile Pro Phe Cys Leu Ala Val Leu Cys Cys Ala
        435                 440                 445

Arg Thr Ala Arg Ala
    450


<210> SEQ ID NO 54
<211> LENGTH: 442
<212> TYPE: PRT
<213> ORGANISM: Artificial Sequence
<220> FEATURE:
<223> OTHER INFORMATION: Synthetic VEEV E1

<400> SEQUENCE: 54

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Val Tyr Val Asn Gly Glu Thr Pro Val Asn Phe Asn Gly Val Lys
145                 150                 155                 160

Ile Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
            180                 185                 190

Gly Ala Gly Gln Pro Gly Ala Phe Gly Asp Ile Gln Ser Arg Thr Val
        195                 200                 205

Ser Ser Ser Asp Leu Tyr Ala Asn Thr Asn Leu Val Leu Gln Arg Pro
    210                 215                 220

Lys Ala Gly Ala Ile His Val Pro Tyr Thr Gln Ala Pro Ser Gly Phe
```

```
225                 230                 235                 240

Glu Gln Trp Lys Lys Asp Lys Ala Pro Ser Leu Lys Phe Thr Ala Pro
                245                 250                 255

Phe Gly Cys Glu Ile Tyr Thr Asn Pro Ile Arg Ala Glu Asn Cys Ala
            260                 265                 270

Val Gly Ser Ile Pro Leu Ala Phe Asp Ile Pro Asp Ala Leu Phe Thr
        275                 280                 285

Arg Val Ser Glu Thr Pro Thr Leu Ser Ala Ala Glu Cys Thr Leu Asn
    290                 295                 300

Glu Cys Val Tyr Ser Ser Asp Phe Gly Gly Ile Ala Thr Val Lys Tyr
305                 310                 315                 320

Ser Ala Ser Lys Ser Gly Lys Cys Ala Val His Val Pro Ser Gly Thr
                325                 330                 335

Ala Thr Leu Lys Glu Ala Ala Val Glu Leu Thr Glu Gln Gly Ser Ala
            340                 345                 350

Thr Ile His Phe Ser Thr Ala Asn Ile His Pro Glu Phe Arg Leu Gln
        355                 360                 365

Ile Cys Thr Ser Tyr Val Thr Cys Lys Gly Asp Cys His Pro Pro Lys
    370                 375                 380

Asp His Ile Val Thr His Pro Gln Tyr His Ala Gln Thr Phe Thr Ala
385                 390                 395                 400

Ala Val Ser Lys Thr Ala Trp Thr Trp Leu Thr Ser Leu Leu Gly Gly
                405                 410                 415

Ser Ala Val Ile Ile Ile Ile Gly Leu Val Leu Ala Thr Ile Val Ala
            420                 425                 430

Met Tyr Val Leu Thr Asn Gln Lys His Asn
        435                 440


<210> SEQ ID NO 55
<211> LENGTH: 275
<212> TYPE: PRT
<213> ORGANISM: Artificial Sequence
<220> FEATURE:
<223> OTHER INFORMATION: Synthetic VEEV Capsid

<400> SEQUENCE: 55

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
```

```
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275


<210> SEQ ID NO 56
<211> LENGTH: 414
<212> TYPE: PRT
<213> ORGANISM: Plasmodium falciparum

<400> SEQUENCE: 56

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Val Asp Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240
```

-continued

```
Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285

Lys Asn Asn Gln Gly Asn Gly Gln Gly His Asn Met Pro Asn Asp Pro
    290                 295                 300

Asn Arg Asn Val Asp Glu Asn Ala Asn Ala Asn Asn Ala Val Lys Asn
305                 310                 315                 320

Asn Asn Asn Glu Glu Pro Ser Asp Lys His Ile Glu Gln Tyr Leu Lys
                325                 330                 335

Lys Ile Lys Asn Ser Ile Ser Thr Glu Trp Ser Pro Cys Ser Val Thr
            340                 345                 350

Cys Gly Asn Gly Ile Gln Val Arg Ile Lys Pro Gly Ser Ala Asn Lys
        355                 360                 365

Pro Lys Asp Glu Leu Asp Tyr Glu Asn Asp Ile Glu Lys Lys Ile Cys
    370                 375                 380

Lys Met Glu Lys Cys Ser Ser Val Phe Asn Val Val Asn Ser Ser Ile
385                 390                 395                 400

Gly Leu Ile Met Val Leu Ser Phe Leu Phe Leu Asn Thr Arg
                405                 410
```

Malaria Vaccine Program, http://www.globalvaccines.org/content/malaria+vaccine+program/19614, 4 pages total (2012).
Communication, dated Jul. 5, 2016, issued by the European Patent Office in counterpart European Application No. 14807026.1.
Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.
Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.
Shiratsuchi T. et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.

* cited by examiner

MALARIA VACCINE

This application claims benefit from U.S. Provisional Application No. 61/830,436 filed Jun. 3, 2013 and U.S. Provisional Application No. 61/906,583 filed Nov. 20, 2013.

TECHNICAL FIELD

The present invention relates to a particle comprising a polypeptide and at least one malaria antigen, and a composition or vaccine comprising thereof, its use in medicine, particularly in the prevention or treatment of malaria.

BACKGROUND

Malaria is one of the world's most prevalent serious infectious diseases, with approximately 250 million cases and 1 million deaths per year (WHO, 2009). Mortality is primarily in children under the age of five and in pregnant women. Every 45 seconds, an African child dies of malaria. The disease is transmitted from person to person by infected mosquitoes, so past eradication efforts involved massive insecticide campaigns. These were successful in the Southeast U.S. for example, but failed in most poorly developed tropical countries. Current efforts involve distribution of bednets, particularly bednets impregnated with insecticide, to prevent mosquito bites at night. However, resistance to insecticides and to anti-malarial drugs for both prevention and treatment is rapidly rising. Thus, the need for a malaria vaccine is imperative for protection of millions of people from disease (http://www.globalvaccines.org/content/malaria+vaccine+program/19614).

Malaria caused by *Plasmodium falciparum* remains a major public health threat, especially among children and pregnant women in Africa. An effective malaria vaccine would be a valuable tool to reduce the disease burden and could contribute to elimination of malaria in some regions of the world. Current malaria vaccine candidates are directed against human and mosquito stages of the parasite life cycle, but thus far, relatively few proteins have been studied for potential vaccine development.

The most advanced vaccine candidate, RTS,S, conferred partial protection against malaria in phase II clinical trials and is currently being evaluated in a phase III trial in Africa. (The Journal of Clinical Investigation 120(12) 4168-4178, 2010).

The CSP is the predominant surface antigen on sporozoites. CSP is composed of an N-terminal region that binds heparin sulfate proteoglycans (RI), a central region containing a four-amino-acid (NPNA) repeat, and a GPI-anchored C-terminal region containing a thrombospondin-like domain (RII). The region of the CSP included in the RTS,S vaccine includes the last 16 NPNA repeats and the entire flanking C-terminus. HBsAg particles serve as the matrix carrier for RTS,S, 25% of which is fused to the CSP segment (The Journal of Clinical Investigation 120(12) 4168-4178, 2010).

In a series of phase II clinical trials for RTS,S, 30%-50% of malaria-naive adults immunized with RTS,S were protected against challenge by mosquitoes infected with the homologous *P. falciparum* clone. In phase II field trials in the Gambia and Kenya, RTS,S conferred short-lived protection against malaria infection in approximately 35% of adults, although results from the Kenya trial did not reach statistical significance. Approximately 30%-50% of children and infants immunized with RTS,S in phase II trials conducted in Mozambique, Tanzania, and Kenya were protected from clinical malaria, however, protection was generally short-lived (The Journal of Clinical Investigation 120(12) 4168-4178, 2010). Results from a pivotal, large-scale Phase III trial, published Nov. 9, 2012, online in the *New England Journal of Medicine* (*NEJM*), show that the RTS,S malaria vaccine candidate can help protect African infants against malaria. When compared to immunization with a control vaccine, infants (aged 6-12 weeks at first vaccination) vaccinated with RTS,S had one-third fewer episodes of both clinical and severe malaria and had similar reactions to the injection.

There are currently no licensed vaccines against malaria. Highly effective malaria vaccine is strongly desired.

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasile (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination (Expert Rev. Vaccines 9(10), 1149-1176, 2010).

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya virus structural polypeptides which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF THE INVENTION

In the first aspect, the present invention provides a particle which is capable of being self-assembled, comprising a polypeptide and at least one malaria antigen, wherein said polypeptide comprises at least one first attachment site and said at least one malaria antigen comprises at least one second attachment site, and wherein said polypeptide and said malaria antigen are linked through said at least one first and said at least one second attachment site.

In the second aspect, the present invention provides a nucleic acid molecule which is designed for expression of a particle provided in the first aspect of the present invention.

In the third aspect, the present invention provides a composition or vaccine comprising the particle provided in the first aspect of the present invention and/or the nucleic acid molecule provided in the second aspect of the present invention.

In the fourth aspect, the present invention provides a method of producing an antibody, comprising contacting the particle provided in the first aspect of the present invention and/or the nucleic acid molecule provided in the second aspect of the present invention to a mammal.

In the fifth aspect, the present invention provides a method of immunomodulation, a method of treating malaria, a method of inducing and/or enhancing immune response against a malaria antigen in a mammal, comprising administering the composition provided in the third aspect of the present invention to a mammal.

In sixth aspect, the present invention provides a method of passive immunization against a malaria-causing pathogen, comprising administering the antibody provided in the fourth aspect of the present invention to a mammal.

In seventh aspect, the present invention provides a method of presenting an antigen on macrophage, comprising contacting the particle provided in the first aspect of the present invention and/or the nucleic acid molecule provided in the second aspect of the present invention to a mammal.

In eighth aspect, the present invention provides a method for producing the particle provided in the first aspect of the present invention, comprising preparing a vector which is designed for expression of said particle; culturing a cell which is transfected with said vector to express said particle; and recovering said particle.

BRIEF DESCRIPTION OF THE INVENTION

Figure 7:
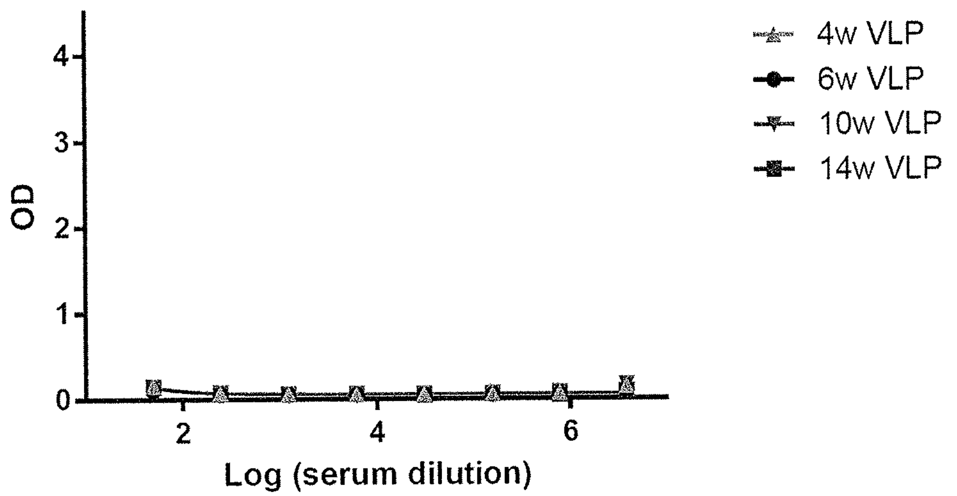

FIG. 7 shows effects of administered VLP fused with no malaria antigen on induction of antibodies against CSP. In the figure, 4 w, 6 w, 10 w and 14 w indicate 4 weeks after immunization, 6 weeks after immunization, 10 weeks after immunization and 14 weeks after immunization, respectively.

Figure 8:
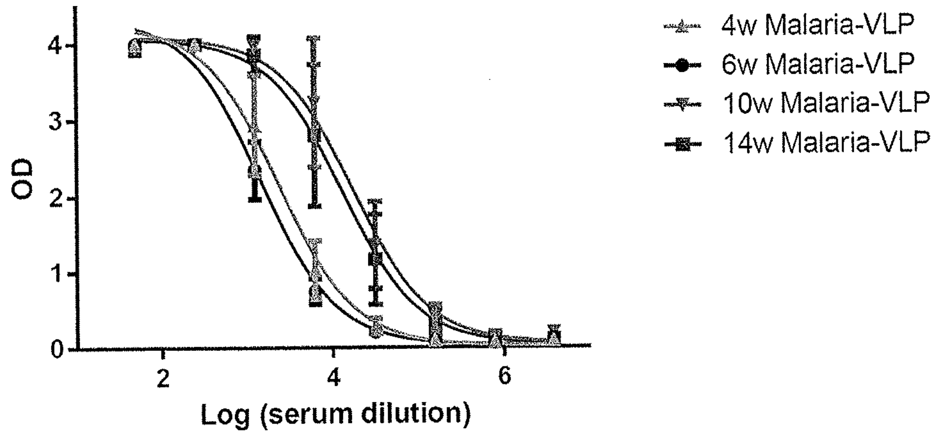

FIG. 8 shows effects of administered VLP fused with malaria antigen on induction of antibodies against CSP. In the figure, 4 w, 6 w, 10 w and 14 w indicate 4 weeks after immunization, 6 weeks after immunization, 10 weeks after immunization and 14 weeks after immunization, respectively.

Figure 9:
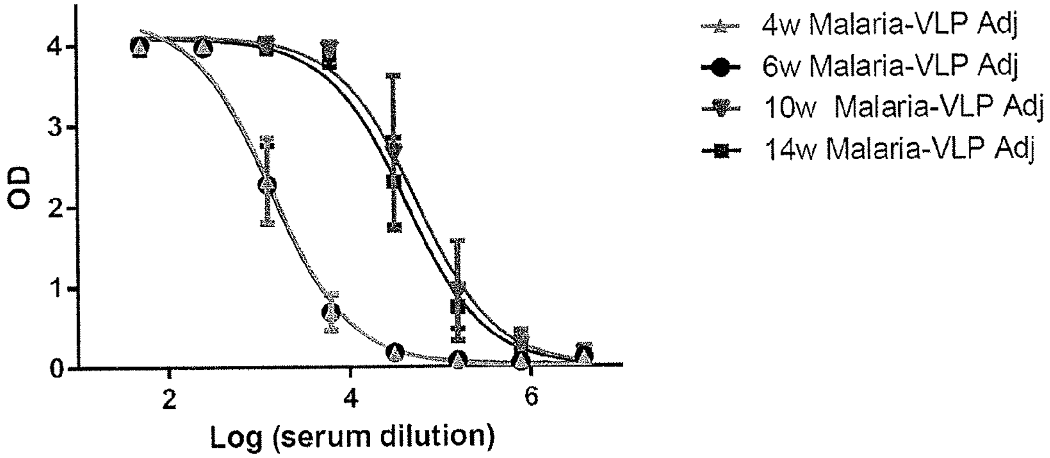

FIG. 9 shows effects of administered VLP fused with malaria antigen together with adjuvant on induction of antibodies against CSP. In the figure, 4 w, 6 w, 10 w and 14 w indicate 4 weeks after immunization, 6 weeks after immunization, 10 weeks after immunization and 14 weeks after immunization, respectively.

Figure 10:
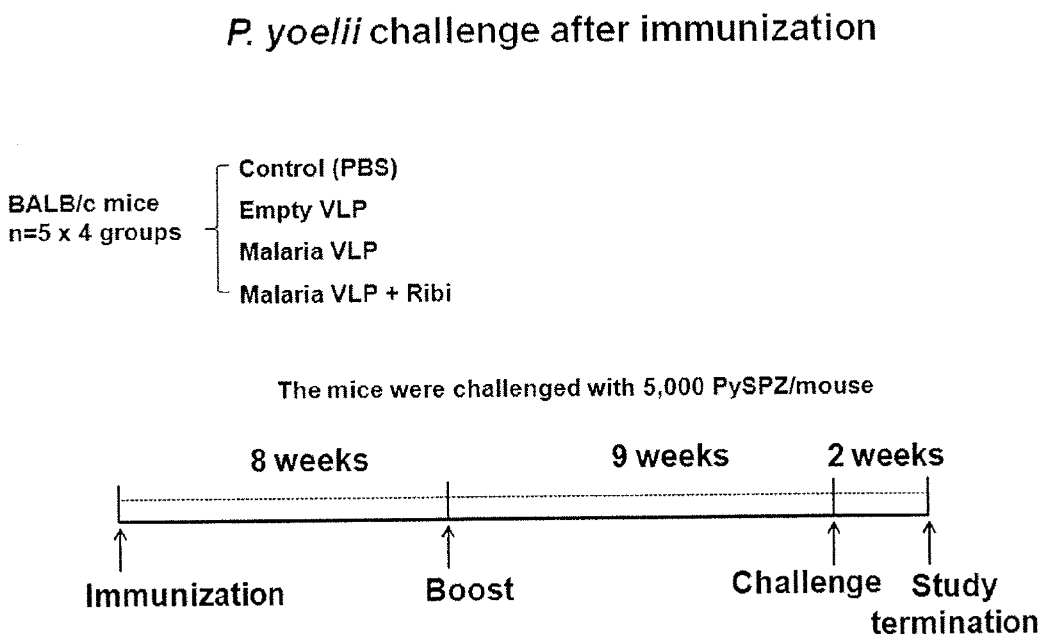

FIG. 10 shows schedule of the experiment.

Figure 11:
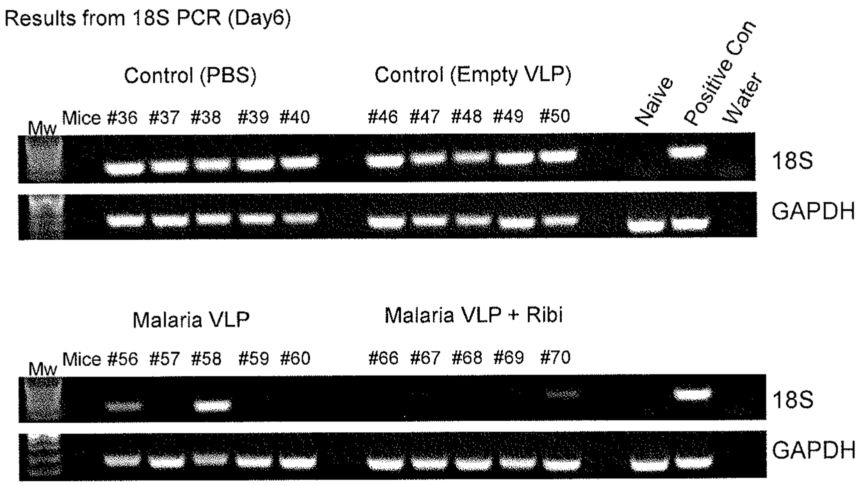

FIG. 11 shows detection of 18S malaria DNA by means of PCR.

DETAILED DESCRIPTION OF THE INVENTION

(1) a Particle Comprising a Polypeptide and at Least One Malaria Antigen

In the first aspect, the present invention provides a particle which is capable of being self-assembled, comprising a polypeptide and at least one malaria antigen, wherein said polypeptide comprises at least one first attachment site and said at least one antigen comprises at least one second attachment site, and wherein said polypeptide and said malaria antigen are linked through said at least one first and said at least one second attachment site.

As used herein, "a particle which is capable of being self-assembled" refers to a particle formed by at least one constituent which is spontaneously assembled. The constituent may be a polypeptide or non-peptide chemical compound. In one embodiment, "a particle which is capable of being self-assembled" may be a particle comprising or consisting of at least one polypeptide. The at least one polypeptide consists of one or more kinds of peptide. In one embodiment, said particle has a diameter of at least 10 nm, for example, at least 20 nm, preferably at least 50 nm. In one embodiment, molecular weight of said particle is from 100 kDa to 100,000 kDa, preferably from 400 kDa to 30,000 kDa.

A polypeptide used for the present invention may be spontaneously assembled. The polypeptide may be a virus structural polypeptide. Thus, the particle provided by the present invention may be a virus like particle.

A virus structural polypeptide may be a naturally occurring viral polypeptide or modified polypeptide thereof. In one embodiment, the modified polypeptide has at least 70%, 75%, 80%, 85%, 90%, 95% or 98% amino acid sequence identity to a naturally occurring viral structural polypeptide including capsid and envelope protein. In one embodiment, the modified polypeptide is a mutant where at most 10% of the amino acids are deleted, substituted, and/or added to a naturally occurring viral structural polypeptide including capsid and envelope protein.

In one embodiment, virus structural polypeptide used for the present invention consists of or comprises capsid and/or envelope protein or fragment thereof. For example, virus structural polypeptide used for the present invention consists of or comprises capsid and E2 and E1. An antigen may be inserted into E2. In one embodiment, a particle provided by the first aspect of the present invention can be formed by assembling 240 capsids, 240 E1 proteins and 240 E2 proteins where a malaria antigen is inserted into each of E2 proteins.

Virus structural polypeptide used for the present invention may be derived from Alphavirus or Flavivirus. Thus, the particle provided by the present invention may be a virus like particle derived from Alphavirus or Flavivirus. Examples of Alphavirus and Flavivirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

Malaria is a disease which human or other animal (e.g. mouse) suffers from. Example of malaria include, but are not limited to, a disease caused by *Plasmodium* (*P.*) species including *P. falciparum, P. malariae, P. ovale, P. vivax, P. knowlesi, P. berghei, P. chabaudi* and *P. yoelii*

As used herein, the term "malaria antigen" refers to any antigen or fragment thereof. The term antigen or fragment thereof, means any peptide-based sequence that can be recognized by the immune system and/or that stimulates a cell-mediated immune response and/or stimulates the generation of antibodies.

According to Scand. J. Immunol. 56, 327-343, 2002, considering the whole parasite life cycle, there are essentially six targets for a malaria vaccine: (1) sporozoites; (2) liver stages; (3) merozoites; (4) infected RBC; (5) parasite toxins; (6) sexual stages.

Table summarizes the main candidate antigens of each stage identified.

Table 1. Main Vaccine Candidates from the Different Phases of *Plasmodium* Life Cycle Targets Candidate Antigens Circumsporozoite protein (CSP)

Thrombospondin-related adhesive protein (TRAP)

Sporozoite

Sporozoite and liver-stage antigen (SALSA)

Sporozoite threonine- and asparagine-rich protein (STARP)

CSP

Liver-stage antigen (LSA)-1 and -3

Liver Stage

SALSA

STARP

Merozoite surface protein (MSP)-1, -2, -3, -4 and -5

Erythrocyte-binding antigen (EBA)-175

Apical membrane antigen (AMA)-1

Merozoite

Rhoptry-associated protein (RAP)-1 and -2

Acidic-basic repeat antigen (ABRA)

Duffy-binding protein (DBP) (*Plasmodium vivax*)

Ring erythrocyte surface antigen (RESA)

Serine-rich protein (SERP)

Blood stage

Erythrocyte membrane protein (EMP)-1, -2 and -3

Glutamate-rich protein (GLURP)

Toxins

Glycosilphosphatidylinositol (GPI)

TABLE 1

1. Main vaccine candidates from the different phases of *Plasmodium* life cycle

| Targets | Candidate antigens |
|---|---|
| Sexual stages | Ps25, Ps28, Ps48/45 and Ps230 |

(Scand. J. Immunol. 56, 327-343, 2002)

According to the present invention, one or more antigens listed above can be used as long as it is formed to a particle. For example, a circumsporozoite protein and a fragment thereof can be used as an antigen. Examples of circumsporozoite protein include, but are not limited to, *Plasmodium falciparum* circumsporozoite protein consisting of amino acid sequence described below (SEQ ID No.: 56):

Mmrklailsyssflfvealfqeyqcygsssntrvinelnydnagtnlynelemnyygkqenwyslkkn
srslgenddgnnnngdngregkdedkrdgnnedneklrkpkhkklkqpgdgnpdpnanpnvdpnanpn
vdpnanpnvdpnanpnanpnanpnanpnanpnanpnanpnanpnanpnanpnanpnanpnanpnanpn
anpnvdpnanpnanpnanpnanpnanpnanpnanpnanpnanpnanpnanpnanpnanpnanpnanpn
anpnanpnanpnanpnknnqgngqghnmpndpnrnvdenanannavknnnneepsdkhiegylkkikn
sistewspcsvtcgngiqvrikpgsankpkdeldyendiekkickmekcssvfnvvnssiglimvlsf
lflntr.

In one embodiment, malaria antigen is a *Plasmodium falciparum* circumsporozoite protein B cell epitope. Example of *Plasmodium falciparum* circumsporozoite protein B cell epitope may be a repeat sequence of NPNA, including $(NPNA)_{4-30}$ (i.e. 4xNPNA, 5xNPNA, 6xNPNA, 7xNPNA, 8xNPNA, 9xNPNA, 10xNPNA, 11xNPNA, 12xNPNA, 13xNPNA 14xNPNA, 15xNPNA, 16xNPNA, 17xNPNA, 18xNPNA, 19xNPNA, 20xNPNA, 21xNPNA, 22xNPNA, 23xNPNA, 24xNPNA, 25xNPNA, 26xNPNA, 27xNPNA, 28xNPNA, 29xNPNA or 30xNPNA).

In one embodiment, malaria antigen is a *Plasmodium yoelii* circumsporozoite protein B cell epitope including $(QGPGAP)_{3-12}$.

In one embodiment, malaria antigen is a *Plasmodium vivax* circumsporozoite protein B cell epitope including $(ANGAGNQPG)_{1-12}$.

In one embodiment, malaria antigen is a *Plasmodium malariae* circumsporozoite protein B cell epitope including $(NAAG)_{4-30}$.

In one embodiment, malaria antigen is a *Plasmodium falciparum* circumsporozoite protein T cell epitope. Example of *Plasmodium falciparum* circumsporozoite protein T cell epitope may be EYLNKIQNSLSTEWSPCSVT (SEQ ID No.:44). $(EYLNKIQNSLSTEWSPCSVT)_{1-6}$ may be also used as a malaria antigen.

In one embodiment, malaria antigen is a *Plasmodium yoelii* circumsporozoite protein T cell epitope which is YNRNIVNRLLGDALNGPEEK (SEQ ID No.45). $(YNRNIVNRLLGDALNGPEEK)_{1-6}$ may be also used as a malaria antigen.

The present invention addresses one or more of the above needs by providing antigens, vectors encoding the antigens, and antibodies (and antibody-like molecules including aptamers and peptides) that specifically bind to the antigen, together with the uses thereof (either alone or in combination) in the prevention or treatment of malaria infections. As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

The antigen used for the present invention can be modified polypeptide derived from a naturally occurring protein. The modified polypeptide may be a fragment of the naturally occurring protein. In one embodiment, the modified polypeptide has at least 70%, 75%, 80%, 85%, 90%, 95% or 98% amino acid sequence identity to a polypeptide derived from a naturally occurring protein. In one embodiment, the modified polypeptide derived is a mutant where at most 10% of the amino acids are deleted, substituted, and/or added based on a polypeptide derived from naturally occurring protein.

In the particle as provided by the present invention, a polypeptide and an antigen may be linked through at least one first attachment site which is present in the polypeptide and at least one second attachment site which is present in the antigen.

As used herein, each of "a first attachment site" and "a second attachment site" refers to a site where more than one substance is linked each other.

In one embodiment, the polypeptide and the antigen are directly fused. Alternatively, one or two linkers may intervene between N-terminal residue of the antigen and the polypeptide and/or between C-terminal residue of the antigen and the polypeptide.

The antigen or the polypeptide can be truncated and replaced by short linkers. In some embodiments, the antigen or the polypeptide include one or more peptide linkers. Typically, a linker consists of from 2 to 25 amino acids. Usually, it is from 2 to 15 amino acids in length, although in certain circumstances, it can be only one, such as a single glycine residue.

In one embodiment, a nucleic acid molecule, in which polynucleotide encoding the polypeptide is genetically fused with polynucleotide encoding the antigen, is expressed in a host cell so that the first attachment site and the second attachment site are linked through a peptide bond. In this case, the polypeptide and the antigen are linked through a peptide bond. Relating to this embodiment, the first attachment site and/or the second attachment site may be genetically modified from the original polypeptide or antigen. For example, the first attachment site is modified from the polypeptide so that through a linker peptide including SG, GS, SGG, GGS and SGSG, the polypeptide is conjugated with the antigen.

When the polypeptide are chemically conjugated with the antigen, the first attachment site and the second attachment site may be linked through a chemical cross-linker which is a chemical compound.

Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

In one embodiment, the particle provided by the present invention comprises a polypeptide linked to an antigen, wherein spatial distance between the N-terminal residue and C-terminal residue of the antigen is 30 Å or less when the distance is determined in a crystal of the antigen or a naturally occurring protein containing the antigen or modified protein therefrom.

The antigen used for the present invention can be designed by a person skilled in the art. For example, the antigen used for the present invention may be a naturally occurring protein or a fragment thereof. Alternatively, the antigen used for the present invention may be a protein modified from a naturally occurring protein or a fragment thereof. A person skilled in the art can design the antigen so that spatial distance between the N-terminal residue and C-terminal residue of the antigen is 30 Å or less when the distance is determined in a crystal of the antigen or a naturally occurring protein containing the antigen or modified protein therefrom. For example, the antigen used for the particle provided by the present invention can be designed using a free software including PyMOL (e.g. PyMOL v0.99: http:/www.pymol.org). In one embodiment, the spatial distance between the N-terminal residue and C-terminal residue of the antigen is 30 Å (angstrom) or less, 20 Å or less, or 10 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

Chikungunya Virus Like Particle or a Venezuelan Equine Encephalitis Virus Like Particle In one embodiment, the present invention provides a Chikungunya virus like particle or a Venezuelan equine encephalitis virus like particle comprising a Chikungunya or Venezuelan equine encephalitis virus structural polypeptide and at least one malaria antigen, wherein said Chikungunya virus structural polypeptide or said Venezuelan equine encephalitis virus structural polypeptide comprises at least one first attachment site and said at least one malaria antigen comprises at least one second attachment site, and wherein said Chikungunya or Venezuelan equine encephalitis virus structural polypeptide and said at least one antigen are linked through said at least one first and said at least one second attachment site.

In one embodiment, a spatial distance between the N-terminal residue and C-terminal residue of the malaria antigen may be 30 Å or less; 25 Å or less; 20 Å or less; 15 Å or less; 14 Å or less; 13 Å or less; 12 Å or less; 11 Å or less; 10 Å or less; 9 Å or less; or 8 Å or less (e.g. from 5 Å to 15 Å, from 5 Å to 12 Å, from 5 Å to 11 Å, from 5 Å to 11 Å, from 5 Å to 8 Å, from 8 Å to 15 Å, from 8 Å to 13 Å, from 8 Å to 12 Å, from 8 Å to 11 Å, from 9 Å to 12 Å, from 9 Å to it Å, from 9 Å to 10 Å or from 10 Å to 11 Å) when the distance is determined in a crystal of the malaria antigen or a naturally occurring protein containing the malaria antigen or modified protein therefrom.

In one embodiment, the malaria antigen is linked to the Chikungunya or Venezuelan equine encephalitis virus structural polypeptide by way of chemical cross-linking or as a fusion protein produced by way of genetic engineering.

A Chikungunya or Venezuelan equine encephalitis virus structural polypeptide used in the present invention may comprise a Chikungunya or Venezuelan equine encephalitis virus envelope protein and/or a capsid.

Examples of Chikungunya virus include, but are not limited to, strains of 37997 and LR2006 OPY-1.

Examples of Venezuelan equine encephalitis virus include, but are not limited to, TC-83.

Chikungunya or Venezuelan equine encephalitis virus structural polypeptide used in the present invention may naturally occurring virus structural polypeptide or modified polypeptide thereof. The modified polypeptide may be a fragment of the naturally occurring virus structural polypeptide. In one embodiment, the modified polypeptide has at least 70%, 75%, 80%, 85%, 90%, 95% or 98% amino acid sequence identity to a naturally occurring viral capsid and/or envelope protein. In one embodiment, the modified polypeptide is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis virus structural polypeptide used in the present invention.

Chikungunya or Venezuelan equine encephalitis virus structural polypeptide may consist of or comprise a capsid, E2 and E1.

Examples of Chikungunya virus structural polypeptide include, but are not limited to, Capsid-E2-E1 of Chikungunya virus Strain 37997, and Capsid-E2-E1 of Chikungunya virus LR2006 OPY-1.

Examples of Venezuelan equine encephalitis virus structural polypeptide include, but are not limited to, Capsid-E2-E1 of Venezuelan equine encephalitis virus Strain TC-83.

An exemplary Chikungunya virus structural polypeptide sequence is provided at Genbank Accession No. ABX40006.1, which is described below (SEQ ID No.:1):

```
mefiptqtfynrryqprpwtprptiqvirprprpqrqagqlaqlisavn
kltmravpqqkprrnrknkkqkqkqqapqnntnqkkqppkkkpaqkkkk
pgrrermcmkiendcifevkhegkvtgyaclvgdkvmkpahvkgtidna
dlaklafkrsskydlecaqipvhmksdaskfthekpegyynwhhgavqy
sggrftiptgagkpgdsgrpifdnkgrvvaivlgganegartalsvvtw
nkdivtkitpegaeewslaipvmcllanttfpcsqppctpccyekepee
tlrmlednvmrpgyyqllgasltcsphrqrrstkdnfnvykatrpylah
cpdcgeghschspvalerirneatdgtlkiqvslqigiktddshdwtkl
rymdnhmpadaeraglfvrtsapctitgtmghfilarcpkgetltvgft
dsrkishscthpfhhdppvigrekfhsrpqhgkelpcstyvqstaatte
eievhmppdtpdrtlmsqqsgnvkitvngqtvrykcncggsnegltttd
kvinnckvdqchaavtnhkkwqynsplvprnaelgdrkgkihipfplan
vtcrvpkarnptvtygknqvimllypdhptllsyrnmgeepnyqeewvm
hkkevvltvpteglevtwgnnepykywpqlstngtahghpheiilyyye
lyptmtvvvvsvatfillsmvgmaagmcmcarrrcitpyeltpgatvpf
llsliccirtakaatyqeaaiylwneqqplfwlqaliplaalivlcncl
rllpccvktlaflavmsvgahtvsayehvtvipntvgvpyktlvnrpgy
spmvlemellsvtleptlsldyitceyktvipspyvkccgtaeckdknl
pdysckvftgvypfmwggaycfcdaentqlseahveksesecktefasay
```

-continued

```
rahtasasaklrvlyqgnnitvtayangdhavtvkdakfivgpmssawt
pfdnkivvykgdvynmdyppfgagrpgqfgdiqsrtpeskdvyantqlv
lqrpavgtvhvpysqapsgfkywlkergaslqhtapfgcqiatnpvrav
ncavgnmpisidipeaaftrvvdapsltdmscevpacthssdfggvaii
kyaaskkgkcavhsmtnavtireaeievegnsqlqisfstalasaefrv
qvcstqvhcaaechppkdhivnypashttlgvqdisatamswvqkitgg
vglvvavaalilivvlcvsfsrh
```

Another exemplary Chikungunya virus structural polypeptide sequence is provided at Genbank Accession No. ABX40011.1, which is described below (SEQ ID No.:2):

```
mefiptqtfynrryqprpwaprptiqvirprprpqrqagqlaqlisavn
kltmravpqqkprrnrknkkqrqkkqapqndpkqkkqppqkkpaqkkkk
pgrrermcmkiendcifevkhegkvmgyaclvgdkvmkpahvkgtidna
dlaklafkrsskydlecaqipvhmksdaskfthekpegyynwhhgavqy
sggrftiptgagkpgdsgrpifdnkgrvvalvlgganegartalsvvtw
nkdivtkitpegaeewslalpvlcllanttfpcsqppctpccyekepes
tlrmlednvmrpgyyqllkasltcsphrqrrstkdnfvnykatrpylah
cpdcgeghschsplalerirneatdgtlkiqvslqiglktddshdwtkl
rymdshtpadaeragllvrtsapctitgtmghfilarcpkgetltvgft
dsrkishtcthpfhheppvigrerfhsrpqhgkelpcstyvqstaatae
eievhmppdtpdrtlmtqqagnvkitvnggtvrykcncggsnegltttd
kvinnckidqchaavtnhknwqynsplvprnaelgdrkgkihipfplan
vtcrvpkarnptvtygknqvtmllypdhptllsyrnmgqepnyheewvt
hkkevtltvpteglevtwgnnepykywpqmstngtahghpheillyyye
lyptmtvvivsvasfvllsmvgtavgmcvcarrrcitpyeltpgatvpf
llsllccvrttkaatyyeaaaylwneqqplfwlqaliplaalivlcnvl
kllpccvktlaflavmsigahtvsayehvtvipntvgvpyktlvnrpgy
spmvlemelqsvtleptlsldyitceyktvipspyvkccgtaeckdksl
pdysckvftgvypfmwggaycfcdaentqlseahveksesecktefasay
rahtasasaklrvlyqgnnitvaayangdhavtvkdakfvvgpmssawt
pfdnkivvykgdvynmdyppfgagrpgqfgdiqartpeskdvyantqlv
lqrpaagtvhvpysqapsgfkywlkergaslqhtapfgcqiatnpvrav
ncavgnipisidipdaaftrvvdapsvtdmscevpacthssdfggvail
kytaskkgkcavhsmtnavtireadvevegnsqlqisfstalasaefrv
qvcstqvhcaaachppkdhlvnypashttlgvqdisttamawvqkitgg
vglivavaalilivvlcvsfsrh.
```

An exemplary Venezuelan equine encephalitis virus structural polypeptide is provided at Genbank Accession No. L01443.1 (http://www.ncbi.nlm.nih.gov/nuccore/L01443.1), which is described below (SEQ ID No.:3):

```
mfpfqpmypmqpmpyrnpfaaprrpwfprtdpflamqvqeltrsmanlt
fkqrrdappegpsaakpkkeasqkqkgggqgkkkknqgkkkaktgppnp
kaqngnkkktnkkpgkrqrmvmklesdktfpimlegkingyacvvggkl
frpmhvegkidndvlaalktkkadkydleyadvpqnmradtfkythekp
qgyyswhhgavqyengrftvpkgvgakgdsgrpildnqgrvvaivlggv
negsrtalsvvmwnekgvtvkytpenceqwslvttmcllanvtfpcaqp
picydrkpaetlamlsvnvdnpgydelleaavkcpgrkrrsteelfney
kltrpymarcircavgschspiaieavksdghdgyvrlqtssqygldss
gnlkgrtmrydmhgtikeiplhqvslytsrpchivdghgyfllarcpag
dsitmefkkdsvrhscsvpyevkfnpvgrelythppehgveqacqvyah
daqnrgayvemhlpgsevdsslvslsgssvtvtppdgtsalvececggt
kisetinktkqfsqctkkeqcrayrlqndkwvynsdklpkaagatlkgk
lhvpflladgkctvplapepmitfgfrsvslklhpknptylitrqlade
phythelisepavrnftvtekgwefvwgnhppkrfwaqetapgnphglp
hevithyyhrypmstilglsicaaiatvsvaastwlfcrsrvacltpyr
ltpnaripfclavlccartaraettwesldhlwnnnqqmfiiqllipla
alivvtrllrcvccvvpflvmagaagagayehattmpsqagisyntivn
ragyaplpisitptkikliptvnleyctchyktgmdspaikccgsqect
ptyrpdeqckvftgvypfmwggaycfcdtentqvskayvmksddcladh
aeaykahtasvqaflnitvgehsivttvyvngetpvnfngvkitagpls
tawtpfdrkivqyageiynydfpeygagqpgafgdiqsrtvsssdlyan
tnlvlqrpkagaihvpytqapsgfeqwkkdkapslkftapfgceiytnp
iraencavgsiplafdipdalftrvsetptlsaaectlnecvyssdfgg
iatvkysasksgkcavhvpsgtatlkeaavelteqgsatihfstanihp
efrlgictsyvtckgdchppkdhivthpqyhaqtftaavsktawtwlts
llggsaviiiiglvlativamyvltnqkhn.
```

In one embodiment, a first attachment site comprises an amino group, preferably an amino group of a lysine residue. In one embodiment, the second attachment site comprises sulfhydryl group, preferably, a sulfhydryl group of a cysteine.

In one embodiment, a conjugation of more than two substances (e.g. antigen and Chikungunya or Venezuelan equine encephalitis virus structural polypeptide) through a first attachment site or a second attachment site is achieved using chemical cross linker. Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

According to the present invention, a Chikungunya or Venezuelan equine encephalitis virus like particle comprising a Chikungunya or Venezuelan equine encephalitis virus structural polypeptide and an antigen, wherein said Chikungunya or Venezuelan equine encephalitis virus structural polypeptide and said antigen are expressed as a fusion protein can be provided.

In one embodiment, the antigen can be fused with any site of the Chikungunya or Venezuelan equine encephalitis virus structural polypeptide. For example, the antigen may be directly or indirectly linked to N- or C-terminal of the Chikungunya or Venezuelan equine encephalitis virus structural polypeptide, or the antigen may be inserted into Chikungunya or Venezuelan equine encephalitis virus structural protein.

In one embodiment, at least one antigen is inserted into E2 of Chikungunya or Venezuelan equine encephalitis virus structural protein. For example, regarding Chikungunya virus structural protein, at least one antigen is inserted between residues 519 and 520 of SEQ ID Nos.1 or 2 (i.e. between G at 519-position and Q at 520-position of SEQ ID Nos.1 or 2); between residues 530 and 531 of SEQ ID Nos.1 or 2 (i.e. between G at 530-position and S at 531-position of SEQ ID Nos.1 or 2); between residues 531 and 532 of SEQ ID Nos.1 or 2 (i.e. between S at 531-position and N at 532-position of SEQ ID Nos.1 or 2); between residues 529 and 530 of SEQ ID Nos.1 or 2 (i.e. between G at 529-position and G at 530-position of SEQ ID Nos.1 or 2); or between residues 510 and 511 of SEQ ID Nos.1 or 2 (i.e. between S at 510-position and G at 511-position of SEQ ID Nos.1 or 2); or between residues 511 and 512 of SEQ ID Nos.1 or 2 (i.e. between G at 511-position and N at 512-position of SEQ ID Nos.1 or 2); or between residues 509 and 510 of SEQ ID Nos.1 or 2 (i.e. between Q at 509-position and S at 510-position of SEQ ID Nos.1 or 2).

For example, regarding Venezuelan equine encephalitis virus structural protein, at least one antigen is inserted between residues 517 and 518 of SEQ ID No.3 (i.e. between G at 517-position and S at 518-position of SEQ ID No.3); between residues 518 and 519 of SEQ ID No.3 (i.e. between S at 518-position and S at 519-position of SEQ ID No.3); between residues 519 and 520 of SEQ ID No.3 (i.e. between S at 519-position and V at 520-position of SEQ ID No.3); between residues 515 and 516 of SEQ ID No.3 (i.e. between L at 515-position and S at 516-position of SEQ ID No.3); between residues 516 and 517 of SEQ ID No.3 (i.e. between S at 516-position and G at 517-position of SEQ ID No.3); between residues 536 and 537 of SEQ ID No.3 (i.e. between C at 536-position and G at 537-position of SEQ ID No.3); between residues 537 and 538 of SEQ ID No.3 (i.e. between G at 537-position and G at 538-position of SEQ ID No.3); between residues 538 and 539 of SEQ ID No.3 (i.e. between G at 538-position and T at 539-position of SEQ ID No.3).

The fusion protein may be expressed using a conventional technique in the art. A variety of expression systems can be used for the expression of the fusion protein. For example, the fusion protein can be expressed in 293 cells, Sf9 cells or *E. coli*.

A polypeptide derived from Chikungunya virus (CHIKV) or Venezuelan equine encephalitis virus (VEEV) may be a naturally occurring viral polypeptide or modified polypeptide thereof. In addition, a polypeptide derived from malaria antigen may be a naturally occurring polypeptide or modified polypeptide of the naturally occurring polypeptide or a fragment of the naturally occurring polypeptide or the modified peptide. The modified polypeptide may be a fragment of the naturally occurring virus structural polypeptide.

In one embodiment, the modified polypeptide derived from malaria antigen has at least 70%, 75%, 80%, 85%, 90%, 95% or 98% amino acid sequence identity to a naturally occurring polypeptide. In one embodiment, the modified peptide derived from malaria antigen is a mutant where at most 10% of the amino acids are deleted, substituted, and/or added based on a naturally occurring polypeptide derived from malaria antigen.

When a polypeptide derived from a virus is conjugated with a polypeptide derived from an antigen, a linker peptide including SG, GS, SGG, GGS SGSG and TRGGS may be used. Examples of conjugation of the polypeptide derived from a virus (referred to as "PFV" below) with the polypeptide derived from the antigen (referred to as "PFA" below) include, but not limited to: PFV-SG-PFA-GS-PFV; PFV-SG-PFA-GGS-PFV; PFV-SSG-PFA-GS-PFV; PFV-SGG-PFA-GGS-PFV; PFV-SGSG-PFA-GS-PFV; and PFA-SGG-PFA-TRGGS-PFV.

In one embodiment, the present invention provides a virus like particle comprising a fusion protein of a polypeptide derived from Chikungunya virus (CHIKV) or Venezuelan equine encephalitis virus (VEEV) and a polypeptide derived from malaria antigen, wherein the virus like particle is prepared by transfecting an expression vector comprising a nucleic acid molecule corresponding to the amino acid sequence represented by SEQ ID NO. 28, 31, 34, 37, 39, 41 or 43 into a mammalian cell (e.g. 293F cell). Regarding this embodiment, modified fusion protein can be also used for a virus like particle provided by the present invention, which can be prepared by transfecting an expression vector comprising a nucleic acid molecule corresponding to the amino acid sequence having at least 70%, 75%, 80%, 85%, 90%, 95% or 98% amino acid sequence identity to SEQ ID NO. 28, 31, 34, 37, 39, 41 or 43 into a mammalian cell (e.g. 293F cell).

In one embodiment, the present invention provides a virus like particle comprising or consisting of:

one or more capsid of Chikungunya virus (CHIKV) or Venezuelan equine encephalitis virus (VEEV);

one or more E1 of Chikungunya virus (CHIKV) or Venezuelan equine encephalitis virus (VEEV); and one or more E2 of Chikungunya virus (CHIKV) or Venezuelan equine encephalitis virus (VEEV), wherein malaria antigen is inserted into E2 of Chikungunya virus (CHIKV) or Venezuelan equine encephalitis virus (VEEV). For example, present invention provides a virus like particle comprising or consisting of:

240 capsids of Chikungunya virus (CHIKV) or Venezuelan equine encephalitis virus (VEEV);

240 E1s of Chikungunya virus (CHIKV) or Venezuelan equine encephalitis virus (VEEV); and 240 E2s of Chikungunya virus (CHIKV) or Venezuelan equine encephalitis virus (VEEV), wherein malaria antigen is inserted into each of E2s of Chikungunya virus (CHIKV) or Venezuelan equine encephalitis virus (VEEV).

In this embodiment, the E2 into which the antigen is inserted may consist of an amino acid sequence represented by SEQ ID No.50; the E1 may consist of an amino acid sequence represented by SEQ ID No.51; and the capsid may consist of an amino acid sequence represented by SEQ ID NO.: 52; or the E2 into which the antigen is inserted may consist of an amino acid sequence represented by SEQ ID NO.53; the E1 may consist of an amino acid sequence represented by SEQ ID NO.54; and the capsid may consist of an amino acid sequence represented by SEQ ID NO.: 55.

Further, regarding this embodiment, modified capsid of Chikungunya virus (CHIKV) or Venezuelan equine encephalitis virus (VEEV), modified E1 of Chikungunya virus (CHIKV) or Venezuelan equine encephalitis virus (VEEV) and modified E2 of Chikungunya virus (CHIKV) or Venezuelan equine encephalitis virus (VEEV) may be used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO.: 52 or SEQ ID No.:55; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO.: 51 or SEQ ID No.:54; and/or the modified E2 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO.: 50 or SEQ ID No.:53.

Also, the modified capsid, E1 or E2 may be a mutant where at most 10% of the amino acids are deleted, substituted, and/or added based on the capsid consisting of an amino acid sequence represented by SEQ ID NO.: 52 or SEQ ID No.:55; E1 consisting of an amino acid sequence represented by SEQ ID NO.: 51 or SEQ ID No.:54; and/or E2 consisting of an amino acid sequence represented by SEQ ID NO.: 50 or SEQ ID No.:53.

(2) Nucleotide, Vector, Host Cell

In the second aspect, the present invention provides a nucleic acid molecule which is designed for expression of a particle as provided in the first aspect of the present invention.

In one embodiment, the present invention provides a nucleic acid molecule comprising a nucleotide sequence that encodes the Chikungunya or Venezuelan equine encephalitis virus like particle as described above.

Examples of the nucleotide sequence that encodes the Chikungunya or Venezuelan equine encephalitis virus like particle include, but are not limited to, a nucleotide sequence encoding envelope of Chikungunya virus Strain 37997, a nucleotide sequence encoding Capsid-envelope of Chikungunya virus Strain 37997, a nucleotide sequence encoding envelope of Chikungunya virus Strain LR2006 OPY-1, a nucleotide sequence encoding Capsid-envelope of Chikungunya virus LR2006 OPY-1, a nucleotide sequence encoding envelope of Venezuelan equine encephalitis virus Strain TC-83 and a nucleotide sequence encoding Capsid-envelope of Venezuelan equine encephalitis virus TC-83.

Regarding Chikungunya virus, an exemplary nucleotide sequence that encodes envelope is described below (SEQ ID No.:4):

```
Atgagcctcgccctcccggtcttgtgcctgttggcaaacactacattcc
cctgctctcagccgccttgcacaccctgctgctacgaaaaggaaccgga
aagcaccttgcgcatgcttgaggacaacgtgatgagacccggatactac
cagctactaaaagcatcgctgacttgctctccccaccgccaaagacgca
gtactaaggacaattttaatgtctataaagccacaagaccatatctagc
tcattgtcctgactgcggagaagggcattcgtgccacagccctatcgca
ttggagcgcatcagaaatgaagcaacggacggaacgctgaaaatccagg
tctctttgcagatcgggataaagacagatgacagccacgattggaccaa
gctgcgctatatggatagccatacgccagcggacgcggagcgagccgga
```

-continued ttgcttgtaaggacttcagcaccgtgcacgatcaccgggaccatgggac
actttattctcgcccgatgcccgaaaggagagacgctgacagtgggatt
tacggacagcagaaagatcagccacacatgcacacacccgttccatcat
gaaccacctgtgataggtagggagaggttccactctcgaccacaacatg
gtaaagagttaccttgcagcacgtacgtgcagagcaccgctgccactgc
tgaggagatagaggtgcatatgcccccagatactcctgaccgcacgctg
atgacgcagcagtctggcaacgtgaagatcacagttaatgggcagacgg
tgcggtacaagtgcaactgcggtggctcaaacgagggactgacaaccac
agacaaagtgatcaataactgcaaaattgatcagtgccatgctgcagtc
actaatcacaagaattggcaatacaactcccctttagtcccgcgcaacg
ctgaactcggggaccgtaaaggaaagatccacatcccattcccattggc
aaacgtgacttgcagagtgccaaaagcaagaaaccctacagtaacttac
ggaaaaaaccaagtcaccatgctgctgtatcctgaccatccgacactct
tgtcttaccgtaacatgggacaggaaccaaattaccacgaggagtgggt
gacacacaagaaggaggttaccttgaccgtgcctactgagggtctggag
gtcacttggggcaacaacgaaccatacaagtactggccgcagatgtcta
cgaacggtactgctcatggtcacccacatgagataatcttgtactatta
tgagctgtaccccactatgactgtagtcattgtgtcggtggcctcgttc
gtgcttctgtcgatggtgggcacagcagtgggaatgtgtgtgtgcgcac
ggcgcagatgcattacaccatatgaattaacaccaggagccactgttcc
cttcctgctcagcctgctatgctgcgtcagaacgaccaaggcggccaca
tattacgaggctgcggcatatctatggaacgaacagcagcccctgttct
ggttgcaggctcttatcccgctggccgccttgatcgtcctgtgcaactg
tctgaaactcttgccatgctgctgtaagaccctggctttttagccgta
ttttgagcatcggtgcccacactgtgagcgcgtacgaacacgtaacagt
gatcccgaacacggtgggagtaccgtataagactcttgtcaacagaccg
ggttacagccccatggtgttggagatggagctacaatcagtcaccttgg
aaccaacactgtcacttgactacatcacgtgcgagtacaaaactgtcat
cccctccccgtacgtgaagtgctgtggtacagcagagtgcaaggacaag
agcctaccagactacagctgcaaggtctttactggagtctacccattta
tgtggggcggcgcctactgcttttgcgacgccgaaaatacgcaattgag
cgaggcacatgtagagaaatctgaatcttgcaaaacagagtttgcatcg
gcctacagagcccacaccgcatcggcgtcggcgaagctccgcgtccttt
accaaggaaacaacattaccgtagctgcctacgctaacggtgaccatgc
cgtcacagtaaaggacgccaagtttgtcgtgggcccaatgtcctccgcc
tggacaccttttgacaacaaaatcgtggtgtacaaaggcgacgtctaca
acatggactacccacctttggcgcaggaagaccaggacaatttggtga
cattcaaagtcgtacaccggaaagtaaagacgtttatgccaacactcag
ttggtactacagaggccagcagcaggcacggtacatgtaccatactctc
aggcaccatctggcttcaagtattggctgaaggaacgaggagcatcgct -continued acagcacacggcaccgttcggttgccagattgcgacaaacccggtaaga
gctgtaaattgcgctgtggggaacataccaatttccatcgacataccgg
atgcggcctttactagggttgtcgatgcaccctctgtaacggacatgtc
atgcgaagtaccagcctgcactcactcctccgactttgggggcgtcgcc
atcatcaaatacacagctagcaagaaaggtaaatgtgcagtacattcga
tgaccaacgccgttaccattcgagaagccgacgtagaagtagaggggaa
ctcccagctgcaaatatccttctcaacagccctggcaagcgccgagttt
gcgcgtgcaagtgtgctccacacaagtacactgcgcagccgcatgccac
cctccaaaggaccacatagtcaattacccagcatcacacaccacccttg
gggtccaggatatccacaacggcaatgtcttgggtgcagaagattacgg
gaggagtaggattaattgttgctgttgctgccttaattttaattgtggt
gctatgcgtgtcgtttagcaggcac Regarding Chikungunya virus, another exemplary nucleotide sequence that encodes envelope is described below (SEQ ID No.:5):

Atgagtcttgccatcccagttatgtgcctgttggcaaacaccacgttcc
cctgctcccagccccttgcacgccctgctgctacgaaaaggaaccgga
ggaaaccctacgcatgcttgaggacaacgtcatgagacctgggtactat
cagctgctacaagcatccttaacatgttctccccaccgccagcgacgca
gacaccaaggacaacttcaatgtctataaagccacaagaccatacttag
ctcactgtcccgactgtggagaagggcactcgtgccatagtcccgtagc
actagaacgcatcagaaatgaagcgacagacgggacgctgaaaatccag
gtctccttgcaaatcggaataaagacggatgacagccacgattggacca
agctgcgttatatggacaaccacatgccagcagacgcagagagggcggg
ctatttgtaagaacatcagcaccgtgtacgattactggaacaatgggac
acttcatcctggcccgatgtccaaaaggggaaactctgacggtgggatt
cactgacagtaggaagattagtcactcatgtacgcacccatttcaccac
gaccctcctgtgataggtcgggaaaaattccattcccgaccgcagcacg
gtaaagagctaccttgcagcacgtacgtgcagagcaccgccgcaactac
cgaggagatagaggtacacatgcccccagacacccctgatcgcacatta
atgtcacaacagtccggcaacgtaaagatcacagtcaatggccagacgg
tgcggtacaagtgtaattgcggtggctcaaatgaaggactaacaactac
agacaaagtgattaataactgcaaggttgatcaatgtcatgccgcggtc
accaatcacaaaaagtggcagtataactcccctctggtcccgcgtaatg
ctgaacttggggaccgaaaaggaaaaattcacatcccgtttccgctggc
aaatgtaacatgcagggtgcctaaagcaaggaaccccaccgtgacgtac
gggaaaaaccaagtcatcatgctactgtatcctgacccaacactcc
tgtcctaccggaatatgggagaagaaccaaactatcaagaagagtgggt
gatgcataagaaggaagtcgtgctaaccgtgccgactgaagggctcgag
gtcacgtggggcaacaacgagccgtataagtattggccgcagttatcta
caaacggtacagcccatggccacccgcatgagataattctgtattatta -continued tgagctgtaccccactatgactgtagtagttgtgtcagtggccacgttc atactcctgtcgatggtgggtatggcagcggggatgtgcatgtgtgcac gacgcagatgcatcacaccgtatgaactgacaccaggagctaccgtccc tttcctgcttgcttagcctaatatgctgcatcagaacagctaaagcggc cacataccaagaggctgcgatatcctgtggaacgagcagcaacctttgt tttggctacaagcccttattccgctggcagccctgattgttctatgcaa ctgtctgagactcttaccatgctgctgtaaaacgttggctttttagcc gtaatgagcgtcggtgcccacactgtgagcgcgtacgaacacgtaacag tgatcccgaacacggtgggagtaccgtataagactctagtcaatagacc tggctacagccccatggtattggagatggaactactgtcagtcactttg gagccaacactatcgcttgattacatcacgtgcgagtacaaaaccgtca tcccgtctccgtacgtgaagtgctgcggtacagcagagtgcaaggacaa aaacctacctgactacagctgtaaggtcttcaccggcgtctacccattt tgtggggcggcgcctactgcttctgcgacgctgaaaacacgcagttgag cgaagcacacgtggagaagtccgaatcatgcaaaacagaatttgcatca gcatacagggctcataccgcatctgcatcagctaagctccgcgtccttt accaaggaaataacatcactgtaactgcctatgcaaacggcgaccatgc cgtcacagttaaggacgccaaattcattgtggggccaatgtcttcagcc -continued tggacacctttcgacaacaaaattgtggtgtacaaaggtgacgtctata acatggactacccgccctttggcgcaggaagaccaggacaatttggcga tatccaaagtcgcacacctgagagtaaagacgtctatgctaatacacaa ctggtactgcagagaccggctgtgggtacggtacacgtgccatactctc aggcaccatctggctttaagtattggctaaaagaacgcggggcgtcgct gcagcacacagcaccatttggctgccaaatagcaacaaacccggtaaga gcggtgaactgcgccgtagggaacatgcccatctccatcgacataccgg aagcggccttcactagggtcgtcgacgcgccctctttaacggacatgtc gtgcgaggtaccagcctgcacccattcctcagactttgggggcgtcgcc attattaaatatgcagccagcaagaaaggcaagtgtgcggtgcattcga tgactaacgccgtcactattcgggaagctgagatagaagttgaagggaa ttctcagctgcaaatctctttctcgacggccttagccagcgccgaattc cgcgtacaagtctgttctacacaagtacactgtgcagccgagtgccacc ccccgaaggaccacatagtcaactacccggcgtcacataccaccctcgg ggtccaggacatctccgctacggcgatgtcatgggtgcagaagatcacg ggaggtgtgggactggttgttgctgttgccgcactgattctaatcgtgg tgctatgcgtgtcgttcagcaggcac Regarding Chikungunya virus, an exemplary nucleotide sequence that encodes a Capsid-envelope is described below (SEQ ID No.:6):

atggagttcatcccgacgcaaactttctataacagaaggtaccaaccccgaccctgggccccacgcccta caattcaagtaattagacctagaccacgtccacagaggcaggctgggcaactcgcccagctgatctccgc agtcaacaaattgaccatgcgcgcggtacctcaacagaagcctcgcagaaatcggaaaaacaagaagcaa aggcagaagaagcaggcgccgcaaaacgacccaaagcaaaagaagcaaccaccacaaaagaagccggctc aaaagaagaagaaaccaggccgtagggagagaatgtgcatgaaaattgaaaatgattgcatcttcgaagt caagcatgaaggcaaagtgatgggctacgcatgcctggtgggggataaagtaatgaaaccagcacatgtg aagggaactatcgacaatgccgatctggctaaactggcctttaagcggtcgtctaaatacgatcttgaat gtgcacagataccggtgcacatgaagtctgatgcctcgaagtttacccacgagaaacccgaggggtacta taactggcatcacggagcagtgcagtattcaggaggccggttcactatcccgacgggtgcaggcaagccg ggagacagcggcagaccgatcttcgacaacaaaggacgggtggtggccatcgtcctaggaggggccaacg aaggtgcccgcacggccctctccgtggtgacgtggaacaaagacatcgtcacaaaaattacccctgaggg agccgaagagtggagcctcgccctcccggtcttgtgcctgttggcaaacactacattcccctgctctcag ccgccttgcacaccctgctgctacgaaaaggaaccggaaagcaccttgcgcatgcttgaggacaacgtga tgagacccggatactaccagctactaaaagcatcgctgacttgctctccccaccgccaaagacgcagtac taaggacaattttaatgtctataaagccacaagaccatatctagctcattgtcctgactgcggagaaggg cattcgtgccacagccctatcgcattggagcgcatcagaaatgaagcaacggacggaacgctgaaaatcc aggtctctttgcagatcgggataaagacagatgacagccacgattggaccaagctgcgctatatggatag ccatacgccagcggacgcggagcgagccggattgcttgtaaggacttcagcaccgtgcacgatcaccggg accatgggacactttattctcgcccgatgcccgaaaggagagacgctgacagtgggatttacggacagca gaaagatcagccacacatgcacacacccgttccatcatgaaccacctgtgataggtagggagaggttcca -continued ctctcgaccacaacatggtaaagagttaccttgcagcacgtacgtgcagagcaccgctgccactgctgag gagatagaggtgcatatgcccccagatactcctgaccgcacgctgatgacgcagcagtctggcaacgtga agatcacagttaatgggcagacggtgcggtacaagtgcaactgcggtggctcaaacgagggactgacaac cacagacaaagtgatcaataactgcaaaattgatcagtgccatgctgcagtcactaatcacaagaattgg caatacaactcccctttagtcccgcgcaacgctgaactcggggaccgtaaaggaaagatccacatcccat tcccattggcaaacgtgacttgcagagtgccaaaagcaagaaaccctacagtaacttacggaaaaaacca agtcaccatgctgctgtatcctgaccatccgacactcttgtcttaccgtaacatgggacaggaaccaaat taccacgaggagtgggtgacacacaagaaggaggttaccttgaccgtgcctactgagggtctggaggtca cttggggcaacaacgaaccatacaagtactggccgcagatgtctacgaacggtactgctcatggtcaccc acatgagataatcttgtactattatgagctgtaccccactatgactgtagtcattgtgtcggtggcctcg ttcgtgcttctgtcgatggtgggcacagcagtgggaatgtgtgtgtgcgcacggcgcagatgcattacac catatgaattaacaccaggagccactgttcccttcctgctcagcctgctatgctgcgtcagaacgaccaa ggcggccacatattacgaggctgcggcatatctatggaacgaacagcagcccctgttctggttgcaggct cttatcccgctggccgccttgatcgtcctgtgcaactgtctgaaactcttgccatgctgctgtaagaccc tggctttttttagccgtaatgagcatcggtgcccacactgtgagcgcgtacgaacacgtaacagtgatccc gaacacggtgggagtaccgtataagactcttgtcaacagaccgggttacagccccatggtgttggagatg gagctacaatcagtcaccttggaaccaacactgtcacttgactacatcacgtgcgagtacaaaactgtca tcccctccccgtacgtgaagtgctgtggtacagcagagtgcaaggacaagagcctaccagactacagctg caaggtctttactggagtctacccatttatgtggggcggcgcctactgcttttgcgacgccgaaaatacg caattgagcgaggcacatgtagagaaatctgaatcttgcaaaacagagtttgcatcggcctacagagccc acaccgcatcggcgtcggcgaagctccgcgtcctttaccaaggaaacaacattaccgtagctgcctacgc taacggtgaccatgccgtcacagtaaaggacgccaagtttgtcgtgggcccaatgtcctccgcctggaca ccttttgacaacaaaatcgtggtgtacaaaggcgacgtctacaacatggactacccaccttttggcgcag gaagaccaggacaatttggtgacattcaaagtcgtacaccggaaagtaaagacgtttatgccaacactca gttggtactacagaggccagcagcaggcacggtacatgtaccatactctcaggcaccatctggcttcaag tattggctgaaggaacgaggagcatcgctacagcacacggcaccgttcggttgccagattgcgacaaacc cggtaagagctgtaaattgcgctgtggggaacataccaatttccatcgacataccggatgcggcctttac tagggttgtcgatgcaccctctgtaacggacatgtcatgcgaagtaccagcctgcactcactcctccgac tttgggggcgtcgccatcatcaaatacacagctagcaagaaaggtaaatgtgcagtacattcgatgacca acgccgttaccattcgagaagccgacgtagaagtagaggggaactcccagctgcaaatatccttctcaac agccctggcaagcgccgagtttcgcgtgcaagtgtgctccacacaagtacactgcgcagccgcatgccac cctccaaaggaccacatagtcaattacccagcatcacacaccacccttggggtccaggatatatccacaa cggcaatgtcttgggtgcagaagattacgggaggagtaggattaattgttgctgttgctgccttaatttt aattgtggtgctatgcgtgtcgtttagcaggcactaa.

Regarding Chikungunya virus, another exemplary nucleotide sequence that encodes a Capsid-envelope is described below (SEQ ID No.:7):

atggagttcatcccaacccaaactttttacaataggaggtaccagcctcgaccctggactccgcgcccta ctatccaagtcatcaggcccagaccgcgccctcagaggcaagctgggcaacttgcccagctgatctcagc agttaataaactgacaatgcgcgcggtaccacaacagaagccacgcaggaatcggaagaataagaagcaa -continued

```
aagcaaaaacaacaggcgccacaaaacaacacaaatcaaaagaagcagccacctaaaaagaaaccggctc
aaaagaaaaagaagccgggccgcagagagaggatgtgcatgaaaatcgaaaatgattgtattttcgaagt
caagcacgaaggtaaggtaacaggttacgcgtgcctggtgggggacaaagtaatgaaaccagcacacgta
aaggggaccatcgataacgcggacctggccaaactggcctttaagcggtcatctaagtatgaccttgaat
gcgcgcagatacccgtgcacatgaagtccgacgcttcgaagttcacccatgagaaaccggaggggtacta
caactggcaccacggagcagtacagtactcaggaggccggttcaccatccctacaggtgctggcaaacca
ggggacagcggcagaccgatcttcgacaacaagggacgcgtggtggccatagtcttaggaggagctaatg
aaggagcccgtacagccctctcggtggtgacctggaataaagacattgtcactaaaatcacccccgaggg
ggccgaagagtggagtcttgccatcccagttatgtgcctgttggcaaacaccacgttcccctgctcccag
cccccttgcacgccctgctgctacgaaaaggaaccggaggaaaccctacgcatgcttgaggacaacgtca
tgagacctgggtactatcagctgctacaagcatccttaacatgttctccccaccgccagcgacgcagcac
caaggacaacttcaatgtctataaagccacaagaccatacttagctcactgtcccgactgtggagaaggg
cactcgtgccatagtcccgtagcactagaacgcatcagaaatgaagcgacagacgggacgctgaaaatcc
aggtctccttgcaaatcggaataaagacggatgacagccacgattggaccaagctgcgttatatggacaa
ccacatgccagcagacgcagagagggcggggctatttgtaagaacatcagcaccgtgtacgattactgga
acaatgggacacttcatcctggcccgatgtccaaaaggggaaactctgacggtgggattcactgacagta
ggaagattagtcactcatgtacgcacccatttcaccacgaccctcctgtgataggtcgggaaaaattcca
ttcccgaccgcagcacggtaaagagctaccttgcagcacgtacgtgcagagcaccgccgcaactaccgag
gagatagaggtacacatgcccccagacacccctgatcgcacattaatgtcacaacagtccggcaacgtaa
agatcacagtcaatggccagacggtgcggtacaagtgtaattgcggtggctcaaatgaaggactaacaac
tacagacaaagtgattaataactgcaaggttgatcaatgtcatgccgcggtcaccaatcacaaaaagtgg
cagtataactcccctctggtcccgcgtaatgctgaacttggggaccgaaaaggaaaaattcacatcccgt
ttccgctggcaaatgtaacatgcagggtgcctaaagcaaggaaccccaccgtgacgtacgggaaaaacca
agtcatcatgctactgtatcctgaccacccaacactcctgtcctaccggaatatgggagaagaaccaaac
tatcaagaagagtgggtgatgcataagaaggaagtcgtgctaaccgtgccgactgaagggctcgaggtca
cgtggggcaacaacgagccgtataagtattggccgcagttatctacaaacggtacagcccatggccaccc
gcatgagataattctgtattattatgagctgtaccccactatgactgtagtagttgtgtcagtggccacg
ttcatactcctgtcgatggtgggtatggcagcggggatgtgcatgtgtgcacgacgcagatgcatcacac
cgtatgaactgacaccaggagctaccgtccctttcctgcttagcctaatatgctgcatcagaacagctaa
agcggccacataccaagaggctgcgatatacctgtggaacgagcagcaacctttgttttggctacaagcc
cttattccgctggcagccctgattgttctatgcaactgtctgagactcttaccatgctgctgtaaaacgt
tggctttttttagccgtaatgagcgtcggtgcccacactgtgagcgcgtacgaacacgtaacagtgatccc
gaacacggtgggagtaccgtataagactctagtcaatagacctggctacagccccatggtattggagatg
gaactactgtcagtcactttggagccaacactatcgcttgattacatcacgtgcgagtacaaaaccgtca
tcccgtctccgtacgtgaagtgctgcggtacagcagagtgcaaggacaaaaacctacctgactacagctg
taaggtcttcaccggcgtctacccatttatgtggggcggcgcctactgcttctgcgacgctgaaaacacg
cagttgagcgaagcacacgtggagaagtccgaatcatgcaaaacagaatttgcatcagcatacagggctc
ataccgcatctgcatcagctaagctccgcgtcctttaccaaggaaataacatcactgtaactgcctatgc
aaacggcgaccatgccgtcacagttaaggacgccaaattcattgtggggccaatgtcttcagcctggaca
cctttcgacaacaaaattgtggtgtacaaaggtgacgtctataacatggactacccgccctttggcgcag
gaagaccaggacaatttggcgatatccaaagtcgcacacctgagagtaaagacgtctatgctaatacaca
```

-continued

```
actggtactgcagagaccggctgtgggtacggtacacgtgccatactctcaggcaccatctggctttaag

tattggctaaaagaacgcggggcgtcgctgcagcacacagcaccatttggctgccaaatagcaacaaacc

cggtaagagcggtgaactgcgccgtagggaacatgcccatctccatcgacataccggaagcggccttcac

tagggtcgtcgacgcgccctctttaacggacatgtcgtgcgaggtaccagcctgcacccattcctcagac

tttgggggcgtcgccattattaaatatgcagccagcaagaaaggcaagtgtgcggtgcattcgatgacta

acgccgtcactattcgggaagctgagatagaagttgaagggaattctcagctgcaaatctctttctcgac

ggccttagccagcgccgaattccgcgtacaagtctgttctacacaagtacactgtgcagccgagtgccac

cccccgaaggaccacatagtcaactacccggcgtcacataccaccctcggggtccaggacatctccgcta

cggcgatgtcatgggtgcagaagatcacgggaggtgtgggactggttgttgctgttgccgcactgattct

aatcgtggtgctatgcgtgtcgttcagcaggcactaa.
```

In one embodiment, the present invention provides a vector comprising the nucleic acid molecule as described above, wherein the vector optionally comprises an expression control sequence operably linked to the nucleic acid molecule.

Examples of an expression control sequence include, but are not limited to, promoter such as CMV promoter, phage lambda PL promoter, the *E. coli* lac, phoA and tac promoters, the SV40 early and late promoters, and promoters of retroviral LTRs.

In this embodiment, the vector comprising an expression control sequence operably linked to the nucleic acid molecule as described above can be used as an expression vector for preparing the particle provided by the first aspect of the present invention.

The expression vectors can be prepared by a person skilled in the art based on WO/2012/006180, the entire contents of which are incorporated by reference herein.

Examples of vectors which can be used for expressing a virus like particle comprising a fusion protein of a polypeptide derived from Chikungunya virus (CHIKV) and a polypeptide of antigen include a vector shown in VLP_CHI 512 vector (SEQ ID No.:8) containing CHIKV VLP polynucleotide (SEQ ID No. 13; corresponding amino acid sequence represented by SEQ ID No.:14); and VLP_CHI 532 vector (SEQ ID No.: 9) containing CHIKV VLP polynucleotide (SEQ ID No. 15; corresponding amino acid sequence represented by SEQ ID No.:16).

The expression vectors can be prepared by a person skilled in the art based on US2012/0003266, the entire contents of which are incorporated by reference herein.

Examples of vectors which can be used for expressing a virus like particle comprising a fusion protein of a polypeptide derived from Venezuelan equine encephalitis virus (VEEV) and a polypeptide of antigen include a vector shown in VLP_VEEV VLP 518 vector (SEQ ID No.:10) containing VEEV VLP polynucleotide (SEQ ID No. 17; corresponding amino acid sequence represented by SEQ ID No.:18); VLP_VEEV VLP 519 vector (SEQ ID No.11) containing VEEV VLP polynucleotide (SEQ ID No. 19; corresponding amino acid sequence represented by SEQ ID No.:20); and VLP_VEEV VLP 538 vector (SEQ ID No.: 12) containing VEEV VLP polynucleotide (SEQ ID No. 21; corresponding amino acid sequence represented by SEQ ID No.:22).

In one embodiment, the present invention provides a nucleic acid molecule which is designed for expression of a virus like particle comprising a fusion protein of a polypeptide derived from Chikungunya virus (CHIKV) or Venezuela equine encephalitis virus (VEEV) and a polypeptide derived from malaria antigen, which consists of a nucleotide sequence represented by SEQ ID Nos.26-27, 29-30, 32-33, 35-36, 38, 40 or 42.

In one embodiment, the present invention provides a nucleic acid molecule which is modified from the nucleic acid molecule having a nucleotide sequence represented by any one of SEQ ID Nos.26-27, 29-30, 32-33 or 35-36, 38, 40 or 42. The modified nucleic acid molecule may have at least 70%, 75%, 80%, 85%, 90%, 95% or 98% nucleotide sequence identity to the nucleic acid molecule having a nucleotide sequence represented by any one of SEQ ID Nos.26-27, 29-30, 32-33, 35-36, 38, 40 or 42. Also, the modified nucleic acid molecule may be a mutant where at most 10% of the amino acids are deleted, substituted, and/or added based on the nucleic acid molecule having a nucleotide sequence represented by any one of SEQ ID Nos.26-27, 29-30, 32-33, 35-36, 38, 40 or 42.

(3) Composition or Vaccine

In the third aspect, the present invention provides a composition or vaccine comprising the particle provided in the first aspect of the present invention and/or the nucleic acid molecule provided in the second aspect of the present invention.

In one embodiment, the present invention provides a composition or vaccine comprising the Alphavirus or Flavivirus virus like particle (e.g. Chikungunya virus like particle or Venezuelan equine encephalitis virus like particle) as described above or the nucleic acid molecule as described above. The content of the Alphavirus or Flavivirus virus like particle and the content of the nucleic acid molecule may be 0.00001-1 w/w %.

Dosage amount of the particle provided in the first aspect of the present invention (e.g. CHIKV VLP or VEEV VLP) may be 1-500 μg/day.

One or more malaria antigens may be used for one composition or one vaccine provided by the third aspect of the present invention.

The composition or vaccine may further comprise a pharmaceutical acceptable carrier and/or adjuvant. Examples of adjuvant include, but are not limited to, aluminium salts, sodium hydroxide, Freund's complete adjuvant, Freund's incomplete adjuvant and Ribi solution (Sigma Adjuvant system, Sigma-Aldrich). The composition or vaccine provided in the third aspect of the present invention may contain buffering agent such as dibasic sodium phosphate hydrate, sodium dihydrogen phosphate and sodium chloride; and preserving agent such as thimerosal. In one embodiment, the composition or vaccine is an aqueous solution containing 0.001-1 w/w % of the particle provided in the first aspect of the present invention (e.g. CHIKV VLP or VEEV VLP), 1-10 w/w % of buffering agent, 0.01-1 w/w % of adjuvant and 0.00001-0.001 w/w % of preserving agent.

A skilled person can prepare the pharmaceutical composition and vaccine using conventional technique. For example, the particle provided in the first aspect of the present invention is mixed with buffer solution having physiological pH (e.g. pH 5-9, pH7) to prepare the pharmaceutical composition and vaccine provided in the third aspect of the present invention.

The pharmaceutical composition of the present invention may contain a single active ingredient or a combination of two or more active ingredients, as far as they are not contrary to the objects of the present invention. For example, cytokines including chemokines, anti-body of cytokines such as anti TNF antibody (e.g. infliximab, adalimumab), anti-VEGF antibody (e.g. bevacizumab and ranibizumab), cytokine receptor antagonist such as anti HER2 antibody (e.g. Trastuzumab), anti EGF receptor antibody (e.g. Cetuximab), anti VEGF aptamer (e.g. Pegaptanib) and immunomodulator such as cyclosporine, tacrolimus, ubenimex may be used for the combination therapy.

In a combination of plural active ingredients, their respective contents may be suitably increased or decreased in consideration of their therapeutic effects and safety.

The term "combination" used herein means two or more active ingredient are administered to a patient simultaneously in the form of a single entity or dosage, or are both administered to a patient as separate entities either simultaneously or sequentially with no specific time limits, wherein such administration provides therapeutically effective levels of the two components in the body, preferably at the same time.

In one embodiment, the composition is a vaccine composition including a DNA vaccine. In one embodiment, the DNA vaccine provided by the present invention comprises CpG containing oligonucleotide.

The composition or vaccine provided in the third aspect of the present invention can be administered one or more times. When the composition or vaccine provided in the third aspect of the present invention is administered more than one time, different particle provided in the first aspect of the present invention (e.g. CHIKV VLP or VEEV VLP) may be used for each of the administration. In one embodiment, combination of immunization using CHIKV VLP provided in the first aspect of the invention and immunization using VEEV VLP provided in the first aspect of the invention is employed. For example, CHIKV VLP provided in the first aspect of the present invention may be used for the 1st immunization and VEEV VLP provided in the first aspect of the present invention may be used for the 2nd immunization, or VEEV VLP provided in the first aspect of the present invention may be used for the 1st immunization and CHIKV VLP provided in the first aspect of the present invention may be used for the 2nd immunization.

A skilled person can determine timing of immunization using the composition or vaccine provided in the third aspect of the present invention. For example, 2nd immunization is performed 1, 2, 3, 4, 5, 6, 7, 8, 9 or 10 weeks after 1st immunization.

In one embodiment, the present invention provides a kit comprising (a) a vaccine composition comprising the particle provided in the first aspect of the present invention; and (b) another vaccine composition comprising the particle provided in the first aspect of the present invention, wherein the particle contained in (a) is a virus like particle which is different from the particle contained in (b). In this embodiment, the particle contained in (a) may be Chikungunya virus like particle and the particle contained in (b) may be Venezuelan equine encephalitis virus like particle.

In one embodiment, the present invention provides a kit comprising (a) a vaccine composition comprising the particle provided in the first aspect of the present invention; and (b) another vaccine composition comprising the particle provided in the first aspect of the present invention, (c) one or more vaccine composition, each of which comprises the particle provided in the first aspect of the present invention, wherein (a) is used for priming immunization and (b) and (c) are used for boosting immunization; and the particle contained in (a) is a virus like particle which is different from the particle contained in (b); and the particle contained in (c) is different from the particle contained in (a) and (b), or the same as the particle contained in (a) or (b).

The respective vaccine compositions contained in the above-described kit may be administered simultaneously, separately or sequentially.

The Alphavirus or Flavivirus virus like particle (e.g. Chikungunya virus or Venezuelan equine encephalitis virus) provided in the first aspect of the present invention or the nucleic acid molecule provided by the second aspect of the invention can be used for the composition and vaccine provided in the third aspect of the present invention.

For example, Chikungunya or Venezuelan equine encephalitis virus like particle comprising or consisting of:

one or more (e.g. 240) capsid of Chikungunya virus (CHIKV) or Venezuelan equine encephalitis virus (VEEV);

one or more (e.g. 240) E1 of Chikungunya virus (CHIKV) or Venezuelan equine encephalitis virus (VEEV); and one or more (e.g. 240) E2 of Chikungunya virus (CHIKV) or Venezuelan equine encephalitis virus (VEEV), wherein malaria antigen is inserted into E2 of Chikungunya virus (CHIKV) or Venezuelan equine encephalitis virus (VEEV) may be used for preparing the composition or vaccine provided in the third aspect of the present invention. The E2 into which the antigen is inserted may consist of an amino acid sequence represented by SEQ ID No.50; the E1 may consist of an amino acid sequence represented by SEQ ID No.51; and the capsid may consist of an amino acid sequence represented by SEQ ID NO.: 52; or the E2 into which the antigen is inserted may consist of an amino acid sequence represented by SEQ ID NO.53; the E1 may consist of an amino acid sequence represented by SEQ ID NO.54; and the capsid may consist of an amino acid sequence represented by SEQ ID NO.: 55.

The composition or vaccine provided in the third aspect of the present invention can be administered to a mammal (e.g. human) intramuscularly (i.m.), intracutaneously (i.c.), subcutaneously (s.c.), intradermally (i.d.) or intraperitoneally (i.p.).

The composition or vaccine provided in the third aspect of the present invention may be used for treating or preventing malaria.

Thus, use of the Alphavirus or Flavivirus (e.g. Chikungunya virus or Venezuelan equine encephalitis virus) virus like particle provided in the first aspect of the present invention or the nucleic acid molecule provided by the second aspect of the invention for manufacturing a pharmaceutical composition or vaccine for treating or preventing malaria is also provided by the present invention.

(4) Method of Producing an Antibody, Method of Immunomodulation, Method of Treating Malaria, Method of Inducing and/or Enhancing Immune Response Against a Malaria Antigen in a Mammal, Method of Passive Immunization, Method of Presenting an Antigen on Macrophage, and Method for Producing a Particle In the fourth aspect, the present invention provides a method of producing an antibody, comprising contacting the particle provided in the first aspect of the present invention and/or the nucleic acid molecule provided in the second aspect of the present invention to a mammal.

The antibody produced in the fourth aspect of the present invention may be humanized using a conventional technique. Thus, in one embodiment, the method provided in the fourth aspect of the invention further comprises a step of humanizing non-human mammal produced antibody.

The particle provided in the first aspect of the present invention and/or the nucleic acid molecule provided in the second aspect of the present invention may be administered directly into the patient, into the affected organ or systemically, or applied ex vivo to cells derived from the patient or a human cell line which are subsequently administered to the patient, or used in vitro to select a subpopulation from immune cells such as B-cell and T-cell derived from the patient, which are then re-administered to the patient.

According to the present invention, the virus like particle can be applied for the immune therapy.

In the fifth aspect, the present invention provides a method of immunomodulation, a method of treating malaria, a method of inducing and/or enhancing immune response against a malaria antigen in a mammal comprising administering the composition provided in the third aspect of the present invention to a mammal.

In sixth aspect, the present invention provides a method of passive immunization against a malaria-causing pathogen, comprising administering the antibody provided in the fourth aspect of the present invention to a mammal.

In seventh aspect, the present invention provides a method of presenting a malaria antigen on macrophage, comprising contacting the particle provided in the first aspect of the present invention and/or the nucleic acid molecule provided in the second aspect of the present invention to a mammal.

In eighth aspect, the present invention provides a method for producing the particle provided in the first aspect of the present invention, comprising preparing a vector designed for expression of said particle; culturing a cell which is transfected with said vector to express said particle; and recovering said particle.

Examples of mammal include, but are not limited to, a human.

In one embodiment, the present invention provides a method of producing an antibody against malaria antigen, comprising contacting the Chikungunya or Venezuelan equine encephalitis virus like particle as described above and/or the nucleic acid molecule as described above to a mammal. The produced antibody may be an antibody which can specifically bind to a malaria antigen comprised in the Chikungunya or Venezuelan equine encephalitis virus like particle or a malaria antigen encoded by the nucleic acid molecule. The method of producing an antibody provided by the present invention may be a useful for producing a monoclonal or polyclonal antibody against a malaria antigen.

In one embodiment, an antibody against malaria antigen obtained by the method of producing an antibody according to the present invention is used for passive immunization. The method of passive immunization may comprise administering the obtained antibody to a mammal.

In one preferred embodiment, the immunomodulation provided by the present invention is inducing and/or enhancing immune response against malaria antigen in a mammal. Thus, in one embodiment, the present invention provides a method of inducing and/or enhancing immune response against malaria antigen in a mammal, comprising administering an effective amount of the composition as described above to the mammal.

Given the symptom of patients infected with Chikungunya or Venezuelan equine encephalitis together with unusual big molecule of Chikungunya or Venezuelan equine encephalitis, this VLP can act effectively and efficiently to target macrophage and its composition such as cytokines and immunomodulative compounds.

In one aspect, the present invention provides a method of presenting an antigen on macrophage, comprising administering the Chikungunya or Venezuelan equine encephalitis virus like particle as described above and/or the nucleic acid molecule as described above to a mammal. The Chikungunya or Venezuelan equine encephalitis virus like particle provided by the present invention is good to target macrophage. In one embodiment, the Chikungunya or Venezuelan equine encephalitis virus like particle provided by the present invention is a kind of delivery system of the at least one antigen, which is comprised in the Chikungunya or Venezuelan equine encephalitis virus like particle, to macrophage.

In one embodiment, the present invention provides a method for producing Chikungunya or Venezuelan equine encephalitis virus like particle provided in the first aspect of the present invention, comprising preparing a vector designed for expression of said particle; culturing a cell which is transfected with said vector to express said particle; and recovering said particle. In this embodiment, transfection can be conducted using a conventional method. Cells using for the transfection may be 293 cells. Recovering VLP may include collecting a conditioned medium after cells are transfected with a vector, and may further include purify VLP from the conditioned medium using ultracentrifugation.

The present invention will be described in detail with reference to the following example, which, however, is not intended to limit the scope of the present invention.

EXAMPLES

Example 1

Preparation of Chikungunya Virus (CHIKV) Like Particle Comprising a Virus Structural Polypeptide and a Fragment of Malaria Antigen The following polynucleotides of malaria CSP1 proteins are used. N terminal linker is SGG and C terminal linker is GGS.

```
VLP74 (6 repeat of NPNA amino acid sequence)
                                             (SEQ ID No.: 46)
Sggnpnanpnanpnanpnanpnanpnaggs

                                             (SEQ ID No.: 47)
(Tccggaggaaacccgaatgccaatcccaacgcgaaccccaatgctaac
ccaaatgccaacccaaacgccaaccccaacgctggtggatcc)

VLP78 (25 repeat of NPNA amino acid sequence)
                                              (SEQ ID No.: 48
Sggnpnanpnanpnanpnanpnanpnvdpnanpnanpnanpnanpnanp
nanpnanpnanpnanpnanpnanpnanpnanpnanpnanpnanpnanpn
anpnaggs

                                             (SEQ ID No.: 49)
(tccggaggaaacccgaatgccaatcccaacgcgaaccccaacgctaac
cccaacgccaatccgaatgcaaacccgaacgttgacccaaacgccaacc
cgaatgccaatcccaacgcgaaccccaatgctaacccaaatgccaaccc
aaacgccaaccccaacgctaatccaaacgccaaccctaacgccaatccc
aacgcgaatcctaacgctaatcccaacgcaaatcccaatgctaatccga
acgcgaaccctaatgcaaaccccaacgccaacccgaacgctaacccgaa
cgctaatcccaacgccggtggatcc)
```

The respective polynucleotides was inserted between the codons encoding Ser at 531-position and Asn at 532-position of SEQ ID Nos.15 or 16 (SEQ ID Nos.1 or 2) to construct a plasmid (hereinafter referred to as CHIKV-VLP74 or 78) for expressing Chikungunya virus like particle where the modified VLP74 or 78-derived peptide is inserted into E2 of Chikungunya virus structural polypeptide.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising VLP74 or 78 conjugated with Chikungunya virus structural polypeptide was confirmed by Western Blot using an antibody specific for CHIKV (ATCC: VR-1241AF) and an antibody specific for VLP74 or 78.

Example 2

Preparation of Venezuelan Equine Encephalitis Virus (VEEV) Like Particle Comprising a Virus Structural Polypeptide and a Fragment of Malaria Antigen The same polynucleotides of malaria CSP1 proteins (VLP74 and VLP78) used in EXAMPLE 1 are used. N terminal linker is SGG and C terminal linker is GGS.

The respective polynucleotides was inserted between the codons encoding Ser at 518-position and Ser at 519-position of SEQ ID Nos.19 or 20 (SEQ ID No.3) to construct a plasmid (hereinafter referred to as VEEV-VLP74 or 78) for expressing Venezuelan equine encephalitis virus like particle where the modified VLP74 or 78-derived peptide is inserted into E2 of Venezuelan equine encephalitis virus structural polypeptide.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising VLP 74 or 78 conjugated with Venezuelan equine encephalitis virus structural polypeptide was confirmed by Western Blot using an antibody specific for VEEV and an antibody specific for VLP74 or 78.

Example 3

Immunogenicity in Non-Human Primate (Monkey)

The monkeys were immunized with ×25-CHI (80 ug) at 0 week and ×6-VEE (80 ug) at 3 week by intramuscular injection with or without adjuvant (Sigma Adjuvant System, Sigma, S6322). ×25-CHI means 25 times malaria CSP repeat amino acid NPNA on CHIKV VLP particle (VLP78_15). ×6-VEE means 6 times malaria CSP repeat amino acid NPNA on VEEV VLP particle (VLP74_25). The blood is taken at 2 and 5 weeks after the first immunization.

96 well ELISA plate were coated with 50 ng of Recombinant Circumsporozoite Protein (rCSP) (Reagent Proteins, ATG-422) in 100 ul PBS buffer pre well. The Plates after 2 hours incubation were washed three times TBS buffer containing 0.05% Tween-20 and blocked with TBS buffer containing 0.05% Tween-20 and 5% dry milk. The heat inactivated diluted serum from monkeys were added in the blocking buffer and incubated for 1 h at room temperature. After washing three times, peroxidase labeled goat anti-human IgG or anti-mouse IgG was added at 1:4000 dilution and incubated for 1 h at room temperature. After washing three times, Peroxidase substrate was added for development and incubated for 10 mins and 2N H2SO4 was added to stop the development. The data were analyzed using Gen5 (BioTek) and GraphPad Prism6 (GraphPad software Inc).

Figure 1:
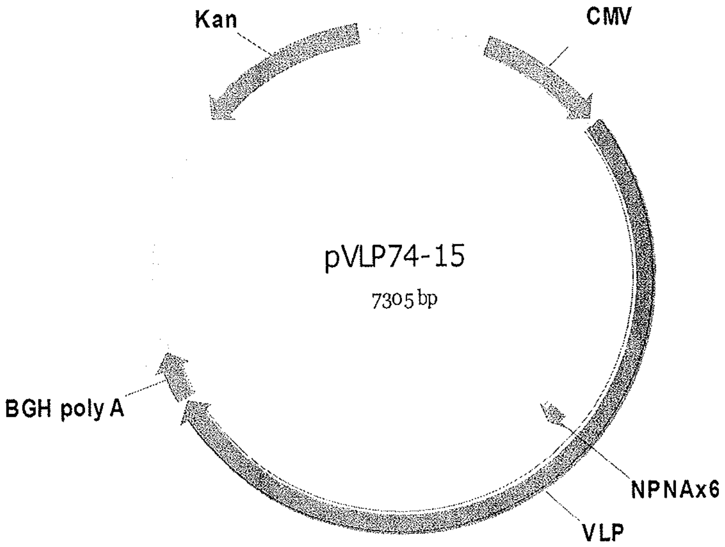
FIG. 1 shows pVLP74_15 (VLP_CHI 532 NPNAx6) vector.
Figure 2:
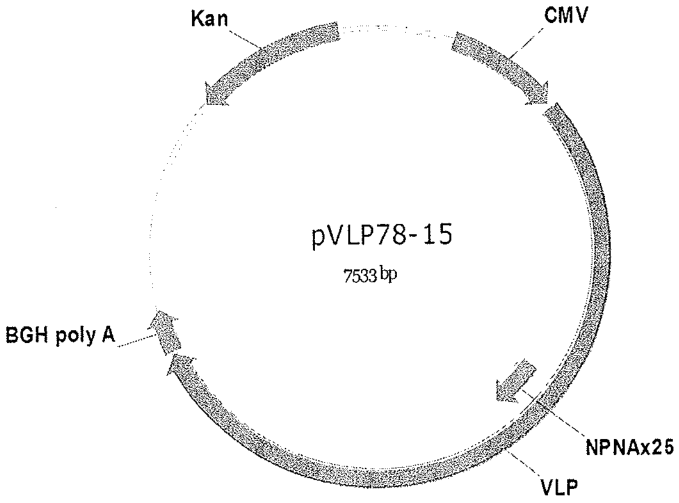
FIG. 2 shows pVLP78_15 (VLP_CHI 532 NPNAx25) vector.
Figure 3:
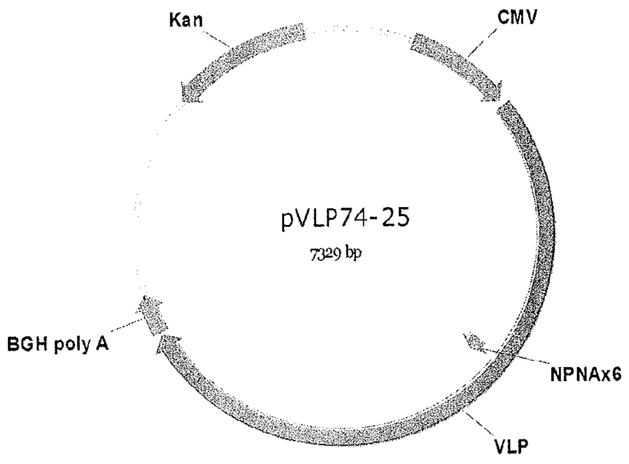
FIG. 3 shows pVLP74_25 (VLP_VEEV 519 NPNAx6) vector.
Figure 4:
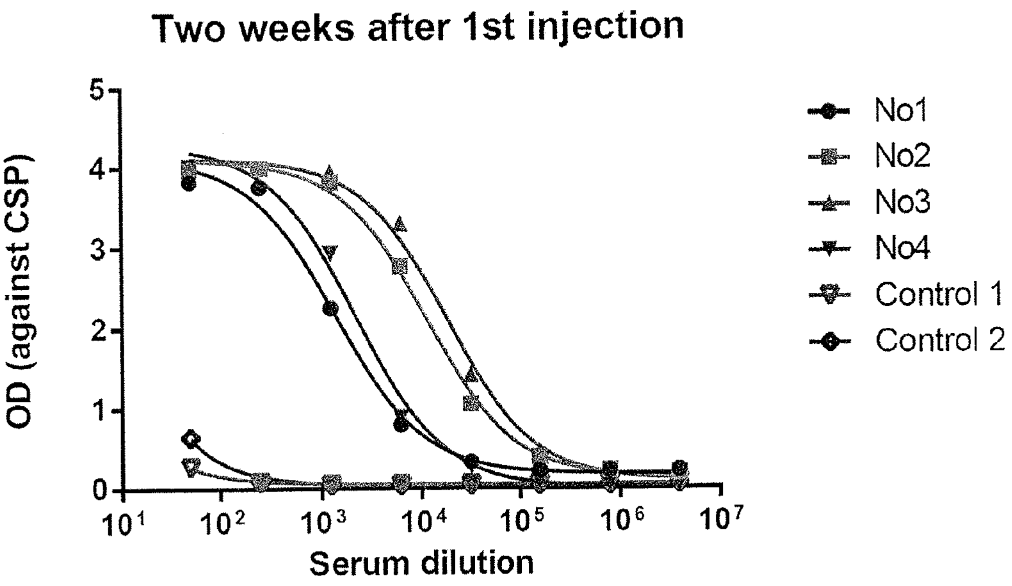
FIG. 4 shows that the serum from individual monkeys immunized with Malaria VLPs after 2 weeks induced high titer of antibodies against CSP.
Figure 5:
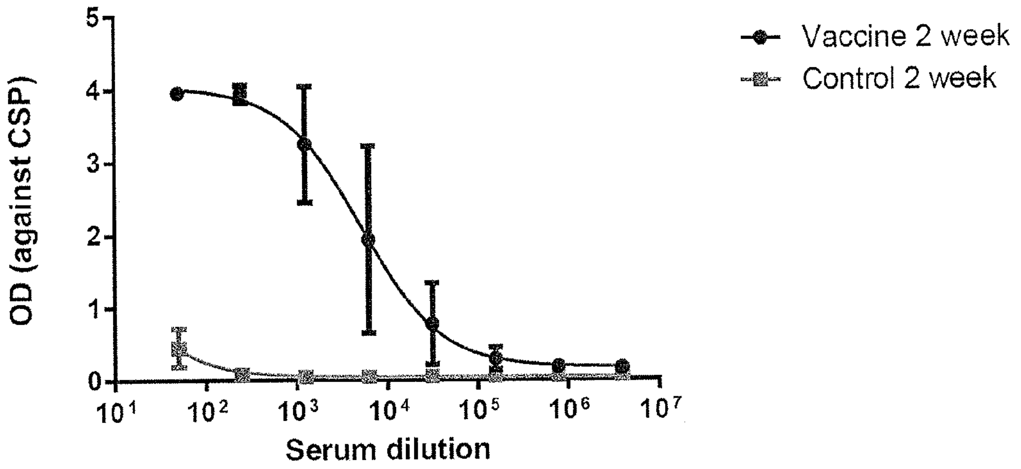
FIG. 5 shows mean value and SD of the data shown in FIG. 4.
Figure 6:
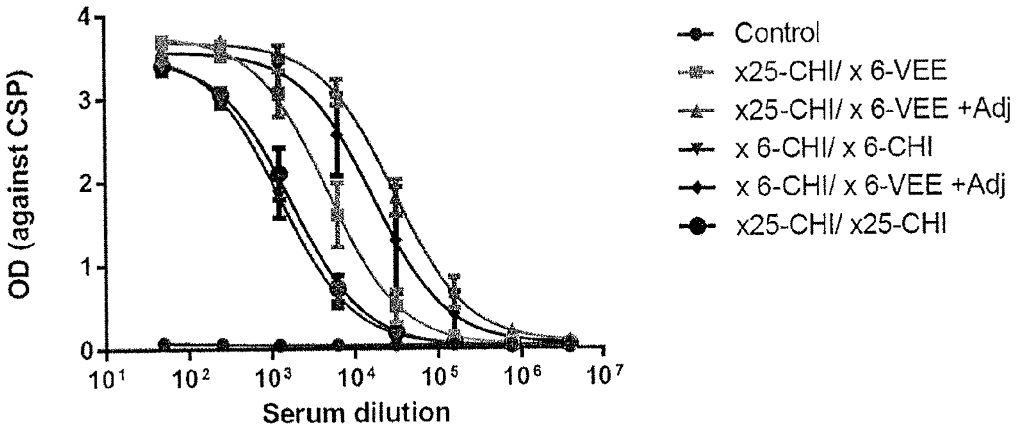
FIG. 6 shows effects of combined immunization of CHIKV VLP and VEEV VLP on induction of antibodies against CSP. In the figure, Adj indicates adjuvant.

The Immunogenicities are shown in FIGS. 4 to 6.

Induction of antibodies against CSP was found in the serum of all monkeys immunized with Malaria VLPs (see FIG. 4). The mean OD values indicating titer of antibodies against CSP is shown in FIG. 5. FIG. 5 shows that the serum from immunized monkeys induced high titer of antibodies against CSP.

As seen in FIG. 6, higher titer of antibodies against CSP was achieved when CHIKV VLP particle comprising NPNA and VEEV VLP particle comprising NPNA were used for the priming immunization and boosting immunization, respectively, compared to when only CHIKV VLP particle comprising NPNA was used for both of the priming immunization and the boosting immunization. In addition, FIG. 6 shows that use of adjuvant further enhanced the titer of antibodies against CSP. Further, FIG. 6 shows that administration of 25-repeats of NPNA induces higher titer of antibodies against CSP compared to administration of 6-repeats of NPNA.

The anti-Pf CSP antibody titer in the serum from the monkeys immunized with ×25-CHI (80 ug) at 0 week and ×6-VEE (80 ug) at 3 week without using adjuvant was measured by ELISA at Malaria Serology Lab Malaria Vaccine Branch, WRAIR. In the ELISA performed at Malaria Serology Lab Malaria Vaccine Branch, WRAIR, the plates were coated with CSPrp ((NPNA)6 Peptide) [0.2 μg/μL]

(Supplier: Eurogentec EP070034) and Goat α-Human IgG (KPL/074-1002 LOT#120714) was used as 2nd antibody. The final titer was determined by the dilution factor that yields an OD of 1.0 (414 nm).

As a result, the anti-Pf CSP antibody titer in the serum from the monkeys was enhanced after 2nd immunization compared to 1st immunization (see Table 2). Compared to the anti-Pf CSP antibody titer in the serum from the monkeys immunized with RTS,S (GlaxoSmithKline), the anti-Pf CSP antibody titer in the serum from the monkeys immunized with ×25-CHI (80 ug) and ×6-VEE (80 ug) in the absence of adjuvant was considered to be higher even though RTS,S (GlaxoSmithKline) contains adjuvant.

TABLE 2

| Animal No. | After 1st immunization Week 2 | After 2nd immunization Week 5 |
|---|---|---|
| 1 | 8990 | 29420 |
| 2 | 48210 | 44100 |
| 3 | 80400 | 51230 |
| 4 | 16260 | 19640 |
| Geometric mean | 27359 | 33801 |

Example 4

Immunogenicity in Mouse

The mice immunized with 10 ug of VLP78_15 at week 0, 10 ug of VLP74_25 at week 3 and 10 ug of VLP78_15 at week 6 with or without adjuvant (Sigma Adjuvant System, Sigma, S6322) by intramuscular injection.

The anti-Pf CSP antibody titer in the serum from the immunized mice were measured by ELISA at Malaria Serology Lab Malaria Vaccine Branch, WRAIR, where plates were coated with CSPrp ((NPNA)6 Peptide) [0.2 μg/μL] (Supplier: Eurogentec EP070034) and Goat α-Mouse IgG (KPL/074-1806 LOT#100737) is used as 2nd antibody to detect the antibodies in the serum.

The final titer was determined by the dilution factor that yields an OD of 1.0 (414 nm).

The Immunogenicity are shown in Tables 3 and 4.

Tables 3 and 4 show that higher titer of antibodies against CSP was achieved after immunizing virus like particle three times. In addition, Tables 3 and 4 show that use of adjuvant enhanced the titer of antibodies against CSP.

TABLE 3

| Mouse Week 3 (after 1st immunization) | | |
|---|---|---|
| Mouse No. | VLP | VLP + Adjuvant |
| 1 | 6070 | QNS |
| 2 | 5850 | 13680 |
| 3 | 9610 | 7610 |
| 4 | 5440 | 23370 |
| 5 | 16320 | 27390 |
| Geometric Mean | 7875 | 16066 |

QNS = Quantity not sufficient to test

TABLE 4

| Mouse Week 9 (after 1st immunization) | | |
|---|---|---|
| Mouse No. | VLP | VLP + Adjuvant |
| 1 | 35510 | 729000 |
| 2 | 15040 | 197800 |
| 3 | 41650 | 106700 |
| 4 | 37250 | 436000 |
| 5 | 48200 | 497600 |
| Geometric Mean | 33134 | 319666 |

Example 5

Immunogenicity of *P. yoelii* CSP Inserted VLP in Mice

QGPGAP seen in the rodent malaria CSP (*P. yoelii* CSP) was used as an antigen. 6×QGPGAP was inserted into CHIKV VLP. The mice were immunized with the CHIKV VLP 2 times at 0 and 8 week (20 ug VLP per mouse) by intramuscle injection with or without Adjuvant Ribi.

Immunogenicity was confirmed at 4, 6, 10 and 14 weeks after the first immunization. The anti-*P. yoelii* CSP antibody were measured by ELISA. The ELISA was performed in the same way as ELISA described in Example 3 except that the plates were coated with *P. Yoelii* CSP repeat sequence peptide at 0.1 ng/μl. The secondary antibody was anti-mouse IgG HRP (Cell signal, #7076S). The results are shown in FIGS. 7-9.

FIGS. 7-9 show that higher titer of antibodies against CSP was achieved by intramuscler administration of CHIKV VLP comprising 6×QGPGAP. In addition, FIGS. 7-9 show that use of adjuvant enhanced the titer of antibodies against CSP.

Example 6

Protection of Mice Against Malaria by Intramuscle Injection of CHIKV VLP Comprising *P. yoelii* CSP Epitope: 6×QGPGAP 6×QGPGAP was inserted into CHIKV VLP. The mice (n=5) were immunized with the CHIKV VLP 2 times at 0 and 8 week (20 ug VLP per mouse) by intramuscle injection with or without Adjuvant Ribi (see FIG. 10). Rodent malaria: *P. yoelii*-challenge (i.v.) was conducted at 17 weeks (see FIG. 10).

Malaria infection was confirmed by PCR. Genomic DNA was purified from the mice blood day 6 after challenge. 18S malaria DNA was amplified by PCR. FIG. 11 shows results of the PCR, indicating that all of 5 control mice (PBS injection) were infected with malaria; all of 5 mice immunized with Control VLP were infected with malaria; among 5 mice immunized with CHIKV VLP comprising 6×QGPGAP, 2 mice were infected with malaria and 3 mice were not infected with malaria; and among 5 mice immunized with CHIKV VLP comprising 6×QGPGAP with adjuvant: Ribi, 1 mouse was infected with malaria and 4 mice were not infected with malaria.

Example 7

Preparation of Vaccine Composition Comprising Chikungunya Virus (CHIKV) Like Particle Comprising NPNA Repeat or Venezuelan Equine Encephalitis Virus (VEEV) Like Particle Comprising NPNA Repeat Chikungunya virus (CHIKV) like particle comprising 6× or 25×NPNA was prepared according to Example 1, and Venezuelan equine encephalitis virus (VEEV) like particle comprising 6×NPNA was prepared according to Example 2. To prepare a vaccine composition, 80 μg of each of the prepared particles was mixed with 1 ml of Sucrose Phosphate Solution, pH 7.2, Endotoxin Free (Teknova, SP buffer).

The invention claimed is:

1. A Chikungunya virus (CHIKV) or Venezuelan equine encephalitis virus (VEEV) virus-like particle, wherein said virus-like particle contains at least one malaria antigen inserted into an E2 envelope protein to form a fusion protein, wherein said at least one malaria antigen is inserted within a CHIKV E2 envelope protein at a site that corresponds in position to a site between residues 509-512, the site between residues 519-520, the site between residues 529-530, or the site between residues 531-532 of SEQ ID NO: 1 or 2; or wherein said at least one antigen is inserted within a VEEV E2 envelope protein at a site that corresponds in position to a site between residues 515-520, or a site between residues 536-539 of SEQ ID NO: 3, and wherein said at least one malaria antigen is selected from the group consisting of (a) and (b):

(a) (NPNA)$_n$, wherein n is from 4 to 30; and (b) (EYLNKIQNSLSTEWSPCSVT)$_y$, wherein y is from 1 to 6.

2. The virus-like particle according to claim 1, which comprises capsid, E1 and E2.

3. The virus-like particle according to claim 1, wherein the virus-like particle comprises E1, E2 and capsid protein, wherein said envelope protein E2 consists of the amino acid sequence of SEQ ID NO: 50;

wherein said envelope protein E1 consists of the amino acid sequence of SEQ ID NO: 51; and wherein said capsid protein consists of the amino acid sequence of SEQ ID NO: 52.

4. The particle according to claim 1, wherein the particle is Venezuelan equine virus like particle consisting of one or more envelope protein E2 into which the antigen is inserted, one or more envelope protein E1 and one or more capsid, and wherein the envelope protein E2 into which the antigen is inserted consists of an amino acid sequence represented by SEQ ID NO.53; the envelope protein E1 consists of an amino acid sequence represented by SEQ ID NO.54; and the capsid consists of an amino acid sequence represented by SEQ ID NO.: 55.

5. An isolated nucleic acid molecule comprising a nucleotide for expressing the particle according to claim 1.

6. An isolated nucleic acid molecule consisting of a nucleotide sequence which has a sequence identity of 90% or more with a nucleotide sequence represented by SEQ ID Nos.26-27, 29-30, 32-33, 35-36, 38, 40 or 42.

7. A vector comprising the nucleic acid molecule according to claim 5, wherein the vector optionally comprises an expression control sequence operably linked to the nucleic acid molecule.

8. A pharmaceutical composition comprising:

particle according to claim 1 and/or a nucleic acid molecule comprising a nucleotide sequence for expressing the particle according to claim 1; and (b) a pharmaceutically acceptable carrier.

9. A vaccine composition comprising the virus-like according to claim 1.

10. A method of treating malaria, comprising administering an effective amount of the composition of claim 8 to a mammal.

11. A vaccine comprising, as separate components, a priming composition comprising at least one first malaria antigen or at least one polynucleotide encoding at least one first malaria antigen; and a boosting composition comprising at least one polypeptide comprising at least one second malaria antigen or at least one polynucleotide encoding at least one second malaria antigen, wherein at least one of said compositions comprises the particle of claim 1, or a nucleic acid encoding said particle.

12. The vaccine of claim 11, wherein the polynucleotide encodes substantially all of the circumsporozoite protein.

13. The vaccine composition according to claim 9, for use in the prevention or treatment of malaria.

14. A kit comprising
(a) a first vaccine composition comprising a virus-like particle according to claim 1; and
(b) a second vaccine composition comprising a virus-like particle according to claim 1,
wherein the virus-like particle contained in said first vaccine composition is a virus-like particle which is different from the virus-like particle contained in said second vaccine composition.

15. The kit according to claim 14, further comprising (c) a third vaccine composition comprising a virus-like particle according to claim 1, wherein said first vaccine composition is used for priming immunization and said second and third vaccine compositions are used for boosting immunization, and wherein the virus-like particle contained in said third vaccine composition is different from the virus-like particle contained in said first and second vaccine compositions, or is the same as a virus-like particle contained in either said first or second vaccine composition.

16. The isolated nucleic acid molecule according to claim 6, which consists of a nucleotide sequence represented by SEQ ID Nos. 26-27, 29-30, 32-33, 35-36, 38, 40 or 42.

17. The virus-like particle according to claim 1, wherein one or two linkers intervene between the N-terminal residue of the at least one malaria antigen and the E2 envelope protein, and/or between the C-terminal residue of the at least one malaria antigen and the E2 envelope protein.

18. The virus-like particle according to claim 1, wherein the virus-like particle comprises an amino acid sequence selected from the group consisting of SEQ ID NOs: 28, 31, 39 and 41.

* * * * *